US008158768B2

(12) United States Patent
Dina et al.

(10) Patent No.: US 8,158,768 B2
(45) Date of Patent: Apr. 17, 2012

(54) IMMUNOSTIMULATORY SEQUENCE OLIGONUCLEOTIDES AND METHODS OF USING THE SAME

(75) Inventors: Dino Dina, Oakland, CA (US); Karen L. Fearon, Lafayette, CA (US); Jason Marshall, Oakland, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 0 days.

(21) Appl. No.: 12/566,521

(22) Filed: Sep. 24, 2009

(65) Prior Publication Data

US 2010/0184834 A1 Jul. 22, 2010

Related U.S. Application Data

(63) Continuation of application No. 10/741,720, filed on Dec. 18, 2003, now Pat. No. 7,745,606.

(60) Provisional application No. 60/436,122, filed on Dec. 23, 2002, provisional application No. 60/447,885, filed on Feb. 13, 2003, provisional application No. 60/467,546, filed on May 1, 2003.

(51) Int. Cl.
*A61K 45/00* (2006.01)
*A61K 47/00* (2006.01)
*A61K 31/70* (2006.01)
*A01N 43/04* (2006.01)
*C07H 21/04* (2006.01)
*C07H 21/02* (2006.01)

(52) U.S. Cl. .............. 536/23.1; 536/24.2; 514/44 R; 424/278.1

(58) Field of Classification Search ............ None
See application file for complete search history.

(56) References Cited

U.S. PATENT DOCUMENTS

| | | | |
|---|---|---|---|
| 4,458,066 A | 7/1984 | Caruthers et al. | |
| 4,650,675 A | 3/1987 | Borel et al. | |
| 4,849,513 A | 7/1989 | Smith et al. | |
| 4,910,300 A | 3/1990 | Urdea et al. | |
| 4,948,882 A | 8/1990 | Ruth | |
| 5,015,733 A | 5/1991 | Smith et al. | |
| 5,093,232 A | 3/1992 | Urdea et al. | |
| 5,118,800 A | 6/1992 | Smith et al. | |
| 5,118,802 A | 6/1992 | Smith et al. | |
| 5,124,246 A | 6/1992 | Urdea et al. | |
| 5,391,723 A | 2/1995 | Priest | |
| 5,453,496 A | 9/1995 | Caruthers et al. | |
| 5,460,831 A | 10/1995 | Kossovsky et al. | |
| 5,484,596 A | 1/1996 | Hanna, Jr. et al. | |
| 5,552,391 A | 9/1996 | Coutts et al. | |
| 5,663,153 A | 9/1997 | Hutcherson et al. | |
| 5,723,335 A | 3/1998 | Hutcherson et al. | |
| 5,849,719 A | 12/1998 | Carson et al. | |
| 5,879,906 A | 3/1999 | Jefferson et al. | |
| 6,090,791 A | 7/2000 | Sato et al. | |
| 6,165,726 A | 12/2000 | Iyyalasomayazula | |
| 6,171,820 B1 * | 1/2001 | Short | 506/1 |
| 6,174,872 B1 | 1/2001 | Carson et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,406,705 B1 | 6/2002 | Davis et al. | |
| 6,426,334 B1 | 7/2002 | Agrawal et al. | |
| 6,426,336 B1 | 7/2002 | Carson et al. | |
| 6,429,199 B1 | 8/2002 | Krieg et al. | |
| 6,476,000 B1 | 11/2002 | Agrawal | |
| 6,482,409 B1 | 11/2002 | Lobb et al. | |
| 6,552,006 B2 | 4/2003 | Raz et al. | |
| 6,589,940 B1 | 7/2003 | Raz et al. | |
| 6,610,661 B1 * | 8/2003 | Carson et al. | 514/44 R |
| 6,613,751 B2 | 9/2003 | Raz et al. | |
| 6,677,115 B2 * | 1/2004 | Short | 435/4 |
| 6,800,744 B1 | 10/2004 | Doucette-Stamm et al. | |
| 7,105,495 B2 | 9/2006 | Agrawal et al. | |
| 7,115,579 B2 | 10/2006 | Agrawal et al. | |
| 7,129,222 B2 | 10/2006 | Van Nest et al. | |
| 7,176,296 B2 | 2/2007 | Agrawal et al. | |
| 7,183,111 B2 | 2/2007 | Van Nest et al. | |
| 7,208,478 B2 | 4/2007 | Carson et al. | |
| 7,250,403 B2 | 7/2007 | Van Nest et al. | |
| 7,255,868 B2 | 8/2007 | Fearon et al. | |
| 7,371,734 B2 | 5/2008 | Phillips et al. | |
| 7,479,285 B1 * | 1/2009 | Van Nest et al. | 424/278.1 |
| 7,485,627 B2 | 2/2009 | Raz et al. | |
| 7,625,872 B2 * | 12/2009 | Fearon | 514/44 R |
| 7,718,622 B2 * | 5/2010 | Tuck et al. | 514/43 |
| 7,727,712 B2 * | 6/2010 | Van Nest et al. | 435/5 |

(Continued)

FOREIGN PATENT DOCUMENTS

| | | |
|---|---|---|
| EP | 0 468 520 A2 | 1/1992 |
| JP | 4-352724 A | 12/1992 |
| JP | 2002-517156 A | 11/2002 |
| WO | WO-96/02555 A1 | 2/1996 |
| WO | WO-97/28259 A1 | 8/1997 |
| WO | WO-98/05770 A2 | 2/1998 |
| WO | WO-98/05770 A3 | 2/1998 |
| WO | WO-98/16247 A1 | 4/1998 |
| WO | WO-98/18810 A1 | 5/1998 |
| WO | WO-98/37919 A1 | 9/1998 |

(Continued)

OTHER PUBLICATIONS

Agrawal, S. et al. et al. (1986). "Efficient Methods for Attaching Non-Radioactive Labels to the 5' ends of Synthetic Oligodeoxyribonucleotides," *Nucleic Acids Res.* 14(15):6227-6245.

Agrawal, S. et al. (Feb. 2000). "Antisense Therapeutics: Is it as Simple as Complementary Base Recognition?" *Molecular Medicine Today* 6:72-81.

(Continued)

*Primary Examiner* — Nita M Minnifield
(74) *Attorney, Agent, or Firm* — Morrison & Foerster LLP

(57) ABSTRACT

The invention provides immunomodulatory polynucleotides and methods for immunomodulation of individuals using the immunomodulatory polynucleotides.

12 Claims, 2 Drawing Sheets

U.S. PATENT DOCUMENTS

| | | | |
|---|---|---|---|
| 7,745,606 B2* | 6/2010 | Dina et al. ............... | 536/24.2 |
| 7,785,610 B2* | 8/2010 | Fearon et al. ............ | 424/278.1 |
| 8,003,115 B2* | 8/2011 | Fearon et al. ............ | 424/280.1 |
| 2002/0042383 A1 | 4/2002 | Yew et al. | |
| 2002/0065236 A1 | 5/2002 | Yew et al. | |
| 2002/0137714 A1 | 9/2002 | Kandimalla et al. | |
| 2003/0049266 A1 | 3/2003 | Fearon et al. | |
| 2003/0060440 A1 | 3/2003 | Klinman et al. | |
| 2003/0133988 A1 | 7/2003 | Fearon et al. | |
| 2003/0148976 A1 | 8/2003 | Krieg et al. | |
| 2003/0175731 A1 | 9/2003 | Fearon et al. | |
| 2003/0199466 A1 | 10/2003 | Fearon et al. | |
| 2003/0212026 A1 | 11/2003 | Krieg et al. | |
| 2003/0212029 A1 | 11/2003 | Agrawal et al. | |
| 2003/0220277 A1 | 11/2003 | Yew et al. | |
| 2003/0225016 A1 | 12/2003 | Fearon et al. | |
| 2004/0006034 A1 | 1/2004 | Raz et al. | |
| 2004/0053870 A1 | 3/2004 | Yew et al. | |
| 2004/0132677 A1 | 7/2004 | Fearon et al. | |
| 2005/0064401 A1 | 3/2005 | Olek et al. | |
| 2006/0058254 A1 | 3/2006 | Dina et al. | |
| 2007/0049550 A1 | 3/2007 | Fearon et al. | |
| 2008/0207550 A1 | 8/2008 | Fearon et al. | |
| 2009/0068208 A1 | 3/2009 | Hessel et al. | |
| 2009/0149411 A1 | 6/2009 | Schwartz | |

FOREIGN PATENT DOCUMENTS

| | | |
|---|---|---|
| WO | WO-98/40100 A1 | 9/1998 |
| WO | WO-98/52581 A1 | 11/1998 |
| WO | WO-98/52962 A1 | 11/1998 |
| WO | WO-98/55495 A2 | 12/1998 |
| WO | WO-98/55495 A3 | 12/1998 |
| WO | WO-98/55495 B1 | 12/1998 |
| WO | WO-98/55609 A1 | 12/1998 |
| WO | WO-99/11275 A2 | 3/1999 |
| WO | WO-99/11275 A3 | 3/1999 |
| WO | WO-99/33488 A2 | 7/1999 |
| WO | WO-99/33868 A2 | 7/1999 |
| WO | WO-99/51259 A2 | 10/1999 |
| WO | WO-99/56755 A1 | 11/1999 |
| WO | WO-99/61056 A2 | 12/1999 |
| WO | WO-99/62923 A2 | 12/1999 |
| WO | WO-00/06588 A1 | 2/2000 |
| WO | WO-00/16804 A1 | 3/2000 |
| WO | WO-00/21556 A1 | 4/2000 |
| WO | WO-00/50006 A2 | 8/2000 |
| WO | WO-00/50006 A3 | 8/2000 |
| WO | WO-00/61151 A2 | 10/2000 |
| WO | WO-00/67023 A1 | 11/2000 |
| WO | WO-00/67787 A2 | 11/2000 |
| WO | WO-01/12223 A2 | 2/2001 |
| WO | WO-01/12804 A2 | 2/2001 |
| WO | WO-01/15726 A2 | 3/2001 |
| WO | WO-01/22972 A2 | 4/2001 |
| WO | WO-01/22990 A2 | 4/2001 |
| WO | WO-01/35991 A2 | 5/2001 |
| WO | WO-01/45750 A1 | 6/2001 |
| WO | WO-01/51500 A1 | 7/2001 |
| WO | WO-01/54720 A1 | 8/2001 |
| WO | WO-01/55341 A2 | 8/2001 |
| WO | WO-01/55370 A2 | 8/2001 |
| WO | WO-01/62207 A2 | 8/2001 |
| WO | WO-01/68077 A2 | 9/2001 |
| WO | WO-01/68078 A2 | 9/2001 |
| WO | WO-01/68103 A2 | 9/2001 |
| WO | WO-01/68116 A2 | 9/2001 |
| WO | WO-01/68117 A2 | 9/2001 |
| WO | WO-01/68143 A2 | 9/2001 |
| WO | WO-01/68144 A2 | 9/2001 |
| WO | WO-01/72123 A1 | 10/2001 |
| WO | WO-01/76642 A1 | 10/2001 |
| WO | WO-01/83503 A2 | 11/2001 |
| WO | WO-01/93902 A2 | 12/2001 |
| WO | WO-02/18631 A2 | 3/2002 |
| WO | WO-02/18631 A3 | 3/2002 |
| WO | WO-02/26757 A2 | 4/2002 |
| WO | WO-02/052002 | 7/2002 |
| WO | WO-02/069369 A2 | 9/2002 |
| WO | WO-02/074922 A2 | 9/2002 |
| WO | WO-03/000922 A2 | 1/2003 |
| WO | WO-03/000922 A3 | 1/2003 |
| WO | WO-03/014316 A2 | 2/2003 |
| WO | WO-03/014316 A3 | 2/2003 |
| WO | WO-03/015711 A2 | 2/2003 |
| WO | WO-03/015711 A3 | 2/2003 |
| WO | WO-03/015816 A1 | 2/2003 |
| WO | WO-03/020884 A2 | 3/2003 |
| WO | WO-03/020884 A3 | 3/2003 |
| WO | WO-2004/014322 A2 | 2/2004 |
| WO | WO-2004/058179 A2 | 7/2004 |
| WO | WO-2004/058179 A3 | 7/2004 |

OTHER PUBLICATIONS

Agrawal, S. et al. (Mar. 2002). "Medicinal Chemistry and Therapeutic Potential CpG DNA," *Trends in Molecular Medicine* 8(3):114-121.

Ahmeida, E.T.S. Ben et al. (1993). "Immunopotentiation of Local and Systemic Humoral Immune Responses by ISCOMs, Liposomes and FCA: Role in Protection Against Influenza A in Mice," *Vaccine* 11(13):1302-1309.

Aramaki, Y. et al. (1995). "Interferon-γ Inductive Effect of Liposomes as an Immunoadjuvant," *Vaccine* 13(18):1809-1814.

Asanuma, H. et al. (1995). "Cross-Protection Against Influenza Virus Infection in Mice Vaccinated by Combined Nasal-Subcutaneous Administration," *Vaccine* 13(1):3-5.

Atherton, E. et al. (Jul. 1981). "Synthesis of a 21-Residue Fragment of Human Proinsulin by the Polyamide Solid Phase Method," *Hoppe-Seylers Z. Physiol. Chem.* 362:833-839.

Ausubel, F.M. et al., eds. (1995). *Current Protocols in Molecular Biology*, vol. 1, John Wiley & Sons, Inc.: pp. iii-xii (Table of Contents).

Ballas, Z.K. et al. (1996). "Induction of NK Activity in Murine and Human Cells by CpG Motifs in Oligodeoxynucleotides and Bacterial DNA," *J. Immunol.* 157:1840-1845.

Bauer, M. et al. (1999). "DNA Activates Human Immune Cells Through a CpG Sequence-Dependent Manner," *Immunology* 97:699-705.

Bauer, M. et al. (2001). "Bacterial CpG-DNA Triggers Activation and Maturation of Human CD11c-, CD123+ Dendritic Cells," *J. Immunol.* 166:5000-5007.

Beaucage, S. L. (1993). "Oligodeoxyribonucleotide Synthesis," Chapter 3 in *Protocols for Oligonucleotides and Analogs, Synthesis and Properties*, Sudhir Agrawal, ed., Humana Press, Totowa, NJ., 20:33-61.

Benoit, R. et al. (1987). "Peptides. Strategies for Antibody Production and Radioimmunoassays," in *Neuromethods*, Alan A. Boulton et al., eds., Humana Press, Clifton, NJ 6:43-72.

Bischoff, R. et al. (1987). "Introduction of 5'-Terminal Functional Groups into Synthetic Oligonucleotides for Selective Immobilization," *Anal. Bioch.* 164:336-344.

Blanks, R. et al. (1988). "An Oligodeoxynucleotide Affinity Column for the Isolation of Sequence Specific DNA Binding Proteins," *Nucleic Acids Res.* 16(21):10282-10299.

Bohle, B. et al. (1999). "Oligodeoxynucleotides Containing CpG Motifs Induce IL-12, IL-18 and IFN-γ Production in Cells from Allergic Individuals and Inhibit IgE Synthesis in vitro," *Eur. J. Immunol.* 29:2344-2353.

Borel, H. et al. (1990). "A Novel Technique to Link Either Proteins or Peptides to Gammaglobulin to Construct Tolerogens," *Immunol. Methods* 126:159-168.

Borel, Y. et al. (1995). "Food Allergens Transformed Into Tolerogens," *Int. Arch. Allergy Immunol.* 107:264-267.

Borel, Y. et al. (1996). "Parenteral and Oral Administation of Tolerogens: Protein-IgG Conjugates," in *Oral Tolerance: Mechanisms and Applications* Ann. N.Y. Acad. Sci., Weiner, H.L. et al. eds., 778:80-87.

Boujrad, N. et al. (Jun. 1993). "Inhibition of Hormone-Stimulated Steroidogenesis in Cultured Leydig Tumor Cells by a Cholesterol-Linked Phosphorothioate Oligodeoxynucleotide Antisense to Diazepam-Binding Inhibitor," *P NAS USA* 90:5728-5731.

Bousquet, Y. et al. (1999). "Molecular Mechanisms of the Adsorption of a Model Protein (Human Serum Albumin) on Poly(Methylidene Malonate 2.1.2) Nanoparticles," *Pharm. Res.* 16(1):141-147.

Branda, R.F. et al. (1993). "Immune Stimulation by an Antisense Oligomer Complementary to the *rev* Gene of HIV-1," *Biochem. Pharmacol.* 45(10):2037-2043.

Branda, R.F. et al. (1996). "Amplification of Antibody Production by Phosphorotioate Oligodeoxynucleotides," *J. Lab. Clin. Med.* 128:329-338.

Braun, R. P. and Lee, J. S. (1988). "Immunogenic Duplex Nucleic Acids are Nuclease Resistant," *J. Immunol.* 141(6):2084-2089.

Brazolot Milan, C.L. et al. (Dec. 22, 1998). "CpG DNA can Induce Strong Th1 Humoral and Cell-Mediated Immune Responses Against Hepatitis B Surface Antigen in Young Men," *Proc. Natl. Acad. Sci. USA* 95(26):15553-15558.

Breiteneder, H. et al. (1989). "The Gene Coding for the Major Birch Pollen Allergen *Betvl*, is Highly Homologous to a Pea Disease Resistance Response Gene," *EMBO J.* 8(7):1935-1938.

Britigan, B.E. et al. (2001). "Lactoferrin Binds CpG-Containing Oligonucleotides and Inhibits Their Immunostimulatory Effects of Human B Cells," *The Journal of Immunology* 167:2921-2928.

Broide, D. et al. (1998). "Immunostimulatory DNA Sequences Inhibit Il-5, Eosinophilic Inflammation, and Airway Hyper-responsiveness in Mice," *J. Immunol.* 161:7054-7062.

Broide, D. et al. (1999). "DNA-Based Immunization for Asthma," *Int. Arch. Allergy Immunol.* 118:453-456.

Broide, D.H. et al. (2001). "Systemic Administration of Immunostimulatory DNA Sequences Mediates Reversible Inhibition of the Th2 Responses in a Mouse Model of Asthma," *J. Clin. Immunol.* 21(3):175-182.

Carson, D.A. et al. (Nov. 17, 1997). "Oligonucleotide Adjuvants for T Helper 1 (Th-1)-Specific Vaccination," *J. Exp. Med.* 186(10):1621-1622.

Chace, J.H. et al. (Aug. 1997). "Bacterial DNA-Induced NK Cell IFN-γ Production is Dependent on Macrophage Secretion of IL-12," *Clin. Immunol. and Immunopathol.* 84(2):185-193.

Chaturvedi, S. et al. (1996). "Stabilization of Triple-Stranded Oligonucleotide Complexes: Use of Probes Containing Alternating Phosphodiester and Stereo-Uniform Cationic Phosphoramidate Linkages," *Nucleic Acids Res.* 24(12):2318-2323.

Chavany, C. et al. (1992). "Polyalkylcyanoacrylate Nanoparticles as Polymeric Carriers for Antisense Oligonucleotides," *Pharm. Res.* 9(4):441-449.

Chavany, C. et al. (1994). "Adsorption of Oligonucleotides onto Polyisohexylcyanoacrylate Nanoparticles Protects Them Against Nucleases and Increases Their Cellular Uptake," *Pharm. Res.* 11(9):1370-1378.

Chen, Z. et al. (1999). "Enhanced Protection Against a Letha Influenza Virus Challenge by Immunization with Both Hemagglutinin- and Neuraminidase-Expressing DNAs," *Vaccine* 17:653-659.

Cho, H.J. et al. (May 2000). "Immunostimulatory DNA-Based Vaccines Induce Cytotoxic Lymphocyte Activity by a T-Helper Cell-Independent Mechanism," *Nat. Biotechnol.* 18:509-514.

Chua, K.Y. et al. (Jan. 1, 1988). "Sequence Analysis of cDNA Coding for a Major House Dust Mite Allergen, *Der p* 1. Homology with Cysteine Proteases," *J. Exp. Med.* 167(1):175-182.

Chua, K.Y. et al. (1990). "Expression of *Dermatophagoides pteronyssinus* Allergen, *Der p* II, in *Escherichia coli* and the Binding Studies with Human IgE," *Int. Arch. Allergy Appl. Immunol.* 91:124-129.

Chu, R.S. et al. (Nov. 17, 1997). "CpG Oligodeoxynucleotides Act as Adjuvants that Switch on T Helper 1 (Th1) Immunity," *J. Exp. Med.* 186(10):1623-1631.

Coligan, J. E. et al., eds. (1998). *Current Protocols in Immunology*, vol. 1, John Wiley & Sons, Inc: pp. 1-9.

Connolly, B.A. (1985). "Chemical Synthesis of Oligonucleotides Containing a Free Sulphydryl Group and Subsequent Attachment of Thiol Specific Probes," *Nucleic Acids Res.* 13(12):4485-4502.

Connolly, B. A. (1987). "The Synthesis of Oligonucleotides Containing a Primary Amino Group at the 5'-Terminus," *Nucleic Acids Res.* 15(7):3131-3139.

Cooke, S.K. et al. (1997). "Allergenic Properties of Ovomucoid in Man," *J. Immunol.* 159:2026-2032.

Corey, D. R. et al. (Dec. 1987). "Generation of a Hybrid Sequence-Specific Single-Stranded Deoxyribonuclease," *Science* 238:1401-1403.

Cowdery, J.S. et al. (1996). "Bacterial DNA Induces NK Cells to Produce IFN-γ in Vivo and Increases the Toxicity of Lipopolysaccharides," *J. Immunol.* 156:4570-4575.

Dalpke, A.H. et al. (2002). "Phosphodiester CpG Oligonucleotides as Adjuvants: Polyguanosine Runs Enhance Cellular Uptake and Improve Immunostimulative Activity of Phosphodiester CpG Oligonucleotides in vitro and in vivo," *Immunology* 106:102-112.

De Martino, M. et al. (Aug. 1999). "Low IgG3 and High IgG4 Subclass Levels in Children with Advanced Human Immunodeficiency Virus-Type 1 Infection and Elevated IgE Levels," *Annals of Allergy, Asthma & Immunol.* 83:160-164.

Douglas, S. J. et al. (1987). "Nanoparticles in Drug Delivery," *Crit. Rev. Ther. Drug. Carrier Syst.* 3(3):233-261.

Dumas, V. et al. (1995). "Induction of Tolerance by Administration of Hapten-Immunoglobulin Conjugates is Associated with Decreased Il-2 and IL-4 Production," *Arch. Dermatol. Res.* 287:123-128.

Elkins, K. L. et al. (1999). "Bacterial DNA Containing CpG Motifs Stimulates Lymphocyte-Dependent Protection of Mice Against Lethal Infection with Intracellular Bacteria," *J. Immunol.* 162:2291-2298.

Elsayed, S. et al. (1991). "The Structural Requirements of Epitopes with IgE Binding Capacity Demonstrated by Three Major Allergens from Fish, Egg and Tree Pollen," *Scand. J. Clin. Lab. Invest.* 51:Suppl. 204:17-31.

EMBL-EBI Database. (May 5, 1999). "HS_5184_A1_A08_SP6E RPCI-11 Human Male BAC Library *Homo sapiens* Genomic Clone Plate=760 col. 15 Row=A, Genomic Survey Sequence," EBI Accession No. AQ514019, one page.

EMBL-EBI Database. (Jun. 19, 1996). "*Halobacterium halobium* Z-DNA-forming Sequence," EBI Accession No. U58476, one page.

Davis, H.L. et al. (2000). "CpG DNA Overcomes Hyporesponsiveness to Hepatitis B Vaccine in Orangutans," *Vaccine* 18:1920-1924.

Dieudonné, F. et al. (May 2001). ISS Linked to Amb a 1 Allergen (AIC) Stimulates IgG Response to Amb a 1 by Ragweed-Allergic Humans, *J. Allergy Clin. Immunol.* 107:S933.

Elkins, K.L. et al. (1999). "Bacterial DNA Containing CpG Motifs Stimulates Lymphocyte-Dependent Protection of Mice Against Lethal Infection with Intracellular Bacteria," *J. Immunol.* 162:2291-2298.

Fearon, K. et al. (2003). "A Minimal Human Immunostimulatory CpG Motif that Potently Induces IFN-Gamma and IFN-Alpha Production," *Eur. J. Immunol.* 33(8):2114-2122.

Fornadley, J. (1998). "Allergy Immunotherapy," *Otolaryngol. Clin. North Am.* 31(1):111-127.

Freidag, B.L. et al. (May 2000). "CpG Oligodeoxynucleotides and Interleukin-12 Improve the Efficacy of *Myobacterium bovis* BCG Vaccination in Mice Challenged with *M. tuberculosis*," *Infect. Immun.* 68(5):2948-2953.

Freshney, R.I., ed. (1987). *Animal Cell Culture: A Practical Approach*, IRL Press: pp. vii-xii (Table of Contents).

Fujieda, S. et al. (2000). "Synthetic Oligodeoxynucleotides Inhibit IgE Induction in Human Lymphocytes," *Am. J. Respir. Crit. Care Med.* 162:232-239.

Gait, M.J., ed. (1984). *Oligonucleotide Synthesis: A Practical Approach*, IRL Press: pp. vii-xii (Table of Contents).

Galland, A.V. et al. (1998). "Purification of a 41 kDa Cod-Allergenic Protein," *J. Chromatogr. B.* 706:63-71.

Gao, H. et al. (1995). "Circularization of Oligonucleotides by Disulfide Bridge Formation," *Nucleic Acids Res.* 23(11):2025-2029.

Geoghegan, K. F. et al. (1992). "Site-Directed Conjugation of Nonpeptide Groups to Peptides and Proteins Via Periodate Oxidation of a 2-Amino Alcohol. Application to Modification at N-Terminal Serine," *Bioconjug. Chem.* 3(2):138-146.

Ghosh, D.K. et al. (Dec. 2001). "Host Response to Infection: The Role of CpG DNA in Induction of Cyclooxygenase 2 and Nitric Oxide Synthase 2 in Murine Macrophages," *Infection and Immunity* 69(12):7703-7710.

Gierynska, M. et al. (Jul. 2002). "Induction of CD8 T-Cell-Specific Systemic and Mucosal Immunity Against Herpes Simplex Virus with CpG-Peptide Complexes," *J. Virol.* 76(13):6568-6576.

Godard, G. et al. (1995). "Antisense Effects of Cholesterol-Oligodeoxynucleotide Conjugates Associated with Poly(Alkylcyanoacrylate) Nanoparticles," *Eur. J. Biochem.* 232:404-410.

Gomis, S. et al. (Feb. 2003). "Protection of Chickens against *Escherichia coli* Infections by DNA Containing CpG Motifs," *Infection and Immunity* 71(2):857-863.

Goodchild, J. (May/Jun. 1990). "Conjugates of Oligonucleotides and Modified Oligonucleotides: A Review of Their Synthesis and Properties," *Bioconjug. Chem.* 1(3):165-187.

Govorkova, E. A. et al. (1997). "Cross-Protection of Mice Immunized with Different Influenza A (H2) Strains and Challenged with Viruses of the Same HA Subtype," *Acta Virol.* 41:251-257.

Grabarek, Z. et al. (1990). "Zero-Length Crosslinking Procedure with the Use of Active Esters," *Anal. Biochem.* 185:131-135.

Gramzinski, R.A. et al. (1998). "Immune Response to a Hepatitis B DNA Vaccine in *Aotus* Monkeys: A Comparison of Vaccine Formulation, Route, and Method of Administration," *Mol. Med.* 4:109-118.

Granoff, D. M. et al. (1993). "Effect of Immunity to the Carrier Protein on Antibody Responses to *Haemophilus influenzae* Type B Conjugate Vaccines," *Vaccine* 11: Suppl.1:46-51.

Gursel, M. et al. (2002). "CpG Oligodeoxynucleotides Induce Human Monocytes to Mature into Functional Dendritic Cells," *Eur. J. Immunol.* 32:2617-2622.

Gursel, M. et al. (May 2002). "Differential and Competitive Activation of Human Immune Cells by Distinct Classes of CpG Oligodeoxynucleotide," *J. Leukoc. Biol.* 71:813-820.

Hafner, M. et al. (Jul. 15, 2001). "Antimetastatic Effect of CpG DNA Mediated by Type I IFN," *Cancer Res.* 61:5523-5528.

Hagiwara, A. et al. (1987). "A New Drug-Delivery-System of Anticancer Agents: Activated Carbon Particles Adsorbing Anticancer Agents," *In Vivo* 1:241-252.

Names, B.D. et al., eds. (1987). *Transcription and Translation: A Practical Approach*, IRL Press: pp. vii-xiv (Table of Contents).

Haralambidis, J. et al. (1990). "The Synthesis of Polyamide-Oligonucleotide Conjugate Molecules," *Nucleic Acids Res.* 18(3):493-499.

Haralambidis, J. et al. (1990). "The Preparation of Polyamide-Oligonucleotide Probes Containing Multiple Non-Radioactive Labels," *Nucleic Acids Res.* 18(3):501-505.

Hartmann, G. et al. (Aug. 1999). "CpG DNA: A Potent Signal for Growth, Activation, and Maturation of Human Dendritic Cells," *Proc. Natl. Acad. Sci. USA* 96:9305-9310.

Hartmann, G. et al. (2000). "Delineation of a CpG Phosphorothioate Oligodeoxynucleotide for Activating Primate Immune Responses in Vitro and in Vivo," *J. Immunol.* 164:1617-1624.

Hartmann, G. et al. (2000). "Mechanism and Function of a Newly Indentified CpG DNA Motif in Human Primary B Cells," *J. Immunol.* 164:944-952.

Hartmann, G. et al. (2003). "Rational Design of New CpG Oligonucleotides that Combine B Cell Activation with High IFN-α Induction in Plasmacytoid Dendritic Cells," *Eur. J. Immmunol.* 33:1633-1641.

Herbert, W.J. et al. eds. (1995). *The Dictionary of Immunology*, Academic Press: London, England, pp. 88 and 93.

Hermanson, G.T. (1996). *Bioconjugate Techniques*, Academic Press, Inc.: pp. ix-xx (Table of Contents).

Horner, A.A. et al. (1998). "Rapid Communication. Immunostimulatory DNA is a Potent Mucosal Adjuvant," *Cell Immunol.* 190:77-82.

Hornung, V. et al. (2002). "Quantitative Expression of Toll-Like Receptor 1-10 mRNA in Cellular Subsets of Human Peripheral Blood Mononuclear Cells and Sensitivity to CpG Oligodeoxynucleotides," *J. Immunol.* 168:4531-4537.

International Search Report mailed on Sep. 10, 2004, for PCT Patent Application No. PCT/US03/41001, filed on Dec. 18, 2003, 6 pages.

Jäger, A. et al. (1988). "Oligonucleotide *N*-Alkylphosphoramidates: Synthesis and Binding to Polynucleotides," *Biochem.* 27(19):7237-7246.

Jahn-Schmid, B. et al. (Nov. 1999). "Oligodeoxynucleotides Containing CpG Motifs Modulate the Allergic TH2 Response of BALB/C Mice to Bet v 1, the Major Birch Pollen Allergen," *J. Allergy Clin. Immunol.* 104(5):1015-1023.

Jakob, T. et al. (1998). "Activation of Cutaneous Dendritic Cells by CpG-Containing Oligodeoxynucleotides: A Role for Dendritic Cells in the Augmentation of Th1 Responses by Immunostimulatory DNA," *J. Immunol.* 161:3042-3049.

Kataoka, T. et al. (Mar. 1992). "Antitumor Activity of Synthetic Oligonucleotides with Sequences from cDNA Enconding Proteins of *Myobacterium bovis* BCG," *Jpn. J. Cancer Res.* 83:244-247.

Kawarada, Y. et al. (2001). "NK- and CD8$^+$ T Cell Mediated Eradication of Established Tumors by Peritumoral Injection of CpG-Containing Oligodeoxynucleotides," *J. Immunol.* 167:5247-5253.

Kendrew, J., ed. (1994). *The Encyclopedia of Molecular Biology* (Table of Contents).

Kessler, C. (Dec. 1992). "Nonradioactive Labeling Methods for Nucleic Acids," Chapter 2 in *Nonisotopic DNA Probe Techniques*, Larry J. Kricka, ed., Academic Press, Inc.: pp. 29-92.

Kikuta, K. et al. (1990). "Cross-Protection Against Influenza B Type Virus Infection by Intranasal Inoculation of the HA Vaccines Combined with Cholera Toxin B Subunit," *Vaccine* 8:595-599.

Kimura, Y. et al. (1994). "Binding of Oligoguanylate to Scavenger Receptors is Required for Oligonucleotides to Augment NK Cell Activity and Induce IFN," *J. Biochem.* (Tokyo) 116(5):991-994.

Kingetsu, I. et al. (2000). "Common Antigenicity between Japanese Cedar (*Cryptomeria japonica*) Pollen and Japanese Cypress (*Chamaecyparis obtusa*) Pollen, I. H-2 Complex Affects Cross Responsiveness to Cry j 1 and Cha o 1 at the T- and B-cell Level in Mice," *Immunol.* 99:625-629.

Kline, J.N. et al. (Feb. 1997). "Immune Redirection by CpG Oligonucleotides:Conversion of a Th2 Response in a Murine Model of Asthma," *J Invest. Med.* 45(2):282A.

Kline, J.N. et al. (Mar. 15, 1998). "Modulation of Airway Inflammation by CpG Oligodeoxynucleotides in a Murine Model of Asthma," *J. Immunol.* 160(6):2555-2559.

Kline, J.N. et al. (Jul. 2002). "Treatment of Established Asthma in a Murine Model Using CpG Oligodeoxynucleotides," *Am. J. Physiol. Lung Cell Mol. Physiol.* 283(1):L170-L179.

Klinman, D.M. et al. (Apr. 2, 1996). "CpG Motifs Present in Bacteria DNA Rapidly Induce Lymphocytes to Secrete Interleukin 6, Interleukin 12, and Interferon Gamma," *Proc. Natl. Acad. Sci. USA.* 93(7):2879-2883.

Klinman, D.M. et al. (1997). "Contribution of CpG Motifs to the Immunogenicity of DNA Vaccines," *J. Immunol.* 158:3635-3639.

Klinman, D.M. et al. (Nov. 1999). "Repeated Administration of Synthetic Oligodeoxynucleotides Expressing CpG Motifs Provides Long-Term Protection Against Bacterial Infection," *Infect. Immun.* 67(11):5658-5663.

Klinman, D.M. et al. (Jan. 1999). "CpG Motifs as Immune Adjuvants," *Vaccine* 17:19-25, Abstract Only.

Klinman, D.M. et al. (2002). "CpG DNA: Recognition by Activation of Monocytes," *Microbes Infect.* 4:897-901.

Klinman et al. (Apr. 2003). "CpG DNA as a Vaccine Adjuvant," *Expert Rev. Vaccines* 2(2):305-315.

Kodihalli, S. et al. (May 1997). "Cross-Protection Among Lethal H5N2 Influenza Viruses Induced by DNA Vaccine to the Hemagglutinin," *J. Virol.* 71(5):3391-3396.

Kovarik, J. et al. (1999). "CpG Oligodeoxynucleotides Can Circumvent the Th2 Polarization of Neonatal Responses to Vaccines But May Fail to Fully Redirect Th2 Responses Established by Neonatal Priming," *J. Immunol.* 162:1611-1617.

Kranzer, K. et al. (2000). "CpG-Oligodeoxynucleotides Enhance T-Cell Receptor-Triggered Interferon-γ Production and Up-Regulation of CD69 via Induction of Antigen-Presenting Cell-Derived Interferon Type 1 and Interleukin-12," *Immunology* 99:170-178.

Kremsky, J. N. et al. (1987). "Immobilization of DNA via Oligonucleotides Containing an Aldehyde or Carboxylic Acid Group at the 5' Terminus," *Nucleic Acids Res.* 15(7):2891-2909.

Krieg, A.M. et al. (Oct. 15, 1989). "A Role for Endogenous Retroviral Sequences in the Regulation of Lymphocyte Activation," *J. Immunol.* 143(8):2448-2451.

Krieg, A.M. et al. (Apr. 6, 1995). "CpG Motifs n Bacterial DNA Trigger Direct B-Cell Activation," *Nature* 374:546-549.

Krieg, A.M. et al. (1996). "Oligodeoxynucleotide Modifications Determine the Magnitude of B Cell Stimulation by CpG Motifs," *Antisense Nucleic Acid Drug Dev.* 6:133-139.

Krieg, A.M. (Feb. 1996) "Lymphocyte Activation by CpG Dinucleotide Motifs in Prokaryotic DNA," *Trends Microbiol.* 4(2):73-77.

Krieg, A.M. et al. (Jan. 1998). "The Role of CpG Dinucleotides in DNA Vaccines," *Trends Microbiol.* 6(1):23-27.

Krieg, A.M. et al. (1998). "CpG DNA Induces Sustained Il-12 Expression in Vivo and Resistance to *Listeria moncytogenes* Challenge," *J. Immunol.* 161:2428-2434.

Krieg, A.M. et al. (Oct. 1998). "Sequence Motifs in Adenoviral DNA Block Immune Activation by Stimulatory CpG Motifs," *Proc. Natl. Acad. Sci. USA* 95:12631-12636.

Krieg, A.M. (1998). "Leuokocyte Stimulation by Oligodeoxynucleotides," Chapter 24 in Applied Antisense Oligonucleotide Technology, Stein, C.A. et al. eds., Wiley-Liss, Inc.: New York, NY, pp. 431-448.

Krieg, A.M. (1999). "Mechanisms and Applications of Immune Stimulatory CpG Oligodeoxynucleotides," *Biochim. Biophys. Acta* 1489:107-116.

Krieg, A.M. (Feb. 1999). "CpG DNA: A Novel Immunomodulator," *Trends Microbiol.* 7(2):64-65.

Krieg, A.M. e al. (Oct. 2000). "Causing a Commotion in the Blood: Immunotherapy Progresses from Bacteria to Bacterial DNA," *Immunology Today* 21(10):521-526.

Krieg, A.M. (Jun. 2001). "Now I Know My CpGs," *Trends in Microbiology* 9(6):249-252.

Krieg, A.M. (2002). "CpG Motifs in Bacterial DNA and Their Immune Effects," *Annu. Rev. Immunol.* 20:709-760.

Krug, A. et al. (2001). "Identification of CpG Oligonucleotide Sequences with High Induction of IFN-α/β in Plasmacytoid Dendritic Cells," *Eur. J. Immunol.* 31:2154-2163.

Krug, A. et al. (2001). "Toll-Like Receptor Expression Reveals CpG DNA as a Unique Microbial Stimulus for Plasmacytoid Dendritic Cells Which Synergizes with CD40 Ligand to Induce High Amounts of II-12," *Eur. J. Immunol.* 31:3026-3037.

Kullman, W. (1997). *Enzymatic Peptide Synthesis*, CRC Press, Inc. Boca Raton, FL: (Table of Contents).

Lambert, G. et al. (1998). "Effect of Polyisobutylcyanoacrylate Nanoparticles and Lipofectin® Loaded with Oligonucleotides on Cell Viability and PKCα Neosynthesis in HepG2 Cells," *Biochimie* 80:969-976.

Langenberg, A.G.M. (Jun. 1995). "A Recombinant Glycoprotein Vaccine for Herpes Simplex Type 2: Safety and Efficacy," *Ann. Intern. Med.* 122(12):889-898.

Lasic, D.D. (1993). *Liposomes: From Physics to Applications*, Elsevier, Amsterdam: pp. xi-xvii (Table of Contents).

Latimer, L.J.P. et al. (1995). "Specificity of Monoclonal Antibodies Produced Against Phosphorothioate and Ribo Modified DNAs," *Mol. Immunol.* 32(14/15):1057-1064.

Lea, I. A. et al., (1996). "Cloning and Sequencing of cDNAs Encoding the Human Sperm Protein, Sp17," *Biochim. et Biophys. Acta* 1307:263-266.

Leclerc, C. et al. (1997). "The Preferential Induction of a Th1 Immune Response by DNA-Based Immunization is Mediated by the Immunostimulatory Effect of Plasmid DNA," *Cell. Immunol.* 179:97-106.

Lee, S.W. et al. (2000). "Effects of a Hexameric Deoxyriboguanosine Run Conjugation into CpG Oligodeoxynucleotides on Their Immunostimulatory Potentials," *J. Immunol.* 165:3631-3639.

Liang, H. et al. (Sep. 1, 1996). "Activation of Human B Cells by Phosphorothioate Oligodeoxynucleotides," *J. Clin. Invest.* 98(5):1119-1129.

Liang, H. et al. (2000). "The Role of Cell Surface Receptors in the Activation of Human B Cells by Phosphorothioate Oligonucleotides," *The Journal of Immunology* 165:1438-1445.

Lipford, G.B. et al. (1997). "CpG-Containing Synthetic Oligonucleotides Promote B and Cytotoxic T Cell Responses to Protein Antigen: A New Class of Vaccine Adjuvants," *Eur. J. Immunol.* 27:2340-2344.

Lipford, G.B. et al. (1997). "Immunostimulatory DNA: Sequence-Dependent Production of Potentially Harmful or Useful Cytokines," *Eur. J. Immunol.* 27:3420-3426.

Lipford, G.B. et al. (2000). "CpG DNA-Mediated Transient Lymphadenopathy is Associated with a State of Th1 Predisposition to Antigen-Driven Respones," *J. Immunol.* 165:1228-1235.

Liu, H-M. et al. (Nov. 15, 1998). "Immunostimulatory CpG Oligodeoxynucleotides Enhance the Immune Response to Vaccine Strategies Involving Granulocyte-Macrophage Colony-Stimulating Factor," *Blood* 92(10):3730-3736.

MacFarlane, D.E. et al. (1997). "Unmethylated CpG-Containing Oligodeoxynucleotides Inhibit Apoptosis in WEHI 231 B Lymphocytes Induced by Several Agents: Evidence for Blockade of Apoptosis at a Distal Signalling Step," *Immunology* 91:586-593.

Magone, M.T. et al. (2000). "Systemic or Mucosal Administration of Immunostimulatory DNA Inhibits Early and Late Phases of Murine Allergic Conjunctivitis," *Eur. J. Immunol.* 30:1841.

Manzel, L. et al. (1999). "Lack of Immune Stimulation by Immobilized CpG-Oligodeoxynucleotide," *Antisense Nucl. Acid Drug Dev.* 9:459-464.

Marshall, J.D. et al. (Jun. 2003). "Identification of a Novel CpG DNA Class and Motif that Optimally Stimulate B Cell and Plasmacytoid Dendritic Cell Functions," *Journal of Leukocyte Biology* 73(6):781-782.

Martin-Orozco, E. et al. (Jul. 1999). "Enhancement of Antigen-Presenting Cell Surface Molecules Involved in Cognate Interactions by Immunostimulatory DNA," *Int. Immunol.* 11(7):1111-1118.

Masseyeff, R.F., ed. (1993). *Methods of Immunological Analysis*. vol. 1: *Fundamentals*, Verlagsgesellschaft mbH, D-6940, Weinheim, Germany: pp. xi-xxii (Table of Contents).

Matteucci, M. (1997). "Oligonucleotide Analogs: An Overview," In *Oligonucleotides as Therapeutic Agents.* D.J. Chadwick and G. Cardew, eds., John Wiley and Sons, New York, NY., pp. 5-18.

Mbawuike, I. N. et al. (1994). "Influenza: A Subtype Cross-Protection After Immunization of Outbred Mice with a Purified Chimeric $NS_1/HA_2$ Influenza Virus Protein," *Vaccine* 12(14):1340-1348.

McCluskie, M.J. et al. (1998). "Cutting Edge: CpG DNA is a Potent Enhancer of Systemic and Mucosal Immune Responses Against Hepatitis B Surface Antigen with Intranasal Administration to Mice," *J. Immunol.* 161(9):4463-4466.

McCluskie, M.J. et al. (May 1999). "Route and Method of Delivery of DNA Vaccine Influence Immune Responses in Mice and Non-Human Primates," *Molecular Med.* 5(5):287-300.

The Merck Manual (1999). In "Section 6—Pulmonary Disorders," in Chapter 68, "Chronic Obstructive Airway Disorders," pp. 556-567.

The Merck Manual (1999). In "Section 12—Immunology; Allergic Disorders," in Chapter 148—Hypersensitivity Disorders, pp. 1042-1058.

Miller, P. S. et al. (1971). "Syntheses and Properties of Adenine and Thymine Nucleoside Alkyl Phosphotriesters, the Neutral Analogs of Dinucleoside Monophosphates," *JACS* 93(24):6657-6665.

Miller, J.H. et al., eds. (1987). "Gene Transfer Vectors for Mammalian Cells," in *Current Communications in Molecular Biology*, Cold Spring Harbor Laboratory: pp. vii-ix (Table of Contents).

Mishell, B.B. et al., eds. (1980). *Selected Methods in Cellular Immunology*, W.H. Freeman & Co., San Francisco: pp. vii-xiv (Table of Contents).

Mitragotri, S. et al. (Aug. 1995). "Ultrasound-Mediated Transdermal Protein Delivery," *Science* 269:850-853.

Mojcik, C. F. et al. (May 1993). "Administration of a Phosphorothioate Oligonucleotide Antisense to Murine Endogenous Retroviral MCF *Env* Causes Immune Effects in Vivo in a Sequence-Specific Manner," *Clin. Immunol. and Immunopathol.* 67(2):130-136.

Moldoveanu, Z. et al. (1998). "CpG DNA, A Novel Immune Enhancer for Systemic and Mucosal Immunization with Influenza Virus," *Vaccine* 16(11/12):1216-1224.

Mullis, K.B. et al., eds. (1994). *PCR: The Polymerase Chain Reaction*, Birkhäuser: pp. xv-xvii (Table of Contents).

Nelson, P. S. et al. (1989). "Bifunctional Oligonucleotide Probes Synthesized Using a Novel CPG Support are able to Detect Single Base Pair Mutations," *Nucleic Acids Res.* 17(18):7187-7194.

Nelson, J. S. et al. (1997). "N3'→P5' Oligodeoxyribonucleotide Phosphoramidates: A New Method of Synthesis Based on a Phosphoramidite Amine-Exchange Reaction," *J. Org. Chem.* 62(21):7278-7287.

O'Shannessy, D. J. et al. (1985). "Specific Conjugation Reactions of the Oligosaccharide Moieties of Immunoglobulins," *J. Applied Biochem.* 7:347-355.

Pastorello, E.A. et al. (1998). "Sensitization to the Major Allergen of Brazil Nut is Correlated with the Clinical Expression of Allergy," *J. Allergy Clin. Immunol.*102(6):1021-1027.

Peng, Z. et al. (2001). "CpG Oligodeoxynucleotide Vaccination Suppresses IgE Induction but May Fail to Down-Regulate Ongoing IgE Responses in Mice," *International Immunology* 13(1):3-11.

Pertmer, T. M. et al. (Sep. 1996). "Influenza Virus Nucleoprotein-Specific Immunoglobulin G Subclass and Cytokine Responses Elicited by DNA Vaccination are Dependent on the Route of Vector DNA Delivery," *J. Virol.* 70(9):6119-6125.

Peyrottes, S. et al. (1996). "Oligodeoxynucleoside Phosphoramidates (P-NH$_2$): Synthesis and Thermal Stability of Duplexes with DNA and RNA Targets," *Nucleic Acids Res.* 24(10):1841-1848.

Pisetsky, D.S. et al. (1994). "Stimulation of Murine Lymphocyte Proliferation by a Phosphorothioate Oligonucleotide with Antisense Acvitivty for Herpes Simplex Virus," *Life Sci.* 54(2):101-107.

Pisetsky, D.S. et al. (Nov. 1995). "Immunological Properties of Bacterial DNA," *Ann. N.Y. Acad. Sci.* 772:152-163.

Pisetsky, D.S. (Jan. 15, 1996). "Commentary: The Immunologic Properties of DNA,"*J. Immunol.* 156:421-423.

Pisetsky, D.S. (Oct. 1996). "Immune Activation by Bacterial DNA: A New Genetic Code," *Immunity* 5:303-310.

Pyles, R.B. et al. (Nov. 2002). "Use of Immunostimulatory Sequence-Containing Oligonucleotides as Topical Therapy for Genital Herpes Simplex Virus Type 2 Infection," *Journal of Virology* 76(22):11387-11396.

Rafnar, T. et al. (1991). "Cloning of *Amb a I* (Antigen E), the Major Allergen Family of Short Ragweed Pollen," *J. Biol. Chem.* 266:1229-1236.

Raz, E. et al. (Sep. 1994). "Intradermal Gene Immuization: The Possible Role of DNA Uptake in the Induction of Cellular Immunity to Viruses," *Proc. Natl. Acad. Sci. USA* 91:9519-9523.

Raz, E. et al. (May 1996). "Preferential Induction of a Th1 Immune Response and Inhibition of Specific IgE Antibody Formation by Plasmid DNA Immunization," *Proc. Natl. Acad. Sci. USA* 93(10):5141-5145.

Redford, T.W. et al. (1998). "Cyclosporin A Enhances IL-12 Production by CpG Motifs in Bacterial DNA and Synthetic Oligodeoxynucleotides," *J. Immunol.* 161:3930-3935.

Reese, G. et al. (1997). "Characterization of Recombinant Shrimp Allergen Pen a 1 (Tropomyosin)," *Int. Arch. Allergy Immunol.* 113:240-242.

Reynolds, M. A. et al. (1996). "Antisense Oligonucleotides Containing an Internal , Non-Nucleotied-Based Linker Promote Site-Specific Cleavage of RNA," *Nucleic Acids Res.* 24(4):760-765.

Rhodes, A. J. et al., eds. (1953). "Fundamental Characteristics and Technical Methods and Apparatus" in *Textbook of Virology for Students and Practioners of Medicine.* 2nd ed., Williams and Wilkins Company, Baltimore, MD. pp. 66-69.

Rogers, B.L. et al. (1993). "Recombinant *Fel d* I: Expression, Purification, IgE Binding and Reaction with Cat-Allergic Human T Cells," *Mol. Immunol.* 30(6):559-568.

Roget, A. et al. (1989). "Synthesis and Use of Labelled Nucleoside Phosphoramidite Building Blocks Bearing a Reporter Group: Biotinyl, Dinitrophenyl, Pyrenyl and Dansyl," *Nucleic Acids Res.* 17(19):7643-7651.

Romagnani, S. (Jul. 2000). "T-Cell Subsets (Th1 versus Th2)," *Ann. Allergy Asthma Immunol.* 85:9-21.

Roman, M. et al. (Aug. 1997). "Immunostimulatory DNA Sequences Function as T Helper-1-Promoting Adjuvants," *Nature Med.* 3(8):849-854.

Rothenfusser, S. et al. (Apr. 2003). "Recent Advances in Immunostimulatory CpG Oligionucleotides" *Current Opinion in Molecular Therapeutics* 5(2):98-106.

Ruth, J. L. (1991). "Oligodeoxynucleotides with Reporter Groups Attached to the Base," Chapter 11 in *Oligonucleotides and Analogues: A Practical Approach*, F. Eckstein, ed., IRL Press: pp. 255-282.

Sambrook, J. et al., eds. (1989). *Molecular Cloning: A Laboratory Manual*, Second Edition, Cold Spring Harbor Laboratory Press: pp. x-xxxviii (Table of Contents).

Sato, Y. et al. (Jul. 19, 1996). "Immunostimulatory DNA Sequences Necessary for Effective Intradermal Gene Immunization," *Science* 273:352-354.

Schacht, E. et al. (Oct. 1996). "Biomedical Applications of Degradable Polyphosphazenes," *Biotechnol. Bioeng.* 52:102-108.

Scherle, P. A. et al. (Oct. 1986). "Functional Analysis of Influenza Specific-Helper T Cell Clones in Vivo," *J. Exp. Med.* 164:1114-1128.

Scherle, P. A. et al. (Jun. 1988). "Differential Ability of B Cells Specific for External vs. Internal Influenza Virus Proteins to Respond to Help from Influenza Virus-Specific T-cell Clones in Vivo," *PNAS USA* 85:4446-4450.

Schluesener, H.J. et al. (2001). "Transient in vivo Activation of Rat Brain Macrophages/Microglial Cells and Astrocytes by Immunostimulatory Multiple CpG Oligonucleotides," *Journal of Neuroimmunology* 113:89-94.

Schultz, R. G. et al. (Jul. 1996). "Oligo-2'-Fluoro-2'-Deoxynucleotide N3'→P5' Phosphoramidates: Synthesis and Properties," *Nucleic Acids Res.* 24(15):2966-2973.

Schwartz, D.A. et al. (Jul. 1997). "CpG Motifs in Bacterial DNA Cause Inflammation in the Lower Respiratory Tract," *J. Clin. Invest.* 100(1):68-73.

Sélo, I. et al. (1999). "Allergy to Bovine β-Lactoglobulin: Specificity of Human IgE to Tryptic Peptides," *Clin. Exp. Allergy* 29:1055-1063.

Shen, K-Y. et al. (2006, e-pub. Jun. 15, 2005). "A Newly Identified CpG Oligodeoxynucleotide Motif that Stimulates Rainbow Trout (*Oncorhynchus mykiss*) Immune Cells to Produce Immunomodulatory Factors," *Developmental and Comparative Immunology* 30:311-324.

Shimada, S. et al. (Aug. 1986). "In Vivo Augmentation of Natural Killer Cell Activity with a Deoxyribonucleic Acid Fraction of BCG," *Jpn. J. Cancer Res.* 77:808-816.

Shirota, H. et al. (Jun. 1, 2000). "Regulation of Murnie Airway Eosinophilia and Th2 Cells by Antigen-Conjugated CpG Oligodeoxynucleotides as a Novel Antigen-Specific Immunomodulator," *J. Immunol.* 164(11):5575-5582.

Simons et al. (Jun. 30, 2004). "Selective Immune Redirection in Humans with Ragweed Allergy by Injecting Amb a 1 Linked to Immunostimulatory DNA," *J. Allergy. Clin. Immunol.* 113(6):1144-1151.

Sinha, N. D. et al. (1991). "Oligonucleotides with Reporter Groups Attached to the 5'-Terminus," Chapter 8 in *Oligonucleotide Analogues: A Practical Approach*, F. Eckstein, ed., IRL Press: pp. 185-210.

Sonehara, K. et al. (1996). "Hexamer Palindromic Oligonucleotides with 5'-CG-3' Motif(s) Induce Production of Interferon," *J. Interferon and Cytokine Res.* 16:799-803.

Sowka, S. et al. (1998). "cDNA Cloning of the 43-kDa Latex Allergen Hev b 7 with Sequence Similarity to Patatins and its Expression in the Yeast *Pichia pastoris,*" *Eur. J. Biochem.* 255:213-219.

Sparwasser, T. et al. (1997). "Macrophages Sense Pathogens via DNA Motifs: Induction of Tumor Necrosis Factor-α-Mediated Shock," *Eur. J. Immunol.* 27:1671-1679.

Spiegelberg, H.L. et al. (1998). "Inhibition of IgE Formation and Allergic Inflammation by Allergen Gene lmmunzation and by CpG Motif Immunostimulatory Oligodeoxynucleotides," *Allergy* 53(455):93-97.

Spiegelberg, H.L. et al. (1999, e-pub. Oct. 6, 1999). "Inhibition of Allergic Inflammation in the Lung by Plasmid DNA Allergen Immunization," *Pediatr. Pulmonol. Suppl.* 18:118-121.

Stacey, K.J. et al. (1996). "Macrophages Ingest and Are Activated by Bacterial DNA," *J. Immunol.* 157:2116-2122.

Stanley, J.S. et al. (1996). "Peanut Hypersensitivity: IgE Binding Characteristics of a Recombinant *Ara h* 1 Protein," *Adv. Exp. Med. Biol.* 409:213-216.

Staros, J. V. et al. (1986). "Enhancement by *N*-Hydroxysulfosuccinimide of Water-Soluble Carbodiimide-Mediated Coupling Reactions," *Anal. Biochem.* 156:220-222.

Stein, C.A. et al. (1997). "Non-Antisense Effects of Oligodeoxynucleotides," Chapter 11 in *Antisense Technology*, Lichetnsetin, C. et al. eds., IRL Press at Oxford University Press: Oxford, England, pp. 241-264.

Stirchak, E. P. et al. (1989). "Uncharged Stereoregular Nucleic Acid Analogs: 2. Morpholino Nucleoside Oligomers with Carbamate Internucleoside Linkages," *Nucleic Acids Res.* 17(15):6129-6141.

Summons to Attend Oral Proceedings mailed on Aug. 6, 2008, for EP Patent Application No. 03814325.1, filed on Dec. 18, 2003, 10 pages. (33.44).

Supplementary European Search Report mailed on Mar. 15, 2006, for European Patent Application No. 03814325.1, filed on Dec. 18, 2003, 4 pages.

Sur, S. et al. (1999). "Long Term prevention of Allergic Lung Inflammation in a Mouse Model of Asthma by CpG Oiligodeoxynucleotides," *J. Immunol.* 162:6284-6293.

Takahashi, H. et al. (Apr. 1990). "Induction of $CD8^+$ Cytotoxic T Cells by Immunization with Purified HIV-1 Envelope Protein in ISCOMs," *Nature* 344:873-875.

Tamborini, E. et al. (1997). "Biochemical and Immunological Characterization of Recombinant Allergen Lol p 1," *Eur. J. Biochem.* 249:886-894.

Tamura, S-I. et al. (1992). "Superior Cross-Protective Effect of Nasal Vaccination to Subcutaneous Inoculation with Influenza Hemagglutinin Vaccine," *Eur. J. Immunol.* 22:477-481.

Tamura, S-I. et al. (1994). "Formulation of Inactivated Influenza Vaccines for Providing Effective Cross-Protection by Intranasal Vaccination in Mice," *Vaccine* 12(4):310-316.

Teuber, S.S. et al. (1998). "Cloning and Sequencing of a Gene Encoding a 2S Albumin Seed Storage Protein Precursor from English Walnut (*Juglans regia*), a Major Food Allergen," *J. Allergy Clin. Immun.* 101:807-814.

Tighe, H. et al. (Jul. 2000). "Conjugation of Protein to Immunostimulatory DNA Results in a Rapid, Long-Lasting and Potent Induction of Cell-Mediated and Humoral Immunity," *Eur. J. Immunol.* 30(7):1939.

Tokunaga, T. et al. (1992). "Synthetic Oligonuceleotides with Particular Base Sequences from the cDNA Encoding Proteins of *Mycobacterium bovis* BCG Induce Interferons and Activate Natural Killer Cells," *Microbiol. Immunol.* 36(1):55-66.

Tung, C-H. et al. (1991). "Preparation of Oligonucleotide-Peptide Conjugates," *Bioconjug. Chem.* 2:464-465.

Van Do, T. et al. (1999). "Expression and Analysis of Recombinant *Salmon parvalbumin*, the Major Allergen in Atlantic Salmon (*Salmo salar*)," *Scand. J. Immunol.* 50:619-625.

Verthelyi, D. et al. (Feb. 15, 2001). "Human Peripheral Blood Cells Differentially Recognize and Respond to Two Distinct CPG Motifs," *J. Immunol.* 166:2372-2377.

Verthelyi, D. et al. (2002). "CpG Oligodeoxynucleotides as Vaccine Adjuvants in Primates," *J. Immunol.* 168:1659-1663.

Voet, D. et al. (1990). "Table 26-1: Names and Abbreviations of Nucleic Acid Bases, Nucleosides, and Nucleotides," in *Biochemistry*, John Wiley & Sons: New York, NY, p. 742.

Walker, C. et al. (Feb. 2001). "New Trends in Immunotherapy to Prevent Atopic Diseases," *TRENDS in Pharmocological Sciences* 22(2):84-90.

Wang, S. et al. (1994). "Circular RNA Oligonucleotides. Synthesis, Nucleic Acid Binding Properties, and a Comparison with Circular DNAs," *Nucleic Acids Res.* 22(12):2326-2333.

Warner, B.D. et al. (1984). "Laboratory Methods: Construction and Evaluation of an Instrument for the Automated Synthesis of Oligodeoxyribonucleotides," *DNA* 3(5):401-44.

Watwe, R. M. et al. (Apr. 1995). "Manufacture of Liposomes: A Review," *Current Science* 68(7):715-724.

Weeratna, R. et al. (1998). "Reduction of Antien Expression from DNA Vaccine by Coadministered Oligodeoxynucleotides," *Antisense & Nucleic Acid Drug Development* 8:351-356.

Weiner, G.J. et al. (Sep. 1997). "Immunostimulatory Oligodeoxynucleotides in Tumor Antigen Immunization," *Proc. Natl. Acad. Sci. USA* 94:10833-10837.

Weiner, G.J. (Oct. 2000). "The Immunology and Clinical Potential of Immunostimulatory CpG Oligodeoxynucleotides," *J. Leukocyte Biology* 68(4):456-463.

Weir, D.M., ed. (1986). *Handbook of Experimental Immunology in Four Volumes*, "vol. 4: Applications of Immunological Methods in Biomedical Sciences," Blackwell Scientific Publications: pp. v-x (Table of Contents).

Widhe, M. et al. (1998). "IgG Subclasses in Lyme Borreliosis: A Study of Specific IgG Subclass Distribution in an Interferon-γ-Predominated Disease," *Scand. J. Immunol.* 47:575-581.

Wild, D., ed. (1994). *The Immunoassay Handbook*, Stockton Press: pp. v-xvi (Table of Contents).

Wohlleben, G. et al. (Nov. 2001). "Atopic Disorders: A Vaccine Around the Corner?" *Trends in Immunology* 22(11):618-626.

Wooldridge, J.E. et al. (Apr. 15, 1997). "Immunostimulatory Oligodeoxynucleotides Containing CpG Motifs Enhance the Efficacy of Monoclonal Antibody Therapy of Lymphoma," *Blood* 89(8):2994-2998.

Written Opinion mailed on Nov. 30, 2004, for PCT Patent Application No. PCT/US03/41001, filed on Dec. 18, 2003, 5 pages.

Yamamoto, S. et al. (Jun. 15, 1992). "Unique Palindromic Sequences in Synthetic Oligonucleotides are Required to Induce IFN and Augment IFN-Mediated Natural Killer Activity," *J. Immunol.* 148(12):4072-4076.

Yamamoto, T. et al. (1994). "Ability of Oligonucleotides with Certain Palindromes to Induce Interferon Production and Augment Natural Killer Cell Activity is Associated with Their Base Length," *Antisense Research and Development*. 4:119-122.

Yamamoto, T. et al. (Aug. 1994). "Synthetic Oligonucleotides with Certain Palindromes Stimulate Interferon Production of Human Peripheral Blood Lymphocyts in vitro," *Jpn. J. Cancer Res.* 85:775-779.

Yamamoto, S. et al. (2000). "Activation of NK Cell (Human and Mouse) by Immunostimulatory DNA Sequence," *Springer Semin. Immunopathol.* 22:35-43.

Yanagawa, H. et al. (Feb. 1988). "Analysis of Superhelical Structures of Nucleic Acid-Lipid Conjugates by Image Processing," *Nucleic Acids Symp. Series* 19:189-192.

Yi, A-K. et al. (1996). "INF-γ Promotes IL-6 and IgM Secretion in Response to CpG Motifs in Bacterial DNA and Oligodeoxynucleotides," *J. Immunol.* 156:558-564.

Yi, A-K. et al. (1998). "CpG DNA Rescue from Anti-IgM-Induced WEHI-231 B Lymphoma Apoptosis via Modulation of I-κBα and IκBα and Sustained Activation of Nuclear Factor-κB/c-Rel," *J. Immunol.* 160:1240-1245.

Yi, A-K. et al. (1998). "CpG Motifs in Bacterial DNA Activate Luekocytes Through the pH-Dependant Generation of Reactive Oxygen Species," *J. Immunol.* 160:4755-4761.

Yi, A-K. et al. (1998). "CpG Oligodeoxyribonucleotides Rescue Mature Spleen B Cells from Spontaneous Apoptosis and Promote Cell Cycle Entry," *J. Immunol.* 160:5898-5906.

Yi, A.K. et al. (Nov. 1, 1998). "Rapid Induction of Mitogen-Activated Protein Kinases by Immune Stimulatory CpG DNA," *J. Immunol.* 161(9):4493-4497.

Yu, D. et al. (2002). "Potent CpG Oligonucleotides Containing Phosphodiester Linkages: in Vitro and in Vivo Immunostimulatory Properties," *Biochem. Biophys. Res. Commun.* 297:83-90.

Zhao, Q. et al. (1996). "Effect of Different Chemically Modified Oligodeoxynucleotides on Immune Stimulation," *Biochem. Pharmacol.* 51:173-182.

Zhu, F-G. et al. (2001). "The Role of Macrophage Scavenger Receptor in Immune Stimulation by Bacterial DNA and Synthetic Oligonucleotides," *Immunology* 103:226-234.

Zimmermann, S. et al. (1998). "Cutting Edge: CpG Oligodeoxynucleotides Trigger Protective and Curative Th1 Responses in Lethal Murine Leishmaniasis," *J. Immunol.* 160:3627-3630.

Zon, G. (1993). "Oligonucleoside Phosphorothioates," Chapter 8 in *Protocols for Oligonucleotides and Analogs, Synthesis and Properties*, Sudhir Agrawal, ed., Humana Press, Totowa, N.J., pp. 165-189.

Zuckermann, R. et al. (1987). "Efficient Methods for Attachment of Thiol Specific Probes to the 3'-Ends of Synthetic Oligodeoxyribonucleotides," *Nucleic Acids Res.* 15(13):5305-5321.

Zwaveling, S. et al. (2002). "Established Human Papillomavirus Type 16-Expressing Tumors Are Effectively Eradicated Following Vaccination with Long Peptides," *J. Immunol.* 169:350-358.

\* cited by examiner

SEQUENCE LISTING

```
<160> NUMBER OF SEQ ID NOS: 228

<210> SEQ ID NO 1
<211> LENGTH: 22
<212> TYPE: DNA
<213> ORGANISM: Artificial Sequence
<220> FEATURE:
<223> OTHER INFORMATION: Synthetic construct

<400> SEQUENCE: 1
tgactgtgaa cgttcgagat ga                                    22

<210> SEQ ID NO 2
<211> LENGTH: 22
<212> TYPE: DNA
<213> ORGANISM: Artificial Sequence
<220> FEATURE:
<223> OTHER INFORMATION: Synthetic construct

<400> SEQUENCE: 2
tgactgtgaa ccttagagat ga                                    22

<210> SEQ ID NO 3
<211> LENGTH: 24
<212> TYPE: DNA
<213> ORGANISM: Artificial Sequence
<220> FEATURE:
<223> OTHER INFORMATION: Synthetic construct

<400> SEQUENCE: 3
tcgtcgtttt gtcgttttgt cgtt                                  24

<210> SEQ ID NO 4
<211> LENGTH: 22
<212> TYPE: DNA
<213> ORGANISM: Artificial Sequence
<220> FEATURE:
<223> OTHER INFORMATION: Synthetic construct
```

```
<400> SEQUENCE: 4
tcaacgttcg ttaacgttcg tt                                          22

<210> SEQ ID NO 5
<211> LENGTH: 24
<212> TYPE: DNA
<213> ORGANISM: Artificial Sequence
<220> FEATURE:
<223> OTHER INFORMATION: Synthetic construct

<400> SEQUENCE: 5
tcgtcgaacg ttcgttaacg ttcg                                        24

<210> SEQ ID NO 6
<211> LENGTH: 24
<212> TYPE: DNA
<213> ORGANISM: Artificial Sequence
<220> FEATURE:
<223> OTHER INFORMATION: Synthetic construct

<400> SEQUENCE: 6
tcgtcgaacg ttccttaacg ttcc                                        24

<210> SEQ ID NO 7
<211> LENGTH: 24
<212> TYPE: DNA
<213> ORGANISM: Artificial Sequence
<220> FEATURE:
<223> OTHER INFORMATION: Synthetic construct

<400> SEQUENCE: 7
tcgtcgaacg ttccttaacg ttcg                                        24

<210> SEQ ID NO 8
<211> LENGTH: 24
<212> TYPE: DNA
<213> ORGANISM: Artificial Sequence
<220> FEATURE:
<223> OTHER INFORMATION: Synthetic construct

<400> SEQUENCE: 8
tgatcgaacg ttcgttaacg ttcg                                        24

<210> SEQ ID NO 9
<211> LENGTH: 24
<212> TYPE: DNA
<213> ORGANISM: Artificial Sequence
<220> FEATURE:
<223> OTHER INFORMATION: Synthetic construct

<400> SEQUENCE: 9
tcgttcaacg ttcgttaacg ttcg                                        24

<210> SEQ ID NO 10
<211> LENGTH: 24
<212> TYPE: DNA
<213> ORGANISM: Artificial Sequence
<220> FEATURE:
<223> OTHER INFORMATION: Synthetic construct

<400> SEQUENCE: 10
tgattcaacg ttcgttaacg ttcg                                        24
```

```
<210> SEQ ID NO 11
<211> LENGTH: 24
<212> TYPE: DNA
<213> ORGANISM: Artificial Sequence
<220> FEATURE:
<223> OTHER INFORMATION: Synthetic construct

<400> SEQUENCE: 11
tcgtcgaacc ttcgttaacc ttcg                                          24

<210> SEQ ID NO 12
<211> LENGTH: 16
<212> TYPE: DNA
<213> ORGANISM: Artificial Sequence
<220> FEATURE:
<223> OTHER INFORMATION: Synthetic construct

<400> SEQUENCE: 12
tcgtcgaacg ttcgtt                                                   16

<210> SEQ ID NO 13
<211> LENGTH: 22
<212> TYPE: DNA
<213> ORGANISM: Artificial Sequence
<220> FEATURE:
<223> OTHER INFORMATION: Synthetic construct

<400> SEQUENCE: 13
tcgtcgtgaa cgttcgagat ga                                            22

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
tcgtcggaac gttcgagatg                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
tcgtcgtaac gttcgagatg                                               20

<210> SEQ ID NO 16
<211> LENGTH: 19
<212> TYPE: DNA
<213> ORGANISM: Artificial Sequence
<220> FEATURE:
<223> OTHER INFORMATION: Synthetic construct

<400> SEQUENCE: 16
tcgtcggacg ttcgagatg                                                19

<210> SEQ ID NO 17
<211> LENGTH: 19
<212> TYPE: DNA
<213> ORGANISM: Artificial Sequence
<220> FEATURE:
<223> OTHER INFORMATION: Synthetic construct
```

```
<400> SEQUENCE: 17
tcgtcgtacg ttcgagatg                                                19

<210> SEQ ID NO 18
<211> LENGTH: 19
<212> TYPE: DNA
<213> ORGANISM: Artificial Sequence
<220> FEATURE:
<223> OTHER INFORMATION: Synthetic construct

<400> SEQUENCE: 18
tcgtcgttcg ttcgagatg                                                19

<210> SEQ ID NO 19
<211> LENGTH: 22
<212> TYPE: DNA
<213> ORGANISM: Artificial Sequence
<220> FEATURE:
<223> OTHER INFORMATION: Synthetic construct

<400> SEQUENCE: 19
tcgtcgaacg ttcgaacgtt cg                                            22

<210> SEQ ID NO 20
<211> LENGTH: 22
<212> TYPE: DNA
<213> ORGANISM: Artificial Sequence
<220> FEATURE:
<223> OTHER INFORMATION: Synthetic construct

<400> SEQUENCE: 20
ttcgaacgtt cgttaacgtt cg                                            22

<210> SEQ ID NO 21
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 1, 4
<223> OTHER INFORMATION: n = um

<400> SEQUENCE: 21
ncgncgaacg ttcgagatg                                                19

<210> SEQ ID NO 22
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 2
<223> OTHER INFORMATION: n = cm

<400> SEQUENCE: 22
tngtcgaacg ttcgagatg                                                19

<210> SEQ ID NO 23
<211> LENGTH: 19
<212> TYPE: DNA
<213> ORGANISM: Artificial Sequence
<220> FEATURE:
<223> OTHER INFORMATION: Synthetic construct
```

```
<220> FEATURE:
<221> NAME/KEY: modified_base
<222> LOCATION: 5
<223> OTHER INFORMATION: n = cm

<400> SEQUENCE: 23
tcgtngaacg ttcgagatg                                              19

<210> SEQ ID NO 24
<211> LENGTH: 22
<212> TYPE: DNA
<213> ORGANISM: Artificial Sequence
<220> FEATURE:
<223> OTHER INFORMATION: Synthetic construct

<400> SEQUENCE: 24
tgatcgtcga acgttcgaga tg                                          22

<210> SEQ ID NO 25
<211> LENGTH: 30
<212> TYPE: DNA
<213> ORGANISM: Artificial Sequence
<220> FEATURE:
<223> OTHER INFORMATION: Synthetic construct

<400> SEQUENCE: 25
accgataacg ttgccggtga cggcaccacg                                  30

<210> SEQ ID NO 26
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1, 2, 16-20
<223> OTHER INFORMATION: Phosphorothioate linkages

<400> SEQUENCE: 26
ggtcgaacgt tcgagggggg                                             20

<210> SEQ ID NO 27
<211> LENGTH: 21
<212> TYPE: DNA
<213> ORGANISM: Artificial Sequence
<220> FEATURE:
<223> OTHER INFORMATION: Synthetic construct

<400> SEQUENCE: 27
tcgtcgaacg ttcgagatga t                                           21

<210> SEQ ID NO 28
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 2, 5, 9, 13
<223> OTHER INFORMATION: n= 5-bromo-2'-deoxycytidine

<400> SEQUENCE: 28
tngtngaang ttngagatga t                                           21
```

```
<210> SEQ ID NO 29
<211> LENGTH: 21
<212> TYPE: DNA
<213> ORGANISM: Artificial Sequence
<220> FEATURE:
<223> OTHER INFORMATION: Synthetic construct

<400> SEQUENCE: 29
atcatctcga acgttcgacg a                                               21

<210> SEQ ID NO 30
<211> LENGTH: 20
<212> TYPE: DNA
<213> ORGANISM: Artificial Sequence
<220> FEATURE:
<223> OTHER INFORMATION: Synthetic construct

<400> SEQUENCE: 30
ggtcgaacgt tcgagggggg                                                 20

<210> SEQ ID NO 31
<211> LENGTH: 20
<212> TYPE: DNA
<213> ORGANISM: Artificial Sequence
<220> FEATURE:
<223> OTHER INFORMATION: Synthetic construct

<400> SEQUENCE: 31
tcgtcgaacg ttttaacgtt                                                 20

<210> SEQ ID NO 32
<211> LENGTH: 21
<212> TYPE: DNA
<213> ORGANISM: Artificial Sequence
<220> FEATURE:
<223> OTHER INFORMATION: Synthetic construct

<400> SEQUENCE: 32
tcgtcgaacg ttcgaggggg g                                               21

<210> SEQ ID NO 33
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1-3, 16-21
<223> OTHER INFORMATION: Phosphorothioate linkages

<400> SEQUENCE: 33
tcgtcgaacg ttcgaggggg g                                               21

<210> SEQ ID NO 34
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1-3, 17-21
<223> OTHER INFORMATION: Phosphorothioate linkages

<400> SEQUENCE: 34
tcgtgcatcg atgcagggggg g                                              21
```

```
<210> SEQ ID NO 35
<211> LENGTH: 21
<212> TYPE: DNA
<213> ORGANISM: Artificial Sequence
<220> FEATURE:
<223> OTHER INFORMATION: Synthetic construct

<400> SEQUENCE: 35
tcgtcgacgt cgagatgata t                                           21

<210> SEQ ID NO 36
<211> LENGTH: 22
<212> TYPE: DNA
<213> ORGANISM: Artificial Sequence
<220> FEATURE:
<223> OTHER INFORMATION: Synthetic construct

<400> SEQUENCE: 36
tgactgtgaa cgttcgaaat ga                                          22

<210> SEQ ID NO 37
<211> LENGTH: 22
<212> TYPE: DNA
<213> ORGANISM: Artificial Sequence
<220> FEATURE:
<223> OTHER INFORMATION: Synthetic construct

<400> SEQUENCE: 37
tgactgtgaa cgttcgaagt ga                                          22

<210> SEQ ID NO 38
<211> LENGTH: 23
<212> TYPE: DNA
<213> ORGANISM: Artificial Sequence
<220> FEATURE:
<223> OTHER INFORMATION: Synthetic construct

<400> SEQUENCE: 38
ttcgaacgtt cgaacgttcg aat                                         23

<210> SEQ ID NO 39
<211> LENGTH: 22
<212> TYPE: DNA
<213> ORGANISM: Artificial Sequence
<220> FEATURE:
<223> OTHER INFORMATION: Synthetic construct

<400> SEQUENCE: 39
tcgaacgttc gaacgttcga at                                          22

<210> SEQ ID NO 40
<211> LENGTH: 24
<212> TYPE: DNA
<213> ORGANISM: Artificial Sequence
<220> FEATURE:
<223> OTHER INFORMATION: Synthetic construct

<400> SEQUENCE: 40
tcgattcgaa cgttcgaacg ttcg                                        24

<210> SEQ ID NO 41
<211> LENGTH: 22
<212> TYPE: DNA
<213> ORGANISM: Artificial Sequence
<220> FEATURE:
<223> OTHER INFORMATION: Synthetic construct
```

```
<400> SEQUENCE: 41
tcgttcgaac gttcgaagtg at                                              22

<210> SEQ ID NO 42
<211> LENGTH: 20
<212> TYPE: DNA
<213> ORGANISM: Artificial Sequence
<220> FEATURE:
<223> OTHER INFORMATION: Synthetic construct

<400> SEQUENCE: 42
tcgttcgaac gttcgaacga                                                 20

<210> SEQ ID NO 43
<211> LENGTH: 22
<212> TYPE: DNA
<213> ORGANISM: Artificial Sequence
<220> FEATURE:
<223> OTHER INFORMATION: Synthetic construct

<400> SEQUENCE: 43
tcgatcgatc gatcgatcga tt                                              22

<210> SEQ ID NO 44
<211> LENGTH: 21
<212> TYPE: DNA
<213> ORGANISM: Artificial Sequence
<220> FEATURE:
<223> OTHER INFORMATION: Synthetic construct

<400> SEQUENCE: 44
tcgtcgagcg ctcgagatga t                                               21

<210> SEQ ID NO 45
<211> LENGTH: 21
<212> TYPE: DNA
<213> ORGANISM: Artificial Sequence
<220> FEATURE:
<223> OTHER INFORMATION: Synthetic construct

<400> SEQUENCE: 45
tcgtcgatcg atcgagatga t                                               21

<210> SEQ ID NO 46
<211> LENGTH: 21
<212> TYPE: DNA
<213> ORGANISM: Artificial Sequence
<220> FEATURE:
<223> OTHER INFORMATION: Synthetic construct

<400> SEQUENCE: 46
tcgtcggtcg accgagatga t                                               21

<210> SEQ ID NO 47
<211> LENGTH: 21
<212> TYPE: DNA
<213> ORGANISM: Artificial Sequence
<220> FEATURE:
<223> OTHER INFORMATION: Synthetic construct

<400> SEQUENCE: 47
tcgtcggacg tccgagatga t                                               21
```

```
<210> SEQ ID NO 48
<211> LENGTH: 21
<212> TYPE: DNA
<213> ORGANISM: Artificial Sequence
<220> FEATURE:
<223> OTHER INFORMATION: Synthetic construct

<400> SEQUENCE: 48
tcgtcgcacg tgcgagatga t                                              21

<210> SEQ ID NO 49
<211> LENGTH: 21
<212> TYPE: DNA
<213> ORGANISM: Artificial Sequence
<220> FEATURE:
<223> OTHER INFORMATION: Synthetic construct

<400> SEQUENCE: 49
tcgtcgcgat cgcgagatga t                                              21

<210> SEQ ID NO 50
<211> LENGTH: 21
<212> TYPE: DNA
<213> ORGANISM: Artificial Sequence
<220> FEATURE:
<223> OTHER INFORMATION: Synthetic construct

<400> SEQUENCE: 50
tcgtcgtcgc gacgagatga t                                              21

<210> SEQ ID NO 51
<211> LENGTH: 21
<212> TYPE: DNA
<213> ORGANISM: Artificial Sequence
<220> FEATURE:
<223> OTHER INFORMATION: Synthetic construct

<400> SEQUENCE: 51
tcgtcgtacg tacgagatga t                                              21

<210> SEQ ID NO 52
<211> LENGTH: 18
<212> TYPE: DNA
<213> ORGANISM: Artificial Sequence
<220> FEATURE:
<223> OTHER INFORMATION: Synthetic construct

<400> SEQUENCE: 52
tcgtcgaacg ttcgacga                                                  18

<210> SEQ ID NO 53
<211> LENGTH: 23
<212> TYPE: DNA
<213> ORGANISM: Artificial Sequence
<220> FEATURE:
<223> OTHER INFORMATION: Synthetic construct

<400> SEQUENCE: 53
tcgttcgaac gttcgaacgt tcg                                            23

<210> SEQ ID NO 54
<211> LENGTH: 17
<212> TYPE: DNA
<213> ORGANISM: Artificial Sequence
<220> FEATURE:
<223> OTHER INFORMATION: Synthetic construct
```

```
<400> SEQUENCE: 54
tcgttcgaac gttcgaa                                                    17

<210> SEQ ID NO 55
<211> LENGTH: 25
<212> TYPE: DNA
<213> ORGANISM: Artificial Sequence
<220> FEATURE:
<223> OTHER INFORMATION: Synthetic construct

<400> SEQUENCE: 55
tcgttcgaac gttcgaacgt tcgaa                                           25

<210> SEQ ID NO 56
<211> LENGTH: 44
<212> TYPE: DNA
<213> ORGANISM: Artificial Sequence
<220> FEATURE:
<223> OTHER INFORMATION: Synthetic construct

<400> SEQUENCE: 56
tcgttcgaac gttcgaacga tttttcgttc gaacgttcga acga                      44

<210> SEQ ID NO 57
<211> LENGTH: 25
<212> TYPE: DNA
<213> ORGANISM: Artificial Sequence
<220> FEATURE:
<223> OTHER INFORMATION: Synthetic construct

<400> SEQUENCE: 57
tttcgaacgt tcgaacgttc gaaat                                           25

<210> SEQ ID NO 58
<211> LENGTH: 27
<212> TYPE: DNA
<213> ORGANISM: Artificial Sequence
<220> FEATURE:
<223> OTHER INFORMATION: Synthetic construct

<400> SEQUENCE: 58
ttttcgaacg ttcgaacgtt cgaaaat                                         27

<210> SEQ ID NO 59
<211> LENGTH: 25
<212> TYPE: DNA
<213> ORGANISM: Artificial Sequence
<220> FEATURE:
<223> OTHER INFORMATION: Synthetic construct

<400> SEQUENCE: 59
ttttcgaacg ttcgaacgtt cgaat                                           25

<210> SEQ ID NO 60
<211> LENGTH: 21
<212> TYPE: DNA
<213> ORGANISM: Artificial Sequence
<220> FEATURE:
<223> OTHER INFORMATION: Synthetic construct

<400> SEQUENCE: 60
tcgtcgacgt cgacgagata t                                               21
```

```
<210> SEQ ID NO 61
<211> LENGTH: 21
<212> TYPE: DNA
<213> ORGANISM: Artificial Sequence
<220> FEATURE:
<223> OTHER INFORMATION: Synthetic construct

<400> SEQUENCE: 61
tcgacgtcga cgtcgacgta t                                      21

<210> SEQ ID NO 62
<211> LENGTH: 21
<212> TYPE: DNA
<213> ORGANISM: Artificial Sequence
<220> FEATURE:
<223> OTHER INFORMATION: Synthetic construct

<400> SEQUENCE: 62
tcgtcgaaac gtttcgacag t                                      21

<210> SEQ ID NO 63
<211> LENGTH: 21
<212> TYPE: DNA
<213> ORGANISM: Artificial Sequence
<220> FEATURE:
<223> OTHER INFORMATION: Synthetic construct

<400> SEQUENCE: 63
tcgtcgagac gtctcgacag t                                      21

<210> SEQ ID NO 64
<211> LENGTH: 22
<212> TYPE: DNA
<213> ORGANISM: Artificial Sequence
<220> FEATURE:
<223> OTHER INFORMATION: Synthetic construct

<400> SEQUENCE: 64
tcgtcgaaaa cgttttcgag at                                     22

<210> SEQ ID NO 65
<211> LENGTH: 22
<212> TYPE: DNA
<213> ORGANISM: Artificial Sequence
<220> FEATURE:
<223> OTHER INFORMATION: Synthetic construct

<400> SEQUENCE: 65
tcgaaaacgt ttcgagatg at                                      22

<210> SEQ ID NO 66
<211> LENGTH: 22
<212> TYPE: DNA
<213> ORGANISM: Artificial Sequence
<220> FEATURE:
<223> OTHER INFORMATION: Synthetic construct

<400> SEQUENCE: 66
tcgaggacgt cctcgagatg at                                     22

<210> SEQ ID NO 67
<211> LENGTH: 23
<212> TYPE: DNA
<213> ORGANISM: Artificial Sequence
<220> FEATURE:
<223> OTHER INFORMATION: Synthetic construct
```

```
<400> SEQUENCE: 67
aacgttcgaa cgttcgaacg ttt                                       23

<210> SEQ ID NO 68
<211> LENGTH: 24
<212> TYPE: DNA
<213> ORGANISM: Artificial Sequence
<220> FEATURE:
<223> OTHER INFORMATION: Synthetic construct

<400> SEQUENCE: 68
tcaacgttcg aacgttcgaa cgtt                                      24

<210> SEQ ID NO 69
<211> LENGTH: 21
<212> TYPE: DNA
<213> ORGANISM: Artificial Sequence
<220> FEATURE:
<223> OTHER INFORMATION: Synthetic construct

<400> SEQUENCE: 69
tcgtcgaccg gtcgagatga t                                         21

<210> SEQ ID NO 70
<211> LENGTH: 21
<212> TYPE: DNA
<213> ORGANISM: Artificial Sequence
<220> FEATURE:
<223> OTHER INFORMATION: Synthetic construct

<400> SEQUENCE: 70
tcgtcgggcg cccgagatga t                                         21

<210> SEQ ID NO 71
<211> LENGTH: 21
<212> TYPE: DNA
<213> ORGANISM: Artificial Sequence
<220> FEATURE:
<223> OTHER INFORMATION: Synthetic construct

<400> SEQUENCE: 71
tcgtcgcgcg cgcgagatga t                                         21

<210> SEQ ID NO 72
<211> LENGTH: 21
<212> TYPE: DNA
<213> ORGANISM: Artificial Sequence
<220> FEATURE:
<223> OTHER INFORMATION: Synthetic construct

<400> SEQUENCE: 72
tcgtcgctcg agcgagatga t                                         21

<210> SEQ ID NO 73
<211> LENGTH: 21
<212> TYPE: DNA
<213> ORGANISM: Artificial Sequence
<220> FEATURE:
<223> OTHER INFORMATION: Synthetic construct

<400> SEQUENCE: 73
tcgtcgcccg ggcgagatga t                                         21
```

```
<210> SEQ ID NO 74
<211> LENGTH: 21
<212> TYPE: DNA
<213> ORGANISM: Artificial Sequence
<220> FEATURE:
<223> OTHER INFORMATION: Synthetic construct

<400> SEQUENCE: 74
tcgtcgtgcg cacgagatga t                                    21

<210> SEQ ID NO 75
<211> LENGTH: 21
<212> TYPE: DNA
<213> ORGANISM: Artificial Sequence
<220> FEATURE:
<223> OTHER INFORMATION: Synthetic construct

<400> SEQUENCE: 75
tcgtcgttcg aacgagatga t                                    21

<210> SEQ ID NO 76
<211> LENGTH: 21
<212> TYPE: DNA
<213> ORGANISM: Artificial Sequence
<220> FEATURE:
<223> OTHER INFORMATION: Synthetic construct

<400> SEQUENCE: 76
tcgtcgtccg gacgagatga t                                    21

<210> SEQ ID NO 77
<211> LENGTH: 20
<212> TYPE: DNA
<213> ORGANISM: Artificial Sequence
<220> FEATURE:
<223> OTHER INFORMATION: Synthetic construct

<400> SEQUENCE: 77
tcgagcgctc gagcgctcga                                      20

<210> SEQ ID NO 78
<211> LENGTH: 20
<212> TYPE: DNA
<213> ORGANISM: Artificial Sequence
<220> FEATURE:
<223> OTHER INFORMATION: Synthetic construct

<400> SEQUENCE: 78
tcggtcgacc ggtcgaccga                                      20

<210> SEQ ID NO 79
<211> LENGTH: 20
<212> TYPE: DNA
<213> ORGANISM: Artificial Sequence
<220> FEATURE:
<223> OTHER INFORMATION: Synthetic construct

<400> SEQUENCE: 79
tcggacgtcc ggacgtccga                                      20

<210> SEQ ID NO 80
<211> LENGTH: 20
<212> TYPE: DNA
<213> ORGANISM: Artificial Sequence
<220> FEATURE:
<223> OTHER INFORMATION: Synthetic construct
```

```
<400> SEQUENCE: 80
tcgaacgtta acgttcgatt                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic construct

<400> SEQUENCE: 81
tcgagcgcta gcgctcgatt                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic construct

<400> SEQUENCE: 82
tcggtcgacg tcgaccgatt                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic construct

<400> SEQUENCE: 83
tcggacgtcg acgtccgatt                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic construct

<400> SEQUENCE: 84
tcgttcgaat tcgaacgatt                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic construct

<400> SEQUENCE: 85
gacgatcgtc gacgatcgtc                                               20

<210> SEQ ID NO 86
<211> LENGTH: 23
<212> TYPE: DNA
<213> ORGANISM: Artificial Sequence
<220> FEATURE:
<223> OTHER INFORMATION: Synthetic construct

<400> SEQUENCE: 86
tcggacgatc gtcgacgatc gtc                                           23
```

```
<210> SEQ ID NO 87
<211> LENGTH: 22
<212> TYPE: DNA
<213> ORGANISM: Artificial Sequence
<220> FEATURE:
<223> OTHER INFORMATION: Synthetic construct

<400> SEQUENCE: 87
tcgtcggacg atcgtcacga cg                                           22

<210> SEQ ID NO 88
<211> LENGTH: 20
<212> TYPE: DNA
<213> ORGANISM: Artificial Sequence
<220> FEATURE:
<223> OTHER INFORMATION: Synthetic construct

<400> SEQUENCE: 88
tcgttcgaac gttcgaacga                                              20

<210> SEQ ID NO 89
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1-3, 15-20
<223> OTHER INFORMATION: Phosphorothioate linkages

<400> SEQUENCE: 89
tcgttcgaac gttcgaacga                                              20

<210> SEQ ID NO 90
<211> LENGTH: 20
<212> TYPE: DNA
<213> ORGANISM: Artificial Sequence
<220> FEATURE:
<223> OTHER INFORMATION: Synthetic construct

<400> SEQUENCE: 90
tgcttgcaag cttgcaagca                                              20

<210> SEQ ID NO 91
<211> LENGTH: 20
<212> TYPE: DNA
<213> ORGANISM: Artificial Sequence
<220> FEATURE:
<223> OTHER INFORMATION: Synthetic construct

<400> SEQUENCE: 91
tcgttgcaag cttgcaacga                                              20

<210> SEQ ID NO 92
<211> LENGTH: 30
<212> TYPE: DNA
<213> ORGANISM: Artificial Sequence
<220> FEATURE:
<223> OTHER INFORMATION: Synthetic construct

<400> SEQUENCE: 92
accgataacg ttgccggtga cggcaccacg                                   30

<210> SEQ ID NO 93
<211> LENGTH: 18
<212> TYPE: DNA
<213> ORGANISM: Artificial Sequence
```

```
<220> FEATURE:
<223> OTHER INFORMATION: Synthetic construct

<400> SEQUENCE: 93
tcgtgcatcg atgcaacg                                               18

<210> SEQ ID NO 94
<211> LENGTH: 18
<212> TYPE: DNA
<213> ORGANISM: Artificial Sequence
<220> FEATURE:
<223> OTHER INFORMATION: Synthetic construct

<400> SEQUENCE: 94
aacaacaacg ttgttgtt                                               18

<210> SEQ ID NO 95
<211> LENGTH: 18
<212> TYPE: DNA
<213> ORGANISM: Artificial Sequence
<220> FEATURE:
<223> OTHER INFORMATION: Synthetic construct

<400> SEQUENCE: 95
aacaacaacg ttgttgtt                                               18

<210> SEQ ID NO 96
<211> LENGTH: 24
<212> TYPE: DNA
<213> ORGANISM: Artificial Sequence
<220> FEATURE:
<223> OTHER INFORMATION: Synthetic construct

<400> SEQUENCE: 96
tcagtcagtc agctgactga ctga                                        24

<210> SEQ ID NO 97
<211> LENGTH: 20
<212> TYPE: DNA
<213> ORGANISM: Artificial Sequence
<220> FEATURE:
<223> OTHER INFORMATION: Synthetic construct

<400> SEQUENCE: 97
tcgaacgttc gaacgttcga                                             20

<210> SEQ ID NO 98
<211> LENGTH: 14
<212> TYPE: DNA
<213> ORGANISM: Artificial Sequence
<220> FEATURE:
<223> OTHER INFORMATION: Synthetic construct

<400> SEQUENCE: 98
ttcgaacgtt cgaa                                                   14

<210> SEQ ID NO 99
<211> LENGTH: 18
<212> TYPE: DNA
<213> ORGANISM: Artificial Sequence
<220> FEATURE:
<223> OTHER INFORMATION: Synthetic construct

<400> SEQUENCE: 99
tcgtcgaacg ttcgagat                                               18
```

```
<210> SEQ ID NO 100
<211> LENGTH: 16
<212> TYPE: DNA
<213> ORGANISM: Artificial Sequence
<220> FEATURE:
<223> OTHER INFORMATION: Synthetic construct

<400> SEQUENCE: 100
tcgtcgaacg ttcgag                                                     16

<210> SEQ ID NO 101
<211> LENGTH: 15
<212> TYPE: DNA
<213> ORGANISM: Artificial Sequence
<220> FEATURE:
<223> OTHER INFORMATION: Synthetic construct

<400> SEQUENCE: 101
tcgtcgaacg ttcga                                                      15

<210> SEQ ID NO 102
<211> LENGTH: 13
<212> TYPE: DNA
<213> ORGANISM: Artificial Sequence
<220> FEATURE:
<223> OTHER INFORMATION: Synthetic construct

<400> SEQUENCE: 102
tcgaacgttc gag                                                        13

<210> SEQ ID NO 103
<211> LENGTH: 12
<212> TYPE: DNA
<213> ORGANISM: Artificial Sequence
<220> FEATURE:
<223> OTHER INFORMATION: Synthetic construct

<400> SEQUENCE: 103
tcgaacgttc ga                                                         12

<210> SEQ ID NO 104
<211> LENGTH: 11
<212> TYPE: DNA
<213> ORGANISM: Artificial Sequence
<220> FEATURE:
<223> OTHER INFORMATION: Synthetic construct

<400> SEQUENCE: 104
tcgaacgttc g                                                          11

<210> SEQ ID NO 105
<211> LENGTH: 10
<212> TYPE: DNA
<213> ORGANISM: Artificial Sequence
<220> FEATURE:
<223> OTHER INFORMATION: Synthetic construct

<400> SEQUENCE: 105
tcgacgtcga                                                            10

<210> SEQ ID NO 106
<211> LENGTH: 21
<212> TYPE: DNA
<213> ORGANISM: Artificial Sequence
<220> FEATURE:
<223> OTHER INFORMATION: Synthetic construct
```

-continued

<400> SEQUENCE: 106
tcgtcgtcga acgttcgaga t                                    21

<210> SEQ ID NO 107
<211> LENGTH: 21
<212> TYPE: DNA
<213> ORGANISM: Artificial Sequence
<220> FEATURE:
<223> OTHER INFORMATION: Synthetic construct

<400> SEQUENCE: 107
tcgtcgtcgt cgaacgttcg a                                    21

<210> SEQ ID NO 108
<211> LENGTH: 24
<212> TYPE: DNA
<213> ORGANISM: Artificial Sequence
<220> FEATURE:
<223> OTHER INFORMATION: Synthetic construct

<400> SEQUENCE: 108
tcgtcgtcga acgttcgacg agat                                 24

<210> SEQ ID NO 109
<211> LENGTH: 27
<212> TYPE: DNA
<213> ORGANISM: Artificial Sequence
<220> FEATURE:
<223> OTHER INFORMATION: Synthetic construct

<400> SEQUENCE: 109
tcgttcgaac gttcgaacgt tcgaacg                              27

<210> SEQ ID NO 110
<211> LENGTH: 21
<212> TYPE: DNA
<213> ORGANISM: Artificial Sequence
<220> FEATURE:
<223> OTHER INFORMATION: Synthetic construct

<400> SEQUENCE: 110
tcgtgcatcg atgcagatga t                                    21

<210> SEQ ID NO 111
<211> LENGTH: 27
<212> TYPE: DNA
<213> ORGANISM: Artificial Sequence
<220> FEATURE:
<223> OTHER INFORMATION: Synthetic construct

<400> SEQUENCE: 111
tcgtgcatcg atgcatgcat cgatgca                              27

<210> SEQ ID NO 112
<211> LENGTH: 21
<212> TYPE: DNA
<213> ORGANISM: Artificial Sequence
<220> FEATURE:
<223> OTHER INFORMATION: Synthetic construct

<400> SEQUENCE: 112
tcgtcggccg gccgagatga t                                    21

```
<210> SEQ ID NO 113
<211> LENGTH: 25
<212> TYPE: DNA
<213> ORGANISM: Artificial Sequence
<220> FEATURE:
<223> OTHER INFORMATION: Synthetic construct

<400> SEQUENCE: 113
tcgaacgttc gaacgttcga acgtt                                        25

<210> SEQ ID NO 114
<211> LENGTH: 20
<212> TYPE: DNA
<213> ORGANISM: Artificial Sequence
<220> FEATURE:
<223> OTHER INFORMATION: Synthetic construct

<400> SEQUENCE: 114
tcggacgtcg acgtgcgatt                                              20

<210> SEQ ID NO 115
<211> LENGTH: 18
<212> TYPE: DNA
<213> ORGANISM: Artificial Sequence
<220> FEATURE:
<223> OTHER INFORMATION: Synthetic construct

<400> SEQUENCE: 115
cttcgaacgt tcgaagtg                                                18

<210> SEQ ID NO 116
<211> LENGTH: 24
<212> TYPE: DNA
<213> ORGANISM: Artificial Sequence
<220> FEATURE:
<223> OTHER INFORMATION: Synthetic construct

<400> SEQUENCE: 116
tgatcgtcga acgttcgacg atca                                         24

<210> SEQ ID NO 117
<211> LENGTH: 25
<212> TYPE: DNA
<213> ORGANISM: Artificial Sequence
<220> FEATURE:
<223> OTHER INFORMATION: Synthetic construct

<400> SEQUENCE: 117
tcgaacgttc gaacgttcga atttt                                        25

<210> SEQ ID NO 118
<211> LENGTH: 25
<212> TYPE: DNA
<213> ORGANISM: Artificial Sequence
<220> FEATURE:
<223> OTHER INFORMATION: Synthetic construct

<400> SEQUENCE: 118
tcgttcgaac gttcgaacga atgat                                        25

<210> SEQ ID NO 119
<211> LENGTH: 22
<212> TYPE: DNA
<213> ORGANISM: Artificial Sequence
<220> FEATURE:
<223> OTHER INFORMATION: Synthetic construct
```

```
<400> SEQUENCE: 119
tcgacgtcga cgtcgacgtc ga                                    22

<210> SEQ ID NO 120
<211> LENGTH: 22
<212> TYPE: DNA
<213> ORGANISM: Artificial Sequence
<220> FEATURE:
<223> OTHER INFORMATION: Synthetic construct

<400> SEQUENCE: 120
acgtcgacgt cgacgtcgac gt                                    22

<210> SEQ ID NO 121
<211> LENGTH: 22
<212> TYPE: DNA
<213> ORGANISM: Artificial Sequence
<220> FEATURE:
<223> OTHER INFORMATION: Synthetic construct

<400> SEQUENCE: 121
tcgtcgacgt cgacgtcgac gt                                    22

<210> SEQ ID NO 122
<211> LENGTH: 22
<212> TYPE: DNA
<213> ORGANISM: Artificial Sequence
<220> FEATURE:
<223> OTHER INFORMATION: Synthetic construct

<400> SEQUENCE: 122
tcgtcggcgc cggcgccggc gc                                    22

<210> SEQ ID NO 123
<211> LENGTH: 22
<212> TYPE: DNA
<213> ORGANISM: Artificial Sequence
<220> FEATURE:
<223> OTHER INFORMATION: Synthetic construct

<400> SEQUENCE: 123
tcgtcgccgg cgccggcgcc gg                                    22

<210> SEQ ID NO 124
<211> LENGTH: 21
<212> TYPE: DNA
<213> ORGANISM: Artificial Sequence
<220> FEATURE:
<223> OTHER INFORMATION: Synthetic construct

<400> SEQUENCE: 124
tcgatacgtc gacgtcgacg t                                     21

<210> SEQ ID NO 125
<211> LENGTH: 21
<212> TYPE: DNA
<213> ORGANISM: Artificial Sequence
<220> FEATURE:
<223> OTHER INFORMATION: Synthetic construct

<400> SEQUENCE: 125
tcgtcgaagc gcttcgacag t                                     21
```

<210> SEQ ID NO 126
<211> LENGTH: 21
<212> TYPE: DNA
<213> ORGANISM: Artificial Sequence
<220> FEATURE:
<223> OTHER INFORMATION: Synthetic construct

<400> SEQUENCE: 126
tcgtcgaatc gattcgacag t                                              21

<210> SEQ ID NO 127
<211> LENGTH: 21
<212> TYPE: DNA
<213> ORGANISM: Artificial Sequence
<220> FEATURE:
<223> OTHER INFORMATION: Synthetic construct

<400> SEQUENCE: 127
tcgtcgagtc gactcgacag t                                              21

<210> SEQ ID NO 128
<211> LENGTH: 21
<212> TYPE: DNA
<213> ORGANISM: Artificial Sequence
<220> FEATURE:
<223> OTHER INFORMATION: Synthetic construct

<400> SEQUENCE: 128
tcgtcgcaac gttgcgacag t                                              21

<210> SEQ ID NO 129
<211> LENGTH: 21
<212> TYPE: DNA
<213> ORGANISM: Artificial Sequence
<220> FEATURE:
<223> OTHER INFORMATION: Synthetic construct

<400> SEQUENCE: 129
tcgtcgccgc gcggcgacag t                                              21

<210> SEQ ID NO 130
<211> LENGTH: 21
<212> TYPE: DNA
<213> ORGANISM: Artificial Sequence
<220> FEATURE:
<223> OTHER INFORMATION: Synthetic construct

<400> SEQUENCE: 130
tcgaaacgtt tcgacagtga t                                              21

<210> SEQ ID NO 131
<211> LENGTH: 22
<212> TYPE: DNA
<213> ORGANISM: Artificial Sequence
<220> FEATURE:
<223> OTHER INFORMATION: Synthetic construct

<400> SEQUENCE: 131
tcgaggtcga cctcgagatg at                                             22

<210> SEQ ID NO 132
<211> LENGTH: 23
<212> TYPE: DNA
<213> ORGANISM: Artificial Sequence
<220> FEATURE:
<223> OTHER INFORMATION: Synthetic construct

```
<400> SEQUENCE: 132
atcgatgtcg acatcgatat gat                                              23

<210> SEQ ID NO 133
<211> LENGTH: 22
<212> TYPE: DNA
<213> ORGANISM: Artificial Sequence
<220> FEATURE:
<223> OTHER INFORMATION: Synthetic construct

<400> SEQUENCE: 133
tcgtcgtcga cgacgagatg at                                               22

<210> SEQ ID NO 134
<211> LENGTH: 23
<212> TYPE: DNA
<213> ORGANISM: Artificial Sequence
<220> FEATURE:
<223> OTHER INFORMATION: Synthetic construct

<400> SEQUENCE: 134
tcggtcgatc gacgtcgatc gac                                              23

<210> SEQ ID NO 135
<211> LENGTH: 23
<212> TYPE: DNA
<213> ORGANISM: Artificial Sequence
<220> FEATURE:
<223> OTHER INFORMATION: Synthetic construct

<400> SEQUENCE: 135
tcggacggcc gtcgacggcc gtc                                              23

<210> SEQ ID NO 136
<211> LENGTH: 23
<212> TYPE: DNA
<213> ORGANISM: Artificial Sequence
<220> FEATURE:
<223> OTHER INFORMATION: Synthetic construct

<400> SEQUENCE: 136
tcggacgtac gtcgacgtac gtc                                              23

<210> SEQ ID NO 137
<211> LENGTH: 23
<212> TYPE: DNA
<213> ORGANISM: Artificial Sequence
<220> FEATURE:
<223> OTHER INFORMATION: Synthetic construct

<400> SEQUENCE: 137
tcgatcgtac gatatcgtac gat                                              23

<210> SEQ ID NO 138
<211> LENGTH: 22
<212> TYPE: DNA
<213> ORGANISM: Artificial Sequence
<220> FEATURE:
<223> OTHER INFORMATION: Synthetic construct

<400> SEQUENCE: 138
tcgtcggacg atcgtccgac ga                                               22
```

```
<210> SEQ ID NO 139
<211> LENGTH: 21
<212> TYPE: DNA
<213> ORGANISM: Artificial Sequence
<220> FEATURE:
<223> OTHER INFORMATION: Synthetic construct

<400> SEQUENCE: 139
tcgtcgcgta cgcgagatga t                                            21

<210> SEQ ID NO 140
<211> LENGTH: 21
<212> TYPE: DNA
<213> ORGANISM: Artificial Sequence
<220> FEATURE:
<223> OTHER INFORMATION: Synthetic construct

<400> SEQUENCE: 140
tcgtcgcggc cgcgagatga t                                            21

<210> SEQ ID NO 141
<211> LENGTH: 20
<212> TYPE: DNA
<213> ORGANISM: Artificial Sequence
<220> FEATURE:
<223> OTHER INFORMATION: Synthetic construct

<400> SEQUENCE: 141
tcgcgatcgc gcgatcgcga                                              20

<210> SEQ ID NO 142
<211> LENGTH: 21
<212> TYPE: DNA
<213> ORGANISM: Artificial Sequence
<220> FEATURE:
<223> OTHER INFORMATION: Synthetic construct

<400> SEQUENCE: 142
tcgtcgacgc gtcgagatga t                                            21

<210> SEQ ID NO 143
<211> LENGTH: 21
<212> TYPE: DNA
<213> ORGANISM: Artificial Sequence
<220> FEATURE:
<223> OTHER INFORMATION: Synthetic construct

<400> SEQUENCE: 143
tcgtcggcgc gccgagatga t                                            21

<210> SEQ ID NO 144
<211> LENGTH: 20
<212> TYPE: DNA
<213> ORGANISM: Artificial Sequence
<220> FEATURE:
<223> OTHER INFORMATION: Synthetic construct

<400> SEQUENCE: 144
tcgtcgatcg cgatcgacga                                              20

<210> SEQ ID NO 145
<211> LENGTH: 22
<212> TYPE: DNA
<213> ORGANISM: Artificial Sequence
<220> FEATURE:
<223> OTHER INFORMATION: Synthetic construct
```

-continued

<400> SEQUENCE: 145
tcgtcgaatc gcgattcgac ga					22

<210> SEQ ID NO 146
<211> LENGTH: 20
<212> TYPE: DNA
<213> ORGANISM: Artificial Sequence
<220> FEATURE:
<223> OTHER INFORMATION: Synthetic construct

<400> SEQUENCE: 146
tcgtcgcgat atcgcgacga					20

<210> SEQ ID NO 147
<211> LENGTH: 25
<212> TYPE: DNA
<213> ORGANISM: Artificial Sequence
<220> FEATURE:
<223> OTHER INFORMATION: Synthetic construct

<400> SEQUENCE: 147
tcgaacgttc gttcgaacga acgtt					25

<210> SEQ ID NO 148
<211> LENGTH: 21
<212> TYPE: DNA
<213> ORGANISM: Artificial Sequence
<220> FEATURE:
<223> OTHER INFORMATION: Synthetic construct

<400> SEQUENCE: 148
tcgaacgttt tcgaaaacgt t					21

<210> SEQ ID NO 149
<211> LENGTH: 18
<212> TYPE: DNA
<213> ORGANISM: Artificial Sequence
<220> FEATURE:
<223> OTHER INFORMATION: Synthetic construct

<400> SEQUENCE: 149
tcgtgcatcg atgcacga					18

<210> SEQ ID NO 150
<211> LENGTH: 21
<212> TYPE: DNA
<213> ORGANISM: Artificial Sequence
<220> FEATURE:
<223> OTHER INFORMATION: Synthetic construct

<400> SEQUENCE: 150
tcgcgaacgt tcgaacgttc g					21

<210> SEQ ID NO 151
<211> LENGTH: 21
<212> TYPE: DNA
<213> ORGANISM: Artificial Sequence
<220> FEATURE:
<223> OTHER INFORMATION: Synthetic construct

<400> SEQUENCE: 151
tcgcgaacgt tcgaacgttt c					21

```
<210> SEQ ID NO 152
<211> LENGTH: 21
<212> TYPE: DNA
<213> ORGANISM: Artificial Sequence
<220> FEATURE:
<223> OTHER INFORMATION: Synthetic construct

<400> SEQUENCE: 152
tcgataacgt tcgaacgtta t                                              21

<210> SEQ ID NO 153
<211> LENGTH: 21
<212> TYPE: DNA
<213> ORGANISM: Artificial Sequence
<220> FEATURE:
<223> OTHER INFORMATION: Synthetic construct

<400> SEQUENCE: 153
tcgataacgt tcgaacgttt c                                              21

<210> SEQ ID NO 154
<211> LENGTH: 20
<212> TYPE: DNA
<213> ORGANISM: Artificial Sequence
<220> FEATURE:
<223> OTHER INFORMATION: Synthetic construct

<400> SEQUENCE: 154
ggtgcatcga tgcagggggg                                                20

<210> SEQ ID NO 155
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (4)...(8)
<223> OTHER INFORMATION: Sequence of bases 4-7 may be repeated up to 4
      times
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (9)...(10)
<223> OTHER INFORMATION: n = absent, A, T, C or G
<220> FEATURE:
<221> NAME/KEY: misc_feature
<222> LOCATION: 11
<223> OTHER INFORMATION: n = A, T, C or G and base is complimentary to
      base 11
<220> FEATURE:
<221> NAME/KEY: misc_feature
<222> LOCATION: (11)...(16)
<223> OTHER INFORMATION: Sequence of bases 11-16 may be repeated up to
      20 times
<220> FEATURE:
<221> NAME/KEY: misc_feature
<222> LOCATION: 14
<223> OTHER INFORMATION: n = A, T,C or G and bases is complimentary to
      base 11
<220> FEATURE:
<221> NAME/KEY: misc_feature
<222> LOCATION: (15)...(16)
<223> OTHER INFORMATION: Bases 15 and 16 may be absent
```

<400> SEQUENCE: 155
nnntcgnnnn ncgncg                                                16

<210> SEQ ID NO 156
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)
<223> OTHER INFORMATION: n = absent or A, T, G or C
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (7)...(8)
<223> OTHER INFORMATION: n = absent or A, T, G or C
<220> FEATURE:
<221> NAME/KEY: misc_feature
<222> LOCATION: (9)...(10)
<223> OTHER INFORMATION: n = absent or A, T, C or G
<220> FEATURE:
<221> NAME/KEY: misc_feature
<222> LOCATION: 11
<223> OTHER INFORMATION: n = A, T, C or G and base is complementary to
      base 12
<220> FEATURE:
<221> NAME/KEY: misc_feature
<222> LOCATION: (11)...(18)
<223> OTHER INFORMATION: Sequence of bases 11-18 may be repeated up to
      20 times
<220> FEATURE:
<221> NAME/KEY: misc_feature
<222> LOCATION: 12
<223> OTHER INFORMATION: n = A, T, C or G and base is complementary to
      base 11
<220> FEATURE:
<221> NAME/KEY: misc_feature
<222> LOCATION: 15
<223> OTHER INFORMATION: n = A, T, C or G and base is complementary to
      base 16
<220> FEATURE:
<221> NAME/KEY: misc_feature
<222> LOCATION: 16
<223> OTHER INFORMATION: n = A, T, C or G and base is complementary to
      base 15
<220> FEATURE:
<221> NAME/KEY: misc_feature
<222> LOCATION: (17)...(18)
<223> OTHER INFORMATION: Bases 17-18 may be absent

<400> SEQUENCE: 156
nnntcgnnnn nncgnncg                                              18

<210> SEQ ID NO 157
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)
<223> OTHER INFORMATION: n = absent or A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times

```
<220> FEATURE:
<221> NAME/KEY: misc_feature
<222> LOCATION: (7)...(8)
<223> OTHER INFORMATION: n = absent or A, T, C or G
<220> FEATURE:
<221> NAME/KEY: misc_feature
<222> LOCATION: (9)...(10)
<223> OTHER INFORMATION: n = absent or A, T, C or G
<220> FEATURE:
<221> NAME/KEY: misc_feature
<222> LOCATION: 11
<223> OTHER INFORMATION: n = absent or A, T, C or G
<220> FEATURE:
<221> NAME/KEY: misc_feature
<222> LOCATION: (11)...(20)
<223> OTHER INFORMATION: Sequence of bases 11-20 may be repeated up to
      20 times
<220> FEATURE:
<221> NAME/KEY: misc_feature
<222> LOCATION: 12
<223> OTHER INFORMATION: n = A, T, C or G and base is complementary to
      base 17
<220> FEATURE:
<221> NAME/KEY: misc_feature
<222> LOCATION: 13
<223> OTHER INFORMATION: n = A, T, C or G and base is complementary to
      base 16
<220> FEATURE:
<221> NAME/KEY: misc_feature
<222> LOCATION: 16
<223> OTHER INFORMATION: n = A, T, C or G and base is complementary to
      base 13
<220> FEATURE:
<221> NAME/KEY: misc_feature
<222> LOCATION: 17
<223> OTHER INFORMATION: n = A, T, C or G and base is complementary to
      base 12
<220> FEATURE:
<221> NAME/KEY: misc_feature
<222> LOCATION: 18
<223> OTHER INFORMATION: n = A, T, C or G and base is complementary to
      base 11
<220> FEATURE:
<221> NAME/KEY: misc_feature
<222> LOCATION: (19)...(20)
<223> OTHER INFORMATION: Bases 19-20 may be absent

<400> SEQUENCE: 157
nnntcgnnnn nnncgnnncg                                              20

<210> SEQ ID NO 158
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)
<223> OTHER INFORMATION: n = absent or A, T, C or G
<220> FEATURE:
<221> NAME/KEY: misc_feature
<222> LOCATION: (4)...(8)
<223> OTHER INFORMATION: Seqeunce of bases 4-8 may be repeated up to 4
      times
<220> FEATURE:
<221> NAME/KEY: misc_feature
<222> LOCATION: (7)...(8)
<223> OTHER INFORMATION: n = absent or A, T, C or G
<220> FEATURE:
<221> NAME/KEY: misc_feature
<222> LOCATION: (9)...(10)
<223> OTHER INFORMATION: n = absent or A, T, C or G
<220> FEATURE:
<221> NAME/KEY: misc_feature
<222> LOCATION: (11)...(22)
<223> OTHER INFORMATION: Sequence of bases 11-22 may be repeated up
      to 20 times
```

```
<220> FEATURE:
<221> NAME/KEY: misc_feature
<222> LOCATION: 11
<223> OTHER INFORMATION: n = A, T, C or G and base is complementary to
      base 20
<220> FEATURE:
<221> NAME/KEY: misc_feature
<222> LOCATION: 12
<223> OTHER INFORMATION: n = A, T, C or G and base is complementary to
      base 19
<220> FEATURE:
<221> NAME/KEY: misc_feature
<222> LOCATION: 13
<223> OTHER INFORMATION: n = A, T, C or G and base is complementary to
      base 18
<220> FEATURE:
<221> NAME/KEY: misc_feature
<222> LOCATION: 14
<223> OTHER INFORMATION: n = A, T, C or G and base is complementary to
      base 17
<220> FEATURE:
<221> NAME/KEY: misc_feature
<222> LOCATION: 17
<223> OTHER INFORMATION: n = A, T, C or G and base is complementary to
      base 14
<220> FEATURE:
<221> NAME/KEY: misc_feature
<222> LOCATION: 18
<223> OTHER INFORMATION: n = A, T, C or G and base is complementary to
      base 13
<220> FEATURE:
<221> NAME/KEY: misc_feature
<222> LOCATION: 19
<223> OTHER INFORMATION: n = A, T, C or G and base is complementary to
      base 12
<220> FEATURE:
<221> NAME/KEY: misc_feature
<222> LOCATION: 20
<223> OTHER INFORMATION: n = A, T, C or G and base is complementary to
      base 11
<220> FEATURE:
<221> NAME/KEY: misc_feature
<222> LOCATION: (21)...(22)
<223> OTHER INFORMATION: Bases 21-22 may be absent

<400> SEQUENCE: 158
nnntcgnnnn nnnncgnnnn cg                                              22

<210> SEQ ID NO 159
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)
<223> OTHER INFORMATION: n = absent or A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (7)...(8)
<223> OTHER INFORMATION: n = absent or A, T, C or G
<220> FEATURE:
<221> NAME/KEY: misc_feature
<222> LOCATION: (9)...(10)
<223> OTHER INFORMATION: n = absent or A, T, C or G
<220> FEATURE:
<221> NAME/KEY: misc_feature
<222> LOCATION: (11)...(22)
<223> OTHER INFORMATION: Sequence of bases 11-22 may be repeated up to
      20 times
```

```
<220> FEATURE:
<221> NAME/KEY: misc_feature
<222> LOCATION: 11
<223> OTHER INFORMATION: n = A, T, C or G and base is complementary to
      base 20
<220> FEATURE:
<221> NAME/KEY: misc_feature
<222> LOCATION: 12
<223> OTHER INFORMATION: n = A, T, C or G and base is complementary to
      base 19
<220> FEATURE:
<221> NAME/KEY: misc_feature
<222> LOCATION: 15
<223> OTHER INFORMATION: n = A, T, C or G and base is complementary to
      base 16
<220> FEATURE:
<221> NAME/KEY: misc_feature
<222> LOCATION: 16
<223> OTHER INFORMATION: n = A, T, C or G and base is complementary to
      base 15
<220> FEATURE:
<221> NAME/KEY: misc_feature
<222> LOCATION: 19
<223> OTHER INFORMATION: n = A, T, C or G and base is complementary to
      base 12
<220> FEATURE:
<221> NAME/KEY: misc_feature
<222> LOCATION: 20
<223> OTHER INFORMATION: n = A, T, C or G and base is complementary to
      base 11
<220> FEATURE:
<221> NAME/KEY: misc_feature
<222> LOCATION: (21)...(22)
<223> OTHER INFORMATION: Bases 21-22 may be absent

<400> SEQUENCE: 159
nnntcgnnnn nncgnncgnn cg                                              22

<210> SEQ ID NO 160
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)
<223> OTHER INFORMATION: n = absent or A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (7)...(8)
<223> OTHER INFORMATION: n = absent or A, T, C or G
<220> FEATURE:
<221> NAME/KEY: misc_feature
<222> LOCATION: (9)...(10)
<223> OTHER INFORMATION: n = absent or A, T, C or G
<220> FEATURE:
<221> NAME/KEY: misc_feature
<222> LOCATION: (11)...(24)
<223> OTHER INFORMATION: Seqeunce of bases 11-24 may be repeated up to
      20 times
<220> FEATURE:
<221> NAME/KEY: misc_feature
<222> LOCATION: 11
<223> OTHER INFORMATION: n = A, T, C or G and base is complementary to
      base 22
<220> FEATURE:
<221> NAME/KEY: misc_feature
<222> LOCATION: 12
<223> OTHER INFORMATION: n = A, T, C or G and base is complementary to
      base 21
```

```
<220> FEATURE:
<221> NAME/KEY: misc_feature
<222> LOCATION: 13
<223> OTHER INFORMATION: n = A, T, C or G and base is complementary to
      base 20
<220> FEATURE:
<221> NAME/KEY: misc_feature
<222> LOCATION: 14
<223> OTHER INFORMATION: n = A, T, C or G and base is complementary to
      base 19
<220> FEATURE:
<221> NAME/KEY: misc_feature
<222> LOCATION: 15
<223> OTHER INFORMATION: n = A, T, C or G and base is complementary to
      base 18
<220> FEATURE:
<221> NAME/KEY: misc_feature
<222> LOCATION: 18
<223> OTHER INFORMATION: n = A, T, C or G and base is complementary to
      base 15
<220> FEATURE:
<221> NAME/KEY: misc_feature
<222> LOCATION: 19
<223> OTHER INFORMATION: n = A, T, C or G and base is complementary to
      base 14
<220> FEATURE:
<221> NAME/KEY: misc_feature
<222> LOCATION: 20
<223> OTHER INFORMATION: n = A, T, C or G and base is complementary to
      base 13
<220> FEATURE:
<221> NAME/KEY: misc_feature
<222> LOCATION: 21
<223> OTHER INFORMATION: n = A, T, C or G and base is complementary to
      base 12
<220> FEATURE:
<221> NAME/KEY: misc_feature
<222> LOCATION: 22
<223> OTHER INFORMATION: n = A, T, C or G and base is complementary to
      base 11
<220> FEATURE:
<221> NAME/KEY: misc_feature
<222> LOCATION: (23)...(24)
<223> OTHER INFORMATION: Bases 23-24 may be absent

<400> SEQUENCE: 160
nnntcgnnnn nnnnncgnnn nncg                                              24

<210> SEQ ID NO 161
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)
<223> OTHER INFORMATION: n = absent or A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (7)...(8)
<223> OTHER INFORMATION: n = absent or A, T, C or G
<220> FEATURE:
<221> NAME/KEY: misc_feature
<222> LOCATION: (9)...(10)
<223> OTHER INFORMATION: n = absent or A, T, C or G
<220> FEATURE:
<221> NAME/KEY: misc_feature
<222> LOCATION: (11)...(18)
<223> OTHER INFORMATION: Sequence of bases 11-18 may be repeated up to
      20 times
```

```
<220> FEATURE:
<221> NAME/KEY: misc_feature
<222> LOCATION: 13
<223> OTHER INFORMATION: n = A, T, C or G and base is complementary to
      base 14
<220> FEATURE:
<221> NAME/KEY: misc_feature
<222> LOCATION: 14
<223> OTHER INFORMATION: n = A, T, C or G and base is complementary to
      base 13
<220> FEATURE:
<221> NAME/KEY: misc_feature
<222> LOCATION: (17)...(18)
<223> OTHER INFORMATION: Bases 17-18 may be absent

<400> SEQUENCE: 161
nnntcgnnnn cgnncgcg                                                    18

<210> SEQ ID NO 162
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)
<223> OTHER INFORMATION: n = absent or A, T, C or G
<220> FEATURE:
<221> NAME/KEY: misc_feature
<222> LOCATION: (4)...(8)
<223> OTHER INFORMATION: Seqeunce of bases 4-8 may be repeated up to 4
      times
<220> FEATURE:
<221> NAME/KEY: misc_feature
<222> LOCATION: (7)...(8)
<223> OTHER INFORMATION: n = absent or A, T, C or G
<220> FEATURE:
<221> NAME/KEY: misc_feature
<222> LOCATION: (9)...(10)
<223> OTHER INFORMATION: n = absent or A, T, C or G
<220> FEATURE:
<221> NAME/KEY: misc_feature
<222> LOCATION: (11)...(18)
<223> OTHER INFORMATION: Sequence of bases 1-18 may be repeated up to
      20 times
<220> FEATURE:
<221> NAME/KEY: misc_feature
<222> LOCATION: 11
<223> OTHER INFORMATION: n = A, T, C or G and base is complementary to
      base 16
<220> FEATURE:
<221> NAME/KEY: misc_feature
<222> LOCATION: 16
<223> OTHER INFORMATION: n = A, T, C or G and base is complementary to
      base 11
<220> FEATURE:
<221> NAME/KEY: misc_feature
<222> LOCATION: (17)...(18)
<223> OTHER INFORMATION: Bases 17-18 may be absent

<400> SEQUENCE: 162
nnntcgnnnn ncgcgncg                                                    18

<210> SEQ ID NO 163
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)
<223> OTHER INFORMATION: n = absent or A, T, C or G
```

```
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (7)...(8)
<223> OTHER INFORMATION: n = absent or A, T, C or G
<220> FEATURE:
<221> NAME/KEY: misc_feature
<222> LOCATION: (9)...(10)
<223> OTHER INFORMATION: n = absent or A, T, C or G
<220> FEATURE:
<221> NAME/KEY: misc_feature
<222> LOCATION: (11)...(20)
<223> OTHER INFORMATION: Sequence of bases 9-18 may be repeated up to
      20 times
<220> FEATURE:
<221> NAME/KEY: misc_feature
<222> LOCATION: 11
<223> OTHER INFORMATION: n = A, T, C or G and base is complementary to
      base 18
<220> FEATURE:
<221> NAME/KEY: misc_feature
<222> LOCATION: 12
<223> OTHER INFORMATION: n = A, T, C or G and base is complementary to
      base 17
<220> FEATURE:
<221> NAME/KEY: misc_feature
<222> LOCATION: 17
<223> OTHER INFORMATION: n = A, T, C or G and base is complementary to
      base 12
<220> FEATURE:
<221> NAME/KEY: misc_feature
<222> LOCATION: 18
<223> OTHER INFORMATION: n = A, T, C or G and base is complementary to
      base 11
<220> FEATURE:
<221> NAME/KEY: misc_feature
<222> LOCATION: (19)...(20)
<223> OTHER INFORMATION: Bases 19-20 may be absent

<400> SEQUENCE: 163
nnntcgnnnn nncgcgnncg                                                  20

<210> SEQ ID NO 164
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)
<223> OTHER INFORMATION: n = absent or A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (7)...(8)
<223> OTHER INFORMATION: n = absent or A, T, C or G
<220> FEATURE:
<221> NAME/KEY: misc_feature
<222> LOCATION: (9)...(10)
<223> OTHER INFORMATION: n = absent or A, T, C or G
<220> FEATURE:
<221> NAME/KEY: misc_feature
<222> LOCATION: (11)...(22)
<223> OTHER INFORMATION: Seqeunce of bases 11-22 may be repeated up to
      20 times
```

```
<220> FEATURE:
<221> NAME/KEY: misc_feature
<222> LOCATION: 11
<223> OTHER INFORMATION: n = A, T, C or G and base is complementary to
      base 20
<220> FEATURE:
<221> NAME/KEY: misc_feature
<222> LOCATION: 12
<223> OTHER INFORMATION: n = A, T, C or G and base is complementary to
      base 19
<220> FEATURE:
<221> NAME/KEY: misc_feature
<222> LOCATION: 13
<223> OTHER INFORMATION: n = A, T, C or G and base is complementary to
      base 18
<220> FEATURE:
<221> NAME/KEY: misc_feature
<222> LOCATION: 18
<223> OTHER INFORMATION: n = A, T, C or G and base is complementary to
      base 13
<220> FEATURE:
<221> NAME/KEY: misc_feature
<222> LOCATION: 19
<223> OTHER INFORMATION: n = A, T, C or G and base is complementary to
      base 12
<220> FEATURE:
<221> NAME/KEY: misc_feature
<222> LOCATION: 20
<223> OTHER INFORMATION: n = A, T, C or G and base is complementary to
      base 11
<220> FEATURE:
<221> NAME/KEY: misc_feature
<222> LOCATION: (21)...(22)
<223> OTHER INFORMATION: Bases 21-22 may be absent

<400> SEQUENCE: 164
nnntcgnnnn nnncgcgnnn cg                                              22

<210> SEQ ID NO 165
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)
<223> OTHER INFORMATION: n = absent or A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (7)...(8)
<223> OTHER INFORMATION: n = absent or A, T, C or G
<220> FEATURE:
<221> NAME/KEY: misc_feature
<222> LOCATION: (9)...(10)
<223> OTHER INFORMATION: n = absent or A, T, C or G
<220> FEATURE:
<221> NAME/KEY: misc_feature
<222> LOCATION: (11)...(20)
<223> OTHER INFORMATION: Sequence of bases 11-20 may be repeated up to
      20 times
<220> FEATURE:
<221> NAME/KEY: misc_feature
<222> LOCATION: 13
<223> OTHER INFORMATION: n = A, T, C or G and base is complementary to
      base 16
<220> FEATURE:
<221> NAME/KEY: misc_feature
<222> LOCATION: 14
<223> OTHER INFORMATION: n = A, T, C or G and base is complementary to
      base 15
```

```
<220> FEATURE:
<221> NAME/KEY: misc_feature
<222> LOCATION: 15
<223> OTHER INFORMATION: n = A, T, C or G and base is complementary to
      base 14
<220> FEATURE:
<221> NAME/KEY: misc_feature
<222> LOCATION: 16
<223> OTHER INFORMATION: n = A, T, C or G and base is complementary to
      base 13
<220> FEATURE:
<221> NAME/KEY: misc_feature
<222> LOCATION: (19)...(20)
<223> OTHER INFORMATION: Bases 19-20 may be absent

<400> SEQUENCE: 165
nnntcgnnnn cgnnnncgcg                                              20

<210> SEQ ID NO 166
<211> LENGTH: 19
<212> TYPE: DNA
<213> ORGANISM: Artificial Sequence
<220> FEATURE:
<223> OTHER INFORMATION: Synthetic construct

<400> SEQUENCE: 166
tcgtcgaacg ttcgagatg                                               19

<210> SEQ ID NO 167
<211> LENGTH: 14
<212> TYPE: DNA
<213> ORGANISM: Artificial Sequence
<220> FEATURE:
<223> OTHER INFORMATION: Synthetic construct

<400> SEQUENCE: 167
tcgtcgaacg ttcg                                                    14

<210> SEQ ID NO 168
<211> LENGTH: 24
<212> TYPE: DNA
<213> ORGANISM: Artificial Sequence
<220> FEATURE:
<223> OTHER INFORMATION: Synthetic construct

<400> SEQUENCE: 168
tcgaacgttc gatcgaacgt tcga                                         24

<210> SEQ ID NO 169
<211> LENGTH: 20
<212> TYPE: DNA
<213> ORGANISM: Artificial Sequence
<220> FEATURE:
<223> OTHER INFORMATION: Synthetic construct

<400> SEQUENCE: 169
tcgaccggtc gaccggtcga                                              20

<210> SEQ ID NO 170
<211> LENGTH: 22
<212> TYPE: DNA
<213> ORGANISM: Artificial Sequence
<220> FEATURE:
<223> OTHER INFORMATION: Synthetic construct

<400> SEQUENCE: 170
tcgaacgttc gaacgttgat gt                                           22
```

```
<210> SEQ ID NO 171
<211> LENGTH: 22
<212> TYPE: DNA
<213> ORGANISM: Artificial Sequence
<220> FEATURE:
<223> OTHER INFORMATION: Synthetic construct

<400> SEQUENCE: 171
tcgaacgttc gaagatgatg at                                              22

<210> SEQ ID NO 172
<211> LENGTH: 30
<212> TYPE: DNA
<213> ORGANISM: Artificial Sequence
<220> FEATURE:
<223> OTHER INFORMATION: Synthetic construct

<400> SEQUENCE: 172
tcgaacgttc gaacgttcga acgttcgaat                                      30

<210> SEQ ID NO 173
<211> LENGTH: 29
<212> TYPE: DNA
<213> ORGANISM: Artificial Sequence
<220> FEATURE:
<223> OTHER INFORMATION: Synthetic construct

<400> SEQUENCE: 173
tcgataacgt tcgaacgttc gaacgttat                                       29

<210> SEQ ID NO 174
<211> LENGTH: 27
<212> TYPE: DNA
<213> ORGANISM: Artificial Sequence
<220> FEATURE:
<223> OTHER INFORMATION: Synthetic construct

<400> SEQUENCE: 174
tcgtaacgtt cgaacgttcg aacgtta                                         27

<210> SEQ ID NO 175
<211> LENGTH: 23
<212> TYPE: DNA
<213> ORGANISM: Artificial Sequence
<220> FEATURE:
<223> OTHER INFORMATION: Synthetic construct

<400> SEQUENCE: 175
tcgaacgttc gaacgttcga acg                                             23

<210> SEQ ID NO 176
<211> LENGTH: 25
<212> TYPE: DNA
<213> ORGANISM: Artificial Sequence
<220> FEATURE:
<223> OTHER INFORMATION: Synthetic construct

<400> SEQUENCE: 176
tcgaccggtc gaccggtcga ccggt                                           25

<210> SEQ ID NO 177
<211> LENGTH: 20
<212> TYPE: DNA
<213> ORGANISM: Artificial Sequence
<220> FEATURE:
<223> OTHER INFORMATION: Synthetic construct
```

```
<400> SEQUENCE: 177
tcgcgcgcgc gcgcgcgcga                                              20

<210> SEQ ID NO 178
<211> LENGTH: 20
<212> TYPE: DNA
<213> ORGANISM: Artificial Sequence
<220> FEATURE:
<223> OTHER INFORMATION: Synthetic construct

<400> SEQUENCE: 178
tcgcccgggc gcccgggcga                                              20

<210> SEQ ID NO 179
<211> LENGTH: 20
<212> TYPE: DNA
<213> ORGANISM: Artificial Sequence
<220> FEATURE:
<223> OTHER INFORMATION: Synthetic construct

<400> SEQUENCE: 179
tcggccggac gtccggacga                                              20

<210> SEQ ID NO 180
<211> LENGTH: 20
<212> TYPE: DNA
<213> ORGANISM: Artificial Sequence
<220> FEATURE:
<223> OTHER INFORMATION: Synthetic construct

<400> SEQUENCE: 180
tcggccggcc ggccggccga                                              20

<210> SEQ ID NO 181
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(22)
<223> OTHER INFORMATION: Polynucleotide is circular

<400> SEQUENCE: 181
tcgaacgttc gaacgttcga at                                           22

<210> SEQ ID NO 182
<211> LENGTH: 9
<212> TYPE: PRT
<213> ORGANISM: Artificial Sequence
<220> FEATURE:
<223> OTHER INFORMATION: Synthetic construct

<400> SEQUENCE: 182

Lys Phe Phe Lys Phe Phe Lys Phe Phe
 1               5

<210> SEQ ID NO 183
<211> LENGTH: 30
<212> TYPE: PRT
<213> ORGANISM: Artificial Sequence
<220> FEATURE:
<223> OTHER INFORMATION: Synthetic construct
```

```
<400> SEQUENCE: 183

Trp Glu Ala Lys Leu Ala Lys Ala Leu Ala Lys Ala Leu Ala Lys His
1               5                   10                  15

Leu Ala Lys Ala Leu Ala Lys Ala Leu Glu Ala Cys Glu Ala
            20                  25                  30

<210> SEQ ID NO 184
<211> LENGTH: 30
<212> TYPE: PRT
<213> ORGANISM: Artificial Sequence
<220> FEATURE:
<223> OTHER INFORMATION: Synthetic construct

<400> SEQUENCE: 184

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 185
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 21
<223> OTHER INFORMATION: n = 5'-DMT-N3-(tBu-SS-ethyl)thymidine-3'-
      phosphoroamidite

<400> SEQUENCE: 185
tcgtcgaacg ttcgagatga n                                     21

<210> SEQ ID NO 186
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = 5'-DMT-N3-(tBu-SS-ethyl)thymidine-3'-
      phosphoroamidite

<400> SEQUENCE: 186
ntcatctcga acgttcgacg a                                     21

<210> SEQ ID NO 187
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 3, 6, 10, 14, 16, 19
<223> OTHER INFORMATION: n = 7-deaza-8-aza-dG

<400> SEQUENCE: 187
tcntcnaacn ttcnanatna t                                     21

<210> SEQ ID NO 188
<211> LENGTH: 21
<212> TYPE: DNA
<213> ORGANISM: Artificial Sequence
```

```
<220> FEATURE:
<223> OTHER INFORMATION: Synthetic construct
<220> FEATURE:
<221> NAME/KEY: modified_base
<222> LOCATION: 7, 8, 15, 17, 20
<223> OTHER INFORMATION: n = 2-amino-dA

<400> SEQUENCE: 188
tcgtcgnncg ttcgngntgn t                                              21

<210> SEQ ID NO 189
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 8
<223> OTHER INFORMATION: n = 2-amino-dA
<220> FEATURE:
<221> NAME/KEY: modified_base
<222> LOCATION: 11
<223> OTHER INFORMATION: n = 2-thio-dT

<400> SEQUENCE: 189
tcgtcgancg ntcgagatga t                                              21

<210> SEQ ID NO 190
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 7, 8
<223> OTHER INFORMATION: n = 2-amino-dA
<220> FEATURE:
<221> NAME/KEY: modified_base
<222> LOCATION: 11, 12
<223> OTHER INFORMATION: n = 2-thio-dT

<400> SEQUENCE: 190
tcgtcgnncg nncgagatga t                                              21

<210> SEQ ID NO 191
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 17
<223> OTHER INFORMATION: n = N6-cystamine-2-dA

<400> SEQUENCE: 191
tcgtcgaacg ttcgagntga t                                              21

<210> SEQ ID NO 192
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 4
<223> OTHER INFORMATION: n = N6-cystamine-2-dA
```

-continued

```
<400> SEQUENCE: 192
atcntctcga acgttcgacg a                                          21

<210> SEQ ID NO 193
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 3, 6, 10, 14
<223> OTHER INFORMATION: n = 7-deaza-dG

<400> SEQUENCE: 193
tcntcnaacn ttcnagatga t                                          21

<210> SEQ ID NO 194
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 3, 7, 11, 15, 19, 23
<223> OTHER INFORMATION: n = 7-deaza-8-aza-dG

<400> SEQUENCE: 194
tcnaacnttc naacnttcna acntt                                      25

<210> SEQ ID NO 195
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 4, 11, 12, 18, 21
<223> OTHER INFORMATION: n = 5-propynyl-dU

<400> SEQUENCE: 195
tcgncgaacg nncgaganga n                                          21

<210> SEQ ID NO 196
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 8, 9, 16, 17, 24, 25
<223> OTHER INFORMATION: n = 5-propynyl-dU

<400> SEQUENCE: 196
tcgaacgnnc gaacgnncga acgnn                                      25

<210> SEQ ID NO 197
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: 4, 5, 12, 13, 20, 21
<223> OTHER INFORMATION: n = 2-amino-dA
```

```
<400> SEQUENCE: 197
tcgnncgttc gnncgttcgn ncgtt                                            25

<210> SEQ ID NO 198
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 4
<223> OTHER INFORMATION: n = A, T, C or G and base is complementary to
      base 9
<220> FEATURE:
<221> NAME/KEY: misc_feature
<222> LOCATION: 5
<223> OTHER INFORMATION: n = A, T, C or G and base is complementary to
      base 8
<220> FEATURE:
<221> NAME/KEY: misc_feature
<222> LOCATION: 8
<223> OTHER INFORMATION: n = A, T, C or G and base is complementary to
      base 5
<220> FEATURE:
<221> NAME/KEY: misc_feature
<222> LOCATION: 9
<223> OTHER INFORMATION: n = A, T, C or G and base is complementary to
      base 4

<400> SEQUENCE: 198
tcgnncgnnc ga                                                          12

<210> SEQ ID NO 199
<211> LENGTH: 12
<212> TYPE: DNA
<213> ORGANISM: Artificial Sequence
<220> FEATURE:
<223> OTHER INFORMATION: Synthetic construct

<400> SEQUENCE: 199
tcgtcgaacg tt                                                          12

<210> SEQ ID NO 200
<211> LENGTH: 19
<212> TYPE: DNA
<213> ORGANISM: Artificial Sequence
<220> FEATURE:
<223> OTHER INFORMATION: Synthesized Primer

<400> SEQUENCE: 200
cacttggtcc tgcgcttga                                                   19

<210> SEQ ID NO 201
<211> LENGTH: 24
<212> TYPE: DNA
<213> ORGANISM: Artificial Sequence
<220> FEATURE:
<223> OTHER INFORMATION: Synthesized Primer

<400> SEQUENCE: 201
caattgggaa tgcaacaact ttat                                             24

<210> SEQ ID NO 202
<211> LENGTH: 23
<212> TYPE: DNA
<213> ORGANISM: Artificial Sequence
<220> FEATURE:
<223> OTHER INFORMATION: Synthesized Primer
```

```
<400> SEQUENCE: 202
agggagcatg aaaacacatt tca                                          23

<210> SEQ ID NO 203
<211> LENGTH: 28
<212> TYPE: DNA
<213> ORGANISM: Artificial Sequence
<220> FEATURE:
<223> OTHER INFORMATION: Synthesized Primer

<400> SEQUENCE: 203
ttgctggtag tttatgacta attccaag                                     28

<210> SEQ ID NO 204
<211> LENGTH: 23
<212> TYPE: DNA
<213> ORGANISM: Artificial Sequence
<220> FEATURE:
<223> OTHER INFORMATION: Synthesized Primer

<400> SEQUENCE: 204
tggaacgtgt gaaagctgag tct                                          23

<210> SEQ ID NO 205
<211> LENGTH: 23
<212> TYPE: DNA
<213> ORGANISM: Artificial Sequence
<220> FEATURE:
<223> OTHER INFORMATION: Synthesized Primer

<400> SEQUENCE: 205
catctgctca ttctttcttt gca                                          23

<210> SEQ ID NO 206
<211> LENGTH: 19
<212> TYPE: DNA
<213> ORGANISM: Artificial Sequence
<220> FEATURE:
<223> OTHER INFORMATION: Synthesized Primer

<400> SEQUENCE: 206
cccaggagga gtttggcaa                                               19

<210> SEQ ID NO 207
<211> LENGTH: 21
<212> TYPE: DNA
<213> ORGANISM: Artificial Sequence
<220> FEATURE:
<223> OTHER INFORMATION: Synthesized Primer

<400> SEQUENCE: 207
tgctggatca tctcatggag g                                            21

<210> SEQ ID NO 208
<211> LENGTH: 21
<212> TYPE: DNA
<213> ORGANISM: Artificial Sequence
<220> FEATURE:
<223> OTHER INFORMATION: Synthesized Primer

<400> SEQUENCE: 208
ctggactggc aatagcaagc t                                            21
```

```
<210> SEQ ID NO 209
<211> LENGTH: 20
<212> TYPE: DNA
<213> ORGANISM: Artificial Sequence
<220> FEATURE:
<223> OTHER INFORMATION: Synthesized Primer

<400> SEQUENCE: 209
agagggtcaa tggcgttctg                                         20

<210> SEQ ID NO 210
<211> LENGTH: 20
<212> TYPE: DNA
<213> ORGANISM: Artificial Sequence
<220> FEATURE:
<223> OTHER INFORMATION: Synthesized Primer

<400> SEQUENCE: 210
ctgctcatgg cagccacttt                                         20

<210> SEQ ID NO 211
<211> LENGTH: 21
<212> TYPE: DNA
<213> ORGANISM: Artificial Sequence
<220> FEATURE:
<223> OTHER INFORMATION: Synthesized Primer

<400> SEQUENCE: 211
agcaggtgat tggaatggaa a                                       21

<210> SEQ ID NO 212
<211> LENGTH: 22
<212> TYPE: DNA
<213> ORGANISM: Artificial Sequence
<220> FEATURE:
<223> OTHER INFORMATION: Synthesized Primer

<400> SEQUENCE: 212
catcttgctg gttctgattg ga                                      22

<210> SEQ ID NO 213
<211> LENGTH: 20
<212> TYPE: DNA
<213> ORGANISM: Artificial Sequence
<220> FEATURE:
<223> OTHER INFORMATION: Synthesized Primer

<400> SEQUENCE: 213
tggtgctgat gcaggaacag                                         20

<210> SEQ ID NO 214
<211> LENGTH: 20
<212> TYPE: DNA
<213> ORGANISM: Artificial Sequence
<220> FEATURE:
<223> OTHER INFORMATION: Synthesized Primer

<400> SEQUENCE: 214
cttctgcctg ctgcactttg                                         20

<210> SEQ ID NO 215
<211> LENGTH: 18
<212> TYPE: DNA
<213> ORGANISM: Artificial Sequence
<220> FEATURE:
<223> OTHER INFORMATION: Synthesized Primer
```

```
<400> SEQUENCE: 215
ctgggccaga gggctgat                                                    18

<210> SEQ ID NO 216
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A, T, C or G and base is complementary to
      base 10
<220> FEATURE:
<221> NAME/KEY: misc_feature
<222> LOCATION: 2
<223> OTHER INFORMATION: n = A, T, C or G and base is complementary to
      base 9
<220> FEATURE:
<221> NAME/KEY: misc_feature
<222> LOCATION: 5
<223> OTHER INFORMATION: n = A, T, C or G and base is complementary to
      base 6
<220> FEATURE:
<221> NAME/KEY: misc_feature
<222> LOCATION: 6
<223> OTHER INFORMATION: n = A, T, C or G and base is complementary to
      base 5
<220> FEATURE:
<221> NAME/KEY: misc_feature
<222> LOCATION: 9
<223> OTHER INFORMATION: n = A, T, C or G and base is complementary to
      base 2
<220> FEATURE:
<221> NAME/KEY: misc_feature
<222> LOCATION: 10
<223> OTHER INFORMATION: n = A, T, C or G and base is complementary to
      base 1

<400> SEQUENCE: 216 nncgnncgnn                                                             10

<210> SEQ ID NO 217
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(12)
<223> OTHER INFORMATION: Sequence of bases 1-12 may be repeated up to 20
      times
<220> FEATURE:
<221> NAME/KEY: misc_feature
<222> LOCATION: 1
<223> OTHER INFORMATION: n = A, T, C or G and bases in complementary to
      base 10
<220> FEATURE:
<221> NAME/KEY: misc_feature
<222> LOCATION: 2
<223> OTHER INFORMATION: n = A, T, C or G and bases in complementary to
      base 9
<220> FEATURE:
<221> NAME/KEY: misc_feature
<222> LOCATION: 5
<223> OTHER INFORMATION: n = A, T, C or G and bases in complementary to
      base 6
<220> FEATURE:
<221> NAME/KEY: misc_feature
<222> LOCATION: 6
<223> OTHER INFORMATION: n = A, T, C or G and bases in complementary to
      base 5
```

```
<220> FEATURE:
<221> NAME/KEY: misc_feature
<222> LOCATION: 9
<223> OTHER INFORMATION: n = A, T, C or G and bases in complementary to
      base 2
<220> FEATURE:
<221> NAME/KEY: misc_feature
<222> LOCATION: 10
<223> OTHER INFORMATION: n = A, T, C or G and bases in complementary to
      base 1
<220> FEATURE:
<221> NAME/KEY: misc_feature
<222> LOCATION: (11)...(12)
<223> OTHER INFORMATION: Bases 11-12 may be absent

<400> SEQUENCE: 217
nncgnncgnn cg                                                               12

<210> SEQ ID NO 218
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A, T, C or G ans base is complementary to
      base 12
<220> FEATURE:
<221> NAME/KEY: misc_feature
<222> LOCATION: 2
<223> OTHER INFORMATION: n = A, T, C or G ans base is complementary to
      base 11
<220> FEATURE:
<221> NAME/KEY: misc_feature
<222> LOCATION: 3
<223> OTHER INFORMATION: n = A, T, C or G ans base is complementary to
      base 10
<220> FEATURE:
<221> NAME/KEY: misc_feature
<222> LOCATION: 4
<223> OTHER INFORMATION: n = A, T, C or G ans base is complementary to
      base 9
<220> FEATURE:
<221> NAME/KEY: misc_feature
<222> LOCATION: 5
<223> OTHER INFORMATION: n = A, T, C or G ans base is complementary to
      base 8
<220> FEATURE:
<221> NAME/KEY: misc_feature
<222> LOCATION: 8
<223> OTHER INFORMATION: n = A, T, C or G ans base is complementary to
      base 5
<220> FEATURE:
<221> NAME/KEY: misc_feature
<222> LOCATION: 9
<223> OTHER INFORMATION: n = A, T, C or G ans base is complementary to
      base 4
<220> FEATURE:
<221> NAME/KEY: misc_feature
<222> LOCATION: 10
<223> OTHER INFORMATION: n = A, T, C or G ans base is complementary to
      base 3
<220> FEATURE:
<221> NAME/KEY: misc_feature
<222> LOCATION: 11
<223> OTHER INFORMATION: n = A, T, C or G ans base is complementary to
      base 2
<220> FEATURE:
<221> NAME/KEY: misc_feature
<222> LOCATION: 12
<223> OTHER INFORMATION: n = A, T, C or G ans base is complementary to
      base 1

<400> SEQUENCE: 218
nnnnncgnnn nn                                                               12
```

```
<210> SEQ ID NO 219
<211> LENGTH: 14
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(14)
<223> OTHER INFORMATION: Sequence of bases 1-14 may be repeated up to 20
      times
<220> FEATURE:
<221> NAME/KEY: misc_feature
<222> LOCATION: 1
<223> OTHER INFORMATION: n = A, T, C or G and base is complementary to
      base 12
<220> FEATURE:
<221> NAME/KEY: misc_feature
<222> LOCATION: 2
<223> OTHER INFORMATION: n = A, T, C or G and base is complementary to
      base 11
<220> FEATURE:
<221> NAME/KEY: misc_feature
<222> LOCATION: 3
<223> OTHER INFORMATION: n = A, T, C or G and base is complementary to
      base 10
<220> FEATURE:
<221> NAME/KEY: misc_feature
<222> LOCATION: 4
<223> OTHER INFORMATION: n = A, T, C or G and base is complementary to
      base 9
<220> FEATURE:
<221> NAME/KEY: misc_feature
<222> LOCATION: 5
<223> OTHER INFORMATION: n = A, T, C or G and base is complementary to
      base 8
<220> FEATURE:
<221> NAME/KEY: misc_feature
<222> LOCATION: 8
<223> OTHER INFORMATION: n = A, T, C or G and base is complementary to
      base 5
<220> FEATURE:
<221> NAME/KEY: misc_feature
<222> LOCATION: 9
<223> OTHER INFORMATION: n = A, T, C or G and base is complementary to
      base 4
<220> FEATURE:
<221> NAME/KEY: misc_feature
<222> LOCATION: 10
<223> OTHER INFORMATION: n = A, T, C or G and base is complementary to
      base 3
<220> FEATURE:
<221> NAME/KEY: misc_feature
<222> LOCATION: 11
<223> OTHER INFORMATION: n = A, T, C or G and base is complementary to
      base 2
<220> FEATURE:
<221> NAME/KEY: misc_feature
<222> LOCATION: 12
<223> OTHER INFORMATION: n = A, T, C or G and base is complementary to
      base 1
<220> FEATURE:
<221> NAME/KEY: misc_feature
<222> LOCATION: (13)...(14)
<223> OTHER INFORMATION: Bases 13-14 may be absent

<400> SEQUENCE: 219
nnnnncgnnn nncg                                                       14

<210> SEQ ID NO 220
<211> LENGTH: 10
<212> TYPE: DNA
<213> ORGANISM: Artificial Sequence
<220> FEATURE:
<223> OTHER INFORMATION: Synthetic construct
```

```
<220> FEATURE:
<221> NAME/KEY: misc_feature
<222> LOCATION: (1)...(10)
<223> OTHER INFORMATION: Sequence of bases 1-10 may be repeated up to 20
      times
<220> FEATURE:
<221> NAME/KEY: misc_feature
<222> LOCATION: 1
<223> OTHER INFORMATION: n = A, T, C or G and base is complementary to
      base 8
<220> FEATURE:
<221> NAME/KEY: misc_feature
<222> LOCATION: 2
<223> OTHER INFORMATION: n = A, T, C or G and base is complementary to
      base 7
<220> FEATURE:
<221> NAME/KEY: misc_feature
<222> LOCATION: 7
<223> OTHER INFORMATION: n = A, T, C or G and base is complementary to
      base 2
<220> FEATURE:
<221> NAME/KEY: misc_feature
<222> LOCATION: 8
<223> OTHER INFORMATION: n = A, T, C or G and base is complementary to
      base 1
<220> FEATURE:
<221> NAME/KEY: misc_feature
<222> LOCATION: (9)...(10)
<223> OTHER INFORMATION: Bases 9-10 may be absent

<400> SEQUENCE: 220 nncgcgnncg                                                            10

<210> SEQ ID NO 221
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A, T, C or G and base is complementary to
      base 10
<220> FEATURE:
<221> NAME/KEY: misc_feature
<222> LOCATION: 2
<223> OTHER INFORMATION: n = A, T, C or G and base is complementary to
      base 9
<220> FEATURE:
<221> NAME/KEY: misc_feature
<222> LOCATION: 3
<223> OTHER INFORMATION: n = A, T, C or G and base is complementary to
      base 8
<220> FEATURE:
<221> NAME/KEY: misc_feature
<222> LOCATION: 8
<223> OTHER INFORMATION: n = A, T, C or G and base is complementary to
      base 3
<220> FEATURE:
<221> NAME/KEY: misc_feature
<222> LOCATION: 9
<223> OTHER INFORMATION: n = A, T, C or G and base is complementary to
      base 2
<220> FEATURE:
<221> NAME/KEY: misc_feature
<222> LOCATION: 10
<223> OTHER INFORMATION: n = A, T, C or G and base is complementary to
      base 1

<400> SEQUENCE: 221 nnncgcgnnn                                                            10
```

```
<210> SEQ ID NO 222
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(12)
<223> OTHER INFORMATION: Sequence of bases 1-12 may be repeated up to 20
      times
<220> FEATURE:
<221> NAME/KEY: misc_feature
<222> LOCATION: 1
<223> OTHER INFORMATION: n = A, T, C or G and base is complementary to
      base 10
<220> FEATURE:
<221> NAME/KEY: misc_feature
<222> LOCATION: 2
<223> OTHER INFORMATION: n = A, T, C or G and base is complementary to
      base
<220> FEATURE:
<221> NAME/KEY: misc_feature
<222> LOCATION: 3
<223> OTHER INFORMATION: n = A, T, C or G and base is complementary to
      base 8
<220> FEATURE:
<221> NAME/KEY: misc_feature
<222> LOCATION: 8
<223> OTHER INFORMATION: n = A, T, C or G and base is complementary to
      base 3
<220> FEATURE:
<221> NAME/KEY: misc_feature
<222> LOCATION: 9
<223> OTHER INFORMATION: n = A, T, C or G and base is complementary to
      base 2
<220> FEATURE:
<221> NAME/KEY: misc_feature
<222> LOCATION: 10
<223> OTHER INFORMATION: n = A, T, C or G and base is complementary to
      base 1
<220> FEATURE:
<221> NAME/KEY: misc_feature
<222> LOCATION: (11)...(12)
<223> OTHER INFORMATION: Bases 11-12 may be absent

<400> SEQUENCE: 222
nnncgcgnnn cg                                                            12

<210> SEQ ID NO 223
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(10)
<223> OTHER INFORMATION: Sequence of bases 1-10 may be repeated up to 20
      times
<220> FEATURE:
<221> NAME/KEY: misc_feature
<222> LOCATION: 3
<223> OTHER INFORMATION: n = A, T, C or G and base is complementary to
      base 6
<220> FEATURE:
<221> NAME/KEY: misc_feature
<222> LOCATION: 4
<223> OTHER INFORMATION: n = A, T, C or G and base is complementary to
      base 5
<220> FEATURE:
<221> NAME/KEY: misc_feature
<222> LOCATION: 5
<223> OTHER INFORMATION: n = A, T, C or G and base is complementary to
      base 4
```

```
<220> FEATURE:
<221> NAME/KEY: misc_feature
<222> LOCATION: 6
<223> OTHER INFORMATION: n = A, T, C or G and base is complementary to
      base 3
<220> FEATURE:
<221> NAME/KEY: misc_feature
<222> LOCATION: (9)...(10)
<223> OTHER INFORMATION: Bases 9-10 may be absent

<400> SEQUENCE: 223 cgnnncgcg                                                                    10

<210> SEQ ID NO 224
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A, T, C or G and base is complementary to
      base 8
<220> FEATURE:
<221> NAME/KEY: misc_feature
<222> LOCATION: 2
<223> OTHER INFORMATION: n = A, T, C or G and base is complementary to
      base 7
<220> FEATURE:
<221> NAME/KEY: misc_feature
<222> LOCATION: 3
<223> OTHER INFORMATION: n = A, T, C or G and base is complementary to
      base 6
<220> FEATURE:
<221> NAME/KEY: misc_feature
<222> LOCATION: 6
<223> OTHER INFORMATION: n = A, T, C or G and base is complementary to
      base 3
<220> FEATURE:
<221> NAME/KEY: misc_feature
<222> LOCATION: 7
<223> OTHER INFORMATION: n = A, T, C or G and base is complementary to
      base 2
<220> FEATURE:
<221> NAME/KEY: misc_feature
<222> LOCATION: 8
<223> OTHER INFORMATION: n = A, T, C or G and base is complementary to
      base 1
<220> FEATURE:
<221> NAME/KEY: misc_feature
<222> LOCATION: (9)...(10)
<223> OTHER INFORMATION: Bases 9-10 may be absent

<400> SEQUENCE: 224 nnncgnnncg                                                                   10

<210> SEQ ID NO 225
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A, T C or G and base is complementary to
      base 10
<220> FEATURE:
<221> NAME/KEY: misc_feature
<222> LOCATION: 2
<223> OTHER INFORMATION: n = A, T C or G and base is complementary to
      base 9
```

-continued

```
<220> FEATURE:
<221> NAME/KEY: misc_feature
<222> LOCATION: 3
<223> OTHER INFORMATION: n = A, T C or G and base is complementary to
      base 8
<220> FEATURE:
<221> NAME/KEY: misc_feature
<222> LOCATION: 4
<223> OTHER INFORMATION: n = A, T C or G and base is complementary to
      base 7
<220> FEATURE:
<221> NAME/KEY: misc_feature
<222> LOCATION: 7
<223> OTHER INFORMATION: n = A, T C or G and base is complementary to
      base 4
<220> FEATURE:
<221> NAME/KEY: misc_feature
<222> LOCATION: 8
<223> OTHER INFORMATION: n = A, T C or G and base is complementary to
      base 3
<220> FEATURE:
<221> NAME/KEY: misc_feature
<222> LOCATION: 9
<223> OTHER INFORMATION: n = A, T C or G and base is complementary to
      base 2
<220> FEATURE:
<221> NAME/KEY: misc_feature
<222> LOCATION: 10
<223> OTHER INFORMATION: n = A, T C or G and base is complementary to
      base 1

<400> SEQUENCE: 225 nnnncgnnnn                                                            10

<210> SEQ ID NO 226
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A, T, C or G and base is complementary to
      base 10
<220> FEATURE:
<221> NAME/KEY: misc_feature
<222> LOCATION: 2
<223> OTHER INFORMATION: n = A, T, C or G and base is complementary to
      base 9
<220> FEATURE:
<221> NAME/KEY: misc_feature
<222> LOCATION: 3
<223> OTHER INFORMATION: n = A, T, C or G and base is complementary to
      base 8
<220> FEATURE:
<221> NAME/KEY: misc_feature
<222> LOCATION: 4
<223> OTHER INFORMATION: n = A, T, C or G and base is complementary to
      base 7
<220> FEATURE:
<221> NAME/KEY: misc_feature
<222> LOCATION: 7
<223> OTHER INFORMATION: n = A, T, C or G and base is complementary to
      base 4
<220> FEATURE:
<221> NAME/KEY: misc_feature
<222> LOCATION: 8
<223> OTHER INFORMATION: n = A, T, C or G and base is complementary to
      base 3
<220> FEATURE:
<221> NAME/KEY: misc_feature
<222> LOCATION: 9
<223> OTHER INFORMATION: n = A, T, C or G and base is complementary to
      base 2
```

```
<220> FEATURE:
<221> NAME/KEY: misc_feature
<222> LOCATION: 10
<223> OTHER INFORMATION: n = A, T, C or G and base is complementary to
      base 1
<220> FEATURE:
<221> NAME/KEY: misc_feature
<222> LOCATION: (11)...(12)
<223> OTHER INFORMATION: Bases 11-12 may be absent

<400> SEQUENCE: 226
nnnncgnnnn cg                                                              12

<210> SEQ ID NO 227
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 4, 27
<223> OTHER INFORMATION: n = 5'-DMT-N3-(tBu-SS-ethyl)thymidine-3'-
      phosphoramidite

<400> SEQUENCE: 227
tcgnaacgtt cgaacgttcg aacgttn                                              27

<210> SEQ ID NO 228
<211> LENGTH: 22
<212> TYPE: DNA
<213> ORGANISM: Artificial Sequence
<220> FEATURE:
<223> OTHER INFORMATION: Synthetic construct

<400> SEQUENCE: 228
aacgttcgaa cgttcgaacg tt                                                   22
```

IMMUNOSTIMULATORY SEQUENCE OLIGONUCLEOTIDES AND METHODS OF USING THE SAME

CROSS-REFERENCE TO RELATED APPLICATIONS

This application is a continuation of U.S. application Ser. No. 10/741,720, filed on Dec. 18, 2003, now U.S. Pat. No. 7,745,606, which claims priority to (1) U.S. Provisional Patent Application No. 60/436,122, filed on Dec. 23, 2002; (2) U.S. Provisional Patent Application No. 60/447,885, filed on Feb. 13, 2003; and (3) U.S. Provisional Patent Application No. 60/467,546, filed on May 1, 2003, the disclosures of which are herein incorporated by reference in their entirety.

TECHNICAL FIELD

The present invention relates to immunomodulatory polynucleotides. It also relates to the administration of the polynucleotides to modulate an immune response.

BACKGROUND OF THE INVENTION

The type of immune response generated to infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets. See, for example, Romagnani (2000) *Ann. Allergy Asthma Immunol.* 85:9-18.

The Th1 subset may be particularly suited to respond to viral infections, intracellular pathogens, and tumor cells because it secretes IL-2 and IFN-γ, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

For many infectious diseases, such as tuberculosis and malaria, Th2-type responses are of little protective value against infection. Proposed vaccines using small peptides derived from the target antigen and other currently used antigenic agents that avoid use of potentially infective intact viral particles, do not always elicit the immune response necessary to achieve a therapeutic effect. Protein-based vaccines typically induce Th2-type immune responses, characterized by high titers of neutralizing antibodies but without significant cell-mediated immunity.

Moreover, some types of antibody responses are inappropriate in certain indications, most notably in allergy where an IgE antibody response can result in anaphylactic shock. Generally, allergic responses also involve Th2-type immune responses. Allergic responses, including those of allergic asthma, are characterized by an early phase response, which occurs within seconds to minutes of allergen exposure and is characterized by cellular degranulation, and a late phase response, which occurs 4 to 24 hours later and is characterized by infiltration of eosinophils into the site of allergen exposure. Specifically, during the early phase of the allergic response, allergen cross-links IgE antibodies on basophils and mast cells, which in turn triggers degranulation and the subsequent release of histamine and other mediators of inflammation from mast cells and basophils. During the late phase response, eosinophils infiltrate into the site of allergen exposure (where tissue damage and dysfunction result).

Antigen immunotherapy for allergic disorders involves the subcutaneous injection of small, but gradually increasing amounts, of antigen. Such immunization treatments present the risk of inducing IgE-mediated anaphylaxis and do not efficiently address the cytokine-mediated events of the allergic late phase response. Thus far, this approach has yielded only limited success.

Administration of certain DNA sequences, generally known as immunostimulatory sequences, induces an immune response with a Th1-type bias as indicated by secretion of Th1-associated cytokines. Administration of an immunostimulatory polynucleotide with an antigen results in a Th1-type immune response to the administered antigen. Roman et al. (1997) *Nature Med.* 3:849-854. For example, mice injected intradermally with *Escherichia coli* (*E. coli*) β-galactosidase (β-Gal) in saline or in the adjuvant alum responded by producing specific IgG1 and IgE antibodies, and CD4$^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding β-Gal and containing an immunostimulatory sequence responded by producing IgG2a antibodies and CD4$^+$ cells that secreted IFN-γ, but not IL-4 and IL-5, demonstrating that the T cells were predominantly of the Th1 subset. Moreover, specific IgE production by the plasmid DNA-injected mice was reduced 66-75%. Raz et al. (1996) *Proc. Natl. Acad. Sci. USA* 93:5141-5145. In general, the response to naked DNA immunization is characterized by production of IL-2, TNFα and IFN-γ by antigen-stimulated CD4$^+$ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495).

References describing immunostimulatory activity of polynucleotides include: Krug et al. (2001) *Eur. J. Immunol.* 31:3026; Bauer et al. (2001) *J. Immunol.* 166:5000; Klinman et al. (1999) *Vaccine* 17:19; Jahn-Schmid et al. (1999) *J. Allergy Clin. Immunol.* 104:1015; Tighe et al. (2000) *Eur. J. Immunol.* 30:1939; Shirota et al. (2000) *J. Immunol.* 164:5575; Klinman et al. (1999) *Infect. Immun.* 67:5658; Sur et al. (1999) *J. Immunol.* 162:6284; Magone et al. (2000) *Eur. J. Immunol.* 30:1841; Kawarada et al. (2001) *J. Immunol.* 167:5247; Kranzer et al. (2000) *Immunology* 99:170; Krug et al. (2001) *Eur. J. Immunol.* 31:2154; Hartmann et al. (2000) *J. Immunol.* 164:944; Bauer et al. (1999) *Immunology* 97:699; Fujieda et al. (2000) *Am. J. Respir. Crit. Care Med.* 162:232; Krieg (2002) *Annu. Rev. Immunol.* 20:709; Verthelyi et al. (2002) *J. Immunol.* 168:1659; Hornung et al. (2002) *J. Immunol.* 168:4531; Yamamoto et al. (2000) *Springer Semin. Immunopathol.* 22:35; Lee et al. (2000) *J. Immunol.* 165:3631; Gursel et al. (2002) *J. Leukoc. Biol.* 71:813; Gursel et al. (2002) *Eur. J. Immunol.* 32:2617; Broide et al. (2001) *J. Clin. Immunol.* 21:175; Zhu et al. (2001) *Immunology* 103:226; Klinman et al. (2002)*Microbes Infect.* 4:897; Hartmann et al. (2000) *J. Immunol.* 164:1617; Krieg (1999) *Biochim.*

Biophys. Acta 1489:107; Dalpke et al. (2002) Immunology 106:102; Yu et al. (2002) Biochem. Biophys. Res. Commun. 297:83; Hafner et al. (2001) Cancer Res. 61:5523; Zwaveling et al. (2002) J. Immunol. 169:350; Davis et al. (2000) Vaccine 18:1920; Gierynska et al. (2002) J. Virol. 76:6568; Lipford et al. (2000) J. Immunol. 165:1228; Freidag et al. (2000) Infect. Immun. 68:2948; Dieudonne et al. (2001) J. Allergy Clin. Immunol. 107:S233.

Other references describing immunostimulatory sequences include: Krieg et al. (1989) J. Immunol. 143:2448-2451; Tokunaga et al. (1992) Microbiol. Immunol. 36:55-66; Kataoka et al. (1992) Jpn. J. Cancer Res. 83:244-247; Yamamoto et al. (1992) J. Immunol. 148:4072-4076; Mojcik et al. (1993) Clin. Immuno. and Immunopathol. 67:130-136; Branda et al. (1993) Biochem. Pharmacol. 45:2037-2043; Pisetsky et al. (1994) Life Sci. 54(2):101-107; Yamamoto et al. (1994a) Antisense Research and Development. 4:119-122; Yamamoto et al. (1994b) Jpn. J. Cancer Res. 85:775-779; Raz et al. (1994) Proc. Natl. Acad. Sci. USA 91:9519-9523; Kimura et al. (1994) J. Biochem. (Tokyo) 116:991-994; Krieg et al. (1995) Nature 374:546-549; Pisetsky et al. (1995) Ann. N.Y. Acad. Sci. 772:152-163; Pisetsky (1996a) J. Immunol. 156:421-423; Pisetsky (1996b) Immunity 5:303-310; Zhao et al. (1996) Biochem. Pharmacol. 51:173-182; Yi et al. (1996) J. Immunol. 156:558-564; Krieg (1996) Trends Microbiol. 4(2):73-76; Krieg et al. (1996) Antisense Nucleic Acid Drug Dev. 6:133-139; Klinman et al. (1996) Proc. Natl. Acad. Sci. USA. 93:2879-2883; Raz et al. (1996); Sato et al. (1996) Science 273:352-354; Stacey et al. (1996) J. Immunol. 157: 2116-2122; Ballas et al. (1996) J. Immunol. 157:1840-1845; Branda et al. (1996) J. Lab. Clin. Med. 128:329-338; Sonehara et al. (1996) J. Interferon and Cytokine Res. 16:799-803; Klinman et al. (1997) J. Immunol. 158:3635-3639; Sparwasser et al. (1997) Eur. J. Immunol. 27:1671-1679; Roman et al. (1997); Carson et al. (1997) J. Exp. Med. 186:1621-1622; Chace et al. (1997) Clin. Immunol. and Immunopathol. 84:185-193; Chu et al. (1997) J. Exp. Med. 186:1623-1631; Lipford et al. (1997a) Eur. J. Immunol. 27:2340-2344; Lipford et al. (1997b) Eur. J. Immunol. 27:3420-3426; Weiner et al. (1997) Proc. Natl. Acad. Sci. USA 94:10833-10837; Macfarlane et al. (1997) Immunology 91:586-593; Schwartz et al. (1997) J. Clin. Invest. 100:68-73; Stein et al. (1997) Antisense Technology, Ch. 11 pp. 241-264, C. Lichtenstein and W. Nellen, Eds., IRL Press; Wooldridge et al. (1997) Blood 89:2994-2998; Leclerc et al. (1997) Cell. Immunol. 179:97-106; Kline et al. (1997) J. Invest. Med. 45(3):282A; Yi et al. (1998a) J. Immunol. 160:1240-1245; Yi et al. (1998b) J. Immunol. 160:4755-4761; Yi et al. (1998c) J. Immunol. 160: 5898-5906; Yi et al. (1998d) J. Immunol. 161:4493-4497; Krieg (1998) Applied Antisense Oligonucleotide Technology Ch. 24, pp. 431-448, C. A. Stein and A. M. Krieg, Eds., Wiley-Liss, Inc.; Krieg et al. (1998a) Trends Microbiol. 6:23-27; Krieg et al. (1998b) J. Immunol. 161:2428-2434; Krieg et al. (1998c) Proc. Natl. Acad. Sci. USA 95:12631-12636; Spiegelberg et al. (1998) Allergy 53(455):93-97; Horner et al. (1998) Cell Immunol. 190:77-82; Jakob et al. (1998) J. Immunol. 161:3042-3049; Redford et al. (1998) J. Immunol. 161: 3930-3935; Weeratna et al. (1998) Antisense & Nucleic Acid Drug Development 8:351-356; McCluskie et al. (1998) J. Immunol. 161(9):4463-4466; Gramzinski et al. (1998) Mol. Med. 4:109-118; Liu et al. (1998) Blood 92:3730-3736; Moldoveanu et al. (1998) Vaccine 16: 1216-1224; Brazolot Milan et al. (1998) Proc. Natl. Acad. Sci. USA 95:15553-15558; Briode et al. (1998) J. Immunol. 161:7054-7062; Briode et al. (1999) Int. Arch. Allergy Immunol. 118:453-456; Kovarik et al. (1999) J. Immunol. 162:1611-1617; Spiegelberg et al. (1999) Pediatr. Pulmonol. Suppl. 18:118-121; Martin-Orozco et al. (1999) Int. Immunol. 11:1111-1118; EP 468,520; WO 96/02555; WO 97/28259; WO 98/16247; WO 98/18810; WO 98/37919; WO 98/40100; WO 98/52581; WO 98/55495; WO 98/55609 and WO 99/11275. See also Elkins et al. (1999) J. Immunol. 162:2291-2298, WO 98/52962, WO 99/33488, WO 99/33868, WO 99/51259 and WO 99/62923. See also Zimmermann et al. (1998) J. Immunol. 160:3627-3630; Krieg (1999) Trends Microbiol. 7:64-65 and U.S. Pat. Nos. 5,663,153, 5,723,335 and 5,849,719. See also Liang et al. (1996) J. Clin. Invest. 98:1119-1129; Bohle et al. (1999) Eur. J. Immunol. 29:2344-2353 and WO 99/56755. See also WO 99/61056; WO 00/06588; WO 00/16804; WO 00/21556; WO 00/54803; WO 00/61151; WO 00/67023; WO 00/67787 and U.S. Pat. No. 6,090,791. See also Manzel et al. (1999) Antisense Nucl. Acid Drug Dev. 9:459-464; Verthelyi et al. (2001) J. Immunol. 166:2372-2377; WO 01/15726; WO 01/12223; WO 01/22972; WO 01/22990; WO 01/35991; WO 01/51500; WO 01/54720; U.S. Pat. Nos. 6,174,872, 6,194, 388, 6,207,646, 6,214,806, 6,218,371, 6,239,116. See also, WO 01/12804; WO 01/45750; WO 01/55341; WO 01/55370; WO 01/62207; WO 01/68077; WO 01/68078; WO 01/68103; WO 01/68116; WO 01/68117; WO 01/68143; WO 01/68144; WO 01/72123; WO 01/76642; WO 01/83503; WO 01/93902; WO 02/026757; WO 02/052002; WO 02/069369; WO 02/074922; U.S. Pat. Nos. 6,339,068, 6,406,705, 6,426,334, 6,426,336, 6,429,199, 6,476,000.

Immunomodulatory polynucleotides generally include a CG sequence. Nucleotides flanking the CG of an IMP also appear to play a role in the immunomodulatory activity of the polynucleotide. There remains a need for continued identification of immunomodulatory polynucleotides.

All patents, patent applications, and publications cited herein are hereby incorporated by reference in their entirety.

DISCLOSURE OF THE INVENTION

The invention relates to immunomodulatory polynucleotides (IMP) and methods for modulating immune responses in individuals using these polynucleotides, particularly humans.

In one aspect, the invention provides immunomodulatory polynucleotides. In certain embodiments, the invention includes compositions which comprise any of the immunomodulatory polynucleotides described herein. The compositions may also include, for example, a pharmaceutically acceptable excipient or any of a number of other components, such as an antigen.

In one aspect, the immunomodulatory polynucleotide of the invention comprises (a) a palindromic sequence comprising at least two CG dinucleotides, wherein the CG dinucleotides are separated by 0, 1, 2, 3, 4 or 5 bases and wherein the palindromic sequence is at least 8 bases in length; and (b) a $(TCG)_y$, wherein y is 1 or 2, wherein the 5' T of the $(TCG)_y$ is positioned 0, 1, 2 or 3 bases from the 5' end of the polynucleotide and wherein the $(TCG)_y$ is separated from the 5' end of the palindromic sequence by 0, 1, or 2 bases. In some immunomodulatory polynucleotides of the invention, whether described in this paragraph or elsewhere in this application, the palindromic sequence has a base composition of less than two-thirds G's and C's. In some embodiments, the palindromic sequence has a base composition of greater than one-third A's and T's.

In another aspect, the immunomodulatory polynucleotide of the invention comprises (a) a palindromic sequence comprising at least two CG dinucleotides, wherein the CG dinucleotides are separated by 0, 1, 2, 3, 4 or 5 bases and wherein the palindromic sequence is at least 8 bases in length;

and (b) a $(TCG)_y$ sequence, wherein y is 1 or 2, wherein the 5' T of the $(TCG)_y$ sequence is positioned 0, 1, 2 or 3 bases from the 5' end of the polynucleotide, and further wherein the palindromic sequence of (a) includes all or part of the $(TCG)_y$ sequence and wherein a CG of the $(TCG)_y$ sequence may be one of the CG dinucleotides of the palindromic sequence of (a).

In another aspect, the immunomodulatory polynucleotide of the invention comprises (a) 5'-$N_x(TCG(N_q))_yN_w$ $(X_1X_2CGX_2'X_1'(CG)_p)_z$ (SEQ ID NO: 156) wherein N are nucleosides, x=0-3, y=1-4, w=−2, −1, 0, 1 or 2, p=0 or 1, q=0, 1 or 2, and z=1-20, $X_1$ and $X_1'$ are self-complimentary nucleosides, $X_2$ and $X_2'$ are self-complimentary nucleosides, and wherein the 5' T of the $(TCG(N_q))_y$ sequence is 0-3 bases from the 5' end of the polynucleotide; and (b) a palindromic sequence at least 8 bases in length wherein the palindromic sequence comprises the first $(X_1X_2CGX_2'X_1')$ of the $(X_1X_2CGX_2'X_1'(CG)_p)_z$ sequences. In some embodiments, $X_1$ and $X_2$ are each either A or T.

In another aspect, the immunomodulatory polynucleotide of the invention comprises (a) 5'-$N_x(TCG(N_q))_yN_w$ $(X_1X_2CGX_3X_3'CGX_2'X_1'(CG)_p)_z$ (SEQ ID NO: 159) wherein N are nucleosides, x=0-3, y=1-4, w=−2, −1, 0, 1 or 2, p=0 or 1, q=0, 1 or 2, and z=1-20, $X_1$ and $X_1'$ are self-complimentary nucleosides, $X_2$ and $X_2'$ are self-complimentary nucleosides, $X_3$ and $X_3'$ are self-complimentary nucleosides and wherein the 5' T of the $(TCG(N_g))_3$ sequence is 0-3 bases from the 5' end of the polynucleotide; and (b) a palindromic sequence at least 10 bases in length wherein the palindromic sequence comprises the first $(X_1X_2CGX_3X_3'CGX_2'X_1')$ (SEQ ID NO:216) of the $(X_1X_2CGX_3X_3'CGX_2'X_1'$ $(CG)_p)_z$ (SEQ ID NO:217) sequences. In some embodiments, when p=1, $X_1$, $X_2$, and $X_3$ are each either A or T. In some embodiments, when p=0, at least two of $X_1$, $X_2$, and $X_3$ are either A or T.

In another aspect, the immunomodulatory polynucleotide of the invention comprises (a) 5'-$N_x(TCG(N_q))_yN_w$ $(X_1X_2X_3X_4X_5CGX_5'X_4'X_3'X_2'X_1'(CG)_p)_z$ (SEQ ID NO:160) wherein N are nucleosides, x=0-3, y=1-4, w=−3, −2, −1, 0, 1 or 2, p=0 or 1, q=0, 1 or 2, and z=1-20, $X_1$ and $X_1'$ are self-complimentary nucleosides, $X_2$ and $X_2'$ are self-complimentary nucleosides, $X_3$ and $X_3'$ are self-complimentary nucleosides, $X_4$ and $X_4'$ are self-complimentary nucleosides, $X_5$ and $X_5'$ are self-complimentary nucleosides, and wherein the 5' T of the $(TCG(N_g))_3$ sequence is 0-3 bases from the 5' end of the polynucleotide; and (b) a palindromic sequence at least 12 bases in length wherein the palindromic sequence comprises the first $(X_1X_2X_3X_4X_5CGX_5'X_4'X_3'X_2'X_1')$ (SEQ ID NO:218) of the $(X_1X_2X_3X_4X_5CGX_5'X_4'X_3'X_2'X_1'$ $(CG)_p$), (SEQ ID NO:219) sequences. In some embodiments, at least three of $X_1$, $X_2$, $X_3$, $X_4$, and $X_5$ are either A or T.

In another aspect, the immunomodulatory polynucleotide of the invention comprises (a) 5'-$N_x(TCG(N_q))_yN_w$ $(CGX_1X_1'CG(CG)_p)_z$ (SEQ ID NO:161) wherein N are nucleosides, x=0-3, y=1-4, w=−2, 0, 1 or 2, p=0 or 1, q=0, 1 or 2, and z=1-20, wherein $X_1$ and $X_1'$ are self-complimentary nucleosides and wherein the 5' T of the $(TCG(N_q))_y$ sequence is 0-3 bases from the 5' end of the polynucleotide; and (b) a palindromic sequence at least 8 bases in length wherein the palindromic sequence comprises the first $(CGX_1X_1'CG)$ of the $(CGX_1X_1'CG(CG)_p)_z$ sequences.

In another aspect, the immunomodulatory polynucleotide of the invention comprises (a) 5'-$N_x(TCG(N_q))_yN_w$ $(X_1CGCGX_1'(CG)_p)_z$ (SEQ ID NO: 162) wherein N are nucleosides, x=0-3, y=1-4, w=−1, 0, 1 or 2, p=0 or 1, q=0, 1 or 2, and z=1-20, $X_1$ and $X_1'$ are self-complimentary nucleosides and wherein the 5' T of the $(TCG(N_q))_z$ sequence is 0-3 bases from the 5' end of the polynucleotide; and (b) a palindromic sequence at least 8 bases in length wherein the palindromic sequence comprises the first $(X_1CGCGX_1')$ of the $(X_1CGCGX_1'(CG)_p)_z$ sequences.

In another aspect, the immunomodulatory polynucleotide of the invention comprises (a) 5'-$N_x(TCG(N_q))_yN_w$ $(X_1X_2CGCGX_2'X_1'(CG)_p)_z$ (SEQ ID NO:163) wherein N are nucleosides, x=0-3, y=1-4, w=−2, −1, 0, 1 or 2, p=0 or 1, q=0, 1 or 2, and z=1-20, $X_1$ and $X_1'$ are self-complimentary nucleosides, $X_2$ and $X_2'$ are self-complimentary nucleosides, and wherein the 5' T of the $(TCG(N_q))_y$ sequence is 0-3 bases from the 5' end of the polynucleotide; and (b) a palindromic sequence at least 8 bases in length wherein the palindromic sequence comprises the first $(X_1X_2CGCGX_2'X_1')$ of the $(X_1X_2CGCGX_2'X_1'(CG)_p)_z$ (SEQ ID NO:220) sequences. In some embodiments, $X_1$ and $X_2$ are each either A or T.

In another aspect, the immunomodulatory polynucleotide of the invention comprises (a) 5'-$N_x(TCG(N_q))_yN_w$ $(X_1X_2X_3CGCGX_3'X_2'X_1'(CG)_p)_z$ (SEQ ID NO:164) wherein N are nucleosides, x=0-3, y=1-4, w=−3, −2, −1, 0, 1 or 2, p=0 or 1, q=0, 1 or 2, and z=1-20, $X_1$ and $X_1'$ are self-complimentary nucleosides, $X_2$ and $X_2'$ are self-complimentary nucleosides, $X_3$ and $X_3'$ are self-complimentary nucleosides, and wherein the 5' T of the $(TCG(N_q))_y$ sequence is 0-3 bases from the 5' end of the polynucleotide; and (b) a palindromic sequence at least 10 bases in length wherein the palindromic sequence comprises the first $(X_1X_2X_3CGCGX_3'X_2'X_1')$ (SEQ ID NO:221) of the $(X_1X_2X_3CGCGX_3'X_2'X_1'(CG)_p)_z$ (SEQ ID NO:222) sequences. In some embodiments, when p=1, $X_1$, $X_2$, and $X_3$ are each either A or T. In some embodiments, when p=0, at least two of $X_1$, $X_2$, and $X_3$ are either A or T.

In another aspect, the immunomodulatory polynucleotide of the invention comprises a) 5'-$N_x(TCG(N_q))_yN_w$ $(CGX_1X_2X_2'X_1'CG(CG)_p)_z$ (SEQ ID NO:165) wherein N are nucleosides, x=0-3, y=1-4, w=−2, 0, 1 or 2, p=0 or 1, q=0, 1 or 2, and z=1-20, $X_1$ and $X_1'$ are self-complimentary nucleosides, $X_2$ and $X_2'$ are self-complimentary nucleosides, and wherein the 5' T of the $(TCG(N_q))_y$ sequence is 0-3 bases from the 5' end of the polynucleotide; and (b) a palindromic sequence at least 8 bases in length wherein the palindromic sequence comprises the first $(CGX_1X_2X_2'X_1'CG)$ of the $(CGX_1X_2X_2'X_1'CG(CG)_p)_z$ (SEQ ID NO:223) sequences. In some embodiments, $X_1$ and $X_2$ are each either A or T.

In another aspect, the invention provides methods of modulating an immune response in an individual, comprising administering to an individual an immunomodulatory polynucleotide of the invention in an amount sufficient to modulate an immune response in said individual. Immunomodulation according to the methods of the invention may be practiced on individuals including those suffering from a disorder associated with a Th2-type immune response (e.g., allergies, allergy-induced asthma, or atopic dermatitis), individuals receiving vaccines such as therapeutic vaccines (e.g., vaccines comprising an allergy epitope, a mycobacterial epitope, or a tumor associated epitope) or prophylactic vaccines, individuals with cancer and individuals having an infectious disease.

In another aspect, the invention provides methods of increasing interferon-gamma (IFN-γ) in an individual, comprising administering an effective amount of an immunomodulatory polynucleotide of the invention to said individual. Administration of an immunomodulatory polynucleotide in accordance with the invention increases IFN-γ in the individual.

In another aspect, the invention provides methods of increasing interferon-alpha (IFN-α) in an individual, comprising administering an effective amount of an immunomodulatory polynucleotide of the invention to said individual. Administration of an immunomodulatory polynucleotide in accordance with the invention increases IFN-α in the individual.

In another aspect, the invention provides methods of ameliorating one or more symptoms of an infectious disease, comprising administering an effective amount of an immunomodulatory polynucleotide of the invention to an individual having an infectious disease. Administration of an immunomodulatory polynucleotide in accordance with the invention ameliorates one or more symptoms of the infectious disease.

In another aspect, the invention provides methods of ameliorating one or more symptoms of an IgE-related disorder, comprising administering an effective amount of an immunomodulatory polynucleotide of the invention to an individual having an IgE-related disorder. Administration of an immunomodulatory polynucleotide in accordance with the invention ameliorates one or more symptoms of the IgE-related disorder.

The invention further relates to kits, preferably for carrying out the methods of the invention. The kits of the invention generally comprise an immunomodulatory polynucleotide of the invention (generally in a suitable container), and may further include instructions for use of the immunomodulatory polynucleotide in immunomodulation of an individual.

MODES FOR CARRYING OUT THE INVENTION

Figure 1:
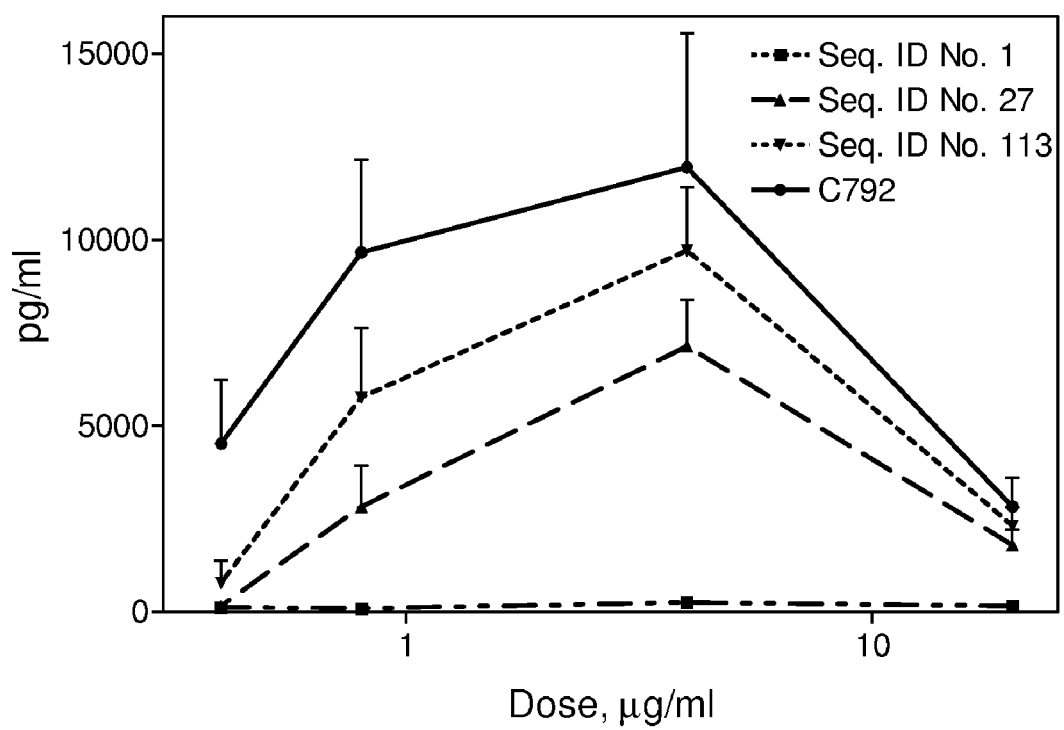
FIG. 1 is a graph depicting the amount of IFN-α produced (pg/ml) from human PBMCs in response to varying doses of four different IMPs: SEQ ID NOs: 1, 27, 113 and 172.

We have discovered immunomodulatory polynucleotides and methods for modulating immune responses in individuals, particularly humans, using these immunomodulatory polynucleotides. The compositions of the invention comprise an immunomodulatory polynucleotide as described herein. The immunomodulatory polynucleotides of the invention include a) a palindromic sequence at least 8 bases in length which contains at least one CG dinucleotide and b) at least one TCG trinucleotide at or near the 5' end of the polynucleotide.

We have found that immunomodulatory polynucleotides of the invention efficiently modulate immune cells, including human cells, in a variety of ways. We have observed that immunomodulatory polynucleotides of the invention can effectively stimulate cytokine, including type I interferons, such as IFN-α and IFN-ω, and IFN-γ, production from human cells. We have also observed that immunomodulatory polynucleotides of the invention can effectively stimulate B cells to proliferate. We have observed that some of the immunomodulatory polynucleotides of the invention activate plasmacytoid dendritic cells to undergo maturation. We have also observed that the presence of some of the immunomodulatory polynucleotides of the invention can result in retardation of plasmacytoid dendritic cell apoptosis in culture.

The invention also provides methods for modulating an immune response in an individual by administering an immunomodulatory polynucleotide of the invention to the individual. Further provided are kits comprising the IMPs of the invention. The kits may further comprise instructions for administering an immunomodulatory polynucleotide of the invention for immunomodulation in a subject and immunomodulatory polynucleotides.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); and *Methods of Immunological Analysis* (R. Masseyeff, W. H. Albert, and N. A. Staines, eds., Weinheim: VCH Verlags gesellschaft mbH, 1993).

DEFINITIONS

As used herein, the singular form "a", "an", and "the" includes plural references unless indicated otherwise. For example, "an" IMP includes one or more IMP.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphodiester linkages, although alternate linkages, such as phosphorothioate esters may also be used in oligonucleotides. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

The term "immunomodulatory polynucleotide" or "IMP" as used herein refers to a polynucleotide that effects and/or contributes to a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Preferably, the IMP sequences preferentially activate a Th1-type response.

The term "immunomodulatory" or "modulating an immune response" as used herein includes immunostimulatory as well as immunosuppressive effects. Immunomodulation is primarily a qualitative alteration in an overall immune response, although quantitative changes may also occur in conjunction with immunomodulation. An immune response that is immunomodulated according to the present invention is one that is shifted towards a "Th1-type" immune response, as opposed to a "Th2-type" immune response. Th1-type responses are typically considered cellular immune system (e.g., cytotoxic lymphocytes) responses, while Th2-type responses are generally "humoral", or antibody-based. Th1-type immune responses are normally characterized by "delayed-type hypersensitivity" reactions to an antigen, and can be detected at the biochemical level by increased levels of Th1-associated cytokines such as IFN-γ, IFN-α, IL-2, IL-12, and TNF-β, as well as IL-6, although IL-6 may also be associated with Th2-type responses as well. Th1-type immune responses are generally associated with the production of cytotoxic lymphocytes (CTLs) and low levels or transient production of antibody. Th2-type immune responses are generally associated with higher levels of antibody production, including IgE production, an absence of or minimal CTL production, as well as expression of Th2-associated cytokines such as IL-4. Accordingly, immunomodulation in accordance with the invention may be recognized by, for example, an increase in IFN-γ and/or IFN-α and/or a decrease in IgE production in an individual treated in accordance with the methods of the invention as compared to the absence of treatment.

The term "3'" generally refers to a region or position in a polynucleotide or oligonucleotide 3' (downstream) from another region or position in the same polynucleotide or oligonucleotide. The term "3' end" refers to the 3' terminus of the polynucleotide.

The term "5'" generally refers to a region or position in a polynucleotide or oligonucleotide 5' (upstream) from another region or position in the same polynucleotide or oligonucleotide. The term "5' end" refers to the 5' terminus of the polynucleotide.

A region, portion, or sequence which is "adjacent" to another sequence directly abuts that region, portion, or sequence. For example, an additional polynucleotide sequence (e.g., a TCG trinucleotide) which is adjacent to a particular portion of an immunomodulatory polynucleotide directly abuts that region.

The term "palindromic sequence" or "palindrome" refers to a nucleic acid sequence that is an inverted repeat, e.g., ABCDD'C'B'A', where the bases, e.g., A, and A', B and B', C and C', D and D', are capable of forming the Watson-Crick base pairs. Such sequences may be single-stranded or may form double-stranded structures or may form hairpin loop structures under some conditions. For example, as used herein, "an 8 base palindrome" refers to a nucleic acid sequence in which the palindromic sequence is 8 bases in length, such as ABCDD'C'B'A'. A palindromic sequence may be part of a polynucleotide which also contains non-palindromic sequences. A polynucleotide may contain one or more palindromic sequence portions and one or more non-palindromic sequence portions. Alternatively, a polynucleotide sequence may be entirely palindromic. In a polynucleotide with more than one palindromic sequence portions, the palindromic sequence portions may overlap with each other or the palindromic sequence portions may not overlap with each other.

The term "conjugate" refers to a complex in which an IMP and an antigen are linked Such conjugate linkages include covalent and/or non-covalent linkages.

The term "antigen" means a substance that is recognized and bound specifically by an antibody or by a T cell antigen receptor. Antigens can include peptides, proteins, glycoproteins, polysaccharides, complex carbohydrates, sugars, gangliosides, lipids and phospholipids; portions thereof and combinations thereof. The antigens can be those found in nature or can be synthetic. Antigens suitable for administration with IMP include any molecule capable of eliciting a B cell or T cell antigen-specific response. Preferably, antigens elicit an antibody response specific for the antigen. Haptens are included within the scope of "antigen." A hapten is a low molecular weight compound that is not immunogenic by itself but is rendered immunogenic when conjugated with an immunogenic molecule containing antigenic determinants. Small molecules may need to be haptenized in order to be rendered antigenic. Preferably, antigens of the present invention include peptides, lipids (e.g., sterols, fatty acids, and phospholipids), polysaccharides such as those used in *Hemophilus influenza* vaccines, gangliosides and glycoproteins.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g., antibody production or cytokine activity whether or not the peptide is a hapten. Typically, the peptides are at least six amino acid residues in length. The term "peptide" further includes modified amino acids (whether or not naturally or non-naturally occurring), such modifications including, but not limited to, phosphorylation, glycosylation, pegylation, lipidization and methylation.

"Antigenic peptides" can include purified native peptides, synthetic peptides, recombinant proteins, crude protein extracts, attenuated or inactivated viruses, cells, micro-organisms, or fragments of such peptides. An "antigenic peptide" or "antigen polypeptide" accordingly means all or a portion of a polypeptide which exhibits one or more antigenic properties. Thus, for example, an "Amb a 1 antigenic polypeptide" or "Amb a 1 polypeptide antigen" is an amino acid sequence from Amb a 1, whether the entire sequence, a portion of the sequence, and/or a modification of the sequence, which exhibits an antigenic property (i.e., binds specifically to an antibody or a T cell receptor).

A "delivery molecule" or "delivery vehicle" is a chemical moiety which facilitates, permits, and/or enhances delivery of an immunomodulatory polynucleotide to a particular site and/or with respect to particular timing. A delivery vehicle may or may not additionally stimulate an immune response.

An "allergic response to antigen" means an immune response generally characterized by the generation of eosinophils and/or antigen-specific IgE and their resultant effects. As is well-known in the art, IgE binds to IgE receptors on mast cells and basophils. Upon later exposure to the antigen recognized by the IgE, the antigen cross-links the IgE on the mast cells and basophils causing degranulation of these cells, including, but not limited, to histamine release. It is understood and intended that the terms "allergic response to antigen", "allergy", and "allergic condition" are equally appropriate for application of some of the methods of the invention. Further, it is understood and intended that the methods of the invention include those that are equally appropriate for prevention of an allergic response as well as treating a pre-existing allergic condition.

As used herein, the term "allergen" means an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule. A number of isolated allergens are known in the art. These include, but are not limited to, those provided in Table 1 herein.

The term "desensitization" refers to the process of the administration of increasing doses of an allergen to which the subject has demonstrated sensitivity. Examples of allergen doses used for desensitization are known in the art, see, for example, Formadley (1998) *Otolaryngol. Clin. North Am.* 31:111-127.

"Antigen-specific immunotherapy" refers to any form of immunotherapy which involves antigen and generates an antigen-specific modulation of the immune response. In the allergy context, antigen-specific immunotherapy includes, but is not limited to, desensitization therapy.

The term "microcarrier" refers to a particulate composition which is insoluble in water and which has a size of less than about 150, 120 or 100 µm, preferably less than about 50-60 µm, preferably less than about 10 µm, preferably less than about 5, 2.5, 2 or 1.5 µm. Microcarriers include "nanocarriers", which are microcarriers having a size of less than about 1 µm, preferably less than about 500 nm. Microcarriers include solid phase particles such as particles formed from biocompatible naturally occurring polymers, synthetic polymers or synthetic copolymers, although microcarriers formed from agarose or cross-linked agarose may be included or excluded from the definition of microcarriers herein as well as other biodegradable materials known in the art. Microcarriers for use in the instant invention may be biodegradable or nonbiodegradable. Nonbiodegradable solid phase microcarriers are formed from polymers or other materials which are non-erodible and/or non-degradable under mammalian physiological conditions, such as polystyrene, polypropylene, silica, ceramic, polyacrylamide, gold, latex, hydroxyapatite, dextran, and ferromagnetic and paramagnetic materials. Biodegradable solid phase microcarriers may be formed from polymers which are degradable (e.g., poly(lactic acid), poly(glycolic acid) and copolymers thereof) or erodible (e.g., poly(ortho esters such as 3,9-diethylidene-2,4,8,10-tetraoxaspiro[5.5]undecane (DETOSU) or poly(anhydrides), such as poly(anhydrides) of sebacic acid) under mammalian physiological conditions. Microcarriers may also be liquid phase (e.g., oil or lipid based), such liposomes, iscoms (immune-stimulating complexes, which are stable complexes of cholesterol, phospholipid and adjuvant-active saponin) without antigen, or droplets or micelles found in oil-in-water or water-in-oil emulsions. Biodegradable liquid phase microcarriers typically incorporate a biodegradable oil, a number of which are known in the art, including squalene and vegetable oils. Microcarriers are typically spherical in shape, but microcarriers which deviate from speherical shape are also acceptable (e.g., ellipsoidal, rod-shaped, etc.). Due to their insoluble nature (with respect to water), microcarriers are filterable from water and water-based (aqueous) solutions.

The term "nonbiodegradable", as used herein, refers to a microcarrier which is not degraded or eroded under normal mammalian physiological conditions. Generally, a microcarrier is considered nonbiodegradable if it not degraded (i.e., loses less than 5% of its mass or average polymer length) after a 72 hour incubation at 37° C. in normal human serum.

A microcarrier is considered "biodegradable" if it is degradable or erodable under normal mammalian physiological conditions. Generally, a microcarrier is considered biodegradable if it is degraded (i.e., loses at least 5% of its mass or average polymer length) after a 72 hour incubation at 37° C. in normal human serum.

The "size" of a microcarrier is generally the "design size" or intended size of the particles stated by the manufacturer. Size may be a directly measured dimension, such as average or maximum diameter, or may be determined by an indirect assay such as a filtration screening assay. Direct measurement of microcarrier size is typically carried out by microscopy, generally light microscopy or scanning electron microscopy (SEM), in comparison with particles of known size or by reference to a micrometer. As minor variations in size arise during the manufacturing process, microcarriers are considered to be of a stated size if measurements show the microcarriers are ± about 5-10% of the stated measurement. Size characteristics may also be determined by dynamic light scattering or obscuration techniques. Alternately, microcarrier size may be determined by filtration screening assays. A microcarrier is less than a stated size if at least 97% of the particles pass through a "screen-type" filter (i.e., a filter in which retained particles are on the surface of the filter, such as polycarbonate or polyethersulfone filters, as opposed to a "depth filter" in which retained particles lodge within the filter) of the stated size. A microcarrier is larger than a stated size if at least about 97% of the microcarrier particles are retained by a screen-type filter of the stated size. Thus, at least about 97% microcarriers of about 10 µm to about 10 nm in size pass through a 10 µm pore screen filter and are retained by a 10 nm screen filter.

As above discussion indicates, reference to a size or size range for a microcarrier implicitly includes approximate variations and approximations of the stated size and/or size range. This is reflected by use of the term "about" when referring to a size and/or size range, and reference to a size or size range without reference to "about" does not mean that the size and/or size range is exact.

The term "immunomodulatory polynucleotide/microcarrier complex" or "IMP/MC complex" refers to a complex of an immunomodulatory polynucleotide and a microcarrier. The components of the complex may be covalently or non-covalently linked. Non-covalent linkages may be mediated by any non-covalent bonding force, including by hydrophobic interaction, ionic (electrostatic) bonding, hydrogen bonds and/or van der Waals attractions. In the case of hydrophobic linkages, the linkage is generally via a hydrophobic moiety (e.g., cholesterol) covalently linked to the IMP.

An "individual" is a vertebrate, such as avian, and is preferably a mammal, more preferably a human. Mammals include, but are not limited to, humans, primates, farm animals, sport animals, rodents and pets.

An "effective amount" or a "sufficient amount" of a substance is that amount sufficient to effect beneficial or desired results, including clinical results, and, as such, an "effective amount" depends upon the context in which it is being applied. In the context of administering a composition that modulates an immune response to a co-administered antigen, an effective amount of an immunomodulatory polynucleotide and antigen is an amount sufficient to achieve such a modulation as compared to the immune response obtained when the antigen is administered alone. An effective amount can be administered in one or more administrations.

The term "co-administration" as used herein refers to the administration of at least two different substances sufficiently close in time to modulate an immune response. Preferably, co-administration refers to simultaneous administration of at least two different substances.

"Stimulation" of a response or parameter includes eliciting and/or enhancing that response or parameter. For example, "stimulation" of an immune response, such as Th1 response, means an increase in the response, which can arise from eliciting and/or enhancement of a response. Similarly, "stimulation" of a cytokine or cell type (such as CTLs) means an increase in the amount or level of cytokine or cell type. B cell "stimulation" includes, for example, enhanced B cell proliferation, induced B cell activation and/or increased production of cytokines, such as IL-6 and/or TNF-$\alpha$, from the stimulated B cell.

An "IgE associated disorder" is a physiological condition which is characterized, in part, by elevated IgE levels, which may or may not be persistent. IgE associated disorders include, but are not limited to, allergy and allergic reactions, food allergies, allergy-related disorders (described below), asthma, rhinitis, atopic dermatitis, conjunctivitis, urticaria, shock, Hymenoptera sting allergies, and drug allergies, and parasite infections. The term also includes related manifestations of these disorders. Generally, IgE in such disorders is antigen-specific.

An "allergy-related disorder" means a disorder resulting from the effects of an antigen-specific IgE immune response. Such effects can include, but are not limited to, hypotension and shock. Anaphylaxis is an example of an allergy-related disorder during which histamine released into the circulation causes vasodilation as well as increased permeability of the capillaries with resultant marked loss of plasma from the circulation. Anaphylaxis can occur systemically, with the associated effects experienced over the entire body, and it can occur locally, with the reaction limited to a specific target tissue or organ.

The term "viral disease", as used herein, refers to a disease which has a virus as its etiologic agent. Examples of viral diseases include hepatitis B, hepatitis C, influenza, acquired immunodeficiency syndrome (AIDS), and herpes zoster.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the allergy context, as is well understood by those skilled in the art, palliation may occur upon modulation of the immune response against an allergen(s). Further, palliation does not necessarily occur by administration of one dose, but often occurs upon administration of a series of doses. Thus, an amount sufficient to palliate a response or disorder may be administered in one or more administrations.

An "antibody titer", or "amount of antibody", which is "elicited" by an immunomodulatory polynucleotide and antigen refers to the amount of a given antibody measured at a time point after administration of immunomodulatory polynucleotide and antigen.

A "Th1-associated antibody" is an antibody whose production and/or increase is associated with a Th1 immune response. For example, IgG2a is a Th1-associated antibody in mouse. For purposes of this invention, measurement of a Th1-associated antibody can be measurement of one or more such antibodies. For example, in human, measurement of a Th1-associated antibody could entail measurement of IgG1 and/or IgG3.

A "Th2-associated antibody" is an antibody whose production and/or increase is associated with a Th2 immune response. For example, IgG1 is a Th2-associated antibody in mouse. For purposes of this invention, measurement of a Th2-associated antibody can be measurement of one or more such antibodies. For example, in human, measurement of a Th2-associated antibody could entail measurement of IgG2 and/or IgG4.

To "suppress" or "inhibit" a function or activity, such as cytokine production, antibody production, or histamine release, is to reduce the function or activity when compared to otherwise same conditions except for a condition or parameter of interest, or alternatively, as compared to another condition. For example, a composition comprising an immunomodulatory polynucleotide and antigen which suppresses histamine release reduces histamine release as compared to, for example, histamine release induced by antigen alone. As another example, a composition comprising an immunomodulatory polynucleotide and antigen which suppresses antibody production reduces extent and/or levels of antibody as compared to, for example, extent and/or levels of antibody produced by antigen alone.

A "serum protein" is a protein that is normally found in the serum of disease-free mammals, particularly disease-free bovines. The most prevalent serum protein is serum albumin.

As used herein, the term "comprising" and its cognates are used in their inclusive sense; that is, equivalent to the term "including" and its corresponding cognates.

Compositions of the Invention

The invention provides immunomodulatory polynucleotides (IMPs) for modulating immune responses in individuals. Compositions of the invention comprise an immunomodulatory polynucleotide alone (or a combination of two or more immunomodulatory polynucleotides) or in conjunction with another immunomodulatory agent, such as a peptide, an antigen (described below) and/or an additional adjuvant. Compositions of the invention may comprise an immunomodulatory polynucleotide and pharmaceutically acceptable excipient. Pharmaceutically acceptable excipients, including buffers, are well known in the art. *Remington: The Science and Practice of Pharmacy,* 20th edition, Mack Publishing (2000).

Upon administration, compositions comprising an antigen, an immunomodulatory polynucleotide of the invention, and optionally an adjuvant can lead to a potentiation of a immune response to the antigen and thus, can result in an enhanced immune response compared to that which results from a composition comprising the IMP and antigen alone. Adjuvants are known in the art and include, but are not limited to, oil-in-water emulsions, water-in oil emulsions, alum (aluminum salts), liposomes and microparticles, including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873-875, as well as, lipid-based adjuvants and others described herein. For veterinary use and for production of antibodies in animals, mitogenic components of Freund's adjuvant (both complete and incomplete) can be used.

IMPs of the invention may be combined with other therapies for particular indications. For example, in addition to an IMP, compositions of the invention may also comprise antimalarial drugs such as chloroquine for malaria patients, leishmanicidal drugs such as pentamidine and/or allopurinol for leishmaniasis patients, anti-mycobacterial drugs such as isoniazid, rifampin and/or ethambutol for tuberculosis patients, or allergen desensitization reagents for atopic (allergy) patients.

As described herein, compositions of the invention may include IMPs and may further comprise one or more additional immunotherapeutic agents (i.e., an agent which acts via the immune system and/or is derived from the immune system) including, but not limited to, cytokine, adjuvants and antibodies. Examples of therapeutic antibodies include those used in the cancer context (e.g., anti-tumor antibodies), such as those described below.

Immunomodulatory Polynucleotides

In accordance with the present invention, the immunomodulatory polynucleotide contains at least one palindromic sequence (i.e., palindrome) of at least 8 bases in length containing at least one CG dinucleotide. The IMP also contains at least one TCG trinucleotide sequence at or near the 5' end of the polynucleotide (i.e., 5'-TCG). In some instances, the palindromic sequence and the 5'-TCG are separated by 0, 1 or 2 bases in the IMP. In some instances the palindromic sequence includes all or part of the 5'-TCG.

IMPs have been described in the art and their activity may be readily identified using standard assays which indicate various aspects of the immune response, such as cytokine secretion, antibody production, NK cell activation, B cell proliferation, T cell proliferation. See, e.g., WO 97/28259; WO 98/16247; WO 99/11275; Krieg et al. (1995) *Nature* 374:546-549; Yamamoto et al. (1992a); Ballas et al. (1996); Klinman et al. (1997); Sato et al. (1996); Pisetsky (1996a); Shimada et al. (1986) *Jpn. J. Cancer Res.* 77:808-816; Cowdery et al. (1996) *J. Immunol.* 156:4570-4575; Roman et al. (1997); Lipford et al. (1997a); WO 98/55495 and WO 00/61151. Accordingly, these and other methods can be used to identify, test and/or confirm immunomodulatory IMPs.

The IMP can be of any length greater than 10 bases or base pairs, preferably greater than 15 bases or base pairs, more preferably greater than 20 bases or base pairs in length.

As is clearly conveyed herein, it is understood that, with respect to formulae described herein, any and all parameters are independently selected. For example, if x=0-2, y may be independently selected regardless of the values of x (or any other selectable parameter in a formula).

In some embodiments, an IMP comprises a) a palindromic sequence at least 8 bases in length which contains at least two CG dinucleotides, where the CG dinucleotides are separated from each other by 0, 1, 2, 3, 4 or 5 bases, and b) a $(TCG)_y$ sequence positioned 0, 1, 2, or 3 bases from the 5' end of the polynucleotide, where y is 1 or 2, and where the 3' end of the $(TCG)_y$ sequence is separated from the 5' end of the palindromic sequence by 0, 1 or 2 bases. In some embodiments, a CG dinucleotide of the $(TCG)_y$ sequence of (b) may count for one of the at least two CG dinucleotides in the palindromic sequence of (a). In some embodiments, the CG dinucleotides of the palindromic sequence are separated from each other by 1, 3 or 4 bases. In some IMPs of the invention, whether described in this paragraph or elsewhere in the application, the palindromic sequence has a base composition of less than two-thirds G's and C's. In some embodiments, the palindromic sequence has a base composition of greater than one-third A's and T's.

In some embodiments, an IMP comprises a) a palindromic sequence at least 8 bases in length which contains at least two CG dinucleotides, where the CG dinucleotides are separated from each other by 0, 1, 2, 3, 4 or 5 bases, and b) a $(TCG)_y$ sequence positioned 0, 1, 2, or 3 bases from the 5' end of the polynucleotide, where y is 1 or 2, where the palindromic sequence includes all or part of the $(TCG)_y$ sequence, and where a CG dinucleotide of the $(TCG)_y$ sequence of (b) may count for one of the CG dinucleotides of the palindromic sequence of (a). Preferably, in some embodiments, the CG dinucleotides of the palindromic sequence are separated from each other by 1, 3 or 4 bases.

Accordingly, in some embodiments, an IMP may comprise a sequence of the formula: 5'-$N_x(TCG(N_g))_y N_w(X_1 CGX_1'(CG)_p)_z$ (SEQ ID NO:155) wherein N are nucleosides with x=0-3, y=1-4, w=-1, 0, 1 or 2, p=0 or 1, q=0, 1 or 2, and z=1-20, wherein $X_1$ and $X_1'$ are self-complimentary and wherein the 5' T of the $(TCG(N_q))_y$ sequence is 0-3 bases from the 5' end of the polynucleotide. The IMP further comprises a palindromic sequence 8 bases in length or greater wherein the palindromic sequence comprises at least one of the $(X_1 CGX_1'(CG)_p)$ sequences. In an IMP with w=-1, the 3' base of the $(TCG(N_q))_y$ sequence is the 5' $X_1$ of the first $(X_1 CGX_1'(CG)_p)$ sequence. In some embodiments, the $(TCG(N_q))_y$ sequence is separated from the palindromic sequence by 0, 1 or 2 bases. In other embodiments, the palindromic sequence includes all or part of the $(TCG(N_q))_y$ sequence. In some embodiments, when p=0, $X_1$ is either A or T.

In some embodiments, the IMP comprises the following sequences (palindromic sequences underlined):

| | |
|---|---|
| 5'-TCG<u>TCGACGTCGA</u>GATGATAT; | (SEQ ID NO: 35) |
| 5'-<u>TCGTCGACGTCGACGA</u>GATAT; | (SEQ ID NO: 60) |
| 5'-<u>TCGACGTCGACGTCGACGTAT</u>; | (SEQ ID NO: 61) |
| 5'-<u>TCGGTCGACGTCGACCGATT</u>; | (SEQ ID NO: 82) |
| 5'-<u>TCGGACGTCGACGTCCGATT</u>; | (SEQ ID NO: 83) |
| 5'-<u>TCGACGTCGA</u>; | (SEQ ID NO: 105) |
| 5'-TCGG<u>ACGTCGACGT</u>GCGATT; | (SEQ ID NO: 114) |
| 5'-<u>TCGACGTCGACGTCGACGTCGA</u>; | (SEQ ID NO: 119) |
| 5'-<u>ACGTCGACGTCGACGTCGACGT</u>; | (SEQ ID NO: 120) |
| 5'-TCGTCG<u>ACGTCGACGTCGACGT</u>; | (SEQ ID NO: 121) |
| 5'-TCGTCG<u>GCGCCGGCGCCGGCGC</u>; | (SEQ ID NO: 122) |
| 5'-TCGTCG<u>CCGGCGCCGGCGCCGG</u>; | (SEQ ID NO: 123) |
| 5'-TCGATA<u>CGTCGACGTCGACGT</u>. | (SEQ ID NO: 124) |

In some embodiments, an IMP may comprise a sequence of the formula: 5'-$N_x(TCG(N_q))_y N_w(X_1 X_2 X_3 CGX_3' X_2' X_1'(CG)_p)_z$ (SEQ ID NO: 157) wherein N are nucleosides with x=0-3, y=1-4, w=-3, -2, -1, 0, 1 or 2, p=0 or 1, q=0, 1 or 2, and z=1-20, wherein $X_1$ and $X_1'$, $X_2$ and $X_2'$, and $X_3$ and $X_3'$ are self-complimentary and wherein the 5' T of the $(TCG(N_q))_y$ sequence is 0-3 bases from the 5' end of the polynucleotide. The IMP further comprises a palindromic sequence 8 bases in length or greater wherein the palindromic sequence comprises the first $(X_1 X_2 X_3 CGX_3' X_2' X_1')$ of the at least one $(X_1 X_2 X_3 CGX_3' X_2' X_1'(CG)_p)$ (SEQ ID NO:224) sequence. In an IMP with w=-1, the 3' base of the $(TCG(N_q))_y$ sequence is the 5' $X_1$ of the first $(X_1 X_2 X_3 CGX_3' X_2' X_1'(CG)_p)$ (SEQ ID NO:224) sequence. In an IMP with w=-2, the penultimate (i.e., second to last) and the ultimate (i.e., last) 3' bases of the $(TCG(N_q))_y$ sequence are the 5' $X_1$ and $X_2$, respectively, of the first $(X_1 X_2 X_3 CGX_3' X_2' X_1'(CG)_p)$ (SEQ ID NO:224) sequence. In an IMP with w=-3, the antepenultimate (i.e., third to last), the penultimate (i.e., second to last) and the ultimate (i.e., last) 3' bases of the $(TCG(N_q))_y$ sequence are the 5' $X_1$, $X_2$, and $X_3$, respectively, of the first $(X_1 X_2 X_3 CGX_3' X_2' X_1'(CG)_p)$ (SEQ ID NO:224) sequence. In some embodiments, the $(TCG(N_q))_y$ sequence is separated from the palindromic sequence by 0, 1 or 2 bases. In other embodiments, the palindromic sequence includes all or part of the (TCG($N_q$))$_y$ sequence. In some embodiments, when p=1, $X_1$, $X_2$, and $X_3$ are each either A or T. In some embodiments, when p=0, at least two of $X_1$, $X_2$, and $X_3$ are either A or T.

In some embodiments, the IMP comprises the following sequences (palindromic sequences underlined):

```
5'-TCGTCGAAACGTTTCGACAGT;     (SEQ ID NO: 62)

5'-TCGTCGAGACGTCTCGAC AGT;    (SEQ ID NO: 63)

5'-TCGTCGAAGCGCTTCGACAGT;     (SEQ ID NO: 125)

5'-TCGTCGAATCGATTCGACAGT;     (SEQ ID NO: 126)

5'-TCGTCGAGTCGACTCGACAGT;     (SEQ ID NO: 127)

5'-TCGTCGCAACGTTGCGACAGT;     (SEQ ID NO: 128)

5'-TCGTCGCCGCGCGGCGACAGT;     (SEQ ID NO: 129)

5'-TCGAAACGTTTCGACAGTGAT.     (SEQ ID NO: 130)
```

In some embodiments, an IMP may comprise a sequence of the formula: 5'-$N_x$(TCG($N_q$))$_y N_w$ ($X_1 X_2 X_3 X_4$CG$X_4'X_3'X_2'X_1'$(CG)$_p$)$_z$ (SEQ ID NO: 158) wherein N are nucleosides with x=0-3, y=1-4, w=−3, −2, −1, 0, 1 or 2, p=0 or 1, q=0, 1 or 2, and z=1-20, wherein $X_1$ and $X_1'$, $X_2$ and $X_2'$, $X_3$ and $X_3'$, and $X_4$ and $X_4'$ are self-complimentary and wherein the 5' T of the (TCG($N_q$))$_y$ sequence is 0-3 bases from the 5' end of the polynucleotide. The IMP further comprises a palindromic sequence 10 bases in length or greater wherein the palindromic sequence comprises the first ($X_1 X_2 X_3 X_4$CG$X_4'X_3'X_2'X_1'$) (SEQ ID NO:225) of the at least one ($X_1 X_2 X_3 X_4$CG$X_4'X_3'X_2'X_1'$(CG)$_p$) (SEQ ID NO:226) sequence. In an IMP with w=−1, the 3' base of the (TCG($N_q$))$_y$ sequence is the 5' $X_1$ of the first ($X_1 X_2 X_3 X_4$CG$X_4'X_3'X_2'X_1'$(CG)$_p$) (SEQ ID NO:226) sequence. In an IMP with w=−2, the penultimate (i.e., second to last) and the ultimate (i.e., last) 3' bases of the (TCG($N_q$))$_y$ sequence are the 5' $X_1$ and $X_2$, respectively, of the first ($X_1 X_2 X_3 X_4$CG$X_4'X_3'X_2'X_1'$(CG)$_p$) (SEQ ID NO:226) sequence. In an IMP with w=−3, the antepenultimate (i.e., third to last), the penultimate (i.e., second to last) and the ultimate (i.e., last) 3' bases of the (TCG($N_q$))$_y$ sequence are the 5' $X_1$, $X_2$, and $X_3$, respectively, of the first ($X_1 X_2 X_3 X_4$CG$X_4'X_3'X_2'X_1'$(CG)$_p$) (SEQ ID NO:226) sequence. In some embodiments, the (TCG($N_q$))$_y$ sequence is separated from the palindromic sequence by 0, 1 or 2 bases. In other embodiments, the palindromic sequence includes all or part of the (TCG($N_q$))$_y$ sequence. In some embodiments, when p=1, at least three of $X_1$, $X_2$, $X_3$, and $X_4$ are either A or T. In some embodiments, when p=0, at least two of $X_1$, $X_2$, $X_3$, and $X_4$ are either A or T.

In some embodiments, the IMP comprises the following sequences (palindromic sequences underlined):

```
5'-TCGTCGAAAACGTTTTCGAGAT;    (SEQ ID NO: 64)

5'-TCGAAAACGTTTTCGAGATGAT;    (SEQ ID NO: 65)

5'-TCGAGGACGTCCTCGAGATGAT;    (SEQ ID NO: 66)

5'-TCGAGGTCGACCTCGAGATGAT;    (SEQ ID NO: 131)

5'-ATCGATGTCGACATCGATATGAT;   (SEQ ID NO: 132)

5'-TCGTCGTCGACGACGAGATGAT.    (SEQ ID NO: 133)
```

In some embodiments, an IMP may comprise a sequence of the formula: 5'-$N_x$(TCG($N_q$))$_y N_w$($X_1$CGCG$X_1'$(CG)$_p$)$_z$ (SEQ ID NO: 162) wherein N are nucleosides with x=0-3, y=1-4, w=−1, 0, 1 or 2, p=0 or 1, q=0, 1 or 2, and z=1-20, wherein $X_1$ and $X_1'$ are self-complimentary and wherein the 5' T of the (TCG($N_q$))$_y$ sequence is 0-3 bases from the 5' end of the polynucleotide. The IMP further comprises a palindromic sequence 8 bases in length or greater wherein the palindromic sequence comprises the first ($X_1$CGCG$X_1'$) of the at least one ($X_1$CGCG$X_1'$(CG)$_p$) sequence. In an IMP with w=−1, the 3' base of the (TCG($N_q$))$_y$ sequence is the 5' $X_1$ of the first ($X_1$CGCG$X_1'$(CG)$_p$) sequence. In some embodiments, the (TCG($N_q$))$_y$ sequence is separated from the palindromic sequence by 0, 1 or 2 bases. In other embodiments, the palindromic sequence includes all or part of the (TCG($N_q$))$_y$ sequence. In some embodiments, the IMP comprises the following sequences (palindromic sequences underlined):

```
5'-TCGTCGTCGCGACGAGATGAT;     (SEQ ID NO: 50)

5'-TCGTCGACGCGTCGAGATGAT;     (SEQ ID NO: 142)

5'-TCGTCGGCGCGCCGAGATGAT.     (SEQ ID NO: 143)
```

In some embodiments, an IMP may comprise a sequence of the formula: 5'-$N_x$(TCG($N_q$))$_y N_w$(CG$X_1 X_1'$CG(CG)$_p$)$_z$ (SEQ ID NO: 161) wherein N are nucleosides with x=0-3, y=1-4, w=−2, 0, 1 or 2, p=0 or 1, q=0, 1 or 2, and z=1-20, wherein $X_1$ and $X_1'$ are self-complimentary and wherein the 5' T of the (TCG($N_q$))$_y$ sequence is 0-3 bases from the 5' end of the polynucleotide. The IMP further comprises a palindromic sequence 8 bases in length or greater wherein the palindromic sequence comprises the first (CG$X_1 X_1'$CG) of the at least one (CG$X_1 X_1'$CG(CG)$_p$) sequence. In an IMP with w=−2, the penultimate (i.e., second to last) and the ultimate (i.e., last) 3' bases of the (TCG($N_q$))$_y$ sequence are CG and are the 5' CG of the first (CG$X_1 X_1'$CG(CG)$_p$) sequence. In some embodiments, the (TCG($N_q$))$_y$ sequence is separated from the palindromic sequence by 0, 1 or 2 bases. In other embodiments, the palindromic sequence includes all or part of the (TCG($N_q$))$_y$ sequence. In some embodiments, the IMP comprises the following sequences (palindromic sequences underlined):

```
5'-TCGTCGCGATCGCGAGATGAT;     (SEQ ID NO: 49)

5'-TCGTCGCGTACGCGAGATGAT;     (SEQ ID NO: 139)

5'-TCGTCGCGGCCGCGAGATGAT;     (SEQ ID NO: 140)

5'-TCGCGATCGCGCGATCGCGA.      (SEQ ID NO: 141)
```

In some embodiments, an IMP may comprise a sequence of the formula: 5'-$N_x$(TCG($N_q$))$_y N_w$($X_1 X_2$CG$X_3 X_3'$CG$X_2'X_1'$(CG)$_p$)$_z$ (SEQ ID NO: 159) wherein N are nucleosides with x=0-3, y=1-4, w=−2, −1, 0, 1 or 2, p=0 or 1, q=0, 1 or 2, and z=1-20, wherein $X_1$ and $X_1'$, $X_2$ and $X_2'$, and $X_3$ and $X_3'$ are self-complimentary and wherein the 5' T of the (TCG($N_q$))$_y$ sequence is 0-3 bases from the 5' end of the polynucleotide. The IMP further comprises a palindromic sequence 10 bases in length or greater wherein the palindromic sequence comprises the first ($X_1 X_2$CG$X_3 X_3'$CG$X_2'X_1'$) (SEQ ID NO:216) of the at least one ($X_1 X_2$CG$X_3 X_3'$CG$X_2'X_1'$(CG)$_p$) (SEQ ID NO:217) sequence. In an IMP with w=−1, the 3' base of the (TCG($N_q$))$_y$ sequence is the 5' $X_1$ of the first ($X_1 X_2$CG$X_3 X_3'$CG$X_2'X_1'$(CG)$_p$) (SEQ ID NO:217) sequence. In an IMP with w=−2, the penultimate (i.e., second to last) and the ultimate (i.e., last) 3' bases of the (TCG($N_q$))$_y$ sequence are the 5' $X_1$ and $X_2$, respectively, of the first ($X_1 X_2$CG$X_3 X_3'$CG$X_2'X_1'$ (CG)$_p$) (SEQ ID NO:217) sequence. In some embodiments, the (TCG($N_q$))$_y$ sequence is separated from the palindromic sequence by 0, 1 or 2 bases. In other embodiments, the palindromic sequence includes all or part of the $(TCG(N_q))_y$ sequence. In some embodiments, when p=1, $X_1$, $X_2$, and $X_3$ are each either A or T. In some embodiments, when p=0, at least two of $X_1$, $X_2$, and $X_3$ are either A or T. In some embodiments, the IMP comprises the following sequences (palindromic sequences underlined):

| | |
|---|---|
| 5'-TCG<u>GACGATCGTCGACGATCGTC</u>; | (SEQ ID NO: 86) |
| 5'-TCGTCG<u>GACGATCGTC</u>ACGACG; | (SEQ ID NO: 87) |
| 5'-TCG<u>GTCGATCGACGTCGATCGAC</u>; | (SEQ ID NO: 134) |
| 5'-TCG<u>GACGGCCGTCGACGGCCGTC</u>; | (SEQ ID NO: 135) |
| 5'-TCG<u>GACGTACGTCGACGTACGTC</u>; | (SEQ ID NO: 136) |
| 5'-TCG<u>ATCGTACGATATCGTACGAT</u>; | (SEQ ID NO: 137) |
| 5'-TCGTCG<u>GACGATCGTCCGACGA</u>. | (SEQ ID NO: 138) |

In some embodiments, an IMP may comprise a sequence of the formula: 5'-$N_x(TCG(N_q))_y N_w (X_1 X_2 CGX_2' X_1'(CG)_p)_z$ (SEQ ID NO: 156) wherein N are nucleosides with x=0-3, y=1-4, w=−2, −1, 0, 1 or 2, p=0 or 1, q=0, 1 or 2, and z=1-20, wherein $X_1$ and $X_1'$, $X_2$ and $X_2'$ are self-complimentary, and wherein the 5' T of the $(TCG(N_q))_y$ sequence is 0-3 bases from the 5' end of the polynucleotide. The IMP further comprises a palindromic sequence 8 bases in length or greater wherein the palindromic sequence comprises the first $(X_1 X_2 CGX_2' X_1')$ of the at least one $(X_1 X_2 CGX_2' X_1'(CG)_p)_z$ sequence. In an IMP with w=−1, the 3' base of the $(TCG(N_q))_y$ sequence is the 5' $X_1$ of the first $(X_1 X_2 CGX_2' X_1'(CG)_p)$ sequence. In the IMP with w=−2, the penultimate (i.e., second to last) and the ultimate (i.e., last) 3' bases of the $(TCG(N_q))_y$ sequence are the 5' $X_1$ and $X_2$, respectively, of the first $(X_1 X_2 CGX_2' X_1'(CG)_p)$ sequence. In some embodiments, the $(TCG(N_q))_y$ sequence is separated from the palindromic sequence by 0, 1 or 2 bases. In other embodiments, the palindromic sequence includes all or part of the $(TCG(N_q))_y$ sequence. In some embodiments, $X_1$ and $X_2$ are each either A or T.

In some embodiments, the IMP comprises the following sequences (palindromic sequences underlined):

| | |
|---|---|
| 5'-TCG<u>AACGTTCGTTCGAACGAACGTT</u>; | (SEQ ID NO: 147) |
| 5'-TCG<u>AACGTTTTCGAAAACGTT</u>; | (SEQ ID NO: 148) |
| 5'-TCGTC<u>GAACGTT</u>CCTTAACGTTCG; | (SEQ ID NO: 7) |
| 5'-TCG<u>AACGTTAACGTTCGATT</u>; | (SEQ ID NO: 80) |
| 5'-TCGT<u>CGAACGTTCGA</u>GATGAT; | (SEQ ID NO: 27) |
| 5'-GG<u>TCGAACGTTCGAGGGGGG</u>; | (SEQ ID NO: 30) |
| 5'-TCGT<u>CGAACGTTCGA</u>GGGGGG; | (SEQ ID NO: 32) |
| 5'-<u>TTCGAACGTTCGAACGTTCGAAT</u>; | (SEQ ID NO: 38) |
| 5'-TCG<u>AACGTTCGAACGTTCGAAT</u>; | (SEQ ID NO: 39) |
| 5'-TCGT<u>CGAACGTTCGACGA</u>; | (SEQ ID NO: 52) |
| 5'-<u>TTTCGAACGTTCGAACGTTCGAAAT</u>; | (SEQ ID NO: 57) |
| 5'-<u>TTTTCGAACGTTCGAACGTTCGAAAAT</u>; | (SEQ ID NO: 58) |
| 5'-<u>TTTTCGAACGTTCGAACGTTCGAAAT</u>; | (SEQ ID NO: 59) |
| 5'-<u>TCGAACGTTCGAACGTTCGA</u>; | (SEQ ID NO: 97) |
| 5'-<u>TTCGAACGTTCGAA</u>; | (SEQ ID NO: 98) |
| 5'-TCGT<u>CGAACGTTCGA</u>GAT; | (SEQ ID NO: 99) |
| 5'-TCGT<u>CGAACGTTCGAG</u>; | (SEQ ID NO: 100) |
| 5'-TCGT<u>CGAACGTTCGA</u>; | (SEQ ID NO: 101) |
| 5'-<u>TCGAACGTTCGAG</u>; | (SEQ ID NO: 102) |
| 5'-<u>TCGAACGTTCGA</u>; | (SEQ ID NO: 103) |
| 5'-T<u>CGAACGTTCG</u>; | (SEQ ID NO: 104) |
| 5'-TCGTC<u>GTCGAACGTTCGA</u>GAT; | (SEQ ID NO: 106) |
| 5'-TCGTCGTC<u>GTCGAACGTTCGA</u>; | (SEQ ID NO: 107) |
| 5'-TCGT<u>CGTCGAACGTTCGACGA</u>GAT; | (SEQ ID NO: 108) |
| 5'-TCG<u>AACGTTCGAACGTTCGAACGTT</u>; | (SEQ ID NO: 113) |
| 5'-<u>CTTCGAACGTTCGAAGTG</u>; | (SEQ ID NO: 115) |
| 5'-<u>TGATCGTCGAACGTTCGACGATCA</u>; | (SEQ ID NO: 116) |
| 5'-<u>TCGAACGTTCGAACGTTCGAATTTT</u>; | (SEQ ID NO: 117) |
| 5'-TCG<u>CGAACGTTCGAACGTTCG</u>; | (SEQ ID NO: 150) |
| 5'-TCGC<u>GAACGTTCGAACGTTTC</u>; | (SEQ ID NO: 151) |
| 5'-TCG<u>ATAACGTTCGAACGTTAT</u>; | (SEQ ID NO: 152) |
| 5'-TCGAT<u>AACGTTCGAACGTTTC</u>; | (SEQ ID NO: 153) |
| 5'-TCGT<u>CGAACGTTCGA</u>GATG; | (SEQ ID NO: 166) |
| 5'-TCGT<u>CGAACGTTCG</u>; | (SEQ ID NO: 167) |
| 5'-<u>TCGAACGTTCGA TCGAACGTTCGA</u>; | (SEQ ID NO: 168) |
| 5'-<u>TCGACCGGTCGACCGGTCGA</u>; | (SEQ ID NO: 169) |
| 5'-TCG<u>AACGTTCGAACGTT</u>GATGT; | (SEQ ID NO: 170) |
| 5'-<u>TCGAACGTTCGA</u>AGATGATGAT; | (SEQ ID NO: 171) |
| 5'-<u>TCGAACGTTCGAACGTTCGAACG</u>; | (SEQ ID NO: 175) |
| 5'-<u>TCGAACGTTCGAACGTTCGAACGTTCGAAT</u>; | (SEQ ID NO: 172) |
| 5'-TCG<u>ATAACGTTCGAACGTTCGAACGTTAT</u>; | (SEQ ID NO: 173) |
| 5'-TCG<u>TAACGTTCGAACGTTCGAACGTTA</u>. | (SEQ ID NO: 174) |

In some embodiments, in an IMP comprising formula of SEQ ID NO:156, $X_1 X_2$ is not AA. In some embodiments, in an IMP comprising formula of SEQ ID NO:156, $X_1$ is not A. Accordingly, in some embodiments, the IMP comprises the following sequences (palindromic sequences underlined):

| | |
|---|---|
| 5'-<u>TCGAGCGCTAGCGCTCGATT</u>; | (SEQ ID NO: 81) |
| 5'-<u>TCGGTCGACGTCGACCGATT</u>; | (SEQ ID NO: 82) |
| 5'-<u>TCGGACGTCGACGTCCGATT</u>; | (SEQ ID NO: 83) |
| 5'-<u>TCGTTCGAATTCGAACGATT</u>. | (SEQ ID NO: 84) |
| 5'-TCGT<u>CGGCCGGCCGA</u>GATGAT; | (SEQ ID NO: 112) |

-continued

5'-TCGGACGTCCGGACGTCCGA; (SEQ ID NO: 79)

5'-TCGTCGCACGTGCGAGATGAT; (SEQ ID NO: 48)

5'-TCGTCGTACGTACGAGATGAT; (SEQ ID NO: 51)

5'-TCGTCGGGCGCCCGAGATGAT; (SEQ ID NO: 70)

5'-TCGTCGCGCGCGCGAGATGAT; (SEQ ID NO: 71)

5'-TCGTCGCTCGAGCGAGATGAT; (SEQ ID NO: 72)

5'-TCGTCGCCCGGGCGAGATGAT; (SEQ ID NO: 73)

5'-TCGTCGTGCGCACGAGATGAT; (SEQ ID NO: 74)

5'-TCGTCGTCCGGACGAGATGAT; (SEQ ID NO: 76)

5'-TCGAGCGCTCGAGCGCTCGA; (SEQ ID NO: 77)

5'-TCGTCGGTCGACCGAGATGAT; (SEQ ID NO: 46)

5'-TCGTCGGACGTCCGAGATGAT; (SEQ ID NO: 47)

5'-TCGTCGAGCGCTCGAGATGAT; (SEQ ID NO: 44)

5'-TCGATTCGAACGTTCGAACGTTCG; (SEQ ID NO: 40)

5'-TCGTTCGAACGTTCGAAGTGAT; (SEQ ID NO: 41)

5'-TCGTTCGAACGTTCGAACGA; (SEQ ID NO: 42)

5'-TCGTTCGAACGTTCGAACGTTCG; (SEQ ID NO: 53)

5'-TCGTTCGAACGTTCGAA; (SEQ ID NO: 54)

5'-TCGTTCGAACGTTCGAACGTTCGAA; (SEQ ID NO: 55)

5'-TCGTTCGAACGTTCGAACGATTTTTCGTTCGAACGTTCGAACGA; (SEQ ID NO: 56)

5'-TCGATCGATCGATCGATCGATT; (SEQ ID NO: 43)

5'-TCGTCGATCGATCGAGATGAT; (SEQ ID NO: 45)

5'-TCGTCGACCGGTCGAGATGAT; (SEQ ID NO: 69)

5'-TCGTCGTTCGAACGAGATGAT; (SEQ ID NO: 75)

5'-TCGGTCGACCGGTCGACCGA; (SEQ ID NO: 78)

5'-TCGTTCGAACGTTCGAACGTTCGAACG; (SEQ ID NO: 109)

5'-TCGTTCGAACGTTCGAACGAATGAT; (SEQ ID NO: 118)

5'-TCGACCGGTCGACCGGTCGACCGGT; (SEQ ID NO: 176)

5'-TCGCGCGCGCGCGCGCGCGA; (SEQ ID NO: 177)

5'-TCGCCCGGGCGCCCGGGCGA; (SEQ ID NO: 178)

5'-TCGGCCGGACGTCCGGACGA; (SEQ ID NO: 179)

5'-TCGGCCGGCCGGCCGGCCGA. (SEQ ID NO: 180)

In some embodiments, an IMP may comprise a sequence of the formula: 5'-$N_x$(TCG($N_q$))$_y$$N_w$ ($X_1X_2X_3X_4X_5$CG$X_5'X_4'X_3'X_2'X_1'$(CG)$_p$)$_z$ (SEQ ID NO:160) wherein N are nucleosides with x=0-3, y=1-4, w=−3, −2, −1, 0, 1 or 2, p=0 or 1, q=0, 1 or 2, and z=1-20, wherein $X_1$ and $X_1'$, $X_2$ and $X_2'$, $X_3$ and $X_3'$, $X_4$ and $X_4'$, and $X_5$ and $X_5'$ are self-complimentary, and wherein the 5' T of the (TCG($N_q$))$_y$ sequence is 0-3 bases from the 5' end of the polynucleotide. The IMP further comprises a palindromic sequence 12 bases in length or greater wherein the palindromic sequence comprises the first ($X_1X_2X_3X_4X_5$CG$X_5'X_4'X_3'X_2'X_1'$) (SEQ ID NO:218) of the at least one (($X_1X_2X_3X_4X_5$CG$X_5'X_4'X_3'X_2'X_1'$(CG)$_p$) (SEQ ID NO:219) sequence. In an IMP with w=−1, the 3' base of the (TCG($N_q$))$_y$ sequence is the 5' $X_1$ of the first ($X_1X_2X_3X_4X_5$CG$X_5'X_4'X_3'X_2'X_1'$(CG)$_p$) (SEQ ID NO:219) sequence. In an IMP with w=−2, the penultimate (i.e., second to last) and the ultimate (i.e., last) 3' bases of the (TCG($N_q$))$_y$ sequence are the 5' $X_1$ and $X_2$, respectively, of the first ($X_1X_2X_3X_4X_5$CG$X_5'X_4'X_3'X_2'X_1'$(CG)$_p$) (SEQ ID NO:219) sequence. In an IMP with w=−3, the antepenultimate (i.e., third to last), the penultimate (i.e., second to last) and the ultimate (i.e., last) 3' bases of the (TCG($N_q$))$_y$ sequence are the 5' $X_1$, $X_2$, and $X_3$, respectively, of the first ($X_1X_2X_3X_4X_5$CG$X_5'X_4'X_3'X_2'X_1'$(CG)$_p$) (SEQ ID NO:219) sequence. In some embodiments, the (TCG($N_q$))$_y$ sequence is separated from the palindromic sequence by 0, 1 or 2 bases. In other embodiments, the palindromic sequence includes all or part of the (TCG($N_q$))$_y$ sequence. In some embodiments, at least three of $X_1$, $X_2$, $X_3$, $X_4$, and $X_5$ are either A or T. In some embodiments, the IMP comprises the following sequences (palindromic sequences underlined):

5'-TCGTGCATCGATGCAACG; (SEQ ID NO: 93)

5'-TCGTGCATCGATGCAGATGAT; (SEQ ID NO: 110)

5'-TCGTGCATCGATGCATGCATCGATGCA; (SEQ ID NO: 111)

5'-TCGTGCATCGATGCACGA. (SEQ ID NO: 149)

In some embodiments, an IMP may comprise a sequence of the formula: 5'-$N_x$(TCG($N_q$))$_y$$N_w$($X_1X_2$CGCG$X_2'X_1'$(CG)$_p$)$_z$ (SEQ ID NO:163) wherein N are nucleosides with x=0-3, y=1-4, w=−2, −1, 0, 1 or 2, p=0 or 1, q=0, 1 or 2, and z=1-20, wherein $X_1$ and $X_1'$, and $X_2$ and $X_2'$ are self-complimentary, and wherein the 5' T of the (TCG($N_q$))$_y$ sequence is 0-3 bases from the 5' end of the polynucleotide. The IMP further comprises a palindromic sequence 8 bases in length or greater wherein the palindromic sequence comprises the first ($X_1X_2$CGCG$X_2'X_1'$) of the at least one ($X_1X_2$CGCG$X_2'X_1'$(CG)$_p$) (SEQ ID NO:220) sequence. In an IMP with w=−1, the 3' base of the (TCG($N_q$))$_y$ sequence is the 5' $X_1$ of the first ($X_1X_2$CGCG$X_2'X_1'$(CG)$_p$) (SEQ ID NO:220) sequence. In an IMP with w=−2, the penultimate (i.e., second to last) and the ultimate (i.e., last) 3' bases of the (TCG(N$_q$))$_y$ sequence are the 5' X$_1$ and X$_2$, respectively, of the first (X$_1$X$_2$CGCGX$_2$'X$_1$'(CG)$_p$) (SEQ ID NO:220) sequence. In some embodiments, the (TCG(N$_q$))$_y$ sequence is separated from the palindromic sequence by 0, 1 or 2 bases. In other embodiments, the palindromic sequence includes all or part of the (TCG(N$_q$))$_y$ sequence. In some embodiments, X$_1$ and X$_2$ are each either A or T. In some embodiments, the IMP comprises the following sequences (palindromic sequence underlined):

5'-<u>TCGTCGATCGCGATCGACGA</u>. (SEQ ID NO: 144)

In some embodiments, an IMP may comprise a sequence of the formula: 5'-N$_x$(TCG(N$_q$))$_y$N$_w$(X$_1$X$_2$X$_3$CGCGX$_3$'X$_2$'X$_1$'(CG)$_p$)$_z$ (SEQ ID NO:164) wherein N are nucleosides with x=0-3, y=1-4, w=−3, −2, −1, 0, 1 or 2, p=0 or 1, q=0, 1 or 2, and z=1-20, wherein X$_1$ and X$_1$', X$_2$ and X$_2$' and X$_3$ and X$_3$' are self-complimentary, and wherein the 5' T of the (TCG(N$_q$))$_y$ sequence is 0-3 bases from the 5' end of the polynucleotide. The IMP further comprises a palindromic sequence 10 bases in length or greater wherein the palindromic sequence comprises the first (X$_1$X$_2$X$_3$CGCGX$_3$'X$_2$'X$_1$') (SEQ ID NO:221) of the at least one (X$_1$X$_2$X$_3$CGCGX$_3$'X$_2$'X$_1$'(CG)$_p$) (SEQ ID NO:222) sequence. In an IMP with w=−1, the 3' base of the (TCG(N$_q$))$_y$ sequence is the 5' X$_1$ of the first (X$_1$X$_2$X$_3$CGCGX$_3$'X$_2$'X$_1$'(CG)$_p$) (SEQ ID NO:222) sequence. In an IMP with w=−2, the penultimate (i.e., second to last) and the ultimate (i.e., last) 3' bases of the (TCG(N$_q$))$_y$ sequence are the 5' X$_1$ and X$_2$, respectively, of the first (X$_1$X$_2$X$_3$CGCGX$_3$'X$_2$'X$_1$'(CG)$_p$) (SEQ ID NO:222) sequence. In an IMP with w=−3, the antepenultimate (i.e., third to last), the penultimate (i.e., second to last) and the ultimate (i.e., last) 3' bases of the (TCG(N$_q$))$_y$ sequence are the 5' X$_1$, X$_2$, and X$_3$, respectively, of the first (X$_1$X$_2$X$_3$CGCGX$_3$'X$_2$:X$_1$' (CG)$_p$) (SEQ ID NO:222) sequence. In some embodiments, the (TCG(N$_q$))$_y$ sequence is separated from the palindromic sequence by 0, 1 or 2 bases. In other embodiments, the palindromic sequence includes all or part of the (TCG(N$_q$))$_y$ sequence. In some embodiments, when p=1, X$_1$, X$_2$, and X$_3$ are each either A or T. In some embodiments, when p=0, at least two of X$_1$, X$_2$, and X$_3$ are either A or T. In some embodiments, the IMP comprises the following sequences (palindromic sequence underlined):

5'-<u>TCGTCGAATCGCGATT</u>CGACGA. (SEQ ID NO: 145)

In some embodiments, an IMP may comprise a sequence of the formula: 5'-N$_x$(TCG(N$_q$))$_y$N$_w$(CGX$_1$X$_2$X$_2$'X$_1$'CG(CG)$_p$)$_z$ (SEQ ID NO: 165) wherein N are nucleosides with x=0-3, y=1-4, w=−2, 0, 1 or 2, p=0 or 1, q=0, 1 or 2, and z=1-20, wherein X$_1$ and X$_1$', and X$_2$ and X$_2$' are self-complimentary, and wherein the 5' T of the (TCG(N$_q$))$_y$ sequence is 0-3 bases from the 5' end of the polynucleotide. The IMP further comprises a palindromic sequence 8 bases in length or greater wherein the palindromic sequence comprises the first (CGX$_1$X$_2$X$_2$'X$_1$'CG) of the at least one (CGX$_1$X$_2$X$_2$'X$_1$'CG(CG)$_p$) (SEQ ID NO:223) sequence. In an IMP with w=−2, the penultimate (i.e., second to last) and the ultimate (i.e., last) 3' bases of the (TCG(N$_q$))$_y$ sequence are CG and are the 5' CG of the first (CGX$_1$X$_2$X$_2$'X$_1$'CG(CG)$_p$) (SEQ ID NO:223) sequence. In some embodiments, the (TCG(N$_q$))$_y$ sequence is separated from the palindromic sequence by 0, 1 or 2 bases. In other embodiments, the palindromic sequence includes all or part of the (TCG(N$_q$))$_y$ sequence. In some embodiments, X$_1$ and X$_2$ are each either A or T. In some embodiments, the IMP comprises the following sequences (palindromic sequence underlined):

5'-<u>TCGTCGCGATATCGCGACGA</u>. (SEQ ID NO: 146)

For IMPs comprising any of the motifs described herein (i.e., SEQ ID NOs:155-165) where y=2 or more, the (N$_q$) in each of the y repetitions of the (TCG(N$_q$)) is independently selected. For example, in an IMP with y=2, the first TCG(N$_q$) may have N=A and q=1 and the second TCG(N$_q$) may have q=0 in which case this portion of the IMP would be . . . TCGATCG . . . . In some embodiments of IMPs comprising any of the motifs described herein (i.e., SEQ ID NOs:155-165) in some embodiments, x is preferably 0 or 1. In some embodiments of IMPs comprising any of the motifs described herein (i.e., SEQ ID NOs:155-165), y is preferably 1 or 2. In some embodiments of IMPs comprising any of the motifs described herein (i.e., SEQ ID NOs:155-165), w is preferably 0. In some embodiments of IMPs comprising any of the motifs described herein (i.e., SEQ ID NOs:155-165), z is preferably 1, 2, 3, 4, 5, 6, 7 or 8.

As noted above, the IMPs contain at least one the palindromic sequence at least 8 bases in length. In some embodiments, an IMP contains at least one palindromic sequence of at least the following lengths (in bases): 10, 12, 14, 16, 18, 20, 22, 24, 26, 28, 30. In some embodiments, the palindromic sequence is repeated at least once in an IMP. In some embodiments, the palindromic sequence also includes bases 5' of the (TCG(N$_q$))$_y$ sequence, if any.

An immunomodulatory polynucleotide may contain modifications. Modifications of IMP include any known in the art, but are not limited to, modifications of the 3'OH or 5'OH group, modifications of the nucleotide base, modifications of the sugar component, and modifications of the phosphate group. Various such modifications are described below. Modified bases may be included in the palindromic sequence of an IMP as long as the modified base(s) maintains the same specificity for its natural complement through Watson-Crick base pairing (e.g., the palindromic portion of the IMP is still self-complementary).

An IMP may be linear, may be circular or include circular portions and/or may include a hairpin loop. In some embodiments, the IMP comprises the following cyclic sequence (palindromic sequences underlined):

(SEQ ID NO: 181)

⌐5'-<u>TCGAACGTTCGAACGTTCGAAT</u>⌐.

An IMP may be single stranded or double stranded DNA, as well as single or double-stranded RNA or other modified polynucleotides. In some embodiments, the IMP comprises the following double-stranded sequences:

5'-TCGTCGAACGTTCGAGATGAT/5'-ATCATCTCGAACGTTCGACGA (SEQ ID NO: 27/SEQ ID NO: 29 duplex)

5'-TCG*TCG*AACG*TTCG*AG*ATG*AT/5'-

ATCATCTCGAACGTTCGACGA (G* = 7-deaza-8-aza-dG, SEQ ID NO: 187/SEQ ID NO: 29 duplex)

-continued

5'-TCGTCGA*A*CGTTCGA*GA*TGA*T/5'-

ATCATCTCGAACGTTCGACGA (A* = 2-amino-dA, SEQ ID NO:

188/SEQ ID NO: 29 duplex)

5'-TCGTCGAA*CGT*TCGAGATGAT/5'-

ATCATCTCGAACGTTCGACGA (A* = 2-amino-dA; T* = 2- thio-dT, SEQ ID NO: 189/SEQ ID NO: 29 duplex)

5'-TCGTCGA*A*CGT*T*CGAGATGAT/5'-

ATCATCTCGAACGTTCGACGA (A* = 2-amino-dA; T* = 2- thio-dT, SEQ ID NO: 190/SEQ ID NO: 29 duplex).

An IMP may contain naturally-occurring or modified, non-naturally occurring bases, and may contain modified sugar, phosphate, and/or termini. For example, in addition to phosphodiester linkages, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. In some embodiments, polynucleotides of the present invention comprise only phosphorothioate backbones. In some embodiments, polynucleotides of the present invention comprise only phosphodiester backbones. In some embodiments, an IMP may comprise a combination of phosphate linkages in the phosphate backbone such as a combination of phosphodiester and phosphorothioate linkages. For example, in some embodiments, the IMP comprises the following sequences ("s" indicates phosphorothioate linkages):

(SEQ ID NO: 62)
5'-TCGTCGAAACGTTTCGACAGT, all phosphorothioate linkages;

(SEQ ID NO: 88)
5'-TCGTTCGAACGTTCGAACGA, all phosphodiester linkages;

(SEQ ID NO: 89)
5'-TsCsGsTTCGAACGTTCGsAsAsCsGsA, phosphorothioate/ phosphodiester chimera;

(SEQ ID NO: 26)
5'-GsGsTCGAACGTTCGAGsGsGsGsGsG, phosphorothioate/ phosphodiester chimera;

(SEQ ID NO: 33)
5'-TsCsGsTCGAACGTTCGAGsGsGsGsGsG, phosphorothioate/phosphodiester chimera;

(SEQ ID NO: 34)
5'-TsCsGsTGCATCGATGCAGGsGsGsGsG, phosphorothioate/ phosphodiester chimera.

Sugar modifications known in the field, such as 2'-alkoxy-RNA analogs, 2'-amino-RNA analogs, 2'-fluoro-DNA, and 2'-alkoxy- or amino-RNA/DNA chimeras and others described herein, may also be made and combined with any phosphate modification. Examples of base modifications (discussed further below) include, but are not limited to, addition of an electron-withdrawing moiety to C-5 and/or C-6 of a cytosine of the IMP (e.g., 5-bromocytosine, 5-chlorocytosine, 5-fluorocytosine, 5-iodocytosine) and C-5 and/or C-6 of a uracil of the IMP (e.g., 5-bromouracil, 5-chlorouracil, 5-fluorouracil, 5-iodouracil). See, for example, International Patent Application No. WO 99/62923. As noted above, use of a base modification in a palidromic sequence of an IMP should not interfere with the self-complimentary ability of the bases involved for Watson-Crick base pairing. However, outside of a palindromic sequence, modified bases may be used without this restriction. For example, in some embodiments, the IMP comprises the following sequences:

(SEQ ID NO: 21)
5'-uCGuCGAACGTTCGAGATG, u = 2'-O-methyl-uridine;

(SEQ ID NO: 22)
5'-TcGTCGAACGTTCGAGATG, c = 2'-O-methyl-cytidine;

(SEQ ID NO: 23)
5'-TCGTcGAACGTTCGAGATG, c = 2'-O-methyl-cytidine;

(SEQ ID NO: 28)
5'-TBGTBGAABGTTBGAGATGAT, B = 5'-bromo-2'- deoxycytidine.

The IMP can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The IMP can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular immunomodulatory polynucleotide can be isolated, synthesized through recombinant methods, or chemically synthesized. Where the circular IMP is obtained through isolation or through recombinant methods, the IMP will preferably be a plasmid. The chemical synthesis of smaller circular oligonucleotides can be performed using any method described in the literature. See, for instance, Gao et al. (1995) *Nucleic Acids Res.* 23:2025-2029; and Wang et al. (1994) *Nucleic Acids Res.* 22:2326-2333.

Duplex (i.e., double stranded) and hairpin forms of most IMPs are in dynamic equilibrium, with the hairpin form generally favored at low polynucleotide concentration and higher temperatures. Covalent interstrand or intrastrand cross-links increases duplex or hairpin stability, respectively, towards thermal-, ionic-, pH-, and concentration-induced conformational changes. Chemical cross-links can be used to lock the polynucleotide into either the duplex or the hairpin form for physicochemical and biological characterization. Cross-linked IMPs that are conformationally homogeneous and are "locked" in their most active form (either duplex or hairpin form) could potentially be more active than their uncross-linked counterparts. Accordingly, some IMPs of the invention contain covalent interstrand and/or intrastrand cross-links.

A variety of ways to chemically cross-link duplex DNA are known in the art. Any cross-linking method may be used as long as the cross-linked polynucleotide product possesses the desired immunomodulatory activity.

One method, for example, results in a disulfide bridge between two opposing thymidines at the terminus of the duplex or hairpin. For this cross-linking method, the oligonucleotide(s) of interest is synthesized with a 5'-DMT-N3-(tBu-SS-ethyl)thymidine-3'-phosphoramidite ("T*"). To form the disulfide bridge, the mixed disulfide bonds are reduced, oligonucleotide purified, the strands hybridized and the compound air-oxidized to form the intrastrand cross-link in the case of a hairpin form or the interstrand cross-link in the case of a duplex form. Alternatively, the oligonucleotides may be hybridized first and then reduced, purified and air-oxidized. Such methods and others are described, for example, in Glick et al. (1991) *J. Org. Chem.* 56:6746-6747, Glick et al. (1992) *J. Am. Chem. Soc.* 114:5447-5448, Goodwin et al. (1994) *Tetrahedron Letters* 35:1647-1650, Wang et al. (1995) *J. Am. Chem. Soc.* 117:2981-2991, Osborne et al. (1996) *Bioorganic & Medicinal Chemistry Letters* 6:2339-2342 and Osborne et al. (1996) *J. Am. Chem. Soc.* 118:11993-12003.

Examples of polynucleotide sequences in which a 5'-DMT-N3-(tBu-SS-ethyl)thymidine-3'-phosphoramidite ("T*") may be incorporated for the purpose of cross-linking include the following. Incorporation of the T* at the 3' end of a SEQ ID NO:27 analog (5'-TCGTCGAACGTTCGAGATGAT*-3', SEQ ID NO: 185) and at the 5' end of a SEQ ID NO:29 analog (5'-T*TCATCTCGAACGTTCGACGA-3', SEQ ID NO:186) would allow a cross-link in a duplex of the two strands at the 3' end of the SEQ ID NO:27 analog. Incorporation of the T* at two locations in a SEQ ID NO:113 analog would allow two cross-links to form a duplex or a single cross-link to hold a hairpin form. For example, folding of the sequence 5'-TCGT*AACGTTCGAACGTTCGAACGTTT*-3 (SEQ ID NO:227) into a hairpin structure and forming a cross-link at the substituted T residues would result in a cross-linked polynucleotide with the following secondary structure.

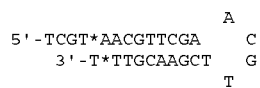

Such a hairpin structure or a duplex structure of the same sequence would have a free 5'-TCG although constrained at two positions (the 3' end and 4 bases in from the 5'-end).

Another cross-linking method forms a disulfide bridge between offset residues in the duplex or hairpin structure. For this cross-linking method, the oligonucleotide(s) of interest is synthesized with convertible nucleosides (commercially available, for example, from Glen Research). This method utilizes, for example, an A-A disulfide or a C-A disulfide bridge and linkages through other bases are also possible. To form the disulfide-modified polynucleotide, the polynucleotide containing the convertible nucleoside is reacted with cystamine (or other disulfide-containing amine). To form the disulfide bridge, the mixed disulfide bonds are reduced, oligonucleotide purified, the strands hybridized and the compound air-oxidized to form the intrastrand cross-link in the case of a hairpin form or the interstrand cross-link in the case of a duplex form. Alternatively, the oligonucleotides may be hybridized first and then reduced, purified and air-oxidized. Such methods are described, for example, in Ferentz et al. (1991) *J. Am. Chem. Soc.* 113:4000-4002 and Ferentz et al. (1993) *J. Am. Chem. Soc.* 115:9006-9014.

Examples of polynucleotide sequences in which offset N6-cystamine-2'-dA (A*) residues are used to crosslink a duplex include the following. Incorporation of the A* at the 3' end of a the sequence 5'-TCGTCGAACGTTCGAGA*TGAT-3', SEQ ID NO:191 and at the 5' end of its complement 5'-ATCA*TCTCGAACGTTCGACGA-3', SEQ ID NO:192 would allow a cross-link in a duplex of the two strands at the 3' end of the SEQ ID NO:191. Such modifications may also be used to cross-link hairpin structures.

The techniques for making polynucleotides and modified polynucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired polynucleotide sequence has been synthesized, the polynucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) *DNA* 3:401 and U.S. Pat. No. 4,458,066.

The IMP can also contain phosphate-modified polynucleotides, some of which are known to stabilize the polynucleotide. Accordingly, some embodiments includes stabilized immunomodulatory polynucleotides. Synthesis of polynucleotides containing modified phosphate linkages or non-phosphate linkages is also known in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the polynucleotides of the present invention can be a monophosphate, diphosphate, triphosphate, alkylphosphonate, phosphorothioate, phosphorodithioate, phosphoramidate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidiates (Nelson et al. (1997) *JOC* 62:7278-7287) and phosphorodithioates (U.S. Pat. No. 5,453,496) has also been described. Other non-phosphorous based modified oligonucleotides can also be used (Stirchak et al. (1989) *Nucleic Acids Res.* 17:6129-6141). Polynucleotides with phosphorothioate backbones can be more immunogenic than those with phosphodiester backbones and appear to be more resistant to degradation after injection into the host. Braun et al. (1988) *J. Immunol.* 141: 2084-2089; and Latimer et al. (1995) *Mol. Immunol.* 32:1057-1064.

IMPs used in the invention can comprise one or more ribonucleotides (containing ribose as the only or principal sugar component), deoxyribonucleotides (containing deoxyribose as the principal sugar component), or, as is known in the art, modified sugars or sugar analogs can be incorporated in the IMP. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the IMP, the sugar moiety is preferably the furanoside of ribose, deoxyribose, arabinose or 2'-O-alkylribose, and the sugar can be attached to the respective heterocyclic bases either in α or β anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification in the IMP includes, but is not limited to, 2'-O-methyl-uridine and 2'-O-methyl-cytidine. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an IMP.

The heterocyclic bases, or nucleic acid bases, which are incorporated in the IMP can be the naturally-occurring principal purine and pyrimidine bases, (namely uracil, thymine, cytosine, adenine and guanine, as mentioned above), as well as naturally-occurring and synthetic modifications of said principal bases. Thus, an IMP may include 2'-deoxyuridine and/or 2-amino-2'-deoxyadenosine.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the IMP can include one or several heterocyclic bases other than the principal five base components of naturally-occurring nucleic acids. Preferably, however, the heterocyclic base in the IMP includes, but is not limited to, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrrolo[2,3-d]pyrimidin-5-yl, 2-amino-4-oxopyrrolo[2,3-d]pyrimidin-3-yl groups, where the purines are attached to the sugar moiety of the IMP via the 9-position, the pyrimidines via the 1-position, the pyrrolopyrimidines via the 7-position and the pyrazolopyrimidines via the 1-position.

The IMP may comprise at least one modified base. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the IMP. Preferably, the electron-withdrawing moiety is a halogen. Such modified cytosines can include, but are not limited to, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, uracil, and any other pyrimidine analog or modified pyrimidine. Other examples of base modifications include, but are not limited to, addition of an electron-withdrawing moiety to C-5 and/or C-6 of a uracil of the immunomodulatory polynucleotide. Preferably, the electron-withdrawing moiety is a halogen. Such modified uracils can include, but are not limited to, 5-bromouracil, 5-chlorouracil, 5-fluorouracil, 5-iodouracil.

Other examples of base modifications include the addition of one or more thiol groups to the base including, but not limited to, 2-amino-adenine, 6-thio-guanine, 2-thio-thymine, 4-thio-thymine, 5-propynyl-uracil, and 4-thio-uracil. Other examples of base modifications include, but are not limited to, N4-ethylcytosine, 7-deazaguanine, 7-deaza-8-azaguanine and 5-hydroxycytosine. See, for example, Kandimalla et al. (2001) *Bioorg. Med. Chem.* 9:807-813. In some embodiments, the IMP comprises the following sequences with modified bases (palindromic sequence underlined):

```
                                              (SEQ ID NO: 193)
5'-TCXTCXAACXTTCXAGATGAT (X = 7-deaza-dG);

(SEQ ID NO: 189)
5'-TCGTCGAA*CGT*TCGAGATGAT (A* = 2-amino-dA; T* =
2-thio-dT);

(SEQ ID NO: 190)
5'-TCGTCGA*A*CGT*T*CGAGATGAT (A* = 2-amino-dA;
T* = 2-thio-dT);

(SEQ ID NO: 187)
5'-TCG*TCG*AACG*TTCG*AG*ATG*AT (G* = 7-deaza-8-
aza-dG);

(SEQ ID NO: 194)
5'-TCG*AACG*TTCG*AACG*TTCG*AACG*TT (G* = 7-deaza-
8-aza-dG);

(SEQ ID NO: 195)
5'-TCGT*CGAACGT*T*CGAGAT*GAT* (T* = 5-propynyl-
dU);

(SEQ ID NO: 196)
5'-TCGAACGT*T*CGAACGT*T*CGAACGT*T* (T* = 5-
propynyl-dU);

(SEQ ID NO: 188)
5'-TCGTCGA*A*CGTTCGA*GA*TGA*T (A* = 2-amino-dA);

(SEQ ID NO: 197)
5'-TCGA*A*CGTTCGA*A*CGTTCGA*A*CGTT (A* = 2-amino-
dA).
```

As exemplified in Example 1, IMPs that maintain a duplex form at low concentration tend to be able to stimulate IFN-α production from human PBMCs. Stabilizing duplex polynucleotide forms through cross-linking has been described above. When in duplex form with their complementary sequence, certain modified bases also can increase the stability of duplexes. For instance, 2-amino-dA (commercially available, for example, from Glen Research) forms 3 hydrogen bonds with T instead of 2 hydrogen bonds, as formed between dA and T. SEQ ID NO:188, an analog of SEQ ID NO:27, contains five 2-amino-dA bases in place of the five dA bases of SEQ ID NO:27 and forms a stronger duplex with itself than SEQ ID NO:27 (size exclusion chromatography data). Incorporation of these modified bases increases the Tm about 3° C. per modification. As demonstrated herein in Example 1, SEQ ID NO:188 also induced production of more IFN-α than SEQ ID NO:27 when human PBMCs were treated with 0.8 μg/ml of IMP. Double-stranded SEQ ID NO:884 induced about three times the IFN-α production as single-stranded SEQ ID NO:188.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

In some embodiments, an immunomodulatory polynucleotide is less than about any of the following lengths (in bases or base pairs): 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10. In some embodiments, an immunomodulatory polynucleotide is greater than about any of the following lengths (in bases or base pairs): 10; 11; 12; 13; 14; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the immunomodulatory polynucleotide can be any of a range of sizes having an upper limit of 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10 and an independently selected lower limit of 10; 11; 12; 13; 14; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit In some embodiments, an IMP is preferably about 200 or less bases in length.

The invention also provides methods of making the immunomodulatory polynucleotides described herein. The methods may be any of those described herein. For example, the method could be synthesizing the IMP (for example, using solid state synthesis) and may further comprise any purification step(s). Methods of purification are known in the art. Other methods of preparation include combining an immunomodulatory polynucleotide and an antigen.

Antigen

Any antigen may be co-administered with an immunomodulatory polynucleotide and/or used in compositions comprising an immunomodulatory polynucleotide and antigen (and preparation of these compositions).

In some embodiments, the antigen is an allergen. Examples of recombinant allergens are provided in Table 1. Preparation of many allergens is well-known in the art, including, but not limited to, preparation of ragweed pollen allergen Antigen E (Amb a I) (Rafnar et al. (1991) *J. Biol. Chem.* 266:1229-1236), grass allergen Lol p 1 (Tamborini et al. (1997) *Eur. J. Biochem.* 249:886-894), major dust mite allergens Der pI and Der PII (Chua et al. (1988) *J. Exp. Med.* 167:175-182; Chua et al. (1990) *Int. Arch. Allergy Appl. Immunol.* 91:124-129), domestic cat allergen Fel d I (Rogers et al. (1993) *Mol. Immunol.* 30:559-568), white birch pollen Bet v1 (Breiteneder et al. (1989) *EMBO J.* 8:1935-1938), Japanese cedar allergens Cry j 1 and Cry j 2 (Kingetsu et al. (2000) *Immunology* 99:625-629), and protein antigens from other tree pollen (Elsayed et al. (1991) *Scand. J. Clin. Lab. Invest. Suppl.* 204:17-31). As indicated, allergens from trees are known, including allergens from birch, juniper and Japanese cedar. Preparation of protein antigens from grass pollen for in vivo administration has been reported.

In some embodiments, the allergen is a food allergen, including, but not limited to, peanut allergen, for example Ara h I (Stanley et al. (1996) *Adv. Exp. Med. Biol.* 409:213-216); walnut allergen, for example, Jug r I (Tueber et al. (1998) *J. Allergy Clin. Immunol.* 101:807-814); brazil nut allergen, for example, albumin (Pastorello et al. (1998) *J. Allergy Clin. Immunol.* 102:1021-1027; shrimp allergen, for example, Pen a I (Reese et al. (1997) *Int. Arch. Allergy Immunol.* 113:240-242); egg allergen, for example, ovomucoid (Crooke et al. (1997) *J. Immunol.* 159:2026-2032); milk allergen, for example, bovine β-lactoglobin (Selot al. (1999) *Clin. Exp. Allergy* 29:1055-1063); fish allergen, for example, parvalbumins (Van Do et al. (1999) *Scand. J. Immunol.* 50:619-625; Galland et al. (1998) *J. Chromatogr. B. Biomed. Sci. Appl.* 706:63-71). In some embodiments, the allergen is a latex allergen, including but not limited to, Hey b 7 (Sowka et al. (1998) *Eur. J. Biochem.* 255:213-219). Table 1 shows an exemplary list of allergens that may be used.

TABLE 1

| Group | Allergen | Reference |
|---|---|---|
| RECOMBINANT ALLERGENS | | |
| ANIMALS: CRUSTACEA | | |
| Shrimp/lobster | tropomyosin | Leung et al. (1996) J. Allergy Clin. Immunol. 98: 954-961 |
| | Pan s I | Leung et al. (1998) Mol. Mar. Biol. Biotechnol. 7: 12-20 |
| INSECTS | | |
| Ant | Sol i 2 (venom) | Schmidt et al. J Allergy Clin Immunol., 1996, 98: 82-8 |
| Bee | Phospholipase A2 (PLA) | Muller et al. J Allergy Clin Immunol, 1995, 96: 395-402 |
| | | Forster et al. J Allergy Clin Immunol, 1995, 95: 1229-35 |
| | | Muller et al. Clin Exp Allergy, 1997, 27: 915-20 |
| | Hyaluronidase (Hya) | Soldatova et al. J Allergy Clin Immunol, 1998, 101: 691-8 |
| Cockroach | Bla g Bd9OK | Helm et al. J Allergy Clin Immunol, 1996, 98: 172-180 |
| | Bla g 4 (a calycin) | Vailes et al. J Allergy Clin Immunol, 1998, 101: 274-280 |
| | Glutathione S-transferase | Arruda et al. J Biol Chem, 1997, 272: 20907-12 |
| | Per a 3 | Wu et al. Mol Immunol, 1997, 34: 1-8 |

TABLE 1-continued

RECOMBINANT ALLERGENS

| Group | Allergen | Reference |
|---|---|---|
| Dust mite | Der p 2 (major allergen) | Lynch et al. J Allergy Clin Immunol, 1998, 101: 562-4 |
| | | Hakkaart et al. Clin Exp Allergy, 1998, 28: 169-74 |
| | | Hakkaart et al. Clin Exp Allergy, 1998, 28: 45-52 |
| | | Hakkaart et al. Int Arch Allergy Immunol, 1998, 115 (2): 150-6 |
| | | Mueller et al. J Biol Chem, 1997, 272: 26893-8 |
| | Der p2 variant | Smith et al. J Allergy Clin Immunol, 1998, 101: 423-5 |
| | Der f2 | Yasue et al. Clin Exp Immunol, 1998, 113: 1-9 |
| | | Yasue et al. Cell Immunol, 1997, 181: 30-7 |
| | Der p10 | Asturias et al. Biochim Biophys Acta, 1998, 1397: 27-30 |
| | Tyr p 2 | Eriksson et al. Eur J Biochem, 1998 |
| Hornet | Antigen 5 aka Dol m V (venom) | Tomalski et al. Arch Insect Biochem Physiol, 1993, 22: 303-13 |
| Mosquito | Aed a I (salivary apyrase) | Xu et al. Int Arch Allergy Immunol, 1998, 115: 245-51 |
| Yellow jacket | antigen 5, hyaluronidase and phospholipase (venom) | King et al. J Allergy Clin Immunol, 1996, 98: 588-600 |
| MAMMALS | | |
| Cat | Fel d I | Slunt et al. J Allergy Clin Immunol, 1995, 95: 1221-8 |
| | | Hoffmann et al. (1997) J Allergy Clin Immunol 99: 227-32 |
| | | Hedlin Curr Opin Pediatr, 1995, 7: 676-82 |
| Cow | Bos d 2 (dander; a lipocalin) | Zeiler et al. J Allergy Clin Immunol, 1997, 100: 721-7 |
| | | Rautiainen et al. Biochem Bioph. Res Comm., 1998, 247: 746-50 |
| | β-lactoglobulin (BLG, major cow milk allergen) | Chatel et al. Mol Immunol, 1996, 33: 1113-8 |
| | | Lehrer et al. Crit Rev Food Sci Nutr, 1996, 36: 553-64 |
| Dog | Can f I and Can f 2, salivary lipocalins | Konieczny et al. Immunology, 1997, 92: 577-86 |
| | | Spitzauer et al. J Allergy Clin Immunol, 1994, 93: 614-27 |
| | | Vrtala et al. J Immunol, 1998, 160: 6137-44 |
| Horse | Equ c1 (major allergen, a lipocalin) | Gregoire et al. J Biol Chem, 1996, 271: 32951-9 |
| Mouse | mouse urinary protein (MUP) | Konieczny et al. Immunology, 1997, 92: 577-86 |
| OTHER MAMMALIAN ALLERGENS | | |
| Insulin | | Ganz et al. J Allergy Clin Immunol, 1990, 86: 45-51 |
| | | Grammer et al. J Lab Clin Med, 1987, 109: 141-6 |
| | | Gonzalo et al. Allergy, 1998, 53: 106-7 |
| Interferons | interferon alpha 2c | Detmar et al. Contact Dermatis, 1989, 20: 149-50 |
| MOLLUSCS | topomyosin | Leung et al. J Allergy Clin Immunol, 1996, 98: 954-61 |
| PLANT ALLERGENS: | | |
| Barley | Hor v 9 | Astwood et al. Adv Exp Med Biol, 1996, 409: 269-77 |
| Birch | pollen allergen, Bet v 4 | Twardosz et al. Biochem Bioph. Res Comm., 1997, 239: 197 |
| | rBet v 1 Bet v 2: (profilin) | Pauli et al. J Allergy Clin Immunol, 1996, 97: 1100-9 |
| | | van Neerven et al. Clin Exp Allergy, 1998, 28: 423-33 |
| | | Jahn-Schmid et al. Immunotechnology, 1996, 2: 103-13 |
| | | Breitwieser et al. Biotechniques, 1996, 21: 918-25 |
| | | Fuchs et al. J Allergy Clin Immunol, 1997, 100: 356-64 |
| Brazil nut | globulin | Bartolome et al. Allergol Immunopathol, 1997, 25: 135-44 |
| Cherry | Pru a I (major allergen) | Scheurer et al. Mol Immunol, 1997, 34: 619-29 |
| Corn | Zml3 (pollen) | Heiss et al. FEBS Lett, 1996, 381: 217-21 |
| | | Lehrer et al. Int Arch Allergy Immunol, 1997, 113: 122-4 |
| Grass | Phl p 1, Phl p 2, Phl p 5 (timothy grass pollen) | Bufe et al. Am J Respir Crit Care Med, 1998, 157: 1269-76 |
| | | Vrtala et al. J Immunol Jun 15, 1998, 160: 6137-44 |
| | | Niederberger et al. J Allergy Clin Immun., 1998, 101: 258-64 |
| | Hol 1 5 velvet grass pollen | Schramm et al. Eur J Biochem, 1998, 252: 200-6 |
| | Bluegrass allergen | Zhang et al. J Immunol, 1993, 151: 791-9 |
| | Cyn d 7 Bermuda grass | Smith et al. Int Arch Allergy Immunol, 1997, 114: 265-71 |
| | Cyn d 12 (a profilin) | Asturias et al. Clin Exp Allergy, 1997, 27: 1307-13 |
| | | Fuchs et al. J Allergy Clin Immunol, 1997, 100: 356-64 |
| Japanese Cedar | Jun a 2 (Juniperus ashei) | Yokoyama et al. Biochem. Biophys. Res. Commun., 2000, 275: 195-202 |
| | Cry j 1, Cry j 2 (Cryptomeria japonica) | Kingetsu et al. Immunology, 2000, 99: 625-629 |
| Juniper | Jun o 2 (pollen) | Tinghino et al. J Allergy Chin Immunol, 1998, 101: 772-7 |
| Latex | Hev b 7 | Sowka et al. Eur J Biochem, 1998, 255: 213-9 |
| | | Fuchs et al. J Allergy Clin Immunol, 1997, 100: 356-64 |

TABLE 1-continued

RECOMBINANT ALLERGENS

| Group | Allergen | Reference |
|---|---|---|
| Mercurialis | Mer a I (profilin) | Vallverdu et al. J Allergy Clin Immunol, 1998, 101: 363-70 |
| Mustard (Yellow) | Sin a I (seed) | Gonzalez de la Pena et al. Biochem Bioph. Res Comm., 1993, 190: 648-53 |
| Oilseed rape | Bra r I pollen allergen | Smith et al. Int Arch Allergy Immunol, 1997, 114: 265-71 |
| Peanut | Ara h I | Stanley et al. Adv Exp Med Biol, 1996, 409: 213-6 |
| | | Burks et al. J Clin Invest, 1995, 96: 1715-21 |
| | | Burks et al. Int Arch Allergy Immunol, 1995, 107: 248-50 |
| Poa pratensis | Poa p9 | Parronchi et al. Eur J Immunol, 1996, 26: 697-703 |
| | | Astwood et al. Adv Exp Med Biol, 1996, 409: 269-77 |
| Ragweed | Amb a I | Sun et al. Biotechnology Aug, 1995, 13: 779-86 |
| | | Hirschwehr et al. J Allergy Clin Immunol, 1998, 101: 196-206 |
| | | Casale et al. J Allergy Clin Immunol, 1997, 100: 110-21 |
| Rye | Lol p I | Tamborini et al. Eur J Biochem, 1997, 249: 886-94 |
| Walnut | Jug r I | Teuber et al. J Allergy Clin Immun., 1998, 101: 807-14 |
| Wheat | allergen | Fuchs et al. J Allergy Clin Immunol, 1997, 100: 356-64 |
| | | Donovan et al. Electrophoresis, 1993, 14: 917-22 |
| FUNGI: | | |
| *Aspergillus* | Asp f 1, Asp f 2, Asp f 3, Asp f 4, rAsp f 6 | Crameri et al. Mycoses, 1998, 41 Suppl 1: 56-60 |
| | | Hemmann et al. Eur J Immunol, 1998, 28: 1155-60 |
| | | Banerjee et al. J Allergy Clin Immunol, 1997, 99: 821-7 |
| | | Crameri Int Arch Allergy Immunol, 1998, 115: 99-114 |
| | | Crameri et al. Adv Exp Med Biol, 1996, 409: 111-6 |
| | | Moser et al. J Allergy Clin Immunol, 1994, 93: 1-11 |
| | Manganese superoxide dismutase (MNSOD) | Mayer et al. Int Arch Allergy Immunol, 1997, 113: 213-5 |
| Blomia | allergen | Caraballo et al. Adv Exp Med Biol, 1996, 409: 81-3 |
| Penicillinium | allergen | Shen et al. Clin Exp Allergy, 1997, 27: 682-90 |
| Psilocybe | Psi c 2 | Horner et al. Int Arch Allergy Immunol, 1995, 107: 298-300 |

In some embodiments, the antigen is from an infectious agent, including protozoan, bacterial, fungal (including unicellular and multicellular), and viral infectious agents. Examples of suitable viral antigens are described herein and are known in the art. Bacteria include *Hemophilus influenza, Mycobacterium tuberculosis* and *Bordetella pertussis*. Protozoan infectious agents include malarial plasmodia, *Leishmania* species, *Trypanosoma species* and *Schistosoma* species. Fungi include *Candida albicans*.

In some embodiments, the antigen is a viral antigen. Viral polypeptide antigens include, but are not limited to, HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like. References discussing influenza vaccination include Scherle and Gerhard (1988) *Proc. Natl. Acad. Sci. USA* 85:4446-4450; Scherle and Gerhard (1986) *J. Exp. Med.* 164:1114-1128; Granoff et al. (1993) *Vaccine* 11:S46-51; Kodihalli et al. (1997) *J. Virol.* 71:3391-3396; Ahmeida et al. (1993) *Vaccine* 11:1302-1309; Chen et al. (1999) *Vaccine* 17:653-659; Govorkova and Smirnov (1997) *Acta Virol.* (1997) 41:251-257; Koide et al. (1995) *Vaccine* 13:3-5; Mbawuike et al. (1994) *Vaccine* 12:1340-1348; Tamura et al. (1994) Vaccine 12:310-316; Tamura et al. (1992) *Eur. J. Immunol.* 22:477-481; Hirabayashi et al. (1990) Vaccine 8:595-599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation or treatment of existing tumors, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with IMP. Lea et al. (1996) *Biochim. Biophys. Acta* 1307:263.

Attenuated and inactivated viruses are suitable for use herein as the antigen. Preparation of these viruses is well-known in the art and many are commercially available (see, e.g., Physicians' Desk Reference (1998) 52nd edition, Medical Economics Company, Inc.). For example, polio virus is available as IPOL® (Pasteur Merieux Connaught) and ORIMUNE® (Lederle Laboratories), hepatitis A virus as VAQTA® (Merck), measles virus as ATTENUVAX® (Merck), mumps virus as MUMPSVAX® (Merck) and rubella virus as MERUVAX®II (Merck). Additionally, attenuated and inactivated viruses such as HIV-1, HIV-2, herpes simplex virus, hepatitis B virus, rotavirus, human and non-human papillomavirus and slow brain viruses can provide peptide antigens.

In some embodiments, the antigen comprises a viral vector, such as vaccinia, adenovirus, and canary pox.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362:833-839. Proteolytic enzymes can also be utilized to couple amino acids to produce peptides. Kullmann (1987) Enzymatic Peptide Synthesis, CRC Press, Inc. Alternatively, the peptide can be obtained by using the biochemical machinery of a cell, or by isolation from a biological source. Recombinant DNA techniques can be employed for the production of peptides. Hames et al. (1987) Transcription and Translation: A Practical Approach, IRL Press. Peptides can also be isolated using standard techniques such as affinity chromatography.

Preferably the antigens are peptides, lipids (e.g., sterols excluding cholesterol, fatty acids, and phospholipids), polysaccharides such as those used in *H. influenza* vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Examples of viral antigens useful in the subject compositions and methods using the compositions include, but are not limited to, HIV antigens. Such antigens include, but are not limited to, those antigens derived from HIV envelope glycoproteins including, but not limited to, gp160, gp120 and gp41. Numerous sequences for HIV genes and antigens are known. For example, the Los Alamos National Laboratory HIV Sequence Database collects, curates and annotates HIV nucleotide and amino acid sequences. This database is accessible via the internet and in a yearly publication, see Human Retroviruses and AIDS Compendium (for example, 2000 edition).

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

IMP-Antigen

When used with antigen, IMP may be administered with antigen in a number of ways. In some embodiments, an IMP and antigen may be administered spatially proximate with respect to each other, or as an admixture (i.e., in solution). As described below, spatial proximation can be accomplished in a number of ways, including conjugation (linkage), encapsidation, via affixation to a platform or adsorption onto a surface. Generally, and most preferably, an IMP and antigen are proximately associated at a distance effective to enhance the immune response generated compared to the administration of the IMP and the antigen as an admixture.

In some embodiments, the IMP is conjugated with the antigen. The IMP portion can be coupled with the antigen portion of a conjugate in a variety of ways, including covalent and/or non-covalent interactions.

The link between the portions can be made at the 3' or 5' end of the IMP, or at a suitably modified base at an internal position in the IMP. If the antigen is a peptide and contains a suitable reactive group (e.g., an N-hydroxysuccinimide ester) it can be reacted directly with the $N^4$ amino group of cytosine residues. Depending on the number and location of cytosine residues in the IMP, specific coupling at one or more residues can be achieved.

Alternatively, modified oligonucleosides, such as are known in the art, can be incorporated at either terminus, or at internal positions in the IMP. These can contain blocked functional groups which, when deblocked, are reactive with a variety of functional groups which can be present on, or attached to, the antigen of interest.

Where the antigen is a peptide or polypeptide, this portion of the conjugate can be attached to the 3'-end of the IMP through solid support chemistry. For example, the IMP portion can be added to a polypeptide portion that has been pre-synthesized on a support. Haralambidis et al. (1990a) *Nucleic Acids Res.* 18:493-499; and Haralambidis et al. (1990b) *Nucleic Acids Res.* 18:501-505. Alternatively, the IMP can be synthesized such that it is connected to a solid support through a cleavable linker extending from the 3'-end. Upon chemical cleavage of the IMP from the support, a terminal thiol group is left at the 3'-end of the oligonucleotide (Zuckermann et al. (1987) *Nucleic Acids Res.* 15:5305-5321; and Corey et al. (1987) *Science* 238:1401-1403) or a terminal amino group is left at the 3'-end of the oligonucleotide (Nelson et al. (1989) *Nucleic Acids Res.* 17:1781-1794). Conjugation of the amino-modified IMP to amino groups of the peptide can be performed as described in Benoit et al. (1987) *Neuromethods* 6:43-72. Conjugation of the thiol-modified IMP to carboxyl groups of the peptide can be performed as described in Sinah et al. (1991) *Oligonucleotide Analogues: A Practical Approach*, IRL Press. Coupling of an oligonucleotide carrying an appended maleimide to the thiol side chain of a cysteine residue of a peptide has also been described. Tung et al. (1991) *Bioconjug. Chem.* 2:464-465.

The peptide or polypeptide portion of the conjugate can be attached to the 5'-end of the IMP through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Subsequent to deprotection, the amine, thiol, and carboxyl functionalities can be used to covalently attach the oligonucleotide to a peptide. Benoit et al. (1987); and Sinah et al. (1991).

An IMP-antigen conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an IMP. Roget et al. (1989) *Nucleic Acids Res.* 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an IMP and residues within the antigen, such as charged amino acids, or through the use of a linker portion comprising charged residues that can interact with both the oligonucleotide and the antigen. For example, non-covalent conjugation can occur between a generally negatively-charged IMP and positively-charged amino acid residues of a peptide, e.g., polylysine, polyarginine and polyhistidine residues.

Non-covalent conjugation between IMP and antigens can occur through DNA binding motifs of molecules that interact with DNA as their natural ligands. For example, such DNA binding motifs can be found in transcription factors and anti-DNA antibodies.

The linkage of the IMP to a lipid can be formed using standard methods. These methods include, but are not limited to, the synthesis of oligonucleotide-phospholipid conjugates (Yanagawa et al. (1988) *Nucleic Acids Symp. Ser.* 19:189-192), oligonucleotide-fatty acid conjugates (Grabarek et al. (1990) *Anal. Biochem.* 185:131-135; and Staros et al. (1986) *Anal. Biochem.* 156:220-222), and oligonucleotide-sterol conjugates. Boujrad et al. (1993) *Proc. Natl. Acad. Sci. USA* 90:5728-5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347-355.

The linkage of a circular IMP to a peptide or antigen can be formed in several ways. Where the circular IMP is synthesized using recombinant or chemical methods, a modified nucleoside is suitable. Ruth (1991) in *Oligonucleotides and Analogues: A Practical Approach*, IRL Press. Standard linking technology can then be used to connect the circular IMP to the antigen or other peptide. Goodchild (1990) *Bioconjug. Chem.* 1:165. Where the circular IMP is isolated, or synthesized using recombinant or chemical methods, the linkage can be formed by chemically activating, or photoactivating, a reactive group (e.g. carbene, radical) that has been incorporated into the antigen or other peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug. Chem.* 3:138-146.

An IMP may be proximately associated with an antigen(s) in other ways. In some embodiments, an IMP and antigen are proximately associated by encapsulation. In other embodiments, an IMP and antigen are proximately associated by linkage to a platform molecule. A "platform molecule" (also termed "platform") is a molecule containing sites which allow for attachment of the IMP and antigen(s). In other embodiments, an IMP and antigen are proximately associated by adsorption onto a surface, preferably a carrier particle.

In some embodiments, the methods of the invention employ an encapsulating agent that can maintain the proximate association of the IMP and first antigen until the complex is available to the target (or compositions comprising such encapsulating agents). Preferably, the composition comprising IMP, antigen and encapsulating agent is in the form of adjuvant oil-in-water emulsions, microparticles and/or liposomes. More preferably, adjuvant oil-in-water emulsions, microparticles and/or liposomes encapsulating an IMP-immunomodulatory molecule are in the form of particles from about 0.04 µm to about 100 µm in size, preferably any of the following ranges: from about 0.1 µm to about 20 µm; from about 0.15 µm to about 10 µm; from about 0.05 µm to about 1.00 µm; from about 0.05 µm to about 0.5 µm.

Colloidal dispersion systems, such as microspheres, beads, macromolecular complexes, nanocapsules and lipid-based system, such as oil-in-water emulsions, micelles, mixed micelles and liposomes can provide effective encapsulation of IMP-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect an IMP-containing composition to preserve the immunomodulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use in the present invention include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The PEGs for use in encapsulation compositions of the present invention are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

A preferred colloidal dispersion system of this invention is a liposome. In mice immunized with a liposome-encapsulated antigen, liposomes appeared to enhance a Th1-type immune response to the antigen. Aramaki et al. (1995) *Vaccine* 13:1809-1814. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Processes for preparing liposomes containing IMP-containing compositions are known in the art. The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715-724. Techniques may be combined in order to provide vesicles with the most desirable attributes.

The invention encompasses use of LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can modulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions of the present invention can additionally comprise surfactants. Surfactants can be cationic, anionic, amphiphilic, or nonionic. A preferred class of surfactants are nonionic surfactants; particularly preferred are those that are water soluble.

In embodiments in which an IMP and antigen are proximately associated by linkage to a platform molecule, the platform may be proteinaceous or non-proteinaceous (i.e., organic). Examples of proteinaceous platforms include, but are not limited to, albumin, gammaglobulin, immunoglobulin (IgG) and ovalbumin Borel et al. (1990) *Immunol. Methods* 126:159-168; Dumas et al. (1995) *Arch. Dematol. Res.* 287: 123-128; Borel et al. (1995) *Int. Arch. Allergy Immunol.* 107: 264-267; Borel et al. (1996) *Ann. N.Y. Acad. Sci.* 778:80-87. A platform is multi-valent (i.e., contains more than one binding, or linking, site) to accommodate binding to both an IMP and antigen. Accordingly, a platform may contain 2 or more, 3 or more, 4 or more, 5 or more, 6 or more, 7 or more, 8 or more, 9 or more, 10 or more binding or linking sites Other examples of polymeric platforms are dextran, polyacrylamide, ficoll, carboxymethylcellulose, polyvinyl alcohol, and poly D-glutamic acid/D-lysine.

The principles of using platform molecules are well understood in the art. Generally, a platform contains, or is derivatized to contain, appropriate binding sites for IMP and antigen. In addition, or alternatively, IMP and/or antigen is derivatized to provide appropriate linkage groups. For example, a simple platform is a bi-functional linker (i.e., has two binding sites), such as a peptide. Further examples are discussed below.

Platform molecules may be biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 1,000,000, preferably any of the following ranges: from about 200 to about 500,000; from about 200 to about 200,000; from about 200 to about 50,000 (or less, such as 30,000). Examples of valency platform molecules are polymers (or are comprised of polymers) such as polyethylene glycol (PEG; preferably having a molecular weight of about 200 to about 8000), poly-D-lysine, polyvinyl alcohol, polyvinylpyrrolidone, D-glutamic acid and D-lysine (in a ratio of 3:2). Other molecules that may be used are albumin and IgG.

Other platform molecules suitable for use within the present invention are the chemically-defined, non-polymeric valency platform molecules disclosed in U.S. Pat. No. 5,552, 391. Other homogeneous chemically-defined valency platform molecules suitable for use within the present invention are derivatized 2,2'-ethylenedioxydiethylamine (EDDA) and triethylene glycol (TEG).

Additional suitable valency platform molecules include, but are not limited to, tetraminobenzene, heptaminobetacyclodextrin, tetraminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Conjugation of an IMP and antigen to a platform molecule may be effected in any number of ways, typically involving one or more crosslinking agents and functional groups on the antigen and IMP platform and platform molecule. Platforms and IMP and antigen must have appropriate linking groups. Linking groups are added to platforms using standard synthetic chemistry techniques. Linking groups may be added to polypeptide antigens and IMP using either standard solid phase synthetic techniques or recombinant techniques. Recombinant approaches may require post-translational modification in order to attach a linker, and such methods are known in the art.

As an example, polypeptides contain amino acid side chain moieties containing functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the antigen is a carbohydrate), functional amino, sulfhydryl and/or aldehyde groups may be incorporated therein by conventional chemistry. For instance, primary amino groups may be incorporated by reaction of the oxidized sugar with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

Hydrophilic linkers of variable lengths are useful for connecting IMP and antigen to platform molecules. Suitable linkers include linear oligomers or polymers of ethylene glycol. Such linkers include linkers with the formula $R^1S(CH_2CH_2O)_nCH_2CH_2O(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. These linkers are flexible with regard to the order of attachment, i.e., the thioether can be formed first or last.

In embodiments in which an IMP and antigen are proximately associated by adsorption onto a surface, the surface may be in the form of a carrier particle (for example, a nanoparticle) made with either an inorganic or organic core. Examples of such nanoparticles include, but are not limited to, nanocrystalline particles, nanoparticles made by the polymerization of alkylcyanoacrylates and nanoparticles made by the polymerization of methylidene malonate. Additional surfaces to which an IMP and antigen may be adsorbed include, but are not limited to, activated carbon particles and protein-ceramic nanoplates. Other examples of carrier particles are provided herein.

Adsorption of polynucleotides and polypeptides to a surface for the purpose of delivery of the adsorbed molecules to cells is well known in the art. See, for example, Douglas et al. (1987) *Crit. Rev. Ther. Drug. Carrier Syst.* 3:233-261; Hagiwara et al. (1987) *In Vivo* 1:241-252; Bousquet et al. (1999) *Pharm. Res.* 16:141-147; and Kossovsky et al., U.S. Pat. No. 5,460,831. Preferably, the material comprising the adsorbent surface is biodegradable. Adsorption of an IMP and/or antigen to a surface may occur through non-covalent interactions, including ionic and/or hydrophobic interactions.

In general, characteristics of carriers such as nanoparticles, such as surface charge, particle size and molecular weight, depend upon polymerization conditions, monomer concentration and the presence of stabilizers during the polymerization process (Douglas et al., 1987). The surface of carrier particles may be modified, for example, with a surface coating, to allow or enhance adsorption of the IMP and/or antigen. Carrier particles with adsorbed IMP and/or antigen may be further coated with other substances. The addition of such other substances may, for example, prolong the half-life of the particles once administered to the subject and/or may target the particles to a specific cell type or tissue, as described herein.

Nanocrystalline surfaces to which an IMP and antigen may be adsorbed have been described (see, for example, U.S. Pat. No. 5,460,831). Nanocrystalline core particles (with diameters of 1 µm or less) are coated with a surface energy modifying layer that promotes adsorption of polypeptides, polynucleotides and/or other pharmaceutical agents. As described in U.S. Pat. No. 5,460,831, for example, a core particle is coated with a surface that promotes adsorption of an oligonucleotide and is subsequently coated with an antigen preparation, for example, in the form of a lipid-antigen mixture. Such nanoparticles are self-assembling complexes of nanometer sized particles, typically on the order of 0.1 µm, that carry an inner layer of IMP and an outer layer of antigen.

Another adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987). For example, oligonucleotides may be adsorbed to polyisobutyl- and polyisohexlcyanoacrylate nanoparticles in the presence of hydrophobic cations such as tetraphenylphosphonium chloride or quaternary ammonium salts, such as cetyltrimethyl ammonium bromide. Oligonucleotide adsorption on these nanoparticles appears to be mediated by the formation of ion pairs between negatively charged phosphate groups of the nucleic acid chain and the hydrophobic cations. See, for example, Lambert et al. (1998) *Biochimie* 80:969-976, Chavany et al. (1994) *Pharm. Res.* 11:1370-1378; Chavany et al. (1992) *Pharm. Res.* 9:441-449. Polypeptides may also be adsorbed to polyalkylcyanoacrylate nanoparticles. See, for example, Douglas et al., 1987; Schroeder et al. (1998) *Peptides* 19:777-780.

Another adsorbent surface are nanoparticles made by the polymerization of methylidene malonate. For example, as described in Bousquet et al., 1999, polypeptides adsorbed to poly(methylidene malonate 2.1.2) nanoparticles appear to do so initially through electrostatic forces followed by stabilization through hydrophobic forces.

IMP/MC Complexes

IMPs may be administered in the form of immunomodulatory polynucleotide/microcarrier (IMP/MC) complexes. Accordingly, the invention provides compositions comprising IMP/MC complexes.

Microcarriers useful in the invention are less than about 150, 120 or 100 µm in size, more commonly less than about 50-60 µm in size, preferably less than about 10 µm in size, and are insoluble in pure water. Microcarriers used in the invention are preferably biodegradable, although nonbiodegradable microcarriers are acceptable. Microcarriers are commonly solid phase, such as "beads" or other particles, although liquid phase microcarriers such as oil in water emulsions comprising a biodegradable polymers or oils are also contemplated. A wide variety of biodegradable and nonbiodegradable materials acceptable for use as microcarriers are known in the art.

Microcarriers for use in the compositions or methods of the invention are generally less than about 10 µm in size (e.g., have an average diameter of less than about 10 µm, or at least about 97% of the particles pass through a 10 µm screen filter), and include nanocarriers (i.e., carriers of less than about 1 µm size). Preferably, microcarriers are selected having sizes within an upper limit of about 9, 7, 5, 2, or 1 µm or 900, 800, 700, 600, 500, 400, 300, 250, 200, or 100 nm and an independently selected lower limit of about 4, 2, or 1 µm or about 800, 600, 500, 400, 300, 250, 200, 150, 100, 50, 25, or 10 nm, where the lower limit is less than the upper limit. In some embodiments, the microcarriers have a size of about 1.0-1.5 µm, about 1.0-2.0 µm or about 0.9-1.6 µm. In certain preferred embodiments, the microcarriers have a size of about 10 nm to about 5 µm or about 25 nm to about 4.5 µm, about 1 µm, about 1.2 µm, about 1.4 µm, about 1.5 µm, about 1.6 µm, about 1.8 µm, about 2.0 µm, about 2.5 µm or about 4.5 µm. When the microcarriers are nanocarriers, preferred embodiments include nanocarriers of about 25 to about 300 nm, 50 to about 200 nm, about 50 nm or about 200 nm.

Solid phase biodegradable microcarriers may be manufactured from biodegradable polymers including, but not limited to: biodegradable polyesters, such as poly(lactic acid), poly(glycolic acid), and copolymers (including block copolymers) thereof, as well as block copolymers of poly(lactic acid) and poly(ethylene glycol); polyorthoesters such as polymers based on 3,9-diethylidene-2,4,8,10-tetraoxaspiro[5.5]undecane (DETOSU); polyanhydrides such as poly(anhydride) polymers based on relatively hydrophilic monomers such as sebacic acid; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al., (1996) *Biotechnol. Bioeng.* 1996:102); and polyamides such as poly(lactic acid-co-lysine).

A wide variety of nonbiodegradable materials suitable for manufacturing microcarriers are also known, including, but not limited to polystyrene, polypropylene, polyethylene, silica, ceramic, polyacrylamide, dextran, hydroxyapatite, latex, gold, and ferromagnetic or paramagnetic materials. Certain embodiments exclude gold, latex, and/or magnetic beads. In certain embodiments, the microcarriers may be made of a first material (e.g., a magnetic material) encapsulated with a second material (e.g., polystyrene).

Solid phase microspheres are prepared using techniques known in the art. For example, they can be prepared by emulsion-solvent extraction/evaporation technique. Generally, in this technique, biodegradable polymers such as polyanhydrates, poly(alkyl-α-cyanoacrylates) and poly(α-hydroxy esters), for example, poly(lactic acid), poly(glycolic acid), poly(D,L-lactic-co-glycolic acid) and poly(caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vacuum, before storing at 4° C.

Physico-chemical characteristics such as mean size, size distribution and surface charge of dried microspheres may be determined. Size characteristics are determined, for example, by dynamic light scattering technique and the surface charge was determined by measuring the zeta potential.

Liquid phase microcarriers include liposomes, micelles, oil droplets and other lipid or oil-based particles which incorporate biodegradable polymers or oils. In certain embodiments, the biodegradable polymer is a surfactant. In other embodiments, the liquid phase microcarriers are biodegradable due to the inclusion of a biodegradable oil such as squalene or a vegetable oil. One preferred liquid phase microcarrier is oil droplets within an oil-in-water emulsion. Preferably, oil-in-water emulsions used as microcarriers comprise biodegradable substituents such as squalene.

IMP/MC complexes comprise an IMP bound to the surface of a microcarrier (i.e., the IMP is not encapsulated in the MC), and preferably comprise multiple molecules of IMP bound to each microcarrier. In certain embodiments, a mixture of different IMPs may be complexed with a microcarrier, such that the microcarrier is bound to more than one IMP species. The bond between the IMP and MC may be covalent or non-covalent. As will be understood by one of skill in the art, the IMP may be modified or derivatized and the composition of the microcarrier may be selected and/or modified to accommodate the desired type of binding desired for IMP/MC complex formation.

Covalently bonded IMP/MC complexes may be linked using any covalent crosslinking technology known in the art. Typically, the IMP portion will be modified, either to incorporate an additional moiety (e.g., a free amine, carboxyl or sulfhydryl group) or incorporate modified (e.g., phosphorothioate) nucleotide bases to provide a site at which the IMP portion may be linked to the microcarrier. The link between the IMP and MC portions of the complex can be made at the 3' or 5' end of the IMP, or at a suitably modified base at an internal position in the IMP. The microcarrier is generally also modified to incorporate moieties through which a covalent link may be formed, although functional groups normally present on the microcarrier may also be utilized. The IMP/MC is formed by incubating the IMP with a microcarrier under conditions which permit the formation of a covalent complex (e.g., in the presence of a crosslinking agent or by use of an activated microcarrier comprising an activated moiety which will form a covalent bond with the IMP).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the IMP and the microcarrier as well as the desired final configuration of the IMP/MC complex. The crosslinker may be either homobifunctional or heterobifunctional. When a homobifunctional crosslinker is used, the crosslinker exploits the same moiety on the IMP and MC (e.g., an aldehyde crosslinker may be used to covalently link an IMP and MC where both the IMP and MC comprise one or more free amines). Heterobifunctional crosslinkers utilize different moieties on the IMP and MC, (e.g., a maleimido-N-hydroxysuccinimide ester may be used to covalently link a free sulfhydryl on the IMP and a free amine on the MC), and are preferred to minimize formation of inter-microcarrier bonds. In most cases, it is preferable to crosslink through a first crosslinking moiety on the microcarrier and a second crosslinking moiety on the IMP, where the second crosslinking moiety is not present on the microcarrier. One preferred method of producing the IMP/MC complex is by 'activating' the microcarrier by incubating with a heterobifunctional crosslinking agent, then forming the IMP/MC complex by incubating the IMP and activated MC under conditions appropriate for reaction. The crosslinker may incorporate a "spacer" arm between the reactive moieties, or the two reactive moieties in the crosslinker may be directly linked.

In one preferred embodiment, the IMP portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the IMP to form the IMP/MC complex.

Non-covalent IMP/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the IMP and MC.

Preferred non-covalent IMP/MC complexes are typically complexed by hydrophobic or electrostatic (ionic) interactions, or a combination thereof, (e.g., through base pairing between an IMP and a polynucleotide bound to an MC use of a binding pair). Due to the hydrophilic nature of the backbone of polynucleotides, IMP/MC complexes which rely on hydrophobic interactions to form the complex generally require modification of the IMP portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of preferred hydrophobic moieties include lipids, steroids, sterols such as cholesterol, and terpenes. The method of linking the hydrophobic moiety to the IMP will, of course, depend on the configuration of the IMP and the identity of the hydrophobic moiety. The hydrophobic moiety may be added at any convenient site in the IMP, preferably at either the 5' or 3' end; in the case of addition of a cholesterol moiety to an IMP, the cholesterol moiety is preferably added to the 5' end of the IMP, using conventional chemical reactions (see, for example, Godard et al. (1995) *Eur. J. Biochem.* 232:404-410). Preferably, microcarriers for use in IMP/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen, the IMP/MC complex is formed by mixing the IMP and the MC after preparation of the MC, in order to avoid encapsulation of the IMP during the MC preparation process.

Non-covalent IMP/MC complexes bound by electrostatic binding typically exploit the highly negative charge of the polynucleotide backbone. Accordingly, microcarriers for use in non-covalently bound IMP/MC complexes are generally positively charged (cationic) at physiological pH (e.g., about pH 6.8-7.4). The microcarrier may intrinsically possess a positive charge, but microcarriers made from compounds not normally possessing a positive charge may be derivatized or otherwise modified to become positively charged (cationic). For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles).

As described herein, to prepare cationic microspheres, cationic lipids or polymers, for example, 1,2-dioleoyl-1,2,3-trimethylammoniopropane (DOTAP), cetyltrimethylammonium bromide (CTAB) or polylysine, are added either to DP or CP, as per their solubility in these phases.

As described herein, IMP/MC complexes can be preformed by adsorption onto cationic microspheres by incubation of polynucleotide and the particles, preferably in an aqueous admixture. Such incubation may be carried out under any desired conditions, including ambient (room) temperature (e.g., approximately 20° C.) or under refrigeration (e.g., 4° C.). Because cationic microspheres and polynucleotides associate relatively quickly, the incubation may be for any convenient time period, such as 5, 10, 15 minutes or more, including overnight and longer incubations. For example, IMPs can be adsorbed onto the cationic microspheres by overnight aqueous incubation of polynucleotide and the particles at 4° C. However, because cationic microspheres and polynucleotides spontaneously associate, the IMP/MC complex can be formed by simple co-administration of the polynucleotide and the MC. Microspheres may be characterized for size and surface charge before and after polynucleotide association. Selected batches may then evaluated for activity against suitable controls in, for example, established human peripheral blood mononuclear cell (PBMC), as described herein, and mouse splenocyte assays. The formulations may also evaluated in suitable animal models.

Non-covalent IMP/MC complexes linked by nucleotide base pairing may be produced using conventional methodologies. Generally, base-paired IMP/MC complexes are produced using a microcarrier comprising a bound, preferably a covalently bound, polynucleotide (the "capture polynucleotide") that is at least partially complementarity to the IMP. The segment of complementarity between the IMP and the capture nucleotide is preferably at least 6, 8, 10 or 15 contiguous base pairs, more preferably at least 20 contiguous base pairs. The capture nucleotide may be bound to the MC by any method known in the art, and is preferably covalently bound to the IMP at the 5' or 3' end.

In other embodiments, a binding pair may be used to link the IMP and MC in an IMP/MC complex. The binding pair may be a receptor and ligand, an antibody and antigen (or epitope), or any other binding pair which binds at high affinity (e.g., Kd less than about 10-8). One type of preferred binding pair is biotin and streptavidin or biotin and avidin, which form very tight complexes. When using a binding pair to mediate IMP/MC complex binding, the IMP is derivatized, typically by a covalent linkage, with one member of the binding pair, and the MC is derivatized with the other member of the binding pair. Mixture of the two derivatized compounds results in IMP/MC complex formation.

Many IMP/MC complex embodiments do not include an antigen, and certain embodiments exclude antigen(s) associated with the disease or disorder which is the object of the IMP/MC complex therapy. In further embodiments, the IMP is also bound to one or more antigen molecules. Antigen may be coupled with the IMP portion of an IMP/MC complex in a variety of ways, including covalent and/or non-covalent interactions, as described, for example, in WO 98/16247. Alternately, the antigen may be linked to the microcarrier. The link between the antigen and the IMP in IMP/MC complexes comprising an antigen bound to the IMP can be made by techniques described herein and known in the art, including, but not limited to, direct covalent linkage, covalent conjugation via a crosslinker moiety (which may include a spacer arm), noncovalent conjugation via a specific binding pair (e.g., biotin and avidin), and noncovalent conjugation via electrostatic or hydrophobic bonding.

IMP Complexes with Cationic Condensing Gent and Stabilizing Agent

IMPs may be administered as a composition comprising a cationic condensing agent, an IMP, and a stabilizing agent (i.e., CIS composition) for modulating an immune response in the recipient. See, U.S. Patent Application No. 60/402,968. In some embodiments, the CIS composition may also comprise an antigen and/or a fatty acid.

The CIS compositions of the invention are typically in particulate form. As will be apparent to those of skill in the art, CIS particulate compositions of the invention will consist of a population of particles of different sizes. Due to this naturally arising variability, the "size" of the particles in the compositions of the invention may be described in ranges or as a maximum or minimum diameter. Particles are considered to be a particular size if at least 95% of the particles (by mass) meet the specified dimension (e.g., if at least 97% of the particles are less than 20 µm in diameter, then the composition is considered to consist of particles of less than 20 µm in diameter). Particle size may be measured by any convenient method known in the art, including filtration (e.g., use of a "depth" filter to capture particles greater than a cutoff size), dynamic light scattering, electron microscopy, including TEM (particularly in combination with freeze-fracture processing) and SEM, and the like.

Preferably, the CIS compositions of the invention comprise particles which are less than about 50 µm in diameter, more preferably less than about 20 µm in diameter, although in some embodiments the particles will be less than about 3, 2 or 1 µm in diameter. Preferred particle size ranges include about 0.01 µm to 50 µm, 0.02 to 20 µm, 0.05 to 5 µm, and 0.05 to 3 µm in diameter.

The components of the CIS compositions may be present in various ratios/quantities in the compositions, although it is contemplated that the amounts of the stabilizing agent(s) and optional components such as fatty acids and antigen will remain relatively invariant, with stabilizing agents generally ranging from about 0.1% to 0.5% (v/v), fatty acids ranging from about 0 to 0.5%, and antigen concentrations ranging from about 0.1 to about 100 µg/mL, preferably about 1 to about 100 µg/mL, more preferably about 10 to 50 µg/mL. The amounts and ratios of the IMP and the cationic condensing agent are subject to a greater range of variation in the compositions of the invention. The amount of IMP will vary to a certain extent as a function of the molecular weight of the IMP, and generally ranges from about 50 µg/mL to about 2 mg/mL, preferably about 100 µg/mL to 1 mg/mL. The cationic condensing agent is generally present in excess (in terms of mass) over the IMP, generally in ratios of about 1:2 (IMP:cationic condensing agent) to about 1:6, more preferably about 2:5 to 1:5.

Particle size in the CIS compositions is a function of a number of variables. The size distribution of particles in the compositions can be modulated by altering the ratio of cationic condensing agent to IMP. For example, altering the ratio of cationic condensing agent to IMP in the exemplary +ISS/0.4% Tween 85/0.4% oleate/polymyxin B compositions can alter mean particle size from about 1.5 µm at cationic condensing agent:IMC=1 to about 45 µm at cationic condensing agent:IMP=10.

In certain embodiments, the CIS compositions comprise a cationic condensing agent, an IMP and a stabilizing agent that is a nonionic detergent. In other embodiments, the compositions comprise a membrane disrupting cationic lipopeptide (preferably a polymyxin, more preferably polymyxin B), an IMP and a stabilizing agent. In some embodiments the stabilizing agent is not a serum protein (particularly not a bovine serum protein). An exemplary composition of this class of embodiments utilizes a polyoxyethylene ether detergent such as Tween 80 or Tween 85 as the stabilizing agent, with oleate as an optional additional stabilizing agent.

In some embodiments, CIS compositions comprise immunomodulatory particles, wherein the particles are made by the process of combining a cationic condensing agent, an IMP and a stabilizing agent that is a nonionic detergent. In other embodiments, compositions of the invention comprise immunomodulatory particles, wherein the particles are made by the process of combining a membrane disrupting cationic lipopeptide (preferably a polymyxin, more preferably polymyxin B), an IMP and a stabilizing agent. In some embodiments the stabilizing agent is not a serum protein (particularly not a bovine serum protein).

In some embodiments, CIS compositions comprise immunomodulatory particles, wherein the particles are formed by the process of combining an IMP and a stabilizing agent that is a nonionic detergent, thereby forming an IMP/stabilizing agent mixture, and combining a cationic condensing agent with the IMP/stabilizing agent mixture. In other embodiments, compositions of the invention comprise immunomodulatory particles, wherein the particles are formed by the process of combining an IMP and a stabilizing agent, thereby forming an IMP/stabilizing agent mixture, and combining a membrane disrupting cationic lipopeptide (preferably a polymyxin, more preferably polymyxin B) with the IMP/stabilizing agent mixture. In some embodiments the stabilizing agent is not a serum protein (particularly not a bovine serum protein).

In some embodiments, CIS compositions comprise immunomodulatory particles, wherein the particles comprise a cationic condensing agent, an IMP and a stabilizing agent that is a nonionic detergent. In other embodiments, compositions of the invention comprise immunomodulatory particles, wherein the particles comprise a membrane disrupting cationic lipopeptide (preferably a polymyxin, more preferably polymyxin B), an IMP and a stabilizing agent. In some embodiments the stabilizing agent is not a serum protein (particularly not a bovine serum protein).

Cationic condensing agents useful in the CIS compositions and methods of using the CIS compositions are molecules which are positively charged at physiological pH (i.e., pH of about 7.0 to about 7.5). Preferably, cationic condensing agents used in the instant invention are not zwitterionic and are polycationic, that is, having more than one positive charge per molecule. Cationic condensing agents useful in the instant invention include hydrophilic or amphipathic polycations.

Preferred cationic condensing agents include: (a) membrane disrupting cationic lipopeptides including, but not limited to polymyxins including polymyxin A, polymyxin B (including polymyxin $B_1$ and polymyxin $B_2$), polymyxin C, polymyxin D, polymyxin E (also known as colistin), polymyxin K, polymyxin M, polymyxin P, polymyxin S and polymyxin T, circulins including circulin A, circulin B, circulin C, circulin D, circulin E and circulin F, octapeptin, amphotericins including amphotericin B, and acylated peptides including octanoyl-KFFKFFKFF (SEQ ID NO:182) and acyl KALA (octanoyl-WEAKLAKALAKALAKHLAKALAKALEACEA (SEQ ID NO:183); (b) membrane disrupting cationic peptides including, but not limited to polymyxin B nonapeptide, cecropins including cecropin A, cecropin B and cecropin P1, KFFKFFKFF (SEQ ID NO:182) and KALA (WEAKLAKALAKALAKHLAKALAKALKACEA) (SEQ ID NO:184); (c) single chain cationic surfactants including, but not limited to cetyltrimethylammonium bromide (CTAB), benzyl-dimethyl-ammonium bromide (BDAB), CpyrB (cetyl-pyridinium bromide), CimB (cetyl imidazolium bromide), and polycationic polymers, including, but not limited to, poly-L-lysine (PLL) and polyethyleneimine (PEI). In certain embodiments, the cationic condensing agent is a membrane disrupting cationic lipopeptide, preferably a polymyxin, more preferably polymyxin B. In some embodiments, cationic condensing agents may exclude fatty acid esters (i.e., lipids) and double chain cationic surfactants.

Stabilizing agents useful in the CIS compositions and methods of using the CIS compositions include those which are suspendable in water and reduce the surface tension of water, although stabilizing agents which are water soluble and/or completely miscible in water are preferred. A number of classes of stabilizing agents are useful in the compositions and methods of the invention, including proteins (preferably hydrophilic proteins), nonionic detergents, polymeric surfactants (e.g., polyvinyl alcohol and polyvinyl pyrrolidone), cationic detergents, anionic detergents and fatty acids, although in certain embodiments, serum proteins (particularly bovine serum proteins), fatty acids, and/or ionic detergents may be excluded from the definition of stabilizing agents.

Any protein may be used as a stabilizing agent in accordance with the invention. In some embodiments, the stabilizing agent is a protein which is not intended as an antigen (see discussion below); in these embodiments, it is preferred that the protein be derived from the same species as the intended recipient of the composition (e.g., if the composition is intended for use in humans, then it is preferred that the protein used as the stabilizing agent be a human protein). Serum albumin is an exemplary protein useful as a stabilizing agent in such embodiments. In other embodiments, an antigen is utilizing as the stabilizing agent, in which case the antigen need not be, and in general is preferably not, species matched with the intended recipient. Antigens useful in the compositions and methods of the invention are disclosed below.

Nonionic detergents useful in the CIS compositions and methods of using the CIS compositions include glucamides such as decyldimethylphosphine oxide (APO-10) and dimethyldodecylphosphine oxide (APO-12), octanoyl-N-methylglucamide (MEGA-8), nonanoyl-N-methylglucamide (MEGA-9) and decanoyl-N-methyl glucamide (MEGA-10), polyoxyethylene ether detergents including polyoxyethylene (10) dodecyl ester (Genapol C100), polyoxyethylene(4) lauryl ether (BRIJ® 30), polyoxyethylene(9) lauryl ether (LUBROL® PX) polyoxyethylene(23) lauryl ether (BRIJ® 35), polyoxyethylene(2) cetyl ether (BRIJ® 52), polyoxyethylene (10) cetyl ether (BRIJ® 56), polyoxyethylene(20) cetyl ether (BRIJ® 58), polyoxyethylene(2) stearyl ether (BRIJ® 72), polyoxyethylene(10) stearyl ether (BRIJ® 76), polyoxyethylene(20) stearyl ether (BRIJ® 78), polyoxyethylene(100) stearyl ether (BRIJ® 700), polyoxyethylene(2) oleyl ether (BRIJ® 92), polyoxyethylene(10) oleyl ether (BRIJ® 97), polyoxyethylene(20) oleyl ether (BRIJ® 98), isotridecylpoly (ethyleneglycolether)$_8$ (Genapol 80), PLURONIC® F-68, PLURONIC® F-127, dodecylpoly(ethyleneglycolether)$_9$ (Thesit) polyoxyethylene(10) isooctylphenyl ether (TRITON® X-100), polyoxyethylene(8) isooctylphenyl ether (TRITON® X-114), polyethylene glycol sorbitan monolaurate (TWEEN® 20), polyoxyethylenesorbitan monopalmitate (TWEEN® 40), polyethylene glycol sorbitan monostearate (TWEEN® 60), polyoxyethylenesorbitan tristearate (TWEEN® 65), polyethylene glycol sorbitan monooleate (TWEEN® 80), polyoxyethylene(20) sorbitan trioleate (TWEEN® 85), poloxamer 188, and polyethyleneglycol-p-isooctylphenyl ether (Nonidet NP40), alkyl maltoside detergents including cyclohexyl-n-ethyl-β-D-maltoside, cyclohexyl-n-hexyl-β-D-maltoside, and cyclohexyl-n-methyl-β-D-maltoside, n-decanoylsucrose, glucopyranosides including methyl 6-O—(N-heptylcarbamoyl)-α-D-glucopyranoside (HECAMEG) and alkyl glucopyranosides such as n-decyl-β-D-glucopyranoside, n-heptyl-β-D-glucopyranoside, n-dodecyl-β-D-glucopyranoside, n-nonyl-β-D-glucopyranoside, n-octyl-α-D-glucopyranoside, and n-octyl-β-D-glucopyranoside, alkyl thioglucopyranosides including n-heptyl-β-D-thioglucopyranoside, alkyl maltopyranosides including n-decyl-β-D-maltopyranoside and n-octyl-β-D-maltopyranoside, n-decyl-β-D-thiomaltoside, digitonin, n-dodecanoyl sucrose, n-dodecyl-β-D-maltoside, heptane 1,2,3-triol, n-octanoyl-β-D-glucosylamine (NOGA), n-octanoyl sucrose, poloxamers (polyoxyethylene/polyoxypropylene block copolymers) such as poloxamer 188 and poloxamer 407, and sulfobetaines including SB-10, SB-12, and SB-14 and n-undecyl-β-D-maltoside. Preferred stabilizing agents include polyoxyethylene ether detergents, particularly polyethylene glycol sorbitan monooleate and polyoxyethylene(20) sorbitan trioleate.

Anionic detergents useful in the CIS compositions and methods of using the CIS compositions include caprylic acid and salts thereof, chenodeoxycholic acid and salts thereof, cholic acid and salts thereof, decanesulfonic acid and salts thereof, deoxycholic acid and salts thereof, glycodeoxycholic acid and salts thereof, lauroylsarcosine and salts thereof, n-dodecyl sulfate and salts thereof (including sodium and lithium salts), taurochenodeoxycholic acid and salts thereof, taurocholic acid and salts thereof, taurodehydrocholic acid and salts thereof, taurodeoxycholic acid and salts thereof, taurolithocholic acid and salts thereof, and tauroursodeoxycholic acid and salts thereof.

Cationic detergents include cetylpyridinium and salts thereof, cetyltrimethylamonia and salts thereof including cetyltrimethylammonium bromide (CTAB), dodecyltrimethylammonia and salts thereof including dedecyltrimethylammonium bromide, alklylammonium imidazolines, quaternary imidazolines, and tetradecyltrimtheylammonia and salts thereof including tetradecyltrimtheylammonium bromide.

Detergents selected for use as stablizing agents are preferably those that are considered oil/water emulsifying detergents. Oil/water emulsifying detergents are known in the art, and are generally characterized by a hydrophobic/lipophilic balance (HLB) value of about 8 to about 18. Preferably, detergents incorporated into the particulate compositions have HLB values of about 10 to about 16, more preferably about 11 to about 15 (e.g., polyethylene glycol sorbitan monooleate, HLB=15.4; polyoxyethylene(10) isooctylphenyl ether, HLB=13.5; polyoxyethylene(20) sorbitan trioleate HLB=11).

In certain embodiments, the CIS compositions may also include one or more fatty acids, or a salt thereof, as an additional component. In those embodiments employing a fatty acid as the stablizing agent component and a fatty acid as an additional component of the composition, the fatty acid utilized as the stablizing agent will be different than the fatty acid used as the 'additional' component. Fatty acids useful in the CIS compositions of the invention may range in size from four to 30 carbon atoms, and may be unsaturated (e.g., stearic acid), monounsaturated (e.g., oleic acid), or polyunsaturated (e.g., linoleic acid), although monounsaturated and polyunsaturated fatty acids are generally preferred.

In some embodiments, the CIS compositions will incorporate a fatty acid having a carbon chain length of at least about 4, 5, 6, 8, 10, 15, 18, or 20 carbon atoms and less than about 30, 25, 20, 19, 15 or 10 carbon atoms. Accordingly, in some embodiments the fatty acids utilized in the invention may have carbon chains with a length in the range of about 4 to 30, 5 to 25, 10 to 20, or 15 to 20 carbon atoms.

Fatty acids useful in the CIS compositions include, but are not limited to, arachidonic acid, decanoic acid, docosanoic acid, docosahexanoic acid eicosanoic acid, heneicosanoic acid, heptadecanoic acid, heptanoic acid, hexanoic acid, lauric acid, linoleic acid, linolenic acid, myristic acid, nonadecanoic acid, nonanoic acid, octanoic acid, oleic acid, palmitic acid, pentadecanoic acid, stearic acid, tetracosanoic acid, tricosanoic acid, tridecanoic acid, and undecanoic acid. Preferred fatty acids for use in the CIS compositions include oleic acid palmitoleic acid, and linoleic acid.

In certain embodiments of the invention, an antigen is incorporated into the CIS composition or administered in combination with a CIS composition. Those CIS compositions incorporating an antigen may incorporate the antigen into the particulate composition itself, or be dissolved or suspended in the solution in which the particulate composition is suspended. Any antigen may be incorporated into or co-administered with a CIS composition of the invention.

METHODS OF THE INVENTION

As described herein, IMPs of the invention may particularly stimulate production of IL-6, TNF-α, IFN-γ and of type I interferons, including IFN-α and IFN-ω, stimulate B cell proliferation and/or activate plasmacytoid dendritic cells to differentiate. The IMPs of the invention may also stimulate production of other cytokines, chemokines and activation-associated proteins including, but not limited to, IP-10 (interferon induced protein 10 kDa), MCP-1 (monocyte chemoattractant protein 1), MCP-2, MCP-3, MIG, MIP-3b, CD80, CD86, CD40, CD54 and MHC class II. The IMPs of the invention may also stimulate expression of IFN-α-inducible genes including, but not limited to 2,5-oligoadenylate synthatse (2,5-OAS), interferon-stimulating gene-54K (ISG-54K) and guanylate-binding protein-1 (GBP-1). The immunomodulatory polynucleotides of the invention also may provide a signal that retards plasmacytoid dendritic cell apoptosis. The immunomodulatory polynucleotides of the invention also may stimulate natural killer (NK) cell lytic activity. Accordingly, the IMPs of the invention are particularly effective in modulating an immune response in an individual.

The invention provides methods of modulating an immune response in an individual, preferably a mammal, more preferably a human, comprising administering to the individual an IMP as described herein. Immunomodulation may include stimulating a Th1-type immune response and/or inhibiting or reducing a Th2-type immune response. The IMP is administered in an amount sufficient to modulate an immune response. As described herein, modulation of an immune response may be humoral and/or cellular, and is measured using standard techniques in the art and as described herein.

For example, the modulation of an immune response of an animal or population of cells, e.g., mammalian, optionally human, blood cells (e.g., PBMCs, lymphocytes, dendritic cells), bronchial alveolar lavage cells, or other cells or cell populations containing ISS-responsive cells, is accomplished by contacting the cells with an IMP or IMP-containing composition described herein (e.g., a composition containing an IMP, IMP and an antigen, an IMP-antigen conjugate, an IMP/microcarrier complex, etc.). The modulation can be accomplished by any form of contacting, including without limitation, co-incubation of cells and IMP in vitro, application of the IMP to skin of a mammal (e.g., of an experimental animal), and parenteral administration.

An immune response in animals or cell populations can be detected in any number of ways, including increased expression of one or more of IFN-γ, IFN-α, IL-2, IL-12, TNF-α, IL-6, IL-4, IL-5, IP-10, ISG-54K, MCP-1, or a change in gene expression profile characteristics of immune stimulation as well as responses such as B cell proliferation and dendritic cell maturation. The ability to stimulate an immune response in a cell population has a number of uses, e.g., in an assay system for immunosuppressive agents.

A number of individuals are suitable for receiving the immunomodulatory polynucleotide(s) described herein. Preferably, but not necessarily, the individual is human.

In certain embodiments, the individual suffers from a disorder associated with a Th2-type immune response, such as allergies or allergy-induced asthma. Administration of an IMP results in immunomodulation, increasing levels of one or more Th1-type response associated cytokines, which may result in a reduction of the Th2-type response features associated with the individual's response to the allergen. Immunomodulation of individuals with Th2-type response associated disorders results in a reduction or improvement in one or more of the symptoms of the disorder. Where the disorder is allergy or allergy-induced asthma, improvement in one or more of the symptoms includes a reduction one or more of the following: rhinitis, allergic conjunctivitis, circulating levels of IgE, circulating levels of histamine and/or requirement for 'rescue' inhaler therapy (e.g., inhaled albuterol administered by metered dose inhaler or nebulizer).

In further embodiments, the individual subject to the immunomodulatory therapy of the invention is an individual receiving a vaccine. The vaccine may be a prophylactic vaccine or a therapeutic vaccine. A prophylactic vaccine comprises one or more epitopes associated with a disorder for which the individual may be at risk (e.g., *M. tuberculosis* antigens as a vaccine for prevention of tuberculosis). Therapeutic vaccines comprise one or more epitopes associated with a particular disorder affecting the individual, such as *M. tuberculosis* or *M. bovis* surface antigens in tuberculosis patients, antigens to which the individual is allergic (i.e., allergy desensitization therapy) in individuals subject to allergies, tumor cells from an individual with cancer (e.g., as described in U.S. Pat. No. 5,484,596), or tumor associated antigens in cancer patients.

The IMP may be given in conjunction with the vaccine (e.g., in the same injection or a contemporaneous, but separate, injection) or the IMP may be administered separately (e.g., at least 12 hours before or after administration of the vaccine). In certain embodiments, the antigen(s) of the vaccine is part of the IMP, by either covalent or non-covalent linkage to the IMP. In other embodiments, the IMP may be administered alone as a prophylactic vaccine to increase resistance to infection by a wide range of bacterial or viral pathogens, including natural or genetically modified organisms employed as agents of biological warfare or terrorism. Administration of immunomodulatory polynucleotide therapy to an individual receiving a vaccine results in an immune response to the vaccine that is shifted towards a Th1-type response as compared to individuals which receive vaccine without IMP. Shifting towards a Th1-type response may be recognized by a delayed-type hypersensitivity (DTH) response to the antigen(s) in the vaccine, increased IFN-γ and other Th1-type response associated cytokines, production of CTLs specific for the antigen(s) of the vaccine, low or reduced levels of IgE specific for the antigen(s) of the vaccine, a reduction in Th2-associated antibodies specific for the antigen(s) of the vaccine, and/or an increase in Th1-associated antibodies specific for the antigen(s) of the vaccine. In the case of therapeutic vaccines, administration of IMP and vaccine results in amelioration of one or more symptoms of the disorder which the vaccine is intended to treat. As will be apparent to one of skill in the art, the exact symptom(s) and manner of their improvement will depend on the disorder sought to be treated. For example, where the therapeutic vaccine is for tuberculosis, IMP treatment with vaccine results in reduced coughing, pleural or chest wall pain, fever, and/or other symptoms known in the art. Where the vaccine is an allergen used in allergy desensitization therapy, the treatment results in a reduction in the symptoms of allergy (e.g., reduction in rhinitis, allergic conjunctivitis, circulating levels of IgE, and/or circulating levels of histamine).

Other embodiments of the invention relate to immunomodulatory therapy of individuals having a pre-existing disease or disorder, such as cancer or an infectious disease. Cancer is an attractive target for immunomodulation because most cancers express tumor-associated and/or tumor specific antigens which are not found on other cells in the body. Stimulation of a Th1-type response against tumor cells results in direct and/or bystander killing of tumor cells by the immune system, leading to a reduction in cancer cells and/or a reduction in symptom(s). Administration of an IMP to an individual having cancer results in stimulation of a Th1-type immune response against the tumor cells. Such an immune response can kill tumor cells, either by direct action of cellular immune system cells (e.g., CTLs, NK cells) or components of the humoral immune system, or by bystander effects on cells proximal to cells targeted by the immune system. See, for example, Cho et al. (2000) *Nat. Biotechnol.* 18:509-514. In the cancer context, administration of IMPs may further comprise administration of one or more additional therapeutic agents such as, for example, anti-tumor antibodies, chemotherapy regimens and/or radiation treatments. Anti-tumor antibodies, including, but not limited to anti-tumor antibody fragments and/or derivatives thereof, and monoclonal anti-tumor antibodies, fragments and/or derivatives thereof, are known in the art as is administration of such antibody reagents in cancer therapy (e.g., Rituxan® (rituximab); Herceptin® (trastuzumab)). Administration of one or more additional therapeutic agents may occur before, after and/or concurrent with administration of the IMPs.

Immunomodulatory therapy in accordance with the invention is also useful for individuals with infectious diseases, particularly infectious diseases which are resistant to humoral immune responses (e.g., diseases caused by mycobacterial infections and intracellular pathogens). Immunomodulatory therapy may be used for the treatment of infectious diseases caused by cellular pathogens (e.g., bacteria or protozoans) or by subcellular pathogens (e.g., viruses). IMP therapy may be administered to individuals suffering from mycobacterial diseases such as tuberculosis (e.g., *M. tuberculosis* and/or *M. bovis* infections), leprosy (i.e., *M. leprae* infections), or *M. marinum* or *M. ulcerans* infections. IMP therapy is also useful for the treatment of viral infections, including infections by influenza virus, respiratory syncytial virus (RSV), hepatitis virus B, hepatitis virus C, herpes viruses, particularly herpes simplex viruses, and papilloma viruses. Diseases caused by intracellular parasites such as malaria (e.g., infection by *Plasmodium vivax, P. ovale, P. falciparum* and/or *P. malariae*), leishmaniasis (e.g., infection by *Leishmania donovani, L. tropica, L. mexicana, L. braziliensis, L. peruviana, L. infantum, L. chagasi,* and/or *L. aethiopica*), and toxoplasmosis (i.e., infection by *Toxoplasmosis gondii*) also benefit from IMP therapy. IMP therapy is also useful for treatment of parasitic diseases such as schistosomiasis (i.e., infection by blood flukes of the genus *Schistosoma* such as *S. haematobium, S. mansoni, S. japonicum,* and *S. mekongi*) and clonorchiasis (i.e., infection by *Clonorchis sinensis*). Administration of an IMP to an individual suffering from an infectious disease results in an amelioration of symptoms of the infectious disease. In some embodiments, the infectious disease is not a viral disease.

The invention further provides methods of increasing or stimulating at least one Th1-associated cytokine in an individual, including IL-2, IL-12, TNF-β, IFN-γ and IFN-α. In certain embodiments, the invention provides methods of increasing or stimulating IFN-γ in an individual, particularly in an individual in need of increased IFN-γ levels, by administering an effective amount of an IMP to the individual such that IFN-γ is increased. Individuals in need of increased IFN-γ are those having disorders which generally respond to the administration of IFN-γ. Such disorders include a number of inflammatory disorders including, but not limited to, ulcerative colitis. Such disorders also include a number of fibrotic disorders, including, but not limited to, idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ. Administration of IMP in accordance with the invention results in an increase in IFN-γ levels, and results in amelioration of one or more symptoms, stabilization of one or more symptoms, and/or prevention or slowing of progression (e.g., reduction or elimination of additional lesions or symptoms) of the disorder which responds to IFN-γ.

The methods of the invention may be practiced in combination with other therapies which make up the standard of care for the disorder, such as administration of anti-inflammatory agents such as systemic corticosteroid therapy (e.g., cortisone) in IPF.

In certain embodiments, the invention provides methods of increasing type I interferon, including IFN-α, IFN-β and IFN-ω, in an individual, particularly in an individual in need of increased type I interferon levels, by administering an effective amount of an IMP to the individual such that type I interferon levels are increased. In certain embodiments, the invention provides methods of increasing IFN-α in an individual, particularly in an individual in need of increased IFN-α levels, by administering an effective amount of an IMP to the individual such that IFN-α levels are increased. Individuals in need of increased IFN-α are those having disorders which generally respond to the administration of IFN-α, including recombinant IFN-α, including, but not limited to, viral infections and cancer. In some embodiments in which increased production of higher levels of IFN-α is desired, the IMP contains at least one palindromic sequence of at least the following lengths (in bases): 10, 12, 14, 16, 18, 20, 22, 24, 26, 28 or 30, and, in some embodiments, the IMP contains at least one palindromic sequence with a length longer than 30 bases.

Administration of IMP in accordance with the invention results in an increase in IFN-α levels, and results in amelioration of one or more symptoms, stabilization of one or more symptoms, and/or prevention or slowing of progression (e.g., reduction or elimination of additional lesions or symptoms) of the disorder which responds to IFN-α. The methods of the invention may be practiced in combination with other therapies which make up the standard of care for the disorder, such as administration of anti-viral agents for viral infections.

Also provided are methods of reducing levels, particularly serum levels, of IgE in an individual having an IgE-related disorder by administering an effective amount of an IMP to the individual. In such methods, the immunomodulatory polynucleotide may be administered alone (e.g., without antigen) or administered with antigen, such as an allergen. Reduction in IgE results in an amelioration of one or more symptoms of the IgE-related disorder. Such symptoms include allergy symptoms such as rhinitis, conjunctivitis, in decreased sensitivity to allergens, a reduction in the symptoms of allergy in an individual with allergies, or a reduction in severity of an allergic response. Accordingly, the invention also provides methods of treating an allergic condition in an individual. In some embodiments, methods of treating an allergic condition include administering the immunomodulatory polynucleotide with a particular amount or dose of antigen. With any additional antigen administration, the amount or dose of antigen administered can remain the same, can decease or can increase (as in conventional desensitization therapy) over the course of treatment.

In some embodiments, the invention provides methods of stimulating CTL production in an individual, particularly in an individual in need of increased number and/or activity of CTLs, comprising administering an effective amount of an IMP to the individual such that CTL production is increased. Individuals in need of increased CTL production are those having disorders which generally respond to CTL activity. Such disorders include, but not limited to, cancer and intracellular infections. Administration of IMP in accordance with the invention results in an increase in CTL levels, and results in amelioration of one or more symptoms, stabilization of one or more symptoms, and/or prevention or slowing of progression (e.g., reduction or elimination of additional lesions or symptoms) of the disorder which responds to CTL activity.

Methods of the invention include any embodiments described herein, such as administering IMPs in the form of immunomodulatory polynucleotide/microcarrier complex (with or without antigen, or with or without antigen over a course of administrations), or in proximate association with an antigen.

As will be apparent to one of skill in the art, the methods of the invention may be practiced in combination with other therapies for the particular indication for which the IMP is administered. For example, IMP therapy may be administered in conjunction with anti-malarial drugs such as chloroquine for malaria patients, in conjunction with leishmanicidal drugs such as pentamidine and/or allopurinol for leishmaniasis patients, in conjunction with anti-mycobacterial drugs such as isoniazid, rifampin and/or ethambutol in tuberculosis patients, or in conjunction with allergen desensitization therapy for atopic (allergy) patients.

As described herein, administration of IMPs may further comprise administration of one or more additional immunotherapeutic agents (i.e., an agent which acts via the immune system and/or is derived from the immune system) including, but not limited to, cytokine, adjuvants and antibodies (including, but not limited to, antibody fragments and/or derivatives and monoclonal antibodies, fragments and/or derivatives thereof). Examples of therapeutic antibodies include those used in the cancer context (e.g., anti-tumor antibodies). Administration of such additional immunotherapeutic agents applies to all the methods described herein.

An IMP may also be administered in conjunction with an adjuvant. Administration of an antigen with an IMP and an adjuvant leads to a potentiation of a immune response to the antigen and thus, can result in an enhanced immune response compared to that which results from a composition comprising the IMP and antigen alone. Adjuvants are known in the art and include, but are not limited to, oil-in-water emulsions, water-in oil emulsions, alum (aluminum salts), liposomes and microparticles, including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) Nature 344:873-875, as well as, lipid-based adjuvants and others described herein. For veterinary use and for production of antibodies in animals, mitogenic components of Freund's adjuvant (both complete and incomplete) can be used.

Administration and Assessment of the Immune Response

The IMP can be administered in combination with other pharmaceutical and/or immunogenic and/or immunostimulatory agents, as described herein, and can be combined with a physiologically acceptable carrier thereof (and as such the invention includes these compositions). The IMP may be any of those described herein.

Accordingly, the IMP can be administered in conjunction with other immunotherapeutic agents including, but not limited to, cytokine, adjuvants and antibodies.

As with all immunogenic compositions, the immunologically effective amounts and method of administration of the particular IMP formulation can vary based on the individual, what condition is to be treated and other factors evident to one skilled in the art. Factors to be considered include the antigenicity of antigen if administered, whether or not the IMP will be administered with or covalently attached to an adjuvant, delivery molecule and/or antigen, route of administration and the number of immunizing doses to be administered. Such factors are known in the art and it is well within the skill of those in the art to make such determinations without undue experimentation. A suitable dosage range is one that provides the desired modulation of immune response (e.g., stimulation of IFN-α and/or IFN-γ). When an immune response to an antigen is desired, a suitable dosage range is one that provides the desired modulation of immune response to the antigen. Generally, dosage is determined by the amount of IMP administered to the patient, rather than the overall quantity of IMP-containing composition administered. Useful dosage ranges of the IMP, given in amounts of IMP delivered, may be, for example, from about any of the following: 1 to 500 µg/kg, 100 to 400 µg/kg, 200 to 300 µg/kg, 1 to 100 µg/kg, 100 to 200 µg/kg, 300 to 400 µg/kg, 400 to 500 µg/kg. The absolute amount given to each patient depends on pharmacological properties such as bioavailability, clearance rate and route of administration.

The effective amount and method of administration of the particular IMP formulation can vary based on the individual patient, desired result and/or type of disorder, the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient IMP-containing composition to attain a tissue concentration of about 1-10 µM as measured by blood levels. The absolute amount given to each patient depends on pharmacological properties such as bioavailability, clearance rate and route of administration.

As described herein, APCs and tissues with high concentration of APCs are preferred targets for the IMP. Thus, administration of IMP to mammalian skin and/or mucosa, where APCs are present in relatively high concentration, is preferred.

The present invention provides IMP formulations suitable for topical application including, but not limited to, physiologically acceptable implants, ointments, creams, rinses and gels. Topical administration is, for instance, by a dressing or bandage having dispersed therein a delivery system, by direct administration of a delivery system into incisions or open wounds, or by transdermal administration device directed at a site of interest. Creams, rinses, gels or ointments having dispersed therein an IMP are suitable for use as topical ointments or wound filling agents.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the IMP to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

For transdermal transmission, iontophoresis is a suitable method. Iontophoretic transmission can be accomplished using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LECTRO PATCH product; those instructions are incorporated herein by this reference. Other occlusive patch systems are also suitable.

For transdermal transmission, low-frequency ultrasonic delivery is also a suitable method. Mitragotri et al. (1995) *Science* 269:850-853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up IMP transferred from the end of the tines. For example, the MONO-VACC old tuberculin test manufactured by Pasteur Merieux of Lyon, France contains a device suitable for introduction of IMP-containing compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of IMP formulation. Use of the device is preferably according to the manufacturer's written instructions included with the device product. Similar devices which can also be used in this embodiment are those which are currently used to perform allergy tests.

Another suitable approach to epidermal administration of IMP is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR. This approach can also be used to achieve epithelial administration in the mucosa. The chemical irritant can also be applied in conjunction with the mechanical irritant (as, for example, would occur if the MONO-VACC type tine were also coated with the chemical irritant). The IMP can be suspended in a carrier which also contains the chemical irritant or coadministered therewith.

Parenteral routes of administration include but are not limited to electrical (iontophoresis) or direct injection such as direct injection into a central venous line, intravenous, intramuscular, intraperitoneal, intradermal, or subcutaneous injection. Formulations of IMP suitable for parenteral administration are generally formulated in USP water or water for injection and may further comprise pH buffers, salts bulking agents, preservatives, and other pharmaceutically acceptable excipients. Immunomodulatory polynucleotide for parenteral injection may be formulated in pharmaceutically acceptable sterile isotonic solutions such as saline and phosphate buffered saline for injection.

Gastrointestinal routes of administration include, but are not limited to, ingestion and rectal. The invention includes formulations IMP suitable for gastrointestinal administration including, but not limited to, pharmaceutically acceptable powders, pills or liquids for ingestion and suppositories for rectal administration. As will be apparent to one of skill in the art, pills or suppositories will further comprise pharmaceutically acceptable solids, such as starch, to provide bulk for the composition.

Naso-pharyngeal and pulmonary administration include are accomplished by inhalation, and include delivery routes such as intranasal, transbronchial and transalveolar routes. The invention includes formulations of IMP suitable for administration by inhalation including, but not limited to, liquid suspensions for forming aerosols as well as powder forms for dry powder inhalation delivery systems. Devices suitable for administration by inhalation of IMP formulations include, but are not limited to, atomizers, vaporizers, nebulizers, and dry powder inhalation delivery devices.

As is well known in the art, solutions or suspensions used for the routes of administration described herein can include any one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

As is well known in the art, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

As is well known in the art, sterile injectable solutions can be prepared by incorporating the active compound(s) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2a, while the epidermal route yielded mostly IgG1. Pertmer et al. (1996) *J. Virol.* 70:6119-6125. Thus, one skilled in the art can take advantage of slight differences in immunogenicity elicited by different routes of administering the immunomodulatory polynucleotides of the present invention.

The above-mentioned compositions and methods of administration are meant to describe but not limit the methods of administering the formulations of IMPs of the invention. The methods of producing the various compositions and devices are within the ability of one skilled in the art and are not described in detail here.

Analysis (both qualitative and quantitative) of the immune response to IMP can be by any method known in the art, including, but not limited to, measuring antigen-specific antibody production (including measuring specific antibody subclasses), activation of specific populations of lymphocytes such as CD4+ T cells, B cells, NK cells or CTLs, maturation of dendritic cells (including plasmacytoid dendritic cells), production of cytokines and chemokines such as IFN-$\gamma$, IFN-$\alpha$, IFN-$\omega$, TNF-$\alpha$, IL-2, IL-4, IL-5, IL-6, IL-10, IL-12, IP-10, MCP-1, MCP-2, MCP-3, MIG or MIP-3$\beta$ and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Measurement of activation of particular populations of cells can be achieved by determining expression of markers, for example, cell surface markers, specific for activation of the particular cell type. Cell marker expression can be measured, for example, by measuring RNA expression or measuring cell surface expression of the particular marker by, for example, FACS analysis. Cytotoxicity and CTL assays can be performed for instance as described in Raz et al. (1994) *Proc. Natl. Acad. Sci. USA* 91:9519-9523 and Cho et al. (2000). Cytokine concentrations can be measured, for example, by ELISA. Measuring maturation of dendritic cells can be performed for instance as described in Hartmann et al. (1999) *Proc. Natl. Acad. Sci. USA* 96:9305-9310. These and other assays to evaluate the immune response to an immunogen are well known in the art. See, for example, Selected Methods in Cellular Immunology (1980) Mishell and Shiigi, eds., W.H. Freeman and Co.

Analysis (both qualitative and quantitative) of the immune response to IMP can also be by measuring the level of cytokines, chemokines and/or other molecules that are induced by cytokines, such as IFN-$\gamma$ and/or IFN-$\alpha$, whose production is stimulated by IMP. Accordingly, the IMPs of the invention may also stimulate expression of IFN-$\gamma$ and/or IFN-$\alpha$ inducible cytokines, chemokines and inflammatory proteins including, but not limited to, IP-10 (interferon induced protein 10 kDa), monokine induced by IFN-$\gamma$, and monocyte chemotactic protein 1 (MCP-1). The immune response to IMP can also be analyzed by measuring the level of cytokines, chemokines and/or other molecules that are known to have antiviral activities, including 2,5-oligoadenylate synthetase (2,5-OAS), interferon-stimulating gene-54K (ISG-54K), MxA, MxB and guanylate-binding protein-1 (GBP-1). Thus, antiviral molecules and molecules induced by IFN-$\gamma$ and/or IFN-$\alpha$ can be used as markers of IMP activity. Measurement of such interferon-induced molecule production and/or gene expression can be by any method known in the art, including, but not limited to, by ELISA and quantitative PCR to measure RNA production.

Preferably, a Th1-type response is stimulated, i.e., elicited and/or enhanced. With reference to the invention, stimulating a Th1-type immune response can be determined in vitro or ex vivo by measuring cytokine production from cells treated with IMP as compared to those treated without IMP. Methods to determine the cytokine production of cells include those methods described herein and any known in the art. The type of cytokines produced in response to IMP treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, IFN-$\gamma$ and IFN-$\alpha$. In contrast, "Th2-type biased cytokines" refers to those associated with a Th2-type immune response, and include, but are not limited to, IL-4, IL-5, and IL-13. Cells useful for the determination of IMP activity include cells of the immune system, primary cells isolated from a host and/or cell lines, preferably APCs and lymphocytes, even more preferably macrophages and T cells.

Stimulating a Th1-type immune response can also be measured in a host treated with an IMP can be determined by any method known in the art including, but not limited to: (1) a reduction in levels of IL-4 or IL-5 measured before and after antigen-challenge; or detection of lower (or even absent) levels of IL-4 or IL-5 in an IMP treated host, optionally as compared to an antigen-primed, or primed and challenged, control treated without IMP; (2) an increase in levels of IL-12, IL-18 and/or IFN ($\alpha$, $\beta$ or $\gamma$) before and after antigen challenge; or detection of higher levels of IL-12, IL-18 and/or IFN ($\alpha$, $\beta$ or $\gamma$) in an IMP treated host as compared to an antigen-primed or, primed and challenged, control treated without IMP; (3) "Th1-type biased" antibody production in an IMP treated host as compared to a control treated without IMP; and/or (4) a reduction in levels of antigen-specific IgE as measured before and after antigen challenge; or detection of lower (or even absent) levels of antigen-specific IgE in an IMP treated host as compared to an antigen-primed, or primed and challenged, control treated without IMP. A variety of these determinations can be made by measuring cytokines made by APCs and/or lymphocytes, preferably macrophages and/or T cells, in vitro or ex vivo using methods described herein or any known in the art. Some of these determinations can be made by measuring the class and/or subclass of antigen-specific antibodies using methods described herein or any known in the art.

The class and/or subclass of antigen-specific antibodies produced in response to IMP treatment indicate a Th1-type or a Th2-type biased immune response by the cells. As used herein, the term "Th1-type biased" antibody production refers to the measurable increased production of antibodies associated with a Th1-type immune response (i.e., Th1-associated antibodies). One or more Th1 associated antibodies may be measured. Examples of such Th1-type biased antibodies include, but are not limited to, human IgG1 and/or IgG3 (see, e.g., Widhe et al. (1998) *Scand. J. Immunol.* 47:575-581 and de Martino et al. (1999) *Ann. Allergy Asthma Immunol.* 83:160-164) and murine IgG2a. In contrast, "Th2-type biased antibodies" refers to those associated with a Th2-type immune response, and include, but are not limited to, human IgG2, IgG4 and/or IgE (see, e.g., Widhe et al. (1998) and de Martino et al. (1999)) and murine IgG1 and/or IgE.

The Th1-type biased cytokine induction which occurs as a result of administration of IMP produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

In some embodiments, a Th2 response is suppressed (reduced). Suppression of a Th2 response may be determined by, for example, reduction in levels of Th2-associated cytokines, such as IL-4 and IL-5, reduction in the levels of Th2-associated antibodies, as well as IgE reduction and reduction in histamine release in response to allergen.

Kits of the Invention

The invention provides kits. In certain embodiments, the kits of the invention generally comprise one or more containers comprising any IMP as described herein. The kits may further comprise a suitable set of instructions, generally written instructions, relating to the use of the IMP for any of the methods described herein (e.g., immunomodulation, ameliorating one or more symptoms of an infectious disease, increasing IFN-γ levels, increasing IFN-α levels, or ameliorating an IgE-related disorder).

The kits may comprise IMP packaged in any convenient, appropriate packaging. For example, if the IMP is a dry formulation (e.g., freeze dried or a dry powder), a vial with a resilient stopper is normally used, so that the IMP may be easily resuspended by injecting fluid through the resilient stopper. Ampoules with non-resilient, removable closures (e.g., sealed glass) or resilient stoppers are most conveniently used for liquid formulations of IMP. Also contemplated are packages for use in combination with a specific device, such as an inhaler, nasal administration device (e.g., an atomizer) or an infusion device such as a minipump.

The instructions relating to the use of IMP generally include information as to dosage, dosing schedule, and route of administration for the intended method of use. The containers of IMP may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, the kits further comprise an antigen (or one or more antigens), which may or may not be packaged in the same container (formulation) as the IMP(s). Antigen have been described herein.

In certain embodiments, the kits of the invention comprise an IMP in the form of an immunomodulatory polynucleotide/microcarrier complex (IMP/MC) and may further comprise a set of instructions, generally written instructions, relating to the use of the IMP/MC complex for any of the methods described herein (e.g., immunomodulation, ameliorating one or more symptoms of an infectious disease, increasing IFN-γ levels, increasing IFN-α levels, or ameliorating an IgE-related disorder).

In some embodiments, kits of the invention comprise materials for production of IMP/MC complex generally include separate containers of IMP and MC, although in certain embodiments materials for producing the MC are supplied rather than preformed MC. The IMP and MC are preferably supplied in a form which allows formation of IMP/MC complex upon mixing of the supplied IMP and MC. This configuration is preferred when the IMP/MC complex is linked by non-covalent bonding. This configuration is also preferred when the IMP and MC are to be crosslinked via a heterobifunctional crosslinker; either IMP or the MC is supplied in an "activated" form (e.g., linked to the heterobifunctional crosslinker such that a moiety reactive with the IMP is available).

Kits for IMP/MC complexes comprising a liquid phase MC preferably comprise one or more containers including materials for producing liquid phase MC. For example, an IMP/MC kit for oil-in-water emulsion MC may comprise one or more containers containing an oil phase and an aqueous phase. The contents of the container are emulsified to produce the MC, which may be then mixed with the IMP, preferably an IMP which has been modified to incorporate a hydrophobic moiety. Such materials include oil and water, for production of oil-in-water emulsions, or containers of lyophilized liposome components (e.g., a mixture of phospholipid, cholesterol and a surfactant) plus one or more containers of an aqueous phase (e.g., a pharmaceutically-acceptable aqueous buffer). In certain embodiments, the kits of the invention comprise an IMP in the form of a cationic condensing agent—IMP—stabilizing agent (CIS) composition in one or more containers comprising any immunomodulatory CIS particulate composition as described herein. Alternately, the kits may comprise one or more containers of the components of the CIS compositions of the invention. Configurations of this embodiment include kits with a container of IMP/stabilizing agent mixture and a container of cationic condensing agent and kits with a container of IMP, a container of stabilizing agent, and a container of cationic condensing agent. The kits may further comprise a suitable set of instructions, generally written instructions, relating to the use of the CIS particulate composition for any of the methods described herein (e.g., immunomodulation, ameliorating one or more symptoms of an infectious disease, increasing IFN-γ levels, increasing IFN-α levels, or ameliorating an IgE-related disorder). The kit embodiments that comprise containers of the components of the CIS compositions will generally include instructions for production of the CIS compositions in accordance with the methods disclosed herein. In addition to the CIS composition and/or components of the CIS composition of the invention, kit embodiments may also enclose instructions for production of the CIS compositions in accordance with the methods disclosed herein and instructions for use of the immunomodulatory CIS compositions for any of the methods described herein.

The following Examples are provided to illustrate, but not limit, the invention.

EXAMPLES

Example 1

Immunomodulation of Human Cells by Immunomodulatory Polynucleotides

Immunomodulatory polynucleotides (IMPs) or control samples, including polynucleotides without an immunomodulatory sequence (5'-TGACTGTGAACCTTAGAGATGAquew-3' (SEQ ID NO: 2)), SAC and media alone, were tested for immunomodulatory activity on human peripheral blood mononuclear cells (PBMCs). Also tested was the standard immunomodulatory polynucleotide 5'-TGACTGT-GAACGTTCGAGATGA. (SEQ ID NO:1). Unless noted otherwise, the polynucleotides tested were fully modified phosphorothioate oligodeoxynucleotides.

Peripheral blood was collected from volunteers by venipuncture using heparinized syringes. Blood was layered onto a FICOLL® (Amersham Pharmacia Biotech) cushion and centrifuged. PBMCs, located at the FICOLL® interface, were collected, then washed twice with cold phosphate buffered saline (PBS). The cells were resuspended and cultured in 48 or 96 well plates at $2\times10^6$ cells/mL in RPMI 1640 with 10% heat-inactivated human AB serum plus 50 units/mL penicillin, 50 µg/mL streptomycin, 300 µg/mL glutamine, 1 mM sodium pyruvate, and 1×MEM non-essential amino acids (NEAA).

The cells were cultured in the presence of test samples (IMPs or controls) at doses ranging from 0.2 to 20 µg/ml for 24 hours, then cell-free medium was collected from each well and assayed for IFN-γ and/or IFN-α concentration. IFN-γ and IFN-α were assayed using CYTOSCREEN™ ELISA kits from BioSource International, Inc., according to the manufacturer's instructions. Generally, the test samples were tested with PBMCs from 4 human donors.

IMPs stimulated IFN-γ and/or IFN-α secretion by human PBMCs. In the human PBMC assay, background levels of IFN-γ can vary, even significantly, with the donor. Other cytokines such as IFN-α, however, demonstrate a generally stable pattern of activation and routinely exhibit low background levels under unstimulated conditions. Examples of results from such assays with PBMCs are summarized in Tables 2-7.

In a dose titration assay, PBMCs from 4 donors were stimulated with 0.2 to 20 µg/ml of SEQ ID NO:27 as described above. The amount of IFN-α and IFN-γ produced was assessed as described above and the results from the 4 donors were averaged and the mean results are presented in Table 2.

TABLE 2

IMP titration - IFN (pg/ml)

| SEQ ID NO: 27 (µg/ml) | IFN-γ | IFN-α |
|---|---|---|
| 20 | 412 | 749 |
| 8 | 583 | 4036 |
| 3.2 | 203 | 4073 |
| 1.3 | 39 | 887 |
| 0.5 | 15 | 108 |
| 0.2 | 11 | 50 |

As can be seen from the results presented in Table 2, the capability to induce IFN-α production increased as the IMP dose decreased and became optimal at approximately 3-8 µg/ml, after which the activity decreased with dose. Additional assays confirmed this result.

PBMCs from four donors were stimulated with 20 µg/ml of IMPs or controls and the stimulation of IFN-α and IFN-γ production was assessed as described above. Among the polynucleotides tested were:

```
5'-TCGTCGAACGTTCGTTAACGTTCG;    (SEQ ID NO: 5)

5'-TCGTCGAACGTTCGTT;            (SEQ ID NO: 12)

5'-TCGTCGGAACGTTCGAGATG;        (SEQ ID NO: 14)

5'-TCGTCGTGAACGTTCGAGATGA;      (SEQ ID NO: 13)

5'-TCGTCGAACGTTCCTTAACGTTCC;    (SEQ ID NO: 6)

5'-TCGTCGTAACGTTCGAGATG;        (SEQ ID NO: 15)

5'-TCGTCGAACGTTTTAACGTT;        (SEQ ID NO: 31)

5'-TCGTTCAACGTTCGTTAACGTTCG;    (SEQ ID NO: 9)

5'-TCGTCGGACGTTCGAGATG;         (SEQ ID NO: 16)

5'-TCGTCGTACGTTCGAGATG;         (SEQ ID NO: 17)

5'-TCGTCGTTCGTTCGAGATG;         (SEQ ID NO: 18)

5'-TCGTCGAACCTTCGTTAACCTTCG;    (SEQ ID NO: 11)

5'-TGATCGTCGAACGTTCGAGATG;      (SEQ ID NO: 24)

5'-TGATCGAACGTTCGTTAACGTTCG;    (SEQ ID NO: 8)

5'-TGATTCAACGTTCGTTAACGTTCG;    (SEQ ID NO: 10)

5'-TCAACGTTCGTTAACGTTCGTT.      (SEQ ID NO: 4)
```

The results of cytokine production from the PBMCs from each donor was averaged and the mean results are presented in Table 3.

TABLE 3

Human PBMC Assays - IFN (pg/ml)

| test or control (SEQ ID NO.) | IFN-γ | IFN-α |
|---|---|---|
| 2 (non-IMP) | 11 | 50 |
| 1 (IMP std) | 205 | 141 |
| 27 | 335 | 842 |
| 5 | 297 | 517 |
| 35 | 308 | 686 |
| 12 | 153 | 157 |
| 14 | 340 | 576 |
| 13 | 297 | 142 |
| 7 | 510 | 594 |
| 6 | 554 | 103 |
| 15 | 204 | 194 |
| 31 | 169 | 178 |
| 9 | 310 | 57 |
| 16 | 274 | 421 |
| 17 | 387 | 208 |
| 18 | 78 | 50 |
| 11 | 36 | 50 |
| 24 | 462 | 708 |
| 8 | 650 | 704 |
| 10 | 111 | 66 |
| 4 | 126 | 50 |
| media | 11 | 50 |

As demonstrated in Table 3, IMPs that stimulated production of more IFN-α than an IMP standard, SEQ ID NO: 1, include at least one TCG sequence at or near the 5' end of the polynucleotide (a 5'-TCG sequence) and a palindromic sequence of at least 8 bases in length either adjacent to or within 3 bases of the 5'-TCG sequence. In general, stimulation of IFN-γ production mirrored stimulation of IFN-α production, although the range of variation in the IFN-γ stimulation was less than for IFN-α. In the polynucleotides in which the palindromic sequence and the 5'-TCG were separated, it was generally preferable for the production of IFN-α that the separation be by or overlapping with a second TCG trinucleotide (see, for example, SEQ ID NO:14). IMPs containing a 5'-TCG but no palindromic sequence as described above induced very low levels of IFN-γ and did not induce IFN-α production (see, for example, SEQ ID NOs: 18 and 11). IMPs containing 6-8 base palindromes but no 5'-TCG trinucleotide induced IFN-γ but only low levels of IFN-α (see, for example, SEQ ID NO: 1 and 4). Notably, IMPs containing a TCG up to three bases removed from the 5' end of the polynucleotide and containing a palindromic sequence of at least 10 bases in length induced a particularly high level of IFN-α compared to an IMP standard without a 5'-TCG, SEQ ID NO: 1 (see, for example, SEQ ID NO: 24 and 8).

An assay was performed to test IMP dose dependence on stimulation of IFN-α production. IMPs tested in this assay varied in the position of the palindromic sequence in the polynucleotide and/or the position of the at least one TCG sequence at the 5' end. Among the polynucleotides tested were some with CG dinucleotides and 5'-TCG sequences but without palindromic sequences 8 bases or greater in length (for example, SEQ ID NO:11; SEQ ID NO:18; 5'-TCGTCGTTTTGTCGTTTTGTCGTT (SEQ ID NO:3)). Also tested were polynucleotides with CG dinucleotides and palindromic sequences 8 bases or greater in length but no 5'-TCG trinucleotides (for example, SEQ ID NO:1; SEQ ID NO:4; 5'-ATCATCTCGAACGTTCGACGA (SEQ ID NO:29); 5'-AACGTTCGAACGTTCGAACGTTT (SEQ ID NO:67); 5'-TCAACGTTCGAACGTTCGAACGTT (SEQ ID NO:68); 5'-GACGATCGTCGACGATCGTC (SEQ ID NO:85)). PBMCs from four donors were stimulated with either 0.8, 4.0 or 20 μg/ml of IMPs or controls. The stimulation of IFN-α production was assessed as described above and the results averaged from the 4 donors are reported in Table 4.

TABLE 4

Human PBMC Assays - IFN-α (pg/ml)

| test or control (SEQ ID NO.) | 20 μg/ml | 4.0 μg/ml | 0.8 μg/ml |
|---|---|---|---|
| 2 (non-IMP) | 52 | 52 | 52 |
| 1 (IMP std) | 52 | 108 | 52 |
| 27 | 8626 | 7908 | 715 |
| 52 | 2425 | 4249 | 1085 |
| 39 | 2388 | 9325 | 3590 |
| 38 | 1874 | 7744 | 4635 |
| 57 | 1991 | 4262 | 9780 |
| 58 | 915 | 1654 | 5965 |
| 59 | 616 | 3221 | 1147 |
| 24 | 1848 | 2233 | 71 |
| 8 | 1023 | 544 | 52 |
| 29 | 1000 | 3325 | 95 |
| 35 | 3507 | 8734 | 63 |
| 60 | 1978 | 517 | 52 |
| 61 | 7256 | 13767 | 599 |
| 62 | 11157 | 16722 | 2254 |
| 63 | 17077 | 12510 | 360 |
| 64 | 569 | 2896 | 80 |
| 65 | 2007 | 1158 | 55 |
| 66 | 3926 | 718 | 64 |
| 67 | 246 | 2399 | 52 |
| 68 | 520 | 1558 | 1254 |
| 85 | 52 | 411 | 52 |
| 4 | 158 | 124 | 52 |
| 18 | 473 | 618 | 52 |
| 11 | 52 | 261 | 756 |
| 3 | 138 | 289 | 53 |
| medium | 52 | | |

The results presented in Table 4 support the importance of a palindromic sequence at least 8 bases in length and at least one TCG sequence at or near the 5' end of the polynucleotide for stimulation of IFN-α from human PBMCs.

Another assay was performed to test IMP dose dependence on stimulation of IFN-☆ production. IMPs tested in this assay varied in the presence of CG dinucleotides and 5'-TCG sequences in the polynucleotide. Among the polynucleotides tested were some with palindromic sequences but without CG dinucleotides (for example, SEQ ID NO:2; 5'-TGCTTGCAAGCTTGCAAGCA (SEQ ID NO: 90), 5'-TCAGTCAGTCAGCTGACTGACTGA (SEQ ID NO:96) and/or without a 5'-TCG sequence (for example, SEQ ID NOs:1, 90, 96; 5'-ACCGATAACGTTGCCGGTGACGGCACCACG (SEQ ID NO:92), 5'-AACAACAACGTTGTTGTT (SEQ ID NO:95), 5'-ACCGATAACGTTGCCGGTGACGGCAC-CACG (SEQ ID NO:25), 5'-AACAACAACGTTGTTGTT (SEQ ID NO:94)). Also tested in this assay was the polynucleotide 5'-TCGTTGCAAGCTTGCAACGA (SEQ ID NO:91). Some of the IMPs varied in phosphate backbone composition. PBMCs from three donors were stimulated with either 0.8, 4.0 or 20 μg/ml of IMPs or controls. The stimulation of IFN-α production was assessed using PBMCs from 3 donors as described above and the averaged results for the 3 donors are reported in Table 5.

TABLE 5

Human PBMC Assays - IFN-α (pg/ml)

| test or control (SEQ ID NO.) | 20 μg/ml | 4.0 μg/ml | 0.8 μg/ml |
|---|---|---|---|
| media | 43 | — | — |
| 2 (non-IMP) | 43 | 43 | 43 |
| 1 (IMP std) | 43 | 371 | 43 |
| 27 | 823 | 4958 | 1893 |
| 53 | 1968 | 13779 | 13550 |
| 54 | 142 | 5090 | 2832 |
| 97 | 1244 | 12097 | 5173 |
| 42 | 1790 | 7923 | 4249 |
| 90 | 43 | 43 | 50 |
| 96 | 58 | 613 | 43 |
| 91 | 1177 | 1539 | 870 |
| 25 | 43 | 43 | 43 |
| 92 | 43 | 903 | 43 |
| 94 | 235 | 56 | 43 |
| 95 | 216 | 84 | 43 |
| 26 | 25420 | 19903 | 4136 |
| 30 | 1125 | 7543 | 5955 |
| 32 | 1483 | 5088 | 2933 |
| 33 | 6031 | 24061 | 14111 |
| 34 | 15012 | 17241 | 6979 |
| 93 | 1355 | 6193 | 1762 |

As can be seen from the results presented in Table 5, inversion of the CG dinucleotides in the highly active sequence SEQ ID NO:42 to GC dinucleotides abolishes the ability of SEQ ID NO:90 to induce IFN-α. Similarly SEQ ID NO:96, a palindromic polynucleotide without CG dinucleotides is also inactive.

As can be seen in Table 5, two representative phosphodiester polynucleotides, SEQ ID NO:25 and SEQ ID NO:94, and their fully modified phosphorothioate versions, SEQ ID NO:92 and SEQ ID NO:95, respectively, were not active in inducing IFN-α from human PBMCs. Although SEQ ID NOs:25 and 92 contain several CG dinucleotides, including the motif AACGTT, they do not include TCG or a palindromic sequence of at least 8 bases. SEQ ID NOs:94 and 95 are 18 base palindromes and contain one CG dinucleotide, but no TCG trinucleotide. Thus, these polynucleotides do not fit the motifs described herein.

SEQ ID NOs:26, 30, 32, and 33, containing all phosphorothioate linkages (SEQ ID NOs:30 and 32) or chimeric phosphorothioate/phosphodiester linkages (SEQ ID NOs:26 and 33), induced high amounts of IFN-α from human PBMCs. Both SEQ ID NOs:34 (which contains chimeric phosphorothioate/phosphodiester linkages) and 93 (all phosphorothioate linkages) induced IFN-α from human PBMCs.

In an assay to test the effect of the length of a palindromic sequence on stimulation of IFN-α, PBMCs from four donors were stimulated with either 2 µg/ml or 20 µg/ml of IMPs or controls, the stimulation of IFN-α production was assessed as described above and the averaged results are reported in Table 6. Among the polynucleotides tested were 5'-TTCGAACGT-TCGTTAACGTTCG (SEQ ID NO:20) and 5'-TCGTC-GAACGTTCGAACGTTCG (SEQ ID NO:19).

TABLE 6

| Human PBMC Assays - IFN-α (pg/ml) | | |
| --- | --- | --- |
| test or control (SEQ ID NO.) | 20 µg/ml | 2 µg/ml |
| 2 (non-IMP) | 26 | 26 |
| 1 (IMP std) | 93 | 34 |
| 5 | 2146 | 4018 |
| 20 | 2350 | 312 |
| 19 | 9844 | 15989 |
| 38 | 1935 | 15217 |
| 39 | 3729 | 14127 |
| 40 | 4584 | 12550 |
| 43 | 4174 | 10362 |
| 27 | 2008 | 10062 |
| 41 | 543 | 12916 |
| 42 | 3935 | 14752 |
| media | 26 | 26 |

The results presented in Table 6 support the importance of a palindromic sequence at least 8 bases in length and at least one TCG sequence at or near the 5' end of the polynucleotide for stimulation of IFN-α from human PBMCs.

In an assay to test IFN-α stimulatory activity of IMPs with a variety of 12 base palindromes, PBMCs from four donors were stimulated with either 0.8, 4 or 20 µg/ml of IMPs or controls, the stimulation of IFN-α production was assessed as described above and the averaged results are reported in Table 7.

TABLE 7

| Human PBMC Assays - IFN-α (pg/ml) | | | |
| --- | --- | --- | --- |
| test or control (SEQ ID NO.) | 20 µg/ml | 4 µg/ml | 0.8 µg/ml |
| 2 (non-IMP) | 169 | 133 | 133 |
| 1 (IMP std) | 190 | 238 | 143 |
| 27 | 3010 | 6473 | 2775 |
| 44 | 4951 | 10420 | 5468 |
| 45 | 3821 | 7221 | 2864 |
| 46 | 1403 | 5296 | 5169 |
| 47 | 2798 | 6731 | 3992 |
| 48 | 3082 | 9190 | 4113 |
| 51 | 2701 | 5699 | 1727 |
| 69 | 1886 | 8299 | 5195 |
| 70 | 7893 | 8429 | 5553 |
| 71 | 10647 | 10525 | 6173 |
| 72 | 9652 | 9101 | 5095 |
| 73 | 10419 | 9376 | 4896 |
| 74 | 9883 | 9085 | 5635 |
| 75 | 10269 | 8153 | 3888 |
| 76 | 10551 | 9773 | 5062 |
| 49 | 5424 | 7762 | 2788 |
| 50 | 6112 | 8517 | 3239 |
| 42 | 7634 | 8208 | 5472 |
| 43 | 6777 | 6768 | 4472 |
| 77 | 3694 | 4725 | 768 |
| 78 | 2542 | 4257 | 4311 |
| 79 | 1201 | 5725 | 5757 |
| 39 | 7454 | 9965 | 6622 |
| 80 | 2938 | 4137 | 1412 |
| 81 | 5914 | 4918 | 865 |
| 82 | 3451 | 4249 | 4170 |
| 84 | 3454 | 5363 | 2255 |
| 86 | 10742 | 11881 | 6332 |

TABLE 7-continued

| Human PBMC Assays - IFN-α (pg/ml) | | | |
| --- | --- | --- | --- |
| test or control (SEQ ID NO.) | 20 µg/ml | 4 µg/ml | 0.8 µg/ml |
| 87 | 5110 | 5950 | 4139 |
| 114 | 4779 | 5491 | 2907 |
| media | 204 | 204 | 204 |

The results presented in Table 7 indicate that any of the IMPs tested with 12 base palindromes were active in stimulating IFN-α from human PBMCs. These IMPs contain a 12 base palindrome with the sequence TCGX$_1$X$_2$CGX$_2$'X$_1$'CGA (SEQ ID NO:198) in which there are no nucleotide limitations for X$_1$ and X$_2$, despite the formation of runs of CGCG, CCGG and GCGC, which have previously been described as immunoinhibitory sequences or immune neutralizing sequences (Krieg et al. (1998) *Proc. Natl. Acad. Sci. USA* 95:12631-12636). For example, SEQ ID NOs:49 and 50 are active in stimulating IFN-α and contain the sequence CGCG. SEQ ID NO:49 exemplifies an immunomodulatory polynucleotide containing SEQ ID NO:161 described above. SEQ ID NO:50 exemplifies an immunomodulatory polynucleotide containing SEQ ID NO:162 described above.

IMPs with longer palindromes induced higher levels of IFN-α from human PBMCs, particularly at lower IMP doses. As can be seen in assay results shown in FIG. 1, the amount of IFN-α produced from the cells in response to SEQ ID NO:172 was significantly higher than SEQ ID NO:113, SEQ ID NO:27 and SEQ ID NO:1 at the 0.4 µg/ml dose of IMP. Also, the amount of IFN-α produced in response to SEQ ID NO:172 was significantly higher than SEQ ID NO:27 and SEQ ID NO:1 at the 0.8 µg/ml dose of IMP (p<0.001). The palindrome length in the IMPs is: 28 bases in SEQ ID NO:172, 22 bases in SEQ ID NO:113, 12 bases in SEQ ID NO:27, and 8 bases in SEQ ID NO:1

In another assay, overall IMP length and IMP palindrome length were compared in the induction of IFN-α production from human PBMCs. Among the polynucleotides tested were:

```
SEQ ID NO: 1, SEQ ID NO: 2, SEQ ID NO: 12, SEQ
ID NO: 27,
5'-TCGTCGAACGTTCGAGATG;     (SEQ ID NO: 166)

5'-TCGTCGAACGTTCGAGAT;      (SEQ ID NO: 99)

5'-TCGTCGAACGTTCGAG;        (SEQ ID NO: 100)

5'-TCGTCGAACGTTCGA;         (SEQ ID NO: 101)

5'-TCGAACGTTCGAG;           (SEQ ID NO: 102)

5'-TCGAACGTTCGA;            (SEQ ID NO: 103)

5'-TCGAACGTTCG;             (SEQ ID NO: 104)

5'-TCGACGTCGA;              (SEQ ID NO: 105)

5'-TCGTCGAACGTTCG;          (SEQ ID NO: 167)

5'-TCGTCGAACGTT;            (SEQ ID NO: 199)

5'-TCGTTCGAACGTTCGAA;       (SEQ ID NO: 54)

5'-TTCGAACGTTCGAA.          (SEQ ID NO: 98)
```

PBMCs from four donors were stimulated with either 0.8, 4.0 or 20 µg/ml of IMPs or controls and the resultant production of IFN-α was assessed as described above. The averaged result for the 4 donors at each IMP concentration are reported in Table 8.

TABLE 8

Human PBMC Assays - IFN-α (pg/ml)

| test (SEQ ID NO.) or control | IFN-α | | | IMP | |
|---|---|---|---|---|---|
| | 20 µg/ml | 4 µg/ml | 0.8 µg/ml | Total length (bases) | Palindrome (bases) |
| 1 (IMP std) | 128 | 412 | 52 | 22 | 8 |
| 2 (non-IMP) | 52 | 52 | 52 | 22 | — |
| 27 | 1181 | 5697 | 1264 | 21 | 12 |
| 166 | 1527 | 4827 | 2095 | 19 | 12 |
| 99 | 204 | 4254 | 2093 | 18 | 12 |
| 100 | 451 | 3835 | 2115 | 16 | 12 |
| 101 | 601 | 3065 | 547 | 15 | 12 |
| 102 | 1016 | 3529 | 533 | 13 | 12 |
| 103 | 484 | 1091 | 83 | 12 | 12 |
| 104 | 321 | 52 | 52 | 11 | 10 |
| 105 | 52 | 52 | 52 | 10 | 10 |
| 12 | 224 | 1692 | 63 | 16 | 10 |
| 167 | 319 | 556 | 69 | 14 | 10 |
| 199 | 52 | 52 | 52 | 12 | 6 |
| 54 | 99 | 3143 | 1133 | 17 | 14 |
| 98 | 1027 | 2321 | 744 | 14 | 14 |
| media | 82 | 82 | 82 | | |

The results presented in Table 8 indicate that, for the polynucleotides tested, the minimum total length of the polynucleotide to stimulate IFN-α production in human PBMCs is about 12 bases with a palindrome of about 10 bases in length. Accordingly, in some embodiments in which production of higher levels of IFN-α is desired, the IMP contains at least one palindromic sequence of at least the following lengths (in bases): 10, 12, 14, 16, 18, 20, 22, 24, 26, 28 or 30, and, in some embodiments, the IMP contains at least one palindromic sequence with a length longer than 30 bases.

In another assay, PBMCs from three donors were stimulated with either 0.8, 4.0 or 20 µg/ml of IMPs or controls. The stimulation of IFN-α, IFN-β and IFN-ω production was assessed as described above. IFN-ω was assayed using an ELISA kit from PBL Biomedical Laboratories and the lower and upper limit of detection of IFN-ω was 48 pg/ml and 6000 pg/ml, respectively. IFN-β was assayed using an ELISA kit from BioSource and the lower and upper limit of detection was 12 IU/ml and 3046 IU/ml, respectively. The averaged result for the 3 donors at each IMP concentration are reported in Table 9.

TABLE 9

Human PBMC Assays - IFN-α or IFN-ω (pg/ml)

| test (SEQ ID NO.) or control | IFN-α | | | IFN-ω | | |
|---|---|---|---|---|---|---|
| | 20 µg/ml | 4.0 µg/ml | 0.8 µg/ml | 20 µg/ml | 4.0 µg/ml | 0.8 µg/ml |
| media | 16 | — | — | 48 | — | — |
| 2 (non-IMP) | 14 | 16 | 14 | 48 | 48 | 48 |
| 1 (IMP std) | 49 | 198 | 19 | 48 | 48 | 48 |
| 27 | 700 | 7394 | 2146 | 76 | 629 | 163 |
| 39 | 2716 | 6180 | 5922 | 284 | 741 | 604 |
| 38 | nd | nd | nd | 228 | 632 | 650 | nd = not determined

As can been seen in Table 9, IMPs of the present invention stimulate production of IFN-ω from human PBMCs as well as production of IFN-α. In the assay described above, IFN-β was not detected.

In another assay, duplex forms of polynucleotides were compared to non-duplex forms in the induction of IFN-α production from human PBMCs. Among the polynucleotides tested were: SEQ ID NO:1, SEQ ID NO:90, SEQ ID NO:27, and 5'-TCGTCGAACGTTCGAGATGAT/5'-ATCATCTC-GAACGTTCGACGA (a duplex of SEQ ID NO:27 and SEQ ID NO:29). PBMCs from three donors were stimulated with either 0.4, 0.8, 4.0 or 20 µg/ml of IMPs or controls and the resultant production of IFN-α was assessed as described above. The duplexes were compared to the single sequences using the same total dose of polynucleotide (e.g., 4 µg/ml of SEQ ID NO:27 was compared to 4 µg/ml of double strand which contained 2 µg/ml SEQ ID NO:27 and 2 µg/ml SEQ ID NO:29). The averaged result for the 3 donors at each IMP concentration are reported in Table 10.

TABLE 10

Human PBMC Assays - IFN-α (pg/ml)

| test (SEQ ID NO.) or control | IFN-α | | | |
|---|---|---|---|---|
| | 20 µg/ml | 4 µg/ml | 0.8 µg/ml | 0.4 µg/ml |
| 27 | 592 | 3719 | 254 | 57 |
| 182 (27/29 dpx) | 386 | 2612 | 4725 | 1027 |
| 1 | 124 | 312 | 52 | 52 |
| 90 | 52 | nd | nd | nd |
| medium | 52 | 52 | 52 | 52 | nd = not determined

As can been seen in Table 10, SEQ ID NO:182, the duplex form of SEQ ID NO:27 is more active than SEQ ID NO:27 in stimulating IFN-α production at lower IMP doses. At higher doses (4 and 20 µg/ml), SEQ ID NO:27 was somewhat more stimulatory.

In another assay, a polynucleotide containing modified bases and polynucleotides without modified bases were compared in the induction of IFN-α production from human PBMCs. Among the polynucleotides tested were: SEQ ID NO:1, SEQ ID NO:2,5'-TCGTCGAACGTTCGAGATGAT (SEQ ID NO:27), and 5'-TCXTCXAACXTTCXAGATGAT (X=7-deaza-dG, SEQ ID NO:193). SEQ ID NO:27 and SEQ ID NO:193 have the same nucleotide sequence except for the deaza-dG substitutions for four dGs in SEQ ID NO:27. PBMCs from four donors were stimulated with either 0.8, 4.0 or 20 µg/ml of IMPs or controls and the resultant production of IFN-α was assessed as described above. The averaged result for the 4 donors at each IMP concentration are reported in Table 11.

TABLE 11

Human PBMC Assays - IFN-α (pg/ml)

| test (SEQ ID NO.) or control | IFN-α | | |
|---|---|---|---|
| | 20 µg/ml | 4 µg/ml | 0.8 µg/ml |
| 1 (IMP std) | 129 | 118 | 80 |
| 2 (non-IMP) | 102 | 102 | 102 |
| 27 | 10248 | 13871 | 3798 |
| 193 | 10754 | 12262 | 193 |
| medium | 102 | | |

As can been seen in Table 11, SEQ ID NO:193 has IFN-α stimulatory activity comparable to SEQ ID NO:27 except at the 0.8 μg/ml dose.

Single and double strand forms of polynucleotides containing modified bases were assayed for activity in the induction of IFN-α production from human PBMCs. Among the polynucleotides tested were: single and double strand SEQ ID NO:1, single strand SEQ ID NO:2, single strand SEQ ID NO:29, single strand and double strand SEQ ID NO:27, single and double strand SEQ ID NO:187, single and double strand SEQ ID NO:188, single and double strand SEQ ID NO:189, single and double strand SEQ ID NO:190, single strand SEQ ID NO:194, and single strand SEQ ID NO:197. SEQ ID NOs: 187, 188, 189, 190, 194 and 197 have the same nucleotide sequence as SEQ ID NO:27 except for the noted substitutions:

```
                                      (SEQ ID NO: 189)
5'-TCGTCGAA*CGT*TCGAGATGAT (A* = 2-amino-dA; T* =
2-thio-dT);

(SEQ ID NO: 190)
5'-TCGTCGA*A*CGT*T*CGAGATGAT (A* = 2-amino-dA;
T* = 2-thio-dT);

(SEQ ID NO: 187)
5'-TCG*TCG*AACG*TTCG*AG*ATG*AT (G* = 7-deaza-8-
aza-dG);

(SEQ ID NO: 194)
5'-TCG*AACG*TTCG*AACG*TTCG*AACG*TT (G* = 7-deaza-
8-aza-dG);

(SEQ ID NO: 188)
5'-TCGTCGA*A*CGTTCGA*GA*TGA*T (A* = 2-amino-dA);

(SEQ ID NO: 197)
5'-TCGA*A*CGTTCGA*A*CGTTCGA*A*CGTT (A* = 2-amino-
dA).
```

PBMCs from eight donors were variously stimulated with either 0.2, 0.4, 0.8, 1.6, 4.0 or 8 μg/ml of IMPs or controls and the resultant production of IFN-α was assessed as described above. The duplexes were compared to the single sequences using the same total dose of polynucleotide (e.g., 4 μg/ml of SEQ ID NO:27 was compared to 4 μg/ml of double strand SEQ ID NO:182 which contained 2 μg/ml SEQ ID NO:27 and 2 μg/ml SEQ ID NO:29). The averaged result for the 8 donors at each IMP concentration are reported in Table 12.

TABLE 12

Human PBMC Assays - IFN-α (pg/ml)

| test (SEQ ID NO.) or control | IFN-α (pg/ml) | | | | | |
|---|---|---|---|---|---|---|
| | 8 μg/ml | 4 μg/ml | 1.6 μg/ml | 0.8 μg/ml | 0.4 μg/ml | 0.2 μg/ml |
| 2 (non-IMP) | nd | 87 | nd | nd | nd | nd |
| 90 | nd | 77 | nd | nd | nd | nd |
| 1 (IMP std) | nd | 288 | nd | 77 | 77 | nd |
| 1 duplex | 81 | 126 | 1988 | 1740 | 258 | 77 |
| 27 | nd | 8850 | nd | 955 | 77 | nd |
| 29 | nd | 6040 | nd | 85 | 77 | nd |
| 182 (27/29 duplex) | 747 | 2162 | 6462 | 7280 | 1862 | 89 |
| 187 | nd | 1050 | nd | 139 | 77 | nd |
| 183 (187/29 duplex) | 91 | 117 | 311 | 1081 | 411 | 119 |
| 188 | nd | 644 | nd | 3360 | 147 | nd |
| 184 (188/29 duplex) | 225 | 978 | 5483 | 10057 | 5022 | 527 |
| 189 | nd | 845 | nd | 302 | 79 | nd |
| 185 (189/29 duplex) | 257 | 638 | 7345 | 7973 | 2711 | 314 |
| 190 | nd | 3064 | nd | 150 | 77 | nd |
| 186 (190/29 duplex) | 491 | 2673 | 6085 | 6603 | 1703 | 194 |
| 194 | nd | 164 | nd | 645 | 77 | nd |
| 197 | nd | 4833 | nd | 5742 | 1224 | nd |
| SAC (1:5000) | 96 | | | | | |
| media | 77 | | | | | | nd = not determined

As can been seen in Table 12, the use of certain modified bases in the IMP can result in polynucleotides which have IFN-α stimulatory activity. With the exception of 183, these results also show that formation of a duplex polynucleotide with the complement sequence leads to a highly active IMP for stimulation of IFN-α production, particularly at lower doses. Polynucleotides which could not form duplexes on their own, e.g., SEQ ID NO:189 and SEQ ID NO:190, induced little IFN-α while longer sequences (e.g., SEQ ID NO:172, a 30-mer with a 28 base palindrome) and the duplex SEQ ID NO:182 induced more IFN-α at low doses (e.g., 0.4 and 0.8 μg/ml) than SEQ ID NO:27 and other IMPs with palindromes less than 28 bases in length (as shown in Table 12 and FIG. 1). As discussed herein, certain modified bases can increase the stability of duplexes formed.

Example 2

Activation of Human B Cells by Immunomodulatory Polynucleotides

The ability of IMPs to activate human B cells was determined by measuring B cell proliferation and IL-6 production in response to incubation with IMPs. Human PBMCs were incubated with CD19 MACS beads (Miltenyi Biotec) and passed through a magnet, separating the CD19+ B cells through positive selection (>98% CD19+ as determined by FACS). For the proliferation assay, B cells were cultured at 1×10^5/well (5×10^5/ml) in 96 well round-bottomed plates. Cells were incubated in triplicate with 2 μg/ml IMP or control for 72 hours. At the end of the culture period, the plates were pulsed with $^3$H-thymidine (1 μCi/well, Amersham) and incubated for an additional 8 hours. The plates were then harvested and radioactive incorporation determined using standard liquid scintillation techniques, and the data was collected in counts per minute (cpm). For IL-6 secretion, B cells were cultured at 0.5–1×10^6/well in 48-well plates with 5 μg/ml IMP or control for 48 hours, then culture supernatants were harvested and assayed for IL-6 using ELISA with CytoSet antibody pairs according to manufacturer's instructions (BioSource). Limits of maximal/minimal detection were 4000/2 pg/ml.

The results of the B cell proliferation assay presented in Table 13 are the mean of the triplicate cell proliferation cpm values for cells from each donor and the mean of the cpm values for both donors. The results of the B cell IL-6 assay presented in Table 13 are the amount of IL-6 produced from cells of each donor and the mean value from both donors.

TABLE 13

Human B Cell Assays

| test (SEQ ID NO.) or control | Proliferation assay (cpm) | | | IL-6 assay (pg/ml) | | |
|---|---|---|---|---|---|---|
| | Donor 1 | Donor 2 | Mean | Donor 1 | Donor 2 | Mean |
| medium | 415 | 575 | 495 | 26 | 28 | 27 |
| 1 (IMP std) | 27,731 | 43,403 | 35,567 | 222 | 531 | 377 |
| 2 (non-IMP) | 6748 | 7704 | 7226 | 52 | 126 | 89 |
| 43 | 22,695 | 26,456 | 24,576 | 187 | 935 | 561 |
| 38 | 45,364 | 27,327 | 36,346 | 248 | 984 | 616 |
| 40 | 60,250 | 52,916 | 56,583 | 172 | 336 | 254 |
| 19 | 22,683 | 29,569 | 26,126 | 173 | 257 | 215 |
| LPS | 1647 | 544 | 1096 | 34 | 21 | 28 |

From the results presented in Table 13, the compounds containing CG dinucleotides induced B cell proliferation and IL-6 production. As can been seen from the results presented in Table 9, although good B cell stimulatory activity in immunostimulatory polynucleotides is dependent on the presence of a CG dinucleotide, it does not appear to require the more specialized motifs described herein for high IFN-α induction.

In another assay, duplex forms of polynucleotides were compared to non-duplex forms in the activation of B cells. Among the polynucleotides tested were: SEQ ID NO:1, SEQ ID NO:90, SEQ ID NO:27, and SEQ ID NO:182-duplex of SEQ ID NO:27 and SEQ ID NO:29. B cells from three donors were stimulated with either 1.0 or 5.0 µg/ml of IMP or control and the resultant cell proliferation and IL-6 production was assessed as described above. The averaged result for the 3 donors at each IMP concentration is reported in Table 14.

TABLE 14

Human B Cell Assays

| test (SEQ ID NO.) or control | Proliferation assay (cpm) | | IL-6 assay (pg/ml) | |
|---|---|---|---|---|
| | 5 µg/ml | 1 µg/ml | 5 µg/ml | 1 µg/ml |
| 1 | 57921 | 11307 | 554 | 73 |
| 27 | 66735 | 24529 | 723 | 322 |
| 182 (27/29 dpx) | 78047 | 25344 | 809 | 281 |
| 90 | 3333 | 2181 | 5 | 4 |
| medium | 2104 | 2104 | 4 | 4 |

From the results presented in Table 14, SEQ ID NO:182, the duplex form of SEQ ID NO:27 is approximately equivalent to SEQ ID NO:27 in activating B cells as measured by stimulating IL-6 production and cell proliferation.

Example 3

Immunomodulation of Murine Cells by Immunomodulatory Polynucleotides

Immunomodulatory polynucleotides or control polynucleotides were assayed for immunomodulatory activity on mouse splenocytes. The polynucleotides tested were fully modified phosphorothioate oligodeoxynucleotides. Among the polynucleotides tested were SEQ ID NO:1 (positive control) and SEQ ID NO:2 (negative control).

Fragments of BALB/c mouse spleen were digested with collagenase/dispase (0.1 U/mL/0.8 U/mL) dissolved in phosphate buffered saline (PBS) for 45 minutes at 37° C., then mechanically dispersed by forcing the digested fragments through metal screens. The dispersed splenocytes were pelleted by centrifugation, then resuspended in fresh medium (RPMI 1640 with 10% fetal calf serum, plus 50 units/mL penicillin, 50 µg/mL streptomycin, 2 mM glutamine, and 0.05 mM β-mercaptoethanol).

Mouse splenocytes were dispensed into wells of 96 well plates ($7 \times 10^7$ cells/ml) and incubated for one hour at 37° C. 100 µL of 2× concentration test sample or control was added and the cells were incubated a further 24 hours. Each test sample or control was tested in duplicate. Medium was harvested from each well and frozen at −80° C. before testing. Harvested medium was thawed and tested for cytokine concentrations by ELISA. Polynucleotides were tested at various concentrations including 5.0, 1.0 and 0.1 µg/ml. Among the polynucleotides tested were 5'-TGACTGTGAACGTTC-GAAATGA (SEQ ID NO:36) and 5'-TGACTGTGAACGT-TCGAAGTGA (SEQ ID NO:37). Control samples included media alone and PANSORBIN® heat-killed, formalin-fixed *Staphylococcus aureus* (SAC) (CalBiochem).

IL-6, IL-12 and IFN-γ was assayed using a sandwich-format ELISA. Medium from the mouse splenocyte assay was incubated in microtiter plates coated with anti-IL-6, anti-IL-12 p40/p70 or anti-IFN-γ monoclonal antibody (Nunc). Bound cytokine (IL-6, IL-12 or IFN-γ) was detected using a biotinylated anti-cytokine antibody (anti-IL-6, anti-IL-12 p40/p70 or anti-IFN-γ) and streptavidin-horseradish peroxidase conjugated secondary antibody, developed with the chromogenic peroxidase substrate 3,3',5,5'-tetramethylbenzidine (TMB) in the presence of peroxidase, and quantitated by measuring absorbance at 450 nm using a Emax precision microplate reader (Molecular Devices). Values of IL-6 less than 45 pg/ml were assigned a value of 45 pg/ml (i.e., 45=<45). Values of IL-12 p40/p70 less than 36 pg/ml were assigned a value of 36 pg/ml (i.e., 36=<36). Values of IFN-γ less than 54 pg/ml were assigned a value of 54 pg/ml (i.e., 54=<54).

Tables 15 and 16 summarize assay results for cytokine production in response to IMPs. Immunomodulatory polynucleotides containing a CG dinucleotide generally stimulated IL-6, IL-12 and IFN-γ secretion by murine splenocytes irrespective of the presence of the more specialized motifs described herein for high IFN-α induction.

TABLE 15

Murine Splenocyte Assay - IL-6 (pg/ml)

| Test (SEQ ID NO.) or Control | Dose (ug/ml) | Rep. 1 | Rep. 2 | Ave. |
|---|---|---|---|---|
| 1 (IMP std) | 5.0 | 4623 | 4655 | 4639 |
| | 1.0 | 999 | 961 | 980 |
| | 0.1 | 47 | 45 | 46 |
| 2 (non-IMP) | 5.0 | 45 | 45 | 45 |
| | 1.0 | 45 | 45 | 45 |
| SAC | | 308 | 296 | 302 |
| Media | | — | — | 45 |
| 5 | 5.0 | 4755 | 4653 | 4704 |
| | 1.0 | 1055 | 985 | 1020 |
| | 0.1 | 45 | 46 | 46 |
| 20 | 5.0 | 4953 | 5464 | 5209 |
| | 1.0 | 1318 | 1413 | 1366 |
| | 0.1 | 90 | 124 | 107 |
| 19 | 5.0 | 4421 | 4726 | 4574 |
| | 1.0 | 645 | 740 | 693 |
| | 0.1 | 45 | 45 | 45 |

TABLE 15-continued

Murine Splenocyte Assay - IL-6 (pg/ml)

| Test (SEQ ID NO.) or Control | Dose (ug/ml) | Rep. 1 | Rep. 2 | Ave. |
|---|---|---|---|---|
| 38 | 5.0 | 4267 | 4350 | 4309 |
|  | 1.0 | 613 | 673 | 643 |
|  | 0.1 | 89 | 160 | 125 |
| 39 | 5.0 | 4775 | 4819 | 4797 |
|  | 1.0 | 802 | 731 | 767 |
|  | 0.1 | 213 | 147 | 180 |
| 40 | 5.0 | 2644 | 2217 | 2431 |
|  | 1.0 | 341 | 251 | 296 |
|  | 0.1 | 45 | 45 | 45 |
| 43 | 5.0 | 101 | 105 | 103 |
|  | 1.0 | 45 | 45 | 45 |
|  | 0.1 | 45 | 45 | 45 |
| 27 | 5.0 | 4809 | 5245 | 5027 |
|  | 1.0 | 2182 | 2693 | 2438 |
|  | 0.1 | 216 | 242 | 229 |
| 41 | 5.0 | 4781 | 5504 | 5143 |
|  | 1.0 | 1979 | 2285 | 2132 |
|  | 0.1 | 316 | 372 | 344 |
| 42 | 5.0 | 2706 | 3242 | 2974 |
|  | 1.0 | 460 | 577 | 519 |
|  | 0.1 | 66 | 70 | 68 |
| 44 | 5.0 | 2458 | 2585 | 2522 |
|  | 1.0 | 358 | 321 | 340 |
|  | 0.1 | 45 | 45 | 45 |
| 45 | 5.0 | 3920 | 3667 | 3794 |
|  | 1.0 | 1177 | 1117 | 1147 |
|  | 0.1 | 45 | 45 | 45 |
| 46 | 5.0 | 45 | 45 | 45 |
|  | 1.01 | 45 | 45 | 45 |
|  | 0.1 | 45 | 45 | 45 |
| 47 | 5.0 | 163 | 213 | 188 |
|  | 1.0 | 45 | 45 | 45 |
|  | 0.1 | 45 | 45 | 45 |
| 48 | 5.0 | 182 | 216 | 199 |
|  | 1.0 | 45 | 45 | 45 |
|  | 0.1 | 45 | 45 | 45 |
| 49 | 5.0 | 690 | 765 | 728 |
|  | 1.0 | 66 | 73 | 70 |
|  | 0.1 | 45 | 45 | 45 |
| 50 | 5.0 | 45 | 45 | 45 |
|  | 1.0 | 45 | 45 | 45 |
|  | 0.1 | 45 | 45 | 45 |
| 51 | 5.0 | 1942 | 1868 | 1905 |
|  | 1.0 | 224 | 197 | 211 |
|  | 0.1 | 45 | 45 | 45 |
| 52 | 5.0 | 1421 | 1234 | 1328 |
|  | 1.0 | 456 | 488 | 472 |
|  | 0.1 | 45 | 45 | 45 |
| 36 | 5.0 | 3656 | 3834 | 3745 |
|  | 1.0 | 858 | 991 | 925 |
|  | 0.1 | 45 | 45 | 45 |
| 36 | 5.0 | 3716 | 3750 | 3733 |
|  | 1.0 | 897 | 934 | 916 |
|  | 0.1 | 45 | 45 | 45 |
| 37 | 5.0 | 4253 | 4643 | 4448 |
|  | 1.0 | 1256 | 1218 | 1237 |
|  | 0.1 | 157 | 190 | 174 |
| 37 | 5.0 | 4457 | 4323 | 4390 |
|  | 1.0 | 1099 | 941 | 1020 |
|  | 0.1 | 88 | 109 | 99 |

TABLE 16

Murine Splenocyte Assay - IL-12 & IFN-γ

| Test (SEQ ID NO) or Control | Dose (ug/ml) | IL-12 (pg/ml) Rep. 1 | IL-12 (pg/ml) Rep. 2 | IL-12 (pg/ml) Ave. | IFN-γ (pg/ml) Rep. 1 | IFN-γ (pg/ml) Rep. 2 | IFN-γ (pg/ml) Ave. |
|---|---|---|---|---|---|---|---|
| 1 (IMP std) | 5.0 | 1915 | 1737 | 1826 | 1858 | 2589 | 2089 |
|  | 1.0 | 1419 | 1424 | 1422 | 1941 | 1954 | 1948 |
|  | 0.1 | 573 | 603 | 588 | 179 | 395 | 287 |
| 2 (non-IMP) | 5.0 | 38 | 36 | 37 | 54 | 54 | 54 |
|  | 1.0 | 36 | 43 | 40 | 54 | 54 | 54 |
| SAC | | 609 | 620 | 615 | 11889 | 13338 | 12614 |
| media | | — | — | 44 | — | — | 54 |
| 5 | 5.0 | 1773 | 1679 | 1726 | 1331 | 1463 | 1397 |
|  | 1.0 | 2099 | 2193 | 2146 | 1878 | 1811 | 1845 |
|  | 0.1 | 651 | 649 | 650 | 271 | 157 | 214 |
| 20 | 5.0 | 1838 | 2023 | 1931 | 2822 | 3342 | 3082 |
|  | 1.0 | 2245 | 2315 | 2280 | 2662 | 3402 | 3032 |
|  | 0.1 | 1016 | 1077 | 1047 | 513 | 1392 | 953 |
| 19 | 5.0 | 1364 | 1458 | 1411 | 1997 | 2686 | 2343 |
|  | 1.0 | 1513 | 1702 | 1608 | 1427 | 2375 | 1901 |
|  | 0.1 | 648 | 597 | 623 | 58 | 54 | 56 |
| 38 | 5.0 | 1822 | 1870 | 1846 | 3168 | 3851 | 3510 |
|  | 1.0 | 1963 | 2239 | 2101 | 3440 | 3721 | 3581 |
|  | 0.1 | 1207 | 1430 | 1319 | 446 | 1364 | 905 |
| 39 | 5.0 | 2476 | 2344 | 2410 | 3578 | 3065 | 3322 |
|  | 1.0 | 2856 | 2504 | 2680 | 2415 | 3497 | 2956 |
|  | 0.1 | 2101 | 2085 | 2093 | 1403 | 1217 | 1310 |
| 40 | 5.0 | 902 | 797 | 850 | 605 | 502 | 554 |
|  | 1.0 | 1244 | 1216 | 1230 | 1116 | 318 | 717 |
|  | 0.1 | 304 | 210 | 257 | 54 | 54 | 54 |
| 43 | 5.0 | 940 | 720 | 830 | 54 | 54 | 54 |
|  | 1.0 | 721 | 852 | 787 | 54 | 54 | 54 |
|  | 0.1 | 37 | 36 | 37 | 54 | 54 | 54 |
| 27 | 5.0 | 1978 | 2295 | 2137 | 3603 | 4546 | 4075 |
|  | 1.0 | 1833 | 2373 | 2103 | 3634 | 4735 | 4185 |
|  | 0.1 | 1761 | 1945 | 1853 | 2401 | 2313 | 2357 |
| 41 | 5.0 | 1590 | 1898 | 1744 | 3328 | 4447 | 3888 |
|  | 1.0 | 1611 | 1910 | 1761 | 4197 | 3402 | 3800 |
|  | 0.1 | 1738 | 1853 | 1796 | 3030 | 3016 | 3023 |
| 42 | 5.0 | 1507 | 1887 | 1697 | 2747 | 3203 | 2975 |
|  | 1.0 | 2185 | 2269 | 2227 | 2609 | 4162 | 3386 |
|  | 0.1 | 669 | 669 | 669 | 192 | 206 | 199 |
| 44 | 5.0 | 1870 | 1805 | 1838 | 2593 | 2802 | 2698 |
|  | 1.0 | 2058 | 1854 | 1956 | 1464 | 1747 | 1606 |
|  | 0.1 | 235 | 214 | 225 | 54 | 54 | 54 |
| 45 | 5.0 | 1716 | 1597 | 1657 | 2153 | 1776 | 1965 |
|  | 1.0 | 1341 | 1175 | 1258 | 1567 | 1368 | 1468 |
|  | 0.1 | 646 | 446 | 546 | 54 | 54 | 54 |
| 46 | 5.0 | 525 | 392 | 459 | 54 | 54 | 54 |
|  | 1.0 | 234 | 132 | 183 | 54 | 54 | 54 |
|  | 0.1 | 36 | 36 | 36 | 54 | 54 | 54 |
| 47 | 5.0 | 746 | 738 | 742 | 54 | 54 | 54 |
|  | 1.0 | 757 | 752 | 755 | 54 | 54 | 54 |
|  | 0.1 | 59 | 64 | 62 | 54 | 54 | 54 |
| 48 | 5.0 | 578 | 676 | 627 | 54 | 54 | 54 |
|  | 1.0 | 697 | 786 | 742 | 54 | 54 | 54 |
|  | 0.1 | 41 | 51 | 46 | 54 | 54 | 54 |
| 49 | 5.0 | 1095 | 1288 | 1192 | 376 | 778 | 577 |
|  | 1.0 | 1510 | 1551 | 1531 | 54 | 54 | 54 |
|  | 0.1 | 79 | 111 | 95 | 54 | 54 | 54 |
| 50 | 5.0 | 586 | 424 | 505 | 54 | 54 | 54 |
|  | 1.0 | 206 | 178 | 192 | 54 | 54 | 54 |
|  | 0.1 | 39 | 44 | 42 | 54 | 54 | 54 |
| 51 | 5.0 | 1341 | 1117 | 1229 | 955 | 1023 | 989 |
|  | 1.0 | 1412 | 1257 | 1335 | 426 | 845 | 636 |
|  | 0.1 | 92 | 75 | 84 | 54 | 54 | 54 |
| 52 | 5.0 | 1855 | 1557 | 1706 | 2408 | 2107 | 2258 |
|  | 1.0 | 2961 | 2821 | 198 | 4421 | 5632 | 5027 |
|  | 0.1 | 205 | 245 | 225 | 54 | 934 | 494 |
| 36 | 5.0 | 1717 | 1656 | 1687 | 3390 | 3338 | 3364 |
|  | 1.0 | 1480 | 1510 | 1495 | 2547 | 2832 | 2690 |
|  | 0.1 | 700 | 571 | 636 | 384 | 264 | 324 |
| 36 | 5.0 | 1478 | 1565 | 1522 | 2281 | 2200 | 2241 |
|  | 1.0 | 1293 | 1235 | 1264 | 2073 | 3112 | 2593 |
|  | 0.1 | 666 | 590 | 628 | 54 | 448 | 251 |
| 37 | 5.0 | 1679 | 1918 | 1799 | 3240 | 3748 | 3494 |
|  | 1.0 | 1603 | 1561 | 1582 | 3950 | 4437 | 4194 |
|  | 0.1 | 1232 | 1235 | 1234 | 1548 | 2044 | 1796 |

TABLE 16-continued

Murine Splenocyte Assay - IL-12 & IFN-γ

| Test (SEQ ID NO) or Control | Dose (ug/ml) | IL-12 (pg/ml) | | | IFN-γ (pg/ml) | | |
|---|---|---|---|---|---|---|---|
| | | Rep. 1 | Rep. 2 | Ave. | Rep. 1 | Rep. 2 | Ave. |
| 37 | 5.0 | 2064 | 3202 | 2633 | 2419 | 2631 | 2525 |
| | 1.0 | 1895 | 2417 | 2156 | 1894 | 3332 | 2613 |
| | 0.1 | 831 | 1430 | 1131 | 293 | 530 | 412 |

From the results presented in Tables 15 and 16, all compounds containing CpG motifs induced IL-12 production from murine splenocytes and most, but not all, compounds containing CpG motifs induced IL-6 and IFN-γ production from murine splenocytes. As can been seen from the results presented in Tables 15 and 16, although IL-6, IL-12 and IFN-γ stimulatory activity of immunostimulatory polynucleotides on murine splenocytes is generally dependent on the presence of a CG dinucleotide, it does not appear to require the more specialized motifs described herein for high IFN-α induction.

Example 4

Stimulation of Interferon-Inducible Gene Expression by Immunomodulatory Polynucleotides As demonstrated herein, immunomodulatory polynucleotides can induce production of IFN-γ and/or IFN-α from PBMCs. IMPs were assayed for activity on human PBMCs for inducing mRNA expression of additional cytokine genes, chemokine genes and other genes using a quantitative PCR technique, the TaqMan technique. The polynucleotides tested were fully modified phosphorothioate oligodeoxynucleotides. Among the polynucleotides tested were SEQ ID NO:1 (positive control) and SEQ ID NO:2 (negative control).

Human PMBCs were prepared as described in Example 1. The cells were cultured in the presence of test samples (IMPs or controls) at 5 µg/ml µg/ml for 24 hours. Total RNA was extracted using the Qiagen RNeasy Mini Protocol (Qiagen) and converted to cDNA using oligo dT (Promega), random hexamers (Promega), and SuperScript RT II (InVitrogen). cDNA was diluted 1:10 and PCR conducted using either QuantiTect SYBR green PCR master mix (Qiagen) and naked primers (synthesized by Operon) or QuantiTect probe PCR master mix (Qiagen) and PDAR primers with labeled probe (Applied BioSystems). Reactions were conducted using the GeneAmp 5700 Sequence Detector (PE BioSystems).

Examples of the sequences for synthesized primers are as follows (listed 5' to 3'):

Ubiquitin
(F: CACTTGGTCCTGCGCTTGA (SEQ ID NO: 200),
R: CAATTGGGAATGCAACAACTTTAT (SEQ ID NO: 201));

2,5-OAS
(F: AGGGAGCATGAAAACACATTTCA (SEQ ID NO: 202),
R: TTGCTGGTAGTTTATGACTAATTCCAAG (SEQ ID NO: 203));

GBP-1
(F: TGGAACGTGTGAAAGCTGAGTCT (SEQ ID NO: 204),
R: CATCTGCTCATTCTTTCTTTGCA (SEQ ID NO: 205));

IFN-α
(F: CCCAGGAGGAGTTTGGCAA (SEQ ID NO: 206),
R: TGCTGGATCATCTCATGGAGG (SEQ ID NO: 207));

ISG-54K
(F: CTGGACTGGCAATAGCAAGCT (SEQ ID NO: 208),
R: AGAGGGTCAATGGCGTTCTG (SEQ ID NO: 209));

MCP-2
(F: CTGCTCATGGCAGCCACTTT (SEQ ID NO: 210),
R: AGCAGGTGATTGGAATGGAAA (SEQ ID NO: 211));

MIG
(F: CATCTTGCTGGTTCTGATTGGA (SEQ ID NO: 212),
R: TGGTGCTGATGCAGGAACAG (SEQ ID NO: 213));

TNF-α
(F: CTTCTGCCTGCTGCACTTTG (SEQ ID NO: 214),
R: CTGGGCCAGAGGGCTGAT (SEQ ID NO: 215)).

IFN-γ, IL-1α, IL-6, IP-10, MCP-3, and MIP-3β, were measured using PDARs supplied by PE BioSystems. Threshold cycle ($C_T$) values for each gene were normalized to ubiquitin using the formula $1.8^{(UBQ-GENE)}(100,000)$, where UBQ is the mean $C_T$ of triplicate ubiquitin runs, GENE is the mean $C_T$ of duplicate runs of the gene of interest, and 100,000 is arbitrarily chosen as a factor to bring all values above 0. The negative control for each experiment, stimulation with medium alone, is assigned a value of 1 and all data is expressed as fold induction over the negative control.

Table 17 summarizes assay results for cytokine, chemokine and inflammatory protein gene expression from PBMCs in response to the IMP SEQ ID NO:27. Also tested was polynucleotide 5'-GGTGCATCGATGCAGGGGGG (SEQ ID NO:154). Data is presented as the mean of fold induction over medium control (given the value of 1.0) with SEM.

TABLE 17

Profile of gene expression modulated by IMP

| Test or Control (SEQ ID NO) | IL-1α | | IP-10 | | MCP-2 | | MCP-3 | | MIG | | MIP-3β | | 2,5-OAS | | GBP-1 | | ISG-54K | |
|---|---|---|---|---|---|---|---|---|---|---|---|---|---|---|---|---|---|---|
| | mean | SEM | mean | SEM | mean | SEM | mean | SEM | mean | SEM | mean | SEM | mean | SEM | mean | SEM | mean | SEM |
| medium | 1.0 | 0.0 | 1.0 | 0.0 | 1.0 | 0.0 | 1.0 | 0.0 | 1.0 | 0.0 | 1.0 | 0.0 | 1.0 | 0.0 | 1.0 | 0.0 | 1.0 | 0.0 |
| 2 | 2.0 | 0.7 | 0.6 | 0.3 | 0.2 | 0.1 | 0.9 | 0.1 | 0.6 | 0.1 | 1.2 | 0.3 | 0.7 | 0.2 | 1.0 | 0.1 | 0.7 | 0.1 |
| 1 | 1.7 | 0.4 | 2.7 | 0.6 | 28.3 | 21.2 | 3.0 | 1.0 | 3.0 | 0.9 | 2.9 | 0.9 | 7.6 | 3.3 | 2.5 | 0.6 | 4.9 | 2.1 |
| 27 | 0.4 | 0.2 | 94.0 | 27.5 | 198.8 | 59.6 | 8.0 | 2.2 | 8.8 | 2.0 | 6.9 | 1.8 | 16.5 | 2.3 | 5.9 | 0.4 | 27.1 | 2.6 |
| 154 | 0.2 | 0.1 | 145.4 | 65.1 | 284.8 | 108.7 | 8.5 | 1.4 | 14.5 | 7.0 | 10.5 | 2.1 | 15.7 | 1.3 | 5.7 | 1.1 | 31.9 | 2.1 |

As shown in Table 17, SEQ ID NO:27 strongly increased expression of the chemokines IP-10, MCP-2, MCP-3, MIG, and MIP-3β. The expression of IL-1α decreased in the presence of SEQ ID NO:27. In addition, SEQ ID NO:27 markedly increased expression of the IFN-α-inducible genes 2,5-oligoadenylate synthetase (2,5-OAS), interferon-stimulating gene-54K (ISG-54K), and guanylate-binding protein-1 (GBP-1).

In these assays, the IMP SEQ ID NO:27 had no significant effect on the expressed mRNA levels of the cytokines G-CSF, IL-1β, IL-6, IL-12 p40, IL-23, TNF-α, or of the chemokines BCA-1, IL-8, LPTN, MCP-1, MDC, MIP-1a, MIP-1b, MIP-3a, RANTES, and TARC.

Example 5

Stimulation of NK Cell Lytic Activity by Immunomodulatory Polynucleotides

IMPs of the present invention stimulate improved natural killer (NK) cell lytic activity as compared to an IMP standard. NK cell lytic activity was assayed through lysis of K562 target cells. In brief, PBMCs were stimulated with 10 mg/ml IMP (previously obtained optimal dose) or negative control polynucleotide for 48 hours in culture. The treated PBMCs were then co-cultured with $^{51}$Cr-loaded K562 tumor target cells at a range of effector:target ratios for 4 hours. $^{51}$Cr released upon cell lysis was measured by a TopCount NXT scintillation counter (Packard) and reported as counts per minute (cpm).

Figure 2:
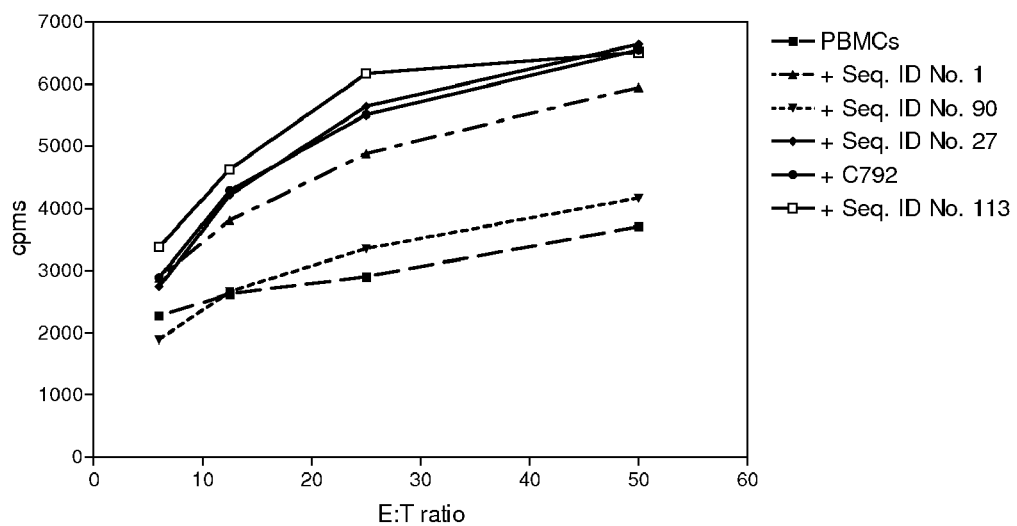
FIG. 2 contains graphs depicting NK cell lytic activity stimulated by IMPs.
Figure 2:
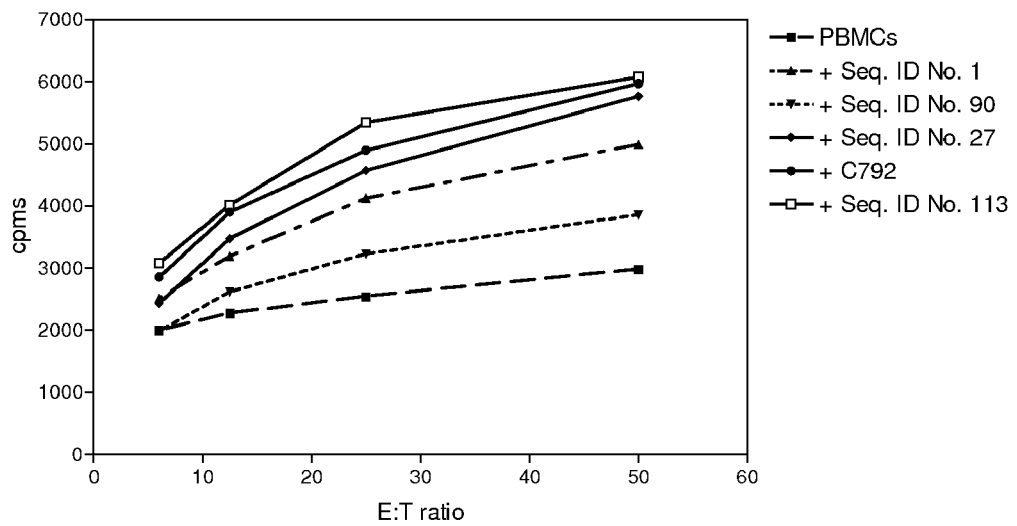

Results of NK cell stimulation from two different PBMC donors is shown in FIG. 2. The IMPs used in the assays were SEQ ID NO:1, SEQ ID NO:90, SEQ ID NO:27, SEQ ID NO:172 and SEQ ID NO:113. The palindrome length in the IMPs is: 28 bases in SEQ ID NO:172, 22 bases in SEQ ID NO:113, 12 bases in SEQ ID NO:27, and 8 bases in SEQ ID NO:1. SEQ ID NO:90, a non-IMP control, has a palindrome length of 20 bases but does not contain a 5'-C, G-3' sequence. In this experiment, IMPs with palindromes of 12 bases in length or longer stimulated an increased amount NK cell lytic activity as compared to the IMP standard SEQ ID NO:1 with a palindrome length of 8 bases.

Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention.

What is claimed is:

1. An immunomodulatory polynucleotide, comprising:
   a) 5'-$N_x(TCG(N_q))_y N_w(X_1 X_2 CGX_2' X_1'(CG)_p)_z$ (SEQ ID NO: 156)
   wherein N are nucleosides, x=0, y=1, w=0, p=0 or 1, q=0, 1 or 2, and z=1-20, $X_1$ and $X_1'$ are self-complimentary nucleosides, $X_2$ and $X_2'$ are self-complimentary nucleosides, and wherein the 5' T of the $(TCG(N_q))_y$ sequence is positioned at the 5' end of the polynucleotide; and
   b) a palindromic sequence at least 8 bases in length wherein the palindromic sequence comprises the first $(X_1 X_2 CGX_2' X_1')$ of the $(X_1 X_2 CGX_2' X_1'(CG)_p)_z$ sequences, wherein the polynucleotide is at least 15 bases in length.

2. An immunomodulatory polynucleotide according to claim 1 wherein the palindromic sequence has a base composition of more than one-third A's and T's.

3. An immunomodulatory polynucleotide according to claim 1 wherein the wherein the IMP comprises a sequence selected from the group consisting of SEQ ID NO: 172, SEQ ID NO: 55, SEQ ID NO: 113, SEQ ID NO: 39, SEQ ID NO: 53, SEQ ID NO: 109, SEQ ID NO: 117, SEQ ID NO: 175, SEQ ID NO: 147, SEQ ID NO: 148, SEQ ID NO: 80, SEQ ID NO: 97, SEQ ID NO: 150, SEQ ID NO: 151, SEQ ID NO: 152, SEQ ID NO: 153, SEQ ID NO: 168, SEQ ID NO: 169, SEQ ID NO: 170, SEQ ID NO: 173, SEQ ID NO: 174, SEQ ID NO: 81, SEQ ID NO: 82, SEQ ID NO: 83, SEQ ID NO: 84, SEQ ID NO: 79, SEQ ID NO: 77, SEQ ID NO: 40, SEQ ID NO: 41, SEQ ID NO: 42, SEQ ID NO: 54, SEQ ID NO: 56, SEQ ID NO: 43, SEQ ID NO: 78, SEQ ID NO: 118, SEQ ID NO: 176, SEQ ID NO: 177, SEQ ID NO: 178, SEQ ID NO: 179, and SEQ ID NO: 180.

4. An immunomodulatory composition comprising an immunomodulatory polynucleotide according to claim 1 or 3.

5. A method of modulating an immune response in an individual comprising: administering to an individual an immunomodulatory polynucleotide according to claim 1 or 3 in an amount sufficient to modulate an immune response in said individual.

6. A method of increasing interferon-gamma (IFN-γ) in an individual, comprising: administering an immunomodulatory polynucleotide according to according to claim 1 or 3 to said individual in an amount sufficient to increase IFN-γ in said individual.

7. A method of increasing interferon-alpha (IFN-α) in an individual, comprising: administering an immunomodulatory polynucleotide according to claim 1 or 3 to said individual in an amount sufficient to increase IFN-α in said individual.

8. A method of ameliorating a symptom of an infectious disease in an individual, comprising: administering an effective amount of an immunomodulatory polynucleotide according to claim 1 or 3 to the individual, wherein an effective amount is an amount sufficient to ameliorate a symptom of said infectious disease.

9. A method of ameliorating a symptom of an IgE-related disorder in an individual, comprising: administering an effective amount of an immunomodulatory polynucleotide according to claim 1 or 3 to an individual having an IgE-related disorder, wherein an effective amount is an amount sufficient to ameliorate a symptom of said IgE-related disorder.

10. An immunomodulatory composition comprising an immunomodulatory polynucleotide according to claim 1 or 3 wherein the immunomodulatory polynucleotide comprises a modification of one or more phosphate groups.

11. The immunomodulatory composition of claim 10 wherein the modification of one or more phosphate groups is a phosphorothioate linkage.

12. The immunomodulatory composition of claim 10 wherein the modification of one or more phosphate groups are phosphorothioate and phosphodiester linkages.

\* \* \* \* \*

UNITED STATES PATENT AND TRADEMARK OFFICE
CERTIFICATE OF CORRECTION

PATENT NO. : 8,158,768 B2
APPLICATION NO. : 12/566521
DATED : April 17, 2012
INVENTOR(S) : Dino Dina et al.

It is certified that error appears in the above-identified patent and that said Letters Patent is hereby corrected as shown below:

ON THE TITLE PAGE:

OTHER PUBLICATIONS:

Page two, in column 2, line 50, delete "Administation" and insert -- Administration --

Page three, in column 1, line 8, delete "Phosphorotioate" and insert -- Phosphorothioate --

Page three, in column 1, line 48, delete "Letha" and insert -- Lethal --

Page three, in column 2, line 49, delete "Myobacterium" and insert -- Mycobacterium --

Page three, in column 1, line 33, delete "Names," and insert -- Hames, --

Page four, in column 1, line 48, delete "Indentified" and insert -- Identified --

Page four, in column 2, line 6, delete "Enconding" and insert -- Encoding --

Page four, in column 2, line 7, delete "Myobacterium" and insert -- Mycobacterium --

Page five, in column 1, line 7, delete "moncytogenes" and insert -- monocytogenes --

Page five, in column 1, line 12, delete "Leuokocyte" and insert -- "Leukocyte --

Page five, in column 2, line 3, delete "Respones,"" and insert -- Responses," --

Page six, in column 1, line 14, delete ""Oligodeoxynucleoside" and insert -- "Oligodeoxynucleotide --

Page six, in column 1, line 20, delete "Acvitivty" and insert -- Activity --

Page six, in column 1, line 34, delete "Immuization:" and insert -- Immunization: --

Page six, in column 1, line 48, delete "Nucleotied" and insert -- Nucleotide --

Page six, in column 1, line 52, delete "Practioners" and insert -- Practitioners --

Page six, in column 1, line 69, delete "Oligionucleotides"" and insert -- Oligonucleotides" --

Page six, in column 2, line 35, delete "Murnie" and insert -- Murine --

Page six, in column 2, line 57, delete "Immunzation" and insert -- Immunization --

Page seven, in column 1, line 7, delete "Internucleoside" and insert -- Internucleotide --

Page seven, in column 1, line 37, delete "Oligonuceleotides" and insert -- Oligonucleotides --

Signed and Sealed this
Eleventh Day of November, 2014

Michelle K. Lee
*Deputy Director of the United States Patent and Trademark Office*

CERTIFICATE OF CORRECTION (continued)
U.S. Pat. No. 8,158,768 B2

Page seven, in column 1, line 55, delete "Pharmocological" and insert -- Pharmacological --

Page seven, in column 1, line 65, delete "Antien" and insert -- Antigen --

Page seven, in column 2, line 28, delete "Lymphocyts" and insert -- Lymphocytes --

Page seven, in column 2, line 44, delete "Luekocytes" and insert -- Leukocytes --

Page seven, in column 2, line 65, delete ""Oligonucleoside" and insert -- "Oligonucleotide --

IN THE SPECIFICATION:

BACKGROUND OF THE INVENTION:

In column 2, line 66, delete "(2002)Microbes" and insert -- (2002) Microbes --

In column 3, line 55, delete "(455)" and insert -- (45S) --

DISCLOSURE OF THE INVENTION:

In column 5, line 18, delete ")$_p$)," and insert -- )$_p$)$_z$ --

In column 5, line 27, delete "(TCG(Ng))$_3$," and insert -- (TCG($N_q$))$_y$ --

In column 5, line 45, delete "(Ng))$_3$," and insert -- ($N_q$))$_y$ --

In column 5, line 50, delete "(CG)$_p$)," and insert -- (CG)$_p$)$_z$ --

In column 5, line 67, delete "($N_q$))z" and insert -- ($N_q$))$_y$ --

In column 6, line 7, delete "$X_1X_2CGCGX_3'X_2'X_1'$" and insert -- $X_1X_2CGCGX_2'X_1'$ --

MODES FOR CARRYING OUT THE INVENTION:

In column 8, line 35, delete "oligonucleosides" and insert -- oligonucleotides --

DEFINITIONS:

In column 9, line 57, delete "linked" and insert -- linked. --

In column 10, lines 9-10, delete "Hemophilus" and insert -- Haemophilus --

In column 11, line 3, delete "Formadley" and insert -- Fornadley --

In column 11, line 45, delete "speherical" and insert -- spherical --

In column 11, line 56, delete "erodable" and insert -- erodible --

In column 16, line 5, delete "($N_g$)" and insert -- ($N_q$) --

In column 16, line 56, delete "$X_2' X_1'$" and insert -- $X_2'X_1'$ --

In column 22, line 15, delete "($N_g$)" and insert -- ($N_q$) --

In column 22, line 56, delete "$X_2X_1$" and insert -- $X_2'X_1'$ --

In column 23, line 38, delete "$X_2:X_1$" and insert -- $X_2X_1$ --

In column 26, line 5, delete "palidromic" and insert -- palindromic --

In column 26, line 21, delete "5'" and insert -- 5 --

In column 28, line 54, delete ""Oligonucleoside" and insert -- "Oligonucleotide --

In column 28, line 60, delete "phosphoramidiates" and insert -- phosphoramidites --

In column 28, line 61, delete "phosphorodithioates" and insert -- phosphorothioates --

In column 31, line 36, delete "limit" and insert -- limit. --

CERTIFICATE OF CORRECTION (continued)
U.S. Pat. No. 8,158,768 B2

In column 32, line 36, delete "lactoglobin" and insert -- lactoglobulin --

In column 32, line 41, delete "Hey" and insert -- Hev --

TABLE 1 RECOMBINANT ALLERGENS:

In column 33, line 44, delete "topomyosin" and insert -- tropomyosin --

In column 34, line 73, delete "Chin" and insert -- Clin --

In column 35, line 36, delete "Hemophilus" and insert -- Haemophilus --

In column 37, line 65, delete "oligonucleosides," and insert -- oligonucleotides, --

In column 40, line 1, delete "myristylation," and insert -- myristoylation, --

In column 42, line 66, delete "maleiamide," and insert -- maleimide, --

In column 43, lines 59-60, delete "polyisohexlcyanoacrylate" and insert -- polyisohexylcyanoacrylate --

In column 45, line 22, delete "polyvinylpirrolidone" and insert -- polyvinylpyrrolidone --

In column 48, line 33, delete "Gent" and insert -- Agent --

In column 51, line 46, delete "glucosylamine" and insert -- glycosylamine --

In column 51, line 50, delete "stablizing" and insert -- stabilizing --

In column 51, line 67, delete "cetyltrimethylamonia" and insert -- cetyltrimethylammonium --

In column 52, lines 2-3, delete "dedecyltrimethylammonium" and insert -- dodecyltrimethylammonium --

In column 52, line 3, delete "alklylammonium" and insert -- alkylammonium --

In column 52, line 4, delete "tetradecyltrimtheylammonia" and insert -- tetradecyltrimethylammonium --

In column 52, line 5, delete "tetradecyltrimtheylammonium" and insert -- tetradecyltrimethylammonium --

In column 52, line 7, delete "stablizing" and insert -- stabilizing --

In column 52, line 21, delete "stablizing" and insert -- stabilizing --

In column 52, line 23, delete "stablizing" and insert -- stabilizing --

In column 52, line 39, delete "docosahexanoic acid" and insert -- docosahexaenoic acid, --

In column 53, lines 2-3, delete "synthatse" and insert -- synthetase --

In column 59, line 52, delete "Noxema" and insert -- Noxzema --

In column 64, line 65, delete "GAquew" and insert -- GA --

In column 67, line 64, delete " IFN-$\alpha$ " and insert -- IFN-α --

IN THE CLAIMS:

In column 179, claim 3, line 57, delete "wherein the wherein the" and insert -- wherein the --

In column 180, claim 6, line 51, delete "according to according to" and insert -- according to --